(12) United States Patent
Estell et al.

(10) Patent No.: US 11,473,075 B2
(45) Date of Patent: Oct. 18, 2022

(54) APRL-CLADE SUBTILISIN PROTEASE VARIANTS AND USES THEREOF

(71) Applicant: DANISCO US INC, Palo Alto, CA (US)

(72) Inventors: David A. Estell, San Mateo, CA (US); Frits Goedegebuur, Vlaardingen (NL); Marc Anton Bernhard Kolkman, Oegstgeest (NL); Rie Mejldal, Ostbirk (DK); Katherine Augustyn, San Francisco, CA (US); Lilia Maria Babe, Emerald Hills, CA (US); Richard R Bott, Kirkland, WA (US); Jian Yao, Sunnyvale, CA (US); Roopa Santosh Ghirnikar, Sunnyvale, CA (US)

(73) Assignee: DANISCO US INC., Palo Alto, CA (US)

( * ) Notice: Subject to any disclaimer, the term of this patent is extended or adjusted under 35 U.S.C. 154(b) by 0 days.

(21) Appl. No.: 16/720,106

(22) Filed: Dec. 19, 2019

(65) Prior Publication Data

US 2020/0123522 A1    Apr. 23, 2020

Related U.S. Application Data

(63) Continuation of application No. 15/572,882, filed as application No. PCT/US2016/032514 on May 13, 2016, now abandoned.

(60) Provisional application No. 62/161,077, filed on May 13, 2015.

(51) Int. Cl.
    *C12N 9/54*     (2006.01)
    *C11D 3/386*    (2006.01)

(52) U.S. Cl.
    CPC .............. *C12N 9/54* (2013.01); *C11D 3/386* (2013.01); *C11D 3/38681* (2013.01); *C12Y 304/21062* (2013.01)

(58) Field of Classification Search
    CPC ............................................. C12Y 304/21062
    USPC ........................................................ 435/222
    See application file for complete search history.

(56) References Cited

U.S. PATENT DOCUMENTS

2016/0312204 A1 * 10/2016 Kolkman ........... C11D 3/38681

FOREIGN PATENT DOCUMENTS

| EP | 0405901 A1 | 1/1991 |
| WO | 1996/28557 A2 | 9/1996 |
| WO | 2010/056640 A2 | 5/2010 |

OTHER PUBLICATIONS

A_Geneseq database Acc# BER84672, result 1202, SID192 from Marquez et al, WO2017210295. Alignment with SID2.*
Published_Applications_AA_Main database result 698, SID79 from Kolkman US-20160312204. Alignment with SID2.*
International Search Report and Written Opinion—PCT/US2016/032514—dated Aug. 22, 2016.

* cited by examiner

Primary Examiner — Sheridan Swope

(57) ABSTRACT

The present disclosure provides AprL-clade protease enzymes, including variant AprL-clade protease enzymes, nucleic acids encoding same, and compositions and methods related to the production and use thereof, including an AprL-clade variant subtilisin enzyme that has improved stability and/or soil removal compared to a parent AprL-clade subtilisin enzyme.

16 Claims, 15 Drawing Sheets

Specification includes a Sequence Listing.

```
                                                     251                        277
                    AprL(SEQ ID NO:2)        (248)  RLSSTATYLGSSFYYGKGLINVEAAAQ
      B_licheniformis_CAA62667 (SEQ ID NO:12) (248) RLSSTATYLGSSFSYRGLINVEAAAQ
     B_licheniformis_AEU12640.1 (SEQ ID NO:13) (248) RLSSTATYLGSSFYYGKGLINVEAAAQ
   B_licheniformis_YP_006712489 (SEQ ID NO:14) (248) RLSSTATYLGSSFYYGKGLINVEAAAQ
                   BliD02339 (SEQ ID NO:9)    (248) RLSSTATYLGSSFYYGKGLINVEAAAQ
       B_licheniformis_DY_P00781 (SEQ ID NO:15) (248) RLSSTATNLGDSFYYGKGLINVEAAAQ
       B_sonorensis_WP_006636716 (SEQ ID NO:16) (248) RLSSTATNLGDSFYYGKGLINVEAAAQ
                  B_lentus_P29600 (SEQ ID NO:17) (243) HLKNTATSLGSNLYGSGLVNAEAATR
             B_clausii_BAD63300 (SEQ ID NO:18) (243) HLKNTATGLGNNLYGSGLVNAEAATR
             B_lehensis_AFK08970 (SEQ ID NO:19) (243) HLKNTATNLGNTTGSGLVNAEAATR
            B_subtilis_AAA87324 (SEQ ID NO:20) (243) HLKNTATNLGNTTGSGLVNAEAATR
           Bacillus_sp_BAA25184 (SEQ ID NO:21) (243) HLKNTATNLGNTNGSGLVNAEAATR
             B_sp_Sendai_BAA06157 (SEQ ID NO:22) (243) HLTSTATSLGNSNGSGLVNAEAATR
             B_clausii_ABI26631 (SEQ ID NO:23) (243) RLNQTATYLGSPSLYGNGLVHAGRATQ
          B_halodurans_BAD04574 (SEQ ID NO:24) (243) RLNQTATYLGSPSLYGNGLVHAGRATQ
           Bacillus_sp_ADD64465 (SEQ ID NO:25) (243) RLNQTATYLGSNLYGNGLVHAGRATQ
         B_pseudofirmus_ADC49870 (SEQ ID NO:26) (247) RLNQTAIPLGNSTYGNGLVDAEYAAQ
            B_sp_sprD_AAC43581 (SEQ ID NO:27) (250) RLRDTATNLGSFNYGNGLINIERALQ
           Bacillus_sp_BAD21128 (SEQ ID NO:28) (250) ILRDTATNLGSSFYYGNGLDVEKALQ
           Bacillus_sp_sprC_AAC43580 (SEQ ID NO:29) (249) HLKNTATNLGDTTYGKGLINVESALQ
           Bacillus_sp_BAD11988 (SEQ ID NO:30) (249) KLNSTATYLGSSFYYGNGLINVERALQ
             B_circulans_ADN04910 (SEQ ID NO:31) (249) RLENTATPLGNSFYYGKGLINVQAASN
             B_lehensis_AFP23380 (SEQ ID NO:32) (250) RLENTATPLGNSFYYGKGLINVQAASN
   B_stratosphericus_WP_007497196 (SEQ ID NO:33) (249) RLENTATPLGNSFYYGKGLINVQAASN
              B_pumilus_ADK11996 (SEQ ID NO:34) (249) RLENTATPLGDSFYYGKGLINVQAASN
         Bac_sp_HYC10_WP008359041 (SEQ ID NO:35) (249) RLENTATPLGSSFYYGKGLINVQAAN
          B_atrophaeus_YP003972439 (SEQ ID NO:36) (249) SLESTATNLGNSFYYGKGLINVQAAAQ
        B_amyloliquefaciens_CAA24990 (SEQ ID NO:37) (249) SLENTTKLGDSFYYGKGLINVQAAAQ
         B_methylotrophicus_AGC81872 (SEQ ID NO:38) (249) SLENTTKLGDAFYYGKGLINVQAAAQ
        G_stearothermophilus_ABY25856 (SEQ ID NO:39) (249) SLENTTKLGDAFYYGKGLINVQAAAQ
         B_vallismortis_WP010329279 (SEQ ID NO:40) (249) RLESTATYLGSSFYYGKGLINVQAAAQ
                B_subtilis_ACJ07037 (SEQ ID NO:41) (249) RLESTATYLGSSFYYGKGLINVQAAAQ
          B_subtilis_str168_CAA74536 (SEQ ID NO:42) (249) RLESTATYLNSFYYGKGLINVQAAAQ
           B_mojavensis_WP010333625 (SEQ ID NO:43) (249) RLESTATYLGSFYYGKGLINVQAAAQ
               B_subtilis_BAN09118 (SEQ ID NO:44) (249) RLESTATNLGSSFYYGKGLINVQAAAQ
                  SEQ ID NO:53 Consensus    (251) RL NTAT LG SFYYGKGLINVEAAAQ
```

Fig. 2F

```
                                            1                                                  50
                  AprL(SEQ ID NO:2)    (1)  AQTVPYGIPLIKADKVQAQGFKGANVKVAVLDTGIQASHPDLNVVGGASF
B_licheniformis_YP_006712489(SEQ ID NO:14) (1)  AQTVPYGIPLIKADKVQAQGFKGANVKVAVLDTGIQASHPDLNVVGGASF
             BLID02339(SEQ ID NO:9)    (1)  AQTVPYGIPLIKADKVQAQGFKGANVKVAVLDTGIQASHPDLNVVGGASF
      B_licheniformis_CAA62667(SEQ ID NO:12) (1)  AQTVPYGIPLIKADKVQAQGFKGANVKVAVLDTGIQASHPDLNVVGGASF
      B_licheniformis_AEU12640(SEQ ID NO:13) (1)  AQTVPYGIPLIKADKVQAQGFKGANVKGAIATGIPSHPDLNVVGGASF
      B_licheniformis_DY_P00781(SEQ ID NO:15) (1)  AQTVPYGIPLIKADKVQAQGFKGANVKVGIIDTGIASHPDLAVVGGASF
      B_sonorensis_WP_006636716(SEQ ID NO:16) (1)  AQTVPYGIPLIKADKVQAQGFKGANVKVIIDTGIASHPDLNVVGGASF
                          Consensus   (1)  AQTVPYGIPLIKADKVQAQGFKGANVKVAVLDTGIQASHPDLNVVGGASF 51                                                100
                  AprL(SEQ ID NO:2)   (51)  VAGEAYNTDGNGHGTHVAGTVAALDNTTGVLGVAPSVSLYAVKVLNSSGS
B_licheniformis_YP_006712489(SEQ ID NO:14) (51)  VAGEAYNTDGNGHGTHVAGTVAALDNTTGVLGVAPNVSLYAVKVLNSSGS
             BLID02339(SEQ ID NO:9)   (51)  VAGEAYNTDGNGHGTHVAGTVAALDNTTGVLGVAPNVSLYAVKVLNSSGS
      B_licheniformis_CAA62667(SEQ ID NO:12) (51)  VAGEAYNTDGNGHGTHVAGTVAALDNTTGVLGVAPSVSLYAVKVLNSSGS
      B_licheniformis_AEU12640(SEQ ID NO:13) (51)  VAGEAYNTDGNGHGTHVAGTVAALDNTTGVLGVAPSVSLYAVKVLNSSGS
      B_licheniformis_DY_P00781(SEQ ID NO:15) (51)  VSGEAYNTDGNGHGTHVAGTVAALDNTTGVLGVAPNVSLYAVKVLNSSGS
      B_sonorensis_WP_006636716(SEQ ID NO:16) (51)  VSGEAYNTDGNGHGTHVAGTVAALDNTTGVLGVAPNVSLYAVKVLNSSGS
                          Consensus  (51)  VAGEAYNTDGNGHGTHVAGTVAALDNTTGVLGVAPNVSLYAVKVLNSSGS 101                                               150
                  AprL(SEQ ID NO:2)  (101)  GSYSGIVSGIEWATTNGMDVINMSLGGASGSTAMKQAVDNAYARGVVVA
B_licheniformis_YP_006712489(SEQ ID NO:14)(101) GSYSGIVSGIEWATTNGMDVINMSLGGPSGSTAMKQAVDNAYARGVVVA
             BLID02339(SEQ ID NO:9)  (101)  GSYSGIVSGIEWATTNGMDVINMSLGGPSGSTAMKQAVDNAYARGVVVA
      B_licheniformis_CAA62667(SEQ ID NO:12)(101) GSYSGIVSGIEWATTNGMDVINMSLGGASGSTAMKQAVDNAYARGAVVA
      B_licheniformis_AEU12640(SEQ ID NO:13)(101) GSYSGIVSGIEWATTNGMDVINMSLGGASGSTAMKQAVDNAYARGVVVA
      B_licheniformis_DY_P00781(SEQ ID NO:15)(101) GSYSGIVSGIEWATQNGMDVINMSLGGPSGSTAMKQAVDKAYASGVVVA
      B_sonorensis_WP_006636716(SEQ ID NO:16)(101) GSYSGIVSGIEWATQNGMDVINMSLGGPSGSTAMKQAVDKAYASGVVVA
                          Consensus (101)  GSYSGIVSGIEWATTNGMDVINMSLGGPSGSTAMKQAVDNAYARGVVVA 151                                               200
                  AprL(SEQ ID NO:2)  (151)  AAGNSGSSGNTNTIGYPAKYDSVIAVGAVDSNSNRASFSSVGAELEVMAP
B_licheniformis_YP_006712489(SEQ ID NO:14)(151) AAGNSGSSGNTNTIGYPAKYDSVIAVGAVDSNSNRASFSSVGAELEVMAP
             BLID02339(SEQ ID NO:9)  (151)  AAGNSGSSGNTNTIGYPAKYDSVIAVGAVDSNSNRASFSSVGAELEVMAP
      B_licheniformis_CAA62667(SEQ ID NO:12)(151) AAGNSGSSGNTNTIGYPAKYDSVIAVGAVDSNSNRASFSSVGAELEVMAP
      B_licheniformis_AEU12640(SEQ ID NO:13)(151) AAGNSGSSGNTNTIGYPAKYDSVIAVGAVDSNSNRASFSSVGAELEVMAP
      B_licheniformis_DY_P00781(SEQ ID NO:15)(151) AAGNSGSSGSQNTIGYPAKYDSVIAVGAVDSNSNRASFSSVGAELEVMAP
      B_sonorensis_WP_006636716(SEQ ID NO:16)(151) AAGNSGSSGSQNTIGYPAKYDSVIAVGAVDSNSNRASFSSVGAELEVMAP
                          Consensus (151)  AAGNSGSSGNTNTIGYPAKYDSVIAVGAVDSNSNRASFSSVGAELEVMAP 201                                               250
                  AprL(SEQ ID NO:2)  (201)  GAGVYSTYPTNTYATLNGTSMASPHVAGAAALILSKHPNLSASQVRNRLS
B_licheniformis_YP_006712489(SEQ ID NO:14)(201) GAGVYSTYPTNTYATLNGTSMASPHVAGAAALILSKHPNLSASQVRNRLS
             BLID02339(SEQ ID NO:9)  (201)  GAGVYSTYPTNTYATLNGTSMASPHVAGAAALILSKHPNLSASQVRNRLS
      B_licheniformis_CAA62667(SEQ ID NO:12)(201) GAGVYSTYPTNTYATLNGTSMASPHVAGAAALILSKHPNLSASQVRNRLS
      B_licheniformis_AEU12640(SEQ ID NO:13)(201) GAGVYSTYPTNTYATLNGTSMASPHVAGAAALILSKHPNLSASQVRNRLS
      B_licheniformis_DY_P00781(SEQ ID NO:15)(201) GVGVYSTYPTNTYATLNGTSMASPHVAGAAALILSKYPTLSASQVRNRLS
      B_sonorensis_WP_006636716(SEQ ID NO:16)(201) GVGVYSTYPTNTYATLNGTSMASPHVAGAAALILSKHPTLSASQVRNRLS
                          Consensus (201)  GAGVYSTYPTNTYATLNGTSMASPHVAGAAALILSKHPNLSASQVRNRLS 251       274
                  AprL(SEQ ID NO:2)  (251)  STATYLGSSFYYGKGLINVEAAQ
B_licheniformis_YP_006712489(SEQ ID NO:14)(251) STATYLGSSFYYGKGLINVEAAQ
             BLID02339(SEQ ID NO:9)  (251)  STATYLGSSFYYGKGLINVEAAQ
      B_licheniformis_CAA62667(SEQ ID NO:12)(251) RTATYLGSSFYYGKGLINVEAAQ
      B_licheniformis_AEU12640(SEQ ID NO:13)(251) STATYLGSSFYYGKGLINVEAAQ
      B_licheniformis_DY_P00781(SEQ ID NO:15)(251) STATNLGSSFYYGKGLINVEAAQ
      B_sonorensis_WP_006636716(SEQ ID NO:16)(251) STATNLGSSFYYGKGLINVEAAQ
                          Consensus (251)  STATYLGSSFYYGKGLINVEAAQ   SEQ ID NO:54
```

Fig. 3

APRL-CLADE SUBTILISIN PROTEASE VARIANTS AND USES THEREOF

CROSS REFERENCE TO RELATED APPLICATIONS

The present application is a Continuation of U.S. application Ser. No. 15/572,882, filed Nov. 9, 2017, which is a 371 of International Application No. PCT/US16/32514, filed May 13, 2016, which claims priority to U.S. Provisional Application No. 62/161,077, filed May 13, 2015, all of which are hereby incorporated by reference in their entirety.

REFERENCE TO SEQUENCE LISTING SUBMITTED ELECTRONICALLY

The official copy of the sequence listing is submitted electronically via EFS-Web 10 as an ASCII formatted sequence listing with a file named 20191217_NB40518USPCN2_SeqLst created on Dec. 17, 2019, and having a size of about 102 kilobytes and is filed concurrently with the specification. The sequence listing contained in this ASCII-formatted document is part of the specification and is herein incorporated by reference in its entirety.

Disclosed herein is one or more AprL-clade protease enzyme, including one or more AprL-clade protease variant, nucleic acids encoding same, and compositions and methods related to the production and use thereof, including an AprL-clade variant subtilisin enzyme that has improved stability and/or soil removal compared to the parent AprL-clade subtilisin enzyme.

Serine proteases are enzymes (EC No. 3.4.21) possessing an active site serine that initiates hydrolysis of peptide bonds of proteins. There are two broad categories of serine proteases, based on their structure: chymotrypsin-like (trypsin-like) and subtilisin-like. The prototypical subtilisin (EC No. 3.4.21.62) was initially obtained from *B. subtilis*. Subtilisins and their homologues are members of the S8 peptidase family of the MEROPS classification scheme. Members of family S8 have a catalytic triad in the order Asp, His and Ser in their amino acid sequence. Although serine proteases have long been known in the art of industrial enzymes, there remains a need for engineered proteases that are suitable for particular conditions and uses.

Some embodiments are directed to an AprL-clade variant subtilisin enzyme or an active fragment thereof comprising one or more amino acid modification to a parent AprL-clade subtilisin enzyme, wherein the modification is selected from: (i) A001C, A001D, A001E, A001Q, A001S, L010M, L010Q, S100G, S102K, S102R, Y103F, Y103M, S104D, G105M, G105R, S108F, S108H, S108K, S108R, E111Q, T114D, T115D, T115E, T115F, T115K, T115Q, N116E, K012C, K012F, K012H, K012M, K012N, K012Q, K012Y, V120S, M123C, M123I, L125I, G127A, G127D, G127I, G127M, G127S, G127T, G127V, A128E, A128H, A128K, A128P, A128R, A128S, A128T, S129H, S129Q, S129R, S129T, S129V, T132C, T132D, T132E, T132K, T132N, T132P, Q136A, Q136C, Q136K, Q136R, V138C, A143D, A143N, G145S, V147L, V148A, V148C, V148M, V148Q, K015A, K015C, K015E, K0151, K015M, K015S, K015T, K015V, S155D, S155F, S155K, S155N, S155R, S157D, S158D, S158I, S158K, S158N, N160C, N160D, N160I, N160M, N160R, T161C, T161D, T161E, T161K, T161Q, T161R, G165A, G165E, G165Q, G165R, G165S, Q017H, A018D, A018E, S181Q, N182D, S183A, S183G, N184C, N184E, N184Q, A186C, S187D, S187E, S187P, Q019D, Q019E, A193D, A193R, A202D, A202E, A202K, A202Q, A202V, G203A, G203C, G203E, G203N, G203Q, Y205E, T210C, T210E, T210I, T210P, T210V, A214E, T215C, L216C, L216H, L216K, L216M, N217S, L234E, L234F, L234Q, L234S, S235D, S235E, P238T, N239A, N239D, N239H, N239M, N239S, N239T, A024E, A024Q, L240D, S241E, S241N, S241Q, S241V, A242G, A242N, S243E, S243Q, S243V, Q244C, Q244E, V245A, V245C, V245T, N247D, N247W, N025D, N025G, N025Q, S250G, S251E, S258C, S258D, S258E, S258H, S258P, S259E, S259P, S259Q, V026A, V026C, V026E, V026H, V026Q, V026R, F260W, K264A, K264C, K264D, K264H, K264M, K264Q, K264S, K264Y, I267C, N268D, N268E, N268Q, V269C, K027C, K027D, K027E, K027M, K027P, A271E, Q274A, Q274C, Q274D, Q274E, Q274G, A029S, T003E, T003I, T003Q, T003V, V030C, I035A, I035S, I035T, I035V, S038T, N043A, N043C, N043F, N043H, N043Q, V044P, V045A, V045C, V045D, V045E, V045F, V045G, V045M, V045N, V045Q, V045R, V045S, V045T, G046D, A048N, A048W, F050H, V0511, A052F, A052G, A052K, A052N, A052P, A052R, A052V, G053N, G053R, A055C, A055D, A055E, A055G, A055H, A055N, A055S, A055V, N057C, N057E, N057G, N057V, T058C, T058I, T058K, T058W, A068C, A068N, A068S, V071A, L074G, D075E, N076K, T077C, T077D, T077H, T077M, T077N, T077P, T077Q, T077S, T078D, T078I, T078V, S086E, S086H, S086R, V087C, V087G, V087S, V087T, S088E, S088N, S088R, L089N, P009C, P009D, P009E, P009N, P009T, L095A, L095V, N096S, S098K, S098R, and G099Q; (ii) A001Q, T003V, K0151, I035A, A068S, V071A, T077N, S086H, V087S, L095A, T115F, M123I, G127T, A128P, A128S, V147L, G165Q, G165S, N184Q, A202V, T210P, N217S, N239S, A242G, S250G, S258P, and Q274A; or (iii) T003V, A068S, T077N, S086H, T115F, M123I, G127T, A128P, G165Q, N184Q, A202V, T210P, N217S, and S258P; wherein the amino acid positions of the AprL-clade subtilisin variant are numbered by correspondence with the amino acid sequence of *Bacillus* sp. AprL subtilisin set forth in SEQ ID NO:2. In some embodiments, one or more AprL-Clade variant described herein has an improved stability when compared to the parent AprL-clade subtilisin enzyme. In other embodiments, the improved stability is (i) a stability PI>1.2, or (ii) a stability PI>1.2 and one or more of an HDD cleaning PI>0.8, an HDL pH 6 or pH 8 cleaning PI>0.8, an ADW cleaning PI>0.8, or an expression PI>0.8. In still other embodiments, the parent AprL-clade subtilisin enzyme and/or said variant comprises: (i) a YNT (SEQ ID NO:46) motif between Asp32 and His63; (ii) a Y56N57T58 (SEQ ID NO:45) motif; (iii) an F50V51X$_1$52 G53E54X$_3$55 Y56N57T58 (SEQ ID NO:48) motif, wherein X$_1$ is an A or S and X$_3$ is an A or S; (iv) an LSX$_4$S (SEQ ID NO:55) motif between Lys236 and Arg246, wherein X$_4$ is A or G; (v) an L240S241A242S243 (SEQ ID NO:50) motif; (vi) an L240S241G242S243 (SEQ ID NO:56) motif; (vii) a KXXXLSX$_4$SQX$_5$R (SEQ ID NO:57) motif, wherein X is any amino acid, X$_4$ is A or G, and X$_5$ is an I or V; (viii) a K236XXXLSASQX$_5$R246 (SEQ ID NO: 52) motif, wherein X is any amino acid and X$_5$ is an I or V; (ix) K236XXXLSGSQX$_5$R246 (SEQ ID NO:60) motif, wherein X is any amino acid and X$_5$ is an I or V; or (viii) a motif 1 selected from (i), (ii), and (iii) in combination with a motif 2 selected from (iv), (v), (vi), (vii), (viii), and (ix).

In some embodiments, the invention is an AprL-clade variant subtilisin enzyme or an active fragment thereof comprising an amino acid modification to a parent AprL-clade enzyme, wherein the modification is at a productive position of the AprL-clade enzyme variant selected from the group consisting of 12, 15, 26, 27, 43, 45, 48, 52, 55, 57, 58, 60, 77, 78, 88, 96, 97, 98, 99, 102, 116, 117, 126, 127, 129, 132, 136, 143, 144, 160, 161, 165, 171, 210, 238, 239, 241, 247, and 274, wherein the amino acid positions of the AprL-clade subtilisin variant are numbered by correspondence with the amino acid sequence of Bacillus sp. AprL subtilisin set forth in SEQ ID NO:2. In some embodiments, the invention is an AprL-clade variant subtilisin enzyme or an active fragment thereof comprising an amino acid modification to a parent AprL-clade enzyme, wherein the modification is at a productive position of the AprL-clade enzyme variant, wherein at least 60% of the modifications tested at the productive position meet at least one of the following criteria: a) a position wherein the minimum performance indices (PI) relative to the parent AprL-clade subtilisin enzyme for: 1) expression; 2) at least one protease activity assay selected from hydrolysis of N-suc-AAPF-pNA, hydrolysis of dimethylcasein (DMC), PAS-38 microswatch cleaning at pH9 or pH10; and EMPA-116 microswatch cleaning at pH6, pH8, or pH10; and 3) detergent stability under stress conditions, are greater than or equal to 0.9, and in addition have a PI for any one of these that is greater than or equal to 1.0; b) a position wherein the minimum performance indices (PI) relative to the parent AprL-clade subtilisin enzyme for: 1) expression; 2) at least one protease activity assay selected from hydrolysis of N-suc-AAPF-pNA, hydrolysis of dimethylcasein (DMC), PAS-38 microswatch cleaning at pH9 or pH10; and EMPA-116 microswatch cleaning at pH6, pH8, or pH10; and 3) detergent stability under stress conditions, are greater than or equal to 0.8, and in addition have a PI for any one of these tests that is greater than or equal to 1.2; or c) a position wherein the minimum performance indices (PI) relative to the parent AprL-clade subtilisin enzyme for: 1) expression; 2) at least one protease activity assay selected from hydrolysis of N-suc-AAPF-pNA, hydrolysis of dimethylcasein (DMC), PAS-38 microswatch cleaning at pH9 or pH10; and EMPA-116 microswatch cleaning at pH6, pH8, or pH10; and 3) detergent stability under stress conditions, are greater than or equal to 0.5, and in addition have a PI for any one of these tests that is greater than or equal to 1.5; and wherein the productive position is selected from the group consisting of 12, 15, 26, 27, 43, 45, 48, 52, 55, 57, 58, 60, 77, 78, 88, 96, 97, 98, 99, 102, 116, 117, 126, 127, 129, 132, 136, 143, 144, 160, 161, 165, 171, 210, 238, 239, 241, 247, and 274, wherein the amino acid positions of the AprL-clade subtilisin variant are numbered by correspondence with the amino acid sequence of Bacillus sp. AprL subtilisin set forth in SEQ ID NO:2. In some embodiments, the modification is selected from the group consisting of 12 (K,A,C,F,G,H,L,M,N,Q,S,Y); 15 (K,A,C,E,F,H,I,M,N,R,S,T,V); 26 (V,A,C,E,H,I,M,N,Q,R,S,T); 27 (K, A, C,D,E,L,M,N,P,Q,R,T); 43 (N,A,C,F,G,H,I,K, L,M,Q,R, S,W, Y); 45 (V,A,C,D,E,F,G,I,K,M, N, P,Q, R, S, T,Y); 48 (A,C,D,E,F,H,I,K,M,N,Q,R,W,Y); 52 (A,C,D,E,F, G, H,K,L,M,N,P,Q,R,S,T,V,Y); 55 (A, C,D,E,F,G,H,I,M,N, P,Q,R,S,T,V); 57 (N,A,C,D,E,G,H,P,R,S,V,Y); 58 (T,C,D,F, H,I,K,L,M,P,R, S,V, W, Y); 60 (G,C,E,F,H,I,K,L,M,Q,R,T, Y); 77 (T,C,D,F,H,K,L,M,N,P,Q, R,S,W); 78 (T,C,D,G, I,L, N,Q, S,V,W,Y); 88 (S,A,E,F,G,L,M,N,Q,R,T,V,W,Y); 96 (N,A,C,D,E,G,H,I,K,L,M,Q,S,V,Y); 97 (S,A,C,D,F, G,H,I, K,M,N,P,Q,R,T,W,Y); 98 (S,A,D,E,F,H,K,L,N,P,R,T,V,Y); 99 (G,A,C,D,E,L,M,Q,S,T,V,W); 102 (S,A,D,E,F,G,K,L,N, P,Q,R,T); 116 (N,A,C,D,E,F,G,H,K,L,M,Q,R,S,T,V,Y); 117 (G,C,D,E,H,K,M,N, Q,R,T,V); 126 (G,A,C,E,H,I,K,M,N,Q, R,S,T,V,W,Y); 127 (G,A,D,E,F,I,L,M,Q,S,T, V,W,Y); 129 (S,C, E,F,H,I,M,N,Q,R,T,V,W,Y); 132 (T,A,C,D,E,F,H,I,K, L,M,N,P,Q,S,V,W,Y); 136 (Q,A,C,D,F,G,H,K,L, N,R,S,T, W); 143 (A,C,D,E,F,G,H,I,K,M,N,S,T,Y); 144 (R,A,C,D,E, F,G,H,L,M,N, Q,V, Y); 160 (N,A,C, D,G,I,K,M,P,R); 161 (T,A,C,D,E,I,K,L,M,Q,R,W); 165 (G,A,E,I,K,L,P,Q,R,S,T, Y); 171 (D,A,C,G,H,I, K, N,P,Q,S,T,V); 210 (T,C,D,E,F,H, I,M,N,P,V,Y); 238 (P,A,C,D,E,F,G,I, L,M,N,Q,R,S,T,W); 239 (N,A, C,D,E,H,I,K,L,M,S,T,V,Y); 241 (S,C,D,E,H,L,N, P,Q,T,V); 247 (N,A,D, E,F,H, I,L,M,Q,S,V,W,Y); and 274 (Q,A,C,D,E,F,G,H,I,L,N,S,T,V,W), wherein the amino acid positions of the AprL-clade variant are numbered by correspondence with the amino acid sequence of AprL protease set forth in SEQ ID NO:2.

In some embodiments, the invention is an AprL-clade variant subtilisin enzyme or an active fragment thereof comprising an amino acid modification to a parent AprL-clade enzyme, wherein the modification is at a productive position of the AprL-clade enzyme variant selected from the group consisting of 1, 9, 22, 24, 25, 53, 86, 89, 95, 100, 105, 108, 114, 115, 119, 125, 128, 140, 146, 155, 158, 187, 202, 203, 234, 237, 240, 243, 244, and 264, wherein the amino acid positions of the AprL-clade subtilisin variant are numbered by correspondence with the amino acid sequence of Bacillus sp. AprL subtilisin set forth in SEQ ID NO:2. In some embodiments, the invention is an AprL-clade variant subtilisin enzyme or an active fragment thereof comprising an amino acid modification to a parent AprL-clade enzyme, wherein the modification is at a productive position of the AprL-clade enzyme variant, wherein at least 40% but less than 60% of the modifications tested at the productive position meet at least one of the following criteria: a) a position wherein the minimum performance indices (PI) relative to the parent AprL-clade subtilisin enzyme for: 1) expression; 2) at least one protease activity assay selected from hydrolysis of N-suc-AAPF-pNA, hydrolysis of dimethylcasein (DMC), PAS-38 microswatch cleaning at pH9 or pH10; and EMPA-116 microswatch cleaning at pH6, pH8, or pH10; and 3) detergent stability under stress conditions, are greater than or equal to 0.9, and in addition have a PI for any one of these that is greater than or equal to 1.0; b) a position wherein the minimum performance indices (PI) relative to the parent AprL-clade subtilisin enzyme for: 1) expression; 2) at least one protease activity assay selected from hydrolysis of N-suc-AAPF-pNA, hydrolysis of dimethylcasein (DMC), PAS-38 microswatch cleaning at pH9 or pH10; and EMPA-116 microswatch cleaning at pH6, pH8, or pH10; and 3) detergent stability under stress conditions, are greater than or equal to 0.8, and in addition have a PI for any one of these tests that is greater than or equal to 1.2; or c) a position wherein the minimum performance indices (PI) relative to the parent AprL-clade subtilisin enzyme for: 1) expression; 2) at least one protease activity assay selected from hydrolysis of N-suc-AAPF-pNA, hydrolysis of dimethylcasein (DMC), PAS-38 microswatch cleaning at pH9 or pH10; and EMPA-116 microswatch cleaning at pH6, pH8, or pH10; and 3) detergent stability under stress conditions, are greater than or equal to 0.5, and in addition have a PI for any one of these tests that is greater than or equal to 1.5; and wherein the productive position is selected from the group consisting of 1, 9, 22, 24, 25, 53, 86, 89, 95, 100, 105, 108, 114, 115, 119, 125, 128, 140, 146, 155, 158, 187, 202, 203, 234, 237, 240, 243, 244, and 264, wherein the amino acid positions of the AprL-clade subtilisin variant are numbered by correspondence with the amino acid sequence of Bacillus sp. AprL subtilisin set forth in SEQ ID NO:2. In some embodiments, the modification is selected from the group consisting of 1 (A,D,E,F,G,N,Q,S,T,V); 9 (P,A,C,D,E, G,N, Q, S,T); 22 (K,A,F,M,Q,R,S,T,VY); 24 (A,C,D,E,G,N,Q,S, W); 25 (N,D,E,F,G,H,L,M, P,Q,R,S); 53 (G, C, D,E,H,K,N, Q,R); 86 (S,C,E,H,K,L,N,R); 89 (L,A,C,F,G,I,M,N,S,V); 95 (L,A,F,G,I, M,Q,S,V); 100 (S, C,F,G,M,N,R,T,Y); 105 (G,A,C,D,I,M,N,R,S,T); 108 (S,E,F,G,H,K,L,N,Q,R,Y); 114 (T,A,C, D, F, I, K, L,N,Q,S,V); 115 (T,D,E,F,H,I,K,Q, S,W); 119 (D,A,E,F,G,H,M,Q,S); 125 (L,A,E,F,I,N, S,V,Y); 128 (A, C,D,E,H,K,N,P,Q,R,S,T); 140 (N,C,D,F,G,H,M,R, T,V); 146 (V,A,E,H,I,K,L,N,Q,S,T); 155 (S, A,D, E, F, G,H,K,N,Q,R,W); 158 (S,A,D,E,I,K,N,Q,R); 187 (S,A,C,D, E,H,K,P,Q,W); 202 (A,C,D, E,I, K, L, M, Q,S,T,V); 203 (G,A,C,E,H,K,M,N,Q,R,S); 234 (L,E,F,H,Q,S,W,Y); 237 (H,A,C,D,G,I,M,N, Q,S); 240 (L,A,D,E,F,I,M,N,Q,T); 243 (S,C,E,F,I,N,Q,T,V,W); 244 (Q,A,C,D,E,G,H,I,N,R,S,V); and 264 (K, A, C, D,H,M,Q,R,S,Y), wherein the amino acid positions of the AprL-clade variant are numbered by correspondence with the amino acid sequence of AprL protease set forth in SEQ ID NO:2.

In some embodiments, the invention is an AprL-clade variant subtilisin enzyme or an active fragment thereof comprising an amino acid modification to a parent AprL-clade enzyme, wherein the modification is at a productive position of the AprL-clade enzyme variant selected from the group consisting of 2, 3, 10, 18, 19, 28, 29, 31, 35, 37, 38, 40, 44, 46, 50, 54, 56, 61, 67, 68, 71, 87, 90, 91, 92, 101, 103, 104, 113, 118, 120, 123, 130, 131, 133, 139, 145, 147, 148, 181, 182, 184, 193, 205, 211, 212, 214, 216, 217, 221, 235, 242, 245, 248, 251, 258, 259, and 268, wherein the amino acid positions of the AprL-clade subtilisin variant are numbered by correspondence with the amino acid sequence of Bacillus sp. AprL subtilisin set forth in SEQ ID NO:2. In some embodiments, the invention is an AprL-clade variant subtilisin enzyme or an active fragment thereof comprising an amino acid modification to a parent AprL-clade enzyme, wherein the modification is at a productive position of the AprL-clade enzyme variant, wherein at least 15% but less than 40% of the modifications tested at the productive position meet at least one of the following criteria: a) a position wherein the minimum performance indices (PI) relative to the parent AprL-clade subtilisin enzyme for: 1) expression; 2) at least one protease activity assay selected from hydrolysis of N-suc-AAPF-pNA, hydrolysis of dimethylcasein (DMC), PAS-38 microswatch cleaning at pH9 or pH10; and EMPA-116 microswatch cleaning at pH6, pH8, or pH10; and 3) detergent stability under stress conditions, are greater than or equal to 0.9, and in addition have a PI for any one of these tests that is greater than or equal to 1.0; b) a position wherein the minimum performance indices (PI) relative to the parent AprL-clade subtilisin enzyme for: 1) expression; 2) at least one protease activity assay selected from hydrolysis of N-suc-AAPF-pNA, hydrolysis of dimethylcasein (DMC), PAS-38 microswatch cleaning at pH9 or pH10; and EMPA-116 microswatch cleaning at pH6, pH8, or pH10; and 3) detergent stability under stress conditions, are greater than or equal to 0.8, and in addition have a PI for any one of these tests that is greater than or equal to 1.2; or c) a position wherein the minimum performance indices (PI) relative to the parent AprL-clade subtilisin enzyme for: 1) expression; 2) at least one protease activity assay selected from hydrolysis of N-suc-AAPF-pNA, hydrolysis of dimethylcasein (DMC), PAS-38 microswatch cleaning at pH9 or pH10; and EMPA-116 microswatch cleaning at pH6, pH8, or pH10; and 3) detergent stability under stress conditions, are greater than or equal to 0.5, and in addition have a PI for any one of these tests that is greater than or equal to 1.5; and wherein the productive position is selected from the group consisting of 2, 3, 10, 18, 19, 28, 29, 31, 35, 37, 38, 40, 44, 46, 50, 54, 56, 61, 67, 68, 71, 87, 90, 91, 92, 101, 103, 104, 113, 118, 120, 123, 130, 131, 133, 139, 145, 147, 148, 181, 182, 184, 193, 205, 211, 212, 214, 216, 217, 221, 235, 242, 245, 248, 251, 258, 259, and 268, wherein the amino acid positions of the AprL-clade subtilisin variant are numbered by correspondence with the amino acid sequence of Bacillus sp. AprL subtilisin set forth in SEQ ID NO:2. In some embodiments, the modification is selected from the group consisting of 2 (Q,A,I,N); 3 (T,E,I, Q,V); 10 (L,F,M,Q); 18 (A,C,D,E,S); 19 (Q,A,D,E,G,M); 28 (V,A,C, S); 29 (A,C,S, T,V); 31 (L,C,I,V); 35 (I,A,C,G,M,S,T,V); 37 (A,E,G,S); 38 (S,A,C,E,G,N,T); 40 (P,A,C, D,E,M,V); 44 (V,C,E,P,S,T); 46 (G,A,C,D,W); 50 (F,H,K,M,Q,R,V,Y); 54 (E,Q,R,T); 56 (Y,C,E,F,H,P); 61 (N,A,D,F,H,K,Q); 67 (V,M, N,Q); 68 (A,C,G,N,S,T); 71 (V,A,G,L,S); 87 (V,C,G,S,T); 90 (Y,A, C,F, H,N,V); 91 (A,G,M,P,V); 92 (V,A, C,I,T); 101 (G,A, C,N,S,T); 103 (Y,A,F,I,L,M,V,W); 104 (S,A,D,E); 113 (A,C, G,S); 118 (M,F, H, P, Q); 120 (V,A,C,I,S,T); 123 (M,C,I,L, N,Q,S); 130 (G,D,E,H,S); 131 (S,D, R,T); 133 (A,G,M,P,S, T,V); 139 (D,G,K,N,S,T); 145 (G,D,N,S); 147 (V,A,L,M,N); 148 (V,A,C,F,M,Q, S); 181 (S,A,C,D,H,Q); 182 (N, C, D,E,Q); 184 (N,C,E,H,M,Q); 193 (A,D,P,Q,R); 205 (Y,C,E, F,I,M,V); 211 (N,C,E,S); 212 (T,A, D, S); 214 (A,E,H,L,T); 216 (L,A,C,H,K,M); 217 (N,C,E,S); 221 (M,C,H,K); 235 (S,C,D,E,G); 242 (A, E, G, N,S); 245 (V,A,C,I,T); 248 (R,A,N,Q,S); 251 (S,A,C,E,G,N); 258 (S,C,D, E,H,P); 259 (S,E,P,Q); and 268 (N,D,E,Q), wherein the amino acid positions of the AprL-clade variant are numbered by correspondence with the amino acid sequence of AprL protease set forth in SEQ ID NO:2.

In some embodiments, the invention is an AprL-clade variant subtilisin enzyme or an active fragment thereof comprising an amino acid modification to a parent AprL-clade enzyme, wherein the modification is at a productive position of the AprL-clade enzyme variant selected from the group consisting of 4, 17, 21, 30, 33, 36, 47, 49, 51, 62, 66, 72, 74, 75, 76, 93, 106, 107, 110, 111, 112, 121, 134, 135, 137, 138, 141, 149, 151, 156, 157, 159, 163, 169, 175, 183, 186, 188, 191, 204, 207, 208, 209, 215, 223, 224, 227, 229, 230, 231, 232, 233, 236, 249, 250, 254, 255, 260, 267, 269, 271, and 273, wherein the amino acid positions of the AprL-clade subtilisin variant are numbered by correspondence with the amino acid sequence of Bacillus sp. AprL subtilisin set forth in SEQ ID NO:2. In some embodiments, the invention is an AprL-clade variant subtilisin enzyme or an active fragment thereof comprising an amino acid modification to a parent AprL-clade enzyme, wherein the modification is at a productive position of the AprL-clade enzyme variant, wherein at least one modification but less than 15% of the modifications tested at the productive position meet at least one of the following criteria: a) a position wherein the minimum performance indices (PI) relative to the parent AprL-clade subtilisin enzyme for: 1) expression; 2) at least one protease activity assay selected from hydrolysis of N-suc-AAPF-pNA, hydrolysis of dimethylcasein (DMC), PAS-38 microswatch cleaning at pH9 or pH10; and EMPA-116 microswatch cleaning at pH6, pH8, or pH10; and 3) detergent stability under stress conditions, are greater than or equal to 0.9, and in addition have a PI for any one of these that is greater than or equal to 1.0; b) a position wherein the minimum performance indices (PI) relative to the parent AprL-clade subtilisin enzyme for: 1) expression; 2) at least one protease activity assay selected from hydrolysis of N-suc-AAPF-pNA, hydrolysis of dimethylcasein (DMC), PAS-38 microswatch cleaning at pH9 or pH10; and EMPA-116 microswatch cleaning at pH6, pH8, or pH10; and 3) detergent stability under stress conditions, are greater than or equal to 0.8, and in addition have a PI for any one of these tests that is greater than or equal to 1.2; or c) a position wherein the minimum performance indices (PI) relative to the parent AprL-clade subtilisin enzyme for: 1) expression; 2) at least one protease activity assay selected from hydrolysis of N-suc-AAPF-pNA, hydrolysis of dimethylcasein (DMC), PAS-38 microswatch cleaning at pH9 or pH10; and EMPA-116 microswatch cleaning at pH6, pH8, or pH10; and 3) detergent stability under stress conditions, are greater than or equal to 0.5, and in addition have a PI for any one of these tests that is greater than or equal to 1.5; and wherein the productive position is selected from the group consisting of 4, 17, 21, 30, 33, 36, 47, 49, 51, 62, 66, 72, 74, 75, 76, 93, 106, 107, 110, 111, 112, 121, 134, 135, 137, 138, 141, 149, 151, 156, 157, 159, 163, 169, 175, 183, 186, 188, 191, 204, 207, 208, 209, 215, 223, 224, 227, 229, 230, 231, 232, 233, 236, 249, 250, 254, 255, 260, 267, 269, 271, and 273, wherein the amino acid positions of the AprL-clade subtilisin variant are numbered by correspondence with the amino acid sequence of *Bacillus* sp. AprL subtilisin set forth in SEQ ID NO:2. In some embodiments, the modification is selected from the group consisting of 4 (V,I); 17 (Q,H,M); 21 (F, Y); 30 (V,C,T); 33 (T,C,M); 36 (Q,E,H); 47 (G,A,M); 49 (S,I,T); 51 (V,C,I); 62 (G,S); 66 (H,R); 72 (A, G,S); 74 (L,G); 75 (D,C,E); 76 (N,K); 93 (K,D); 106 (I,G,M); 107 (V,F,I); 110 (I,F); 111 (E,D,Q); 112 (W,A); 121 (I,L,M); 134 (M,L); 135 (K,E,H); 137 (A,S); 138 (V,C,S); 141 (A,S); 149 (V,C); 151 (A, G, P); 156 (G,E); 157 (S,D,R); 159 (G,A,F); 163 (T,E); 169 (K,R); 175 (A,C); 183 (S,A,G); 186 (A,C); 188 (F,W); 191 (V,C); 204 (V,I); 207 (T,C); 208 (Y,F); 209 (P,S); 215 (T,C,V); 223 (S,A,C); 224 (P,A); 227 (A,S); 229 (A,G,S); 230 (A,\G); 231 (A,C); 232 (L,Q); 233 (I,V); 236 (K,A); 249 (L,I,M); 250 (S,A, G); 254 (T,D); 255 (Y,C,E); 260 (F,C,W); 267 (I,C); 269 (V,A,C); 271 (A,D,E); and 273 (A,S), wherein the amino acid positions of the AprL-clade variant are numbered by correspondence with the amino acid sequence of AprL protease set forth in SEQ ID NO:2.

Some embodiments are directed a composition comprising at least one variant as listed above. Some embodiments are directed to a method of cleaning using a cleaning composition as listed above.

FIG. 1 provides a plasmid map of pHYT-AprL for the expression of AprL wildtype and variant proteases.

Figure 2A:
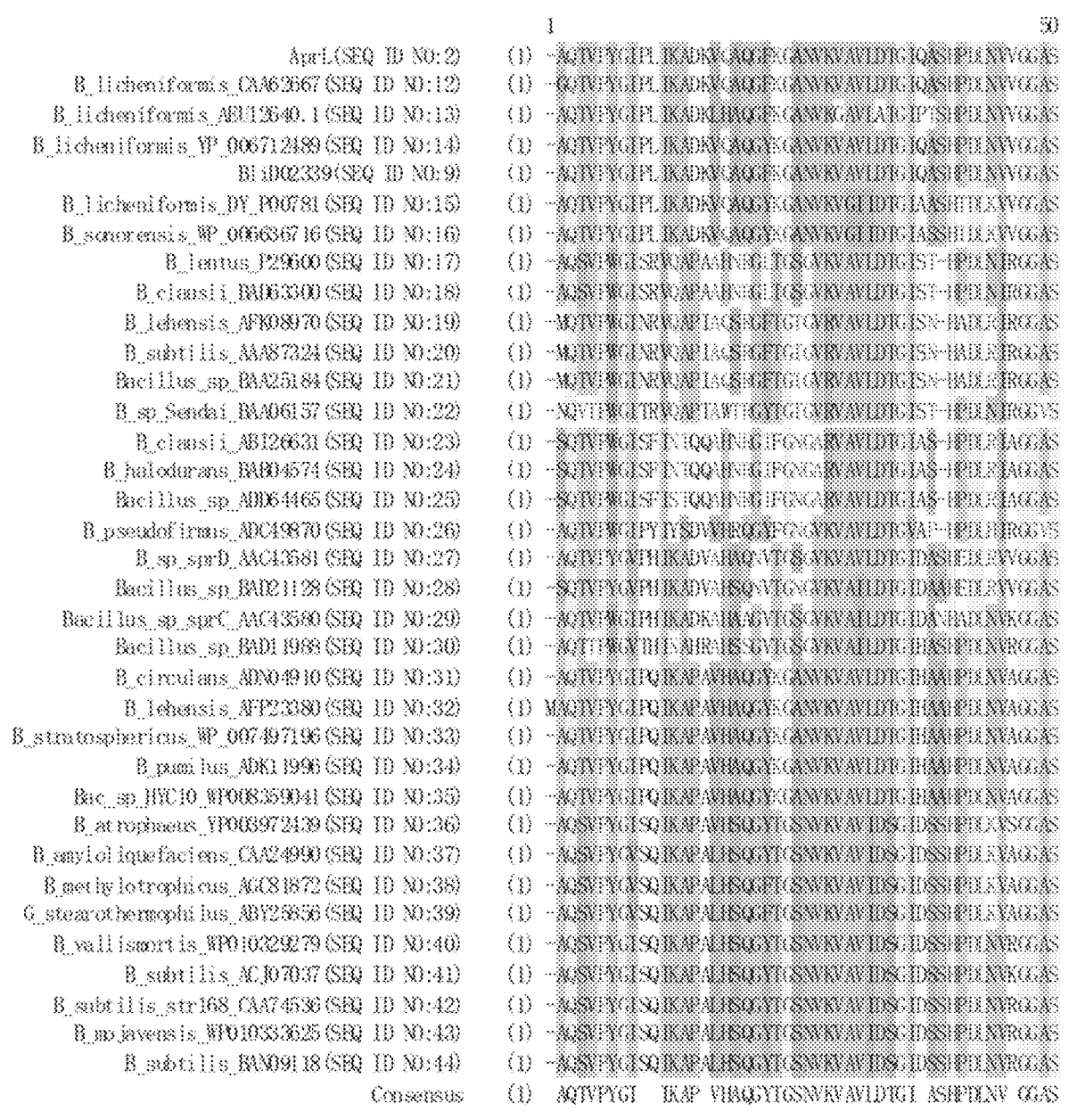
Figure 2B:
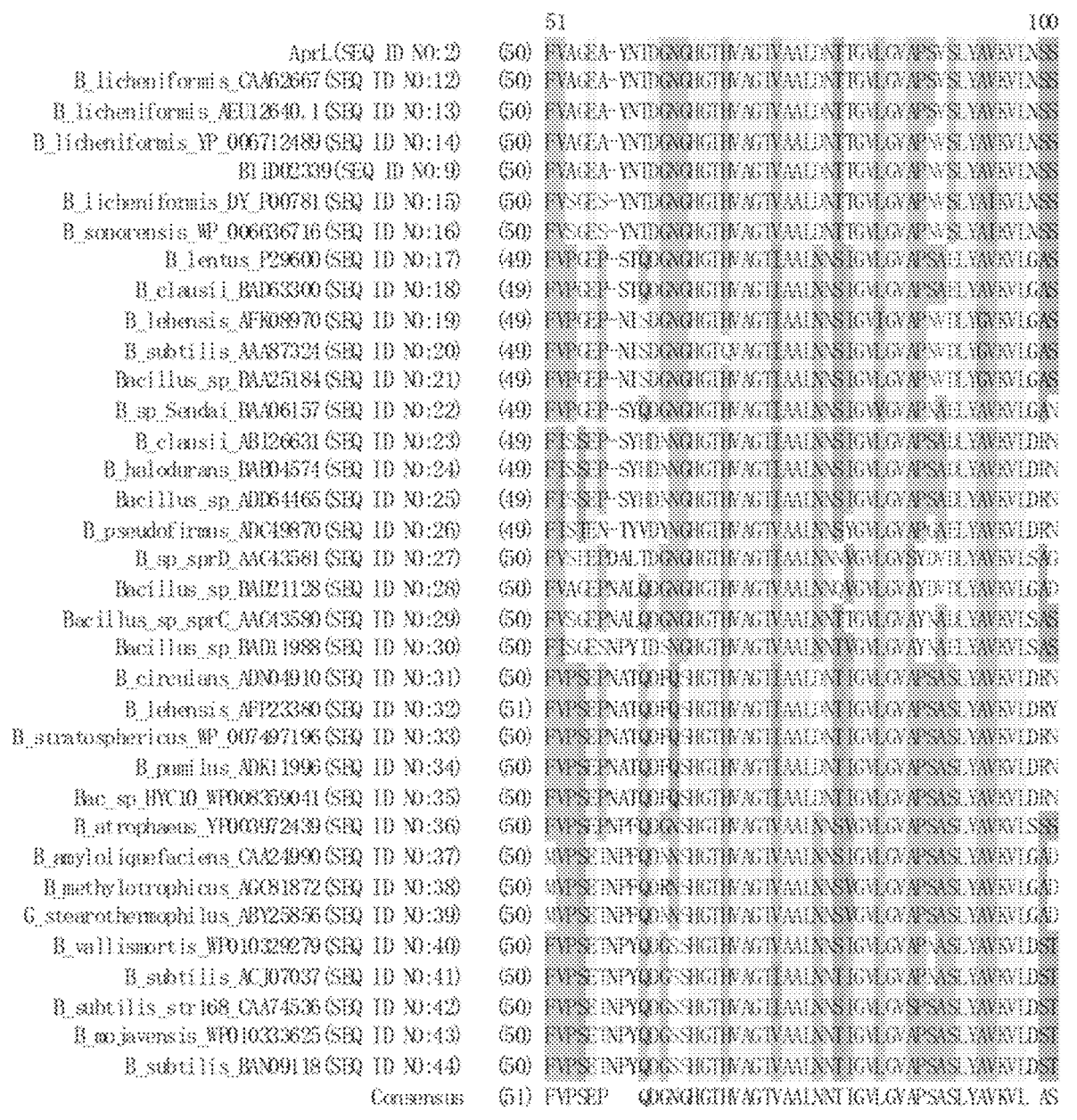
Figure 2C:
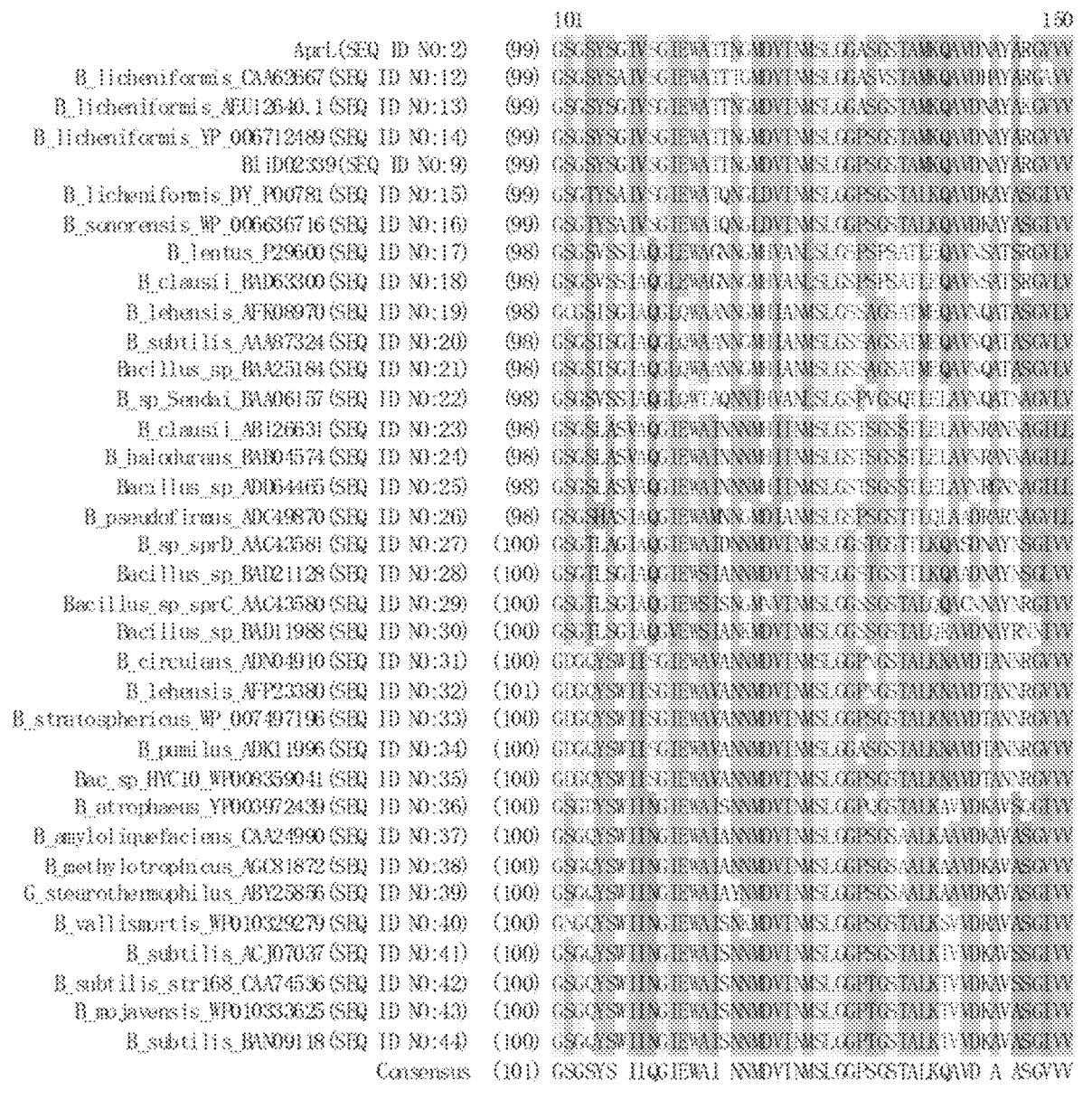
Figure 2D:
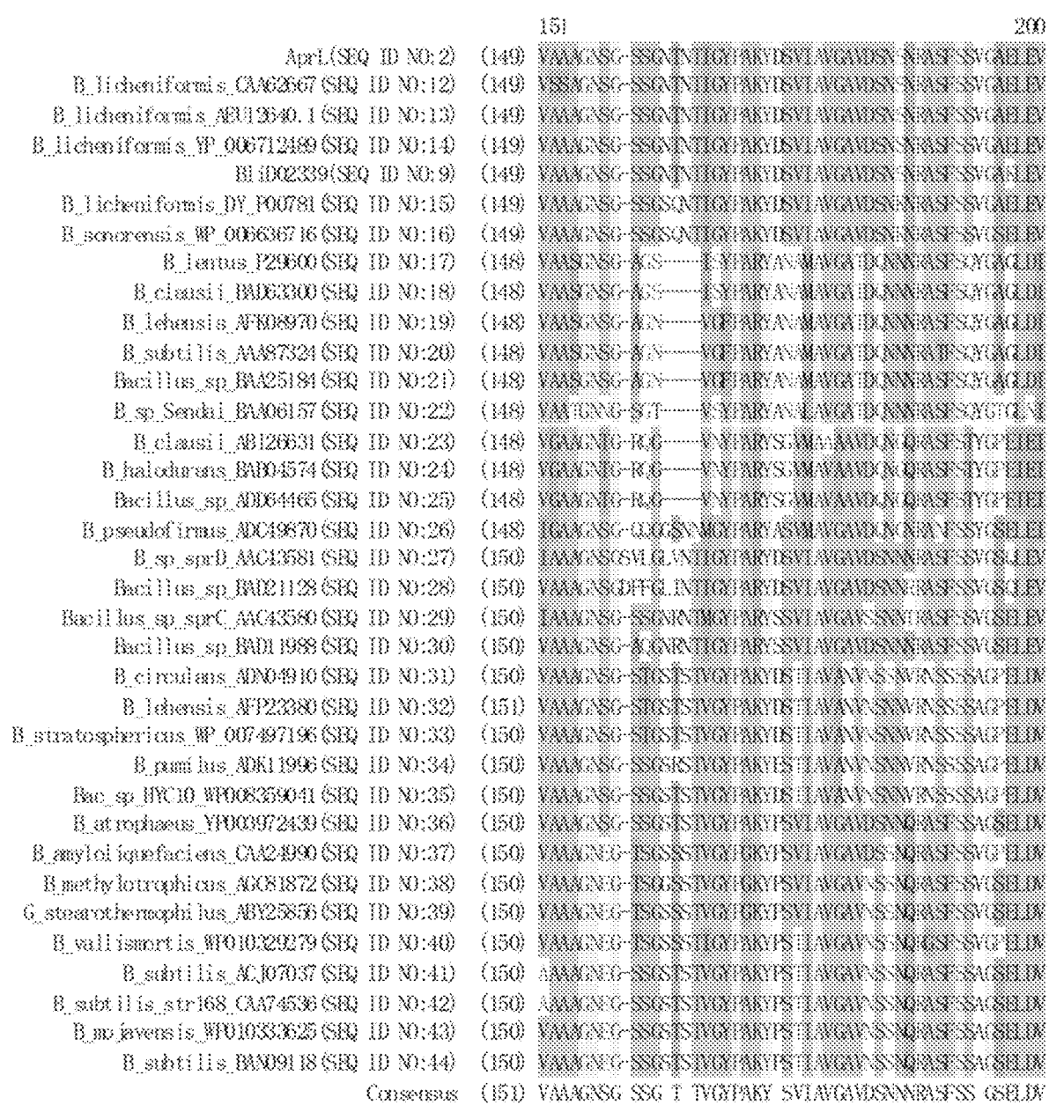
Figure 2E:
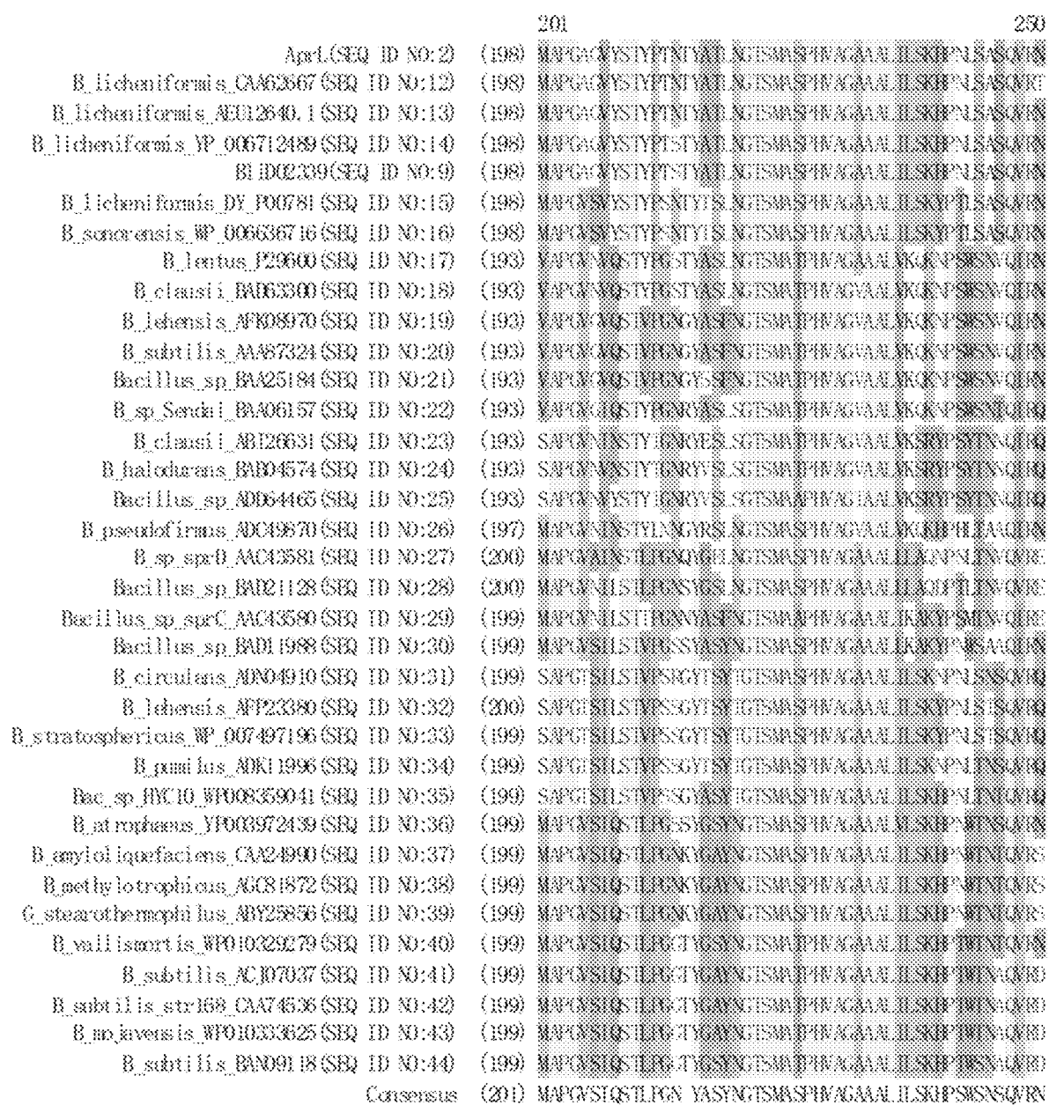

FIG. 2A-F provides the alignment of AprL protein with a subset of multiple subtilisin sequences using CLUSTALW software.

FIG. 3 provides a CLUSTAL W sequence alignment of AprL, Blid02339, and related subtilisins.

FIG. 4 provides a plasmid map of pHYT-BliD02339 for the expression of BliD02339 wildtype and variant proteases.

Figure 11:
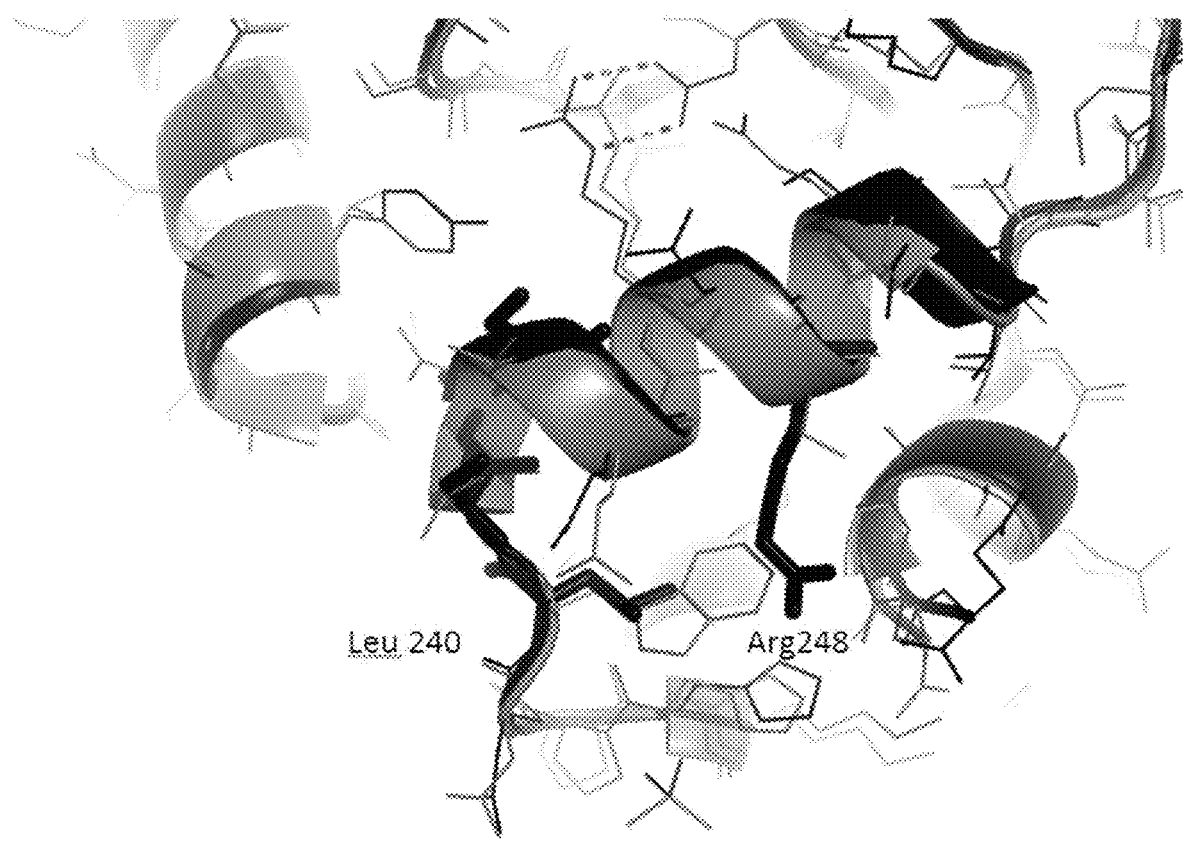

FIG. 11 shows a structural representation of residues L240S241A242S243. In AprL (black), side chain of Leu240 and Arg248 are shown as sticks. For comparison, the remainder of AprL (black) and subtilisin BPN' (gray) side chains are shown as thin lines.

Figure 12:
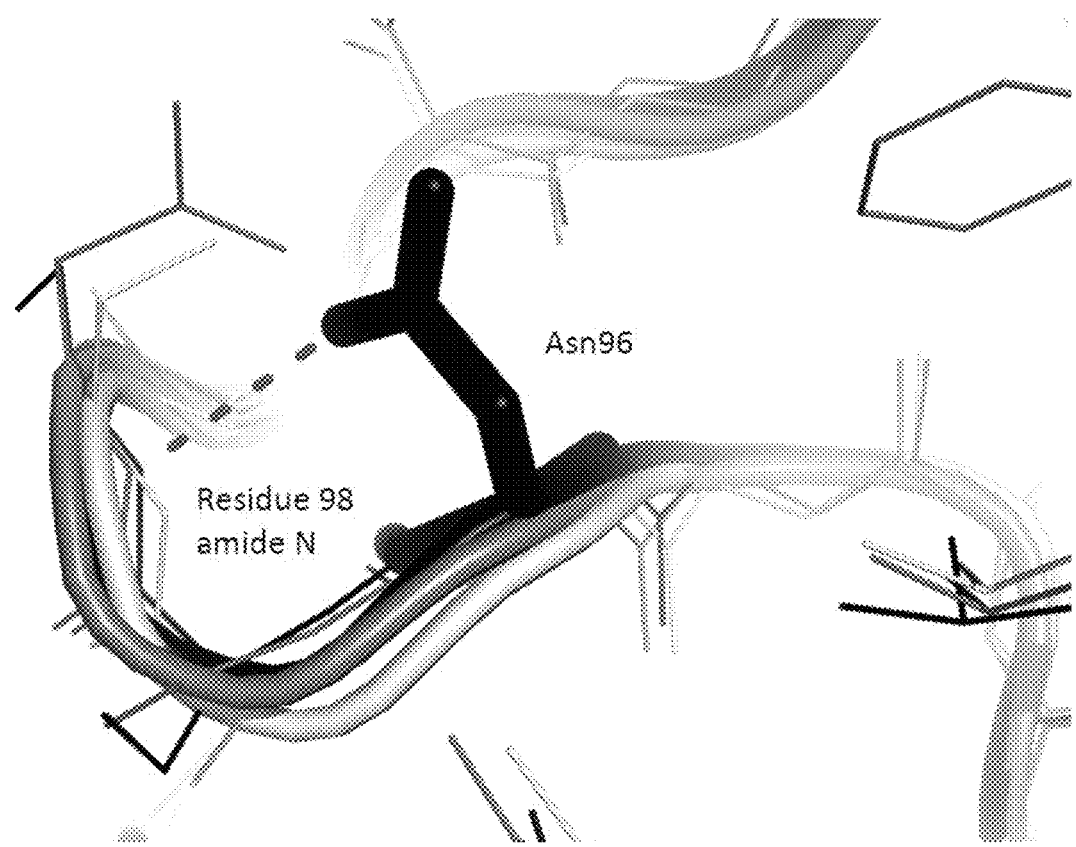

FIG. 12 shows a structural representation of Asn96 in AprL forming a hydrogen bond with main chain amide of Ser98 to stabilize a turn leading to the strand 101-104, which is part of the substrate binding site.

The present invention provides novel serine protease enzymes, particularly variants of the AprL-clade serine proteases and especially enzymes useful for detergent compositions. In some embodiments, the present invention provides serine protease enzyme variants having one or more modifications, such as a substitution, as compared to a parent serine protease enzyme. In some embodiments, the present invention provides novel serine protease enzyme variants of the AprL-clade serine proteases. In each of the above, the serine protease enzymes of the present invention can be useful in several industries, including soil removal, grain ethanol production, animal feed, food processing and digestive aids, leather processing, and personal care. This can be achieved by making improvements to the enzyme by improving cleaning performance, stability of the enzyme the presence of chemical agents, and/or thermostability of the enzyme that improve effectiveness of the enzyme. The present invention provides variant serine protease enzymes, including, but not limited to, variant AprL-clade serine protease enzymes, that are particularly well suited to and useful in a variety of cleaning applications. The invention includes compositions comprising at least one of the variant serine protease enzymes (e.g., AprL-clade variants) set forth herein. Some such compositions comprise detergent compositions. The invention provides various species, including *Bacillus* species variant serine protease enzymes and compositions comprising one or more such variant AprL-clade serine proteases. The serine protease enzyme variants of the present invention can be combined with other enzymes useful in detergent compositions. The invention also provides methods of cleaning using serine protease enzyme variants of the present invention.

The invention includes enzyme variants of serine protease enzymes having one or more modifications from a parent serine protease enzyme. The enzyme variants can be useful in a detergent composition by having a minimum performing index for wash performance, stability of the enzyme in detergent compositions and thermostability of the enzyme, while having at least one of these characteristics improved from a parent serine protease enzyme.

Additionally, the invention provides modifications, such as a substitution, at one or more amino acid positions in a serine protease enzyme which can be useful in a detergent composition where favorable modifications result in a minimum performing index for wash performance, stability of the enzyme in detergent compositions and thermostability of the enzyme, while having at least one of these characteristics improved from a parent serine protease enzyme. These modifications are considered suitable modifications of the invention. These amino acid positions can be considered useful positions for combinatorial modifications to a parent serine protease enzyme. Serine protease enzyme amino acid positions found to be useful positions can be further characterized by having multiple modifications that are suitable for use in a detergent composition. For each position, greater numbers of possible suitable modifications denotes a higher productivity of a particular position.

In addition, the present invention provides compositions comprising these serine protease variants. In some embodiments, the present invention provides cleaning compositions comprising at least one of these serine protease variants.

It is to be appreciated those certain features of the invention, which are, for clarity, described above and below in the context of separate embodiments, may also be provided in combination in a single embodiment. Conversely, various features of the invention that are, for brevity, described in the context of a single embodiment, may also be provided separately or in any sub-combination.

Prior to describing the present compositions and methods in detail, the following terms are defined for clarity. Terms and abbreviations not defined should be accorded their ordinary meaning as used in the art. Unless otherwise indicated, the practice of the present invention involves conventional techniques commonly used in molecular biology, protein engineering, microbiology, and recombinant DNA, which are within the skill of the art. Such techniques are known to those of skill in the art and are described in numerous texts and reference works well known to those of skill in the art. All patents, patent applications, articles and publications mentioned herein, both supra and infra, are hereby expressly incorporated herein by reference.

Unless defined otherwise herein, all technical and scientific terms used herein have the same meaning as commonly understood by one of ordinary skill in the art. Unless otherwise indicated, the practice of the present disclosure involves conventional techniques commonly used in molecular biology, protein engineering, and microbiology. Although any methods and materials similar or equivalent to those described herein find use in the practice of the present disclosure, some suitable methods and materials are described herein. The terms defined immediately below are more fully described by reference to the Specification as a whole.

As used herein, the singular "a," "an" and "the" includes the plural unless the context clearly indicates otherwise. Unless otherwise indicated, nucleic acid sequences are written left to right in 5' to 3' orientation; and amino acid sequences are written left to right in amino to carboxy orientation. It is to be understood that this disclosure is not limited to the particular methodology, protocols, and reagents described herein, absent an indication to the contrary.

The practice of the present invention employs, unless otherwise indicated, conventional techniques of protein purification, molecular biology, microbiology, recombinant DNA techniques and protein sequencing, all of which are within the skill of those in the art.

Furthermore, the headings provided herein are not limitations of the various aspects or embodiments of the invention which can be had by reference to the specification as a whole. Accordingly, the terms defined immediately below are more fully defined by reference to the specification as a whole. Nonetheless, in order to facilitate understanding of the invention, a number of terms are defined below.

It is intended that every maximum numerical limitation given throughout this Specification includes every lower numerical limitation, as if such lower numerical limitations were expressly written herein. Every minimum numerical limitation given throughout this Specification will include every higher numerical limitation, as if such higher numerical limitations were expressly written herein. Every numerical range given throughout this Specification will include every narrower numerical range that falls within such broader numerical range, as if such narrower numerical ranges were all expressly written herein.

As used herein in connection with a numerical value, the term "about" refers to a range of +1-0.5 of the numerical value, unless the term is otherwise specifically defined in context. For instance, the phrase a "pH value of about 6" refers to pH values of from 5.5 to 6.5, unless the pH value is specifically defined otherwise.

As used herein, the terms "protease" and "proteinase" refer to an enzyme that has the ability to break down proteins and peptides. A protease has the ability to conduct "proteolysis," by hydrolysis of peptide bonds that link amino acids together in a peptide or polypeptide chain forming the protein. This activity of a protease as a protein-digesting enzyme is referred to as "proteolytic activity." Many well-known procedures exist for measuring proteolytic activity (See e.g., Kalisz, "Microbial Proteinases," In: Fiechter (ed.), *Advances in Biochemical Engineering/Biotechnology*, (1988)). For example, proteolytic activity may be ascertained by comparative assays that analyze the respective protease's ability to hydrolyze a suitable substrate. Exemplary substrates useful in the analysis of protease or proteolytic activity, include, but are not limited to, di-methyl casein (Sigma C-9801), bovine collagen (Sigma C-9879), bovine elastin (Sigma E-1625), and bovine keratin (ICN Biomedical 902111). Colorimetric assays utilizing these substrates are well known in the art (See e.g., WO 99/34011 and U.S. Pat. No. 6,376,450). The pNA peptidyl assay (See e.g., Del Mar et al., Anal Biochem, 99:316-320, 1979) also finds use in determining the active enzyme concentration. This assay measures the rate at which p-nitroaniline is released as the enzyme hydrolyzes a soluble synthetic substrate, such as succinyl-alanine-alanine-proline-phenylalanine-p-nitroanilide (suc-AAPF-pNA). The rate of production of yellow color from the hydrolysis reaction is measured at 410 nm on a spectrophotometer and is proportional to the active enzyme concentration. In addition, absorbance measurements at 280 nanometers (nm) can be used to determine the total protein concentration in a sample of purified protein. The activity on substrate/protein concentration gives the enzyme specific activity.

As used herein in connection to a polypeptide such as a protease, the term "variant" refers to a polypeptide comprising an amino acid sequence that differs in at least one amino acid residue from the amino acid sequence of a parent or reference polypeptide (including but not limited to wild-type polypeptides). In some embodiments, the polypeptide variant that differs from the amino acid sequence of a parent or reference polypeptide contains one or more naturally-occurring or man-made substitutions, insertions, or deletions of an amino acid. In other embodiments, the polypeptide variant that differs from the amino acid sequence of a parent or reference polypeptide contains one or more naturally-occurring substitutions, insertions, or deletions of an amino acid. In further embodiments the polypeptide variant that differs from the amino acid sequence of a parent or reference polypeptide contains one or more man-made substitutions, insertions, or deletions of an amino acid.

As used herein, "the genus *Bacillus*" includes all species within the genus "*Bacillus*," as known to those of skill in the art, including but not limited to *B. subtilis, B. licheniformis, B. lentus, B. brevis, B. stearothermophilus, B. alkalophilus, B. amyloliquefaciens, B. clausii, B. sonorensis, B. halodurans, B. pumilus, B. gibsonii, B. pabuli, B. cereus, B. agaradhaerens, B. akibai, B. clarkii, B. pseudofirmus, B. lehensis, B. megaterium, B. coagulans, B. circulars, B. lautus*, and *B. thuringiensis*. It is recognized that the genus *Bacillus* continues to undergo taxonomical reorganization. Thus, it is intended that the genus include species that have been reclassified, including but not limited to such organisms as *B. stearothermophilus*, which is now named "*Geobacillus stearothermophilus*." The production of resistant endospores oxygen under stressful environmental conditions is considered the defining feature of the genus *Bacillus*, although this characteristic also applies to the recently named *Alicyclobacillus, Amphibacillus, Aneurinibacillus, Anoxybacillus, Brevibacillus, Filobacillus, Gracilibacillus, Halobacillus, Paenibacillus, Salibacillus, Thermobacillus, Ureibacillus*, and *Virgibacillus*.

The phrase "composition(s) substantially-free of boron" or "detergent(s) substantially-free of boron" refers to composition(s) or detergent(s), respectively, that contain trace amounts of boron, for example, about 1000 ppm (1 mg/kg or litre equals 1 ppm), about 100 ppm, about 50 ppm, about 10 ppm, or about 5 ppm, or about 1 ppm, perhaps from other composition or detergent constituents.

The terms "polynucleotide" and "nucleic acid," which are used interchangeably herein, refer to a polymer of any length of nucleotide monomers covalently bonded in a chain. DNA (deoxyribonucleic acid), a polynucleotide comprising deoxyribonucleotides, and RNA (ribonucleic acid), a polymer of ribonucleotides, are examples of polynucleotides or nucleic acids having distinct biological functions. Polynucleotides or nucleic acids include, but are not limited to, a single-, double- or triple-stranded DNA, genomic DNA, cDNA, RNA, DNA-RNA hybrid, or a polymer comprising purine and pyrimidine bases, or other natural, chemically, biochemically modified, non-natural or derivatized nucleotide bases. The following are non-limiting examples of polynucleotides: genes, gene fragments, chromosomal fragments, expressed sequence tag(s) (EST(s)), exons, introns, messenger RNA (mRNA), transfer RNA (tRNA), ribosomal RNA (rRNA), ribozymes, complementary DNA (cDNA), recombinant polynucleotides, branched polynucleotides, plasmids, vectors, isolated DNA of any sequence, isolated RNA of any sequence, nucleic acid probes, and primers. In some embodiments, polynucleotides comprise modified nucleotides, such as methylated nucleotides and nucleotide analogs, uracyl, other sugars and linking groups such as fluororibose and thioate, and nucleotide branches. In a particular embodiment, a sequence of nucleotides is interrupted by non-nucleotide components.

As used herein, the term "mutation" refers to changes made to a reference amino acid or nucleic acid sequence. It is intended that the term encompass substitutions, insertions and deletions.

As used herein, the term "vector" refers to a nucleic acid construct used to introduce or transfer nucleic acid(s) into a target cell or tissue. A vector is typically used to introduce foreign DNA into a cell or tissue. Vectors include plasmids, cloning vectors, bacteriophages, viruses (e.g., viral vector), cosmids, expression vectors, shuttle vectors, and the like. A vector typically includes an origin of replication, a multicloning site, and a selectable marker. The process of inserting a vector into a target cell is typically referred to as transformation. The present invention includes, in some embodiments, a vector that comprises a DNA sequence encoding a serine protease polypeptide (e.g., precursor or mature serine protease polypeptide) that is operably linked to a suitable prosequence (e.g., secretory, signal peptide sequence, etc.) capable of effecting the expression of the DNA sequence in a suitable host, and the folding and translocation of the recombinant polypeptide chain.

As used herein, the term "expression cassette," "expression plasmid" or "expression vector" refers to a nucleic acid construct or vector generated recombinantly or synthetically for the expression of a nucleic acid of interest in a target cell. An expression vector or expression cassette typically comprises a promoter nucleotide sequence that drives expression of the foreign nucleic acid. The expression vector or cassette also typically includes any other specified nucleic acid elements that permit transcription of a particular nucleic acid in a target cell. A recombinant expression cassette can be incorporated into a plasmid, chromosome, mitochondrial DNA, plastid DNA, virus, or nucleic acid fragment. Many prokaryotic and eukaryotic expression vectors are commercially available.

As used herein, a "plasmid" refers to an extrachromosomal DNA molecule which is capable of replicating independently from the chromosomal DNA. A plasmid is double stranded (ds) and may be circular and is typically used as a cloning vector.

As used herein in the context of introducing a nucleic acid sequence into a cell, the term "introduced" refers to any method suitable for transferring the nucleic acid sequence into the cell. Such methods for introduction include but are not limited to protoplast fusion, transfection, transformation, electroporation, conjugation, and transduction (See e.g., Ferrari et al., "Genetics," in Hardwood et al. (eds.), *Bacillus*, Plenum Publishing Corp., pp. 57-72 [1989]).

Transformation refers to the genetic alteration of a cell which results from the uptake, optional genomic incorporation, and expression of genetic material (e.g., DNA).

As used herein, a nucleic acid is "operably linked" with another nucleic acid sequence when it is placed into a functional relationship with another nucleic acid sequence. For example, a promoter or enhancer is operably linked to a nucleotide coding sequence if the promoter affects the transcription of the coding sequence. A ribosome binding site may be operably linked to a coding sequence if it is positioned so as to facilitate translation of the coding sequence. Typically, "operably linked" DNA sequences are contiguous. However, enhancers do not have to be contiguous. Linking is accomplished by ligation at convenient restriction sites. If such sites do not exist, synthetic oligonucleotide adaptors or linkers may be used in accordance with conventional practice.

As used herein the term "gene" refers to a polynucleotide (e.g., a DNA segment), that encodes a polypeptide and includes regions preceding and following the coding regions. In some instances a gene includes intervening sequences (introns) between individual coding segments (exons).

As used herein, "recombinant" when used with reference to a cell typically indicates that the cell has been modified by the introduction of a foreign nucleic acid sequence or that the cell is derived from a cell so modified. For example, a recombinant cell may comprise a gene not found in identical form within the native (non-recombinant) form of the cell, or a recombinant cell may comprise a native gene (found in the native form of the cell) that has been modified and re-introduced into the cell. A recombinant cell may comprise a nucleic acid endogenous to the cell that has been modified without removing the nucleic acid from the cell; such modifications include those obtained by gene replacement, site-specific mutation, and related techniques known to those of ordinary skill in the art. Recombinant DNA technology includes techniques for the production of recombinant DNA in vitro and transfer of the recombinant DNA into cells where it may be expressed or propagated, thereby producing a recombinant polypeptide. "Recombination" and "recombining" of polynucleotides or nucleic acids refer generally to the assembly or combining of two or more nucleic acid or polynucleotide strands or fragments to generate a new polynucleotide or nucleic acid.

A nucleic acid or polynucleotide is said to "encode" a polypeptide if, in its native state or when manipulated by methods known to those of skill in the art, it can be transcribed and/or translated to produce the polypeptide or a fragment thereof. The anti-sense strand of such a nucleic acid is also said to encode the sequence.

The terms "host strain" and "host cell" refer to a suitable host for an expression vector comprising a DNA sequence of interest.

A "protein" or "polypeptide" comprises a polymeric sequence of amino acid residues. The terms "protein" and "polypeptide" are used interchangeably herein. The single and 3-letter code for amino acids as defined in conformity with the IUPAC-IUB Joint Commission on Biochemical Nomenclature (JCBN) is used throughout this disclosure. The single letter X refers to any of the twenty amino acids. It is also understood that a polypeptide may be coded for by more than one nucleotide sequence due to the degeneracy of the genetic code. Mutations can be named by the one letter code for the parent amino acid, followed by a position number and then the one letter code for the variant amino acid. For example, mutating glycine (G) at position 87 to serine (S) is represented as "G087S" or "G87S". Mutations can also be named by using the three letter code for an amino acid followed by its position in the polypeptide chain as counted from the N-terminus; for example, Ala10 for alanine at position 10. Multiple mutations are indicated by inserting a "-," "+," "/," or ";" between the mutations. Mutations at positions 87 and 90 are represented as either "G087S-A090Y" or "G87S-A90Y" or "G87S +A90Y" or "G087S+A090Y". For insertions, one or more inserted amino acids can be listed after a position. For example, "G087GS" describes a serine inserted after the glycine at position 87; as a second example, "G087GSA" describes a serine and alanine inserted after the glycine at position 87. Insertions can be done in combination with substitutions; thus, "G087RS" describes a substitution at position 87 from glycine to arginine, followed by an inserted serine residue. For deletions, either a "Δ" or "del" is used following the position number. Thus, for example, "G087del" describes deletion of the glycine at position 87. When describing modifications, a position followed by amino acids listed in parentheses indicates a list of substitutions at that position by any of the listed amino acids. For example, 6(L,I) means position 6 can be substituted with a leucine or isoleucine. At times, in a sequence, a slash (/) is used to define substitutions, e.g. F/V, indicates that the particular position may have a phenylalanine or valine at that position.

A "prosequence" or "propeptide sequence" refers to an amino acid sequence between the signal peptide sequence and mature protease sequence that is necessary for the proper folding and secretion of the protease; they are sometimes referred to as intramolecular chaperones. Cleavage of the prosequence or propeptide sequence results in a mature active protease. Bacterial serine proteases are often expressed as pro-enzymes.

The terms "signal sequence" and "signal peptide" refer to a sequence of amino acid residues that may participate in the secretion or direct transport of the mature or precursor form of a protein. The signal sequence is typically located N-terminal to the precursor or mature protein sequence. The signal sequence may be endogenous or exogenous. A signal sequence is normally absent from the mature protein. A signal sequence is typically cleaved from the protein by a signal peptidase after the protein is transported.

The term "mature" form of a protein, polypeptide, or peptide refers to the functional form of the protein, polypeptide, or peptide without the signal peptide sequence and propeptide sequence.

The term "precursor" form of a protein or peptide refers to a mature form of the protein having a prosequence operably linked to the amino or carbonyl terminus of the protein. The precursor may also have a "signal" sequence operably linked to the amino terminus of the prosequence. The precursor may also have additional polypeptides that are involved in post-translational activity (e.g., polypeptides cleaved therefrom to leave the mature form of a protein or peptide).

The term "wild-type" in reference to an amino acid sequence or nucleic acid sequence indicates that the amino acid sequence or nucleic acid sequence is a native or naturally-occurring sequence. As used herein, the term "naturally-occurring" refers to anything (e.g., proteins, amino acids, or nucleic acid sequences) that is found in nature Conversely, the term "non-naturally occurring" refers to anything that is not found in nature (e.g., recombinant nucleic acids and protein sequences produced in the laboratory or modification of the wild-type sequence).

As used herein with regard to amino acid residue positions, "corresponding to" or "corresponds to" or "corresponds" refers to an amino acid residue at the enumerated position in a protein or peptide, or an amino acid residue that is analogous, homologous, or equivalent to an enumerated residue in a protein or peptide. As used herein, "corresponding region" generally refers to an analogous position in a related proteins or a reference protein.

The terms "derived from" and "obtained from" refer to not only a protein produced or producible by a strain of the organism in question, but also a protein encoded by a DNA sequence isolated from such strain and produced in a host organism containing such DNA sequence. Additionally, the term refers to a protein which is encoded by a DNA sequence of synthetic and/or cDNA origin and which has the identifying characteristics of the protein in question. To exemplify, "proteases derived from *Bacillus*" refers to those enzymes having proteolytic activity that are naturally produced by *Bacillus*, as well as to serine proteases like those produced by *Bacillus* sources but which through the use of genetic engineering techniques are produced by other host cells transformed with a nucleic acid encoding the serine proteases.

The term "identical" in the context of two polynucleotide or polypeptide sequences refers to the nucleic acids or amino acids in the two sequences that are the same when aligned for maximum correspondence, as measured using a readily available sequence comparison or analysis algorithm.

As used herein, "homologous genes" refers to a pair of genes from different, but usually related species, which correspond to each other and which are identical or very similar to each other. The term encompasses genes that are separated by speciation (i.e., the development of new species) (e.g., orthologous genes), as well as genes that have been separated by genetic duplication (e.g., paralogous genes).

As used herein, "homology" refers to sequence similarity or identity, with identity being preferred. Homology may be determined using standard techniques known in the art (See e.g., Smith and Waterman, Adv. Appl. Math. 2:482 [1981]; Needleman and Wunsch, J. Mol. Biol. 48:443 [1970]; Pearson and Lipman, Proc. Natl. Acad. Sci. USA 85:2444 [1988]; software programs such as GAP, BESTFIT, FASTA, and TFASTA in the Wisconsin Genetics Software Package (Genetics Computer Group, Madison, Wis.); and Devereux et al., Nucl. Acid Res. 12:387-395 [1984]). One example of a useful algorithm is PILEUP. PILEUP creates a multiple sequence alignment from a group of related sequences using progressive, pair-wise alignments. It can also plot a tree showing the clustering relationships used to create the alignment. PILEUP uses a simplification of the progressive alignment method of Feng and Doolittle (See, Feng and Doolittle, J. Mol. Evol. 35:351-360 [1987]). The method is similar to that described by Higgins and Sharp (See, Higgins and Sharp, CABIOS 5:151-153 [1989]). Useful PILEUP parameters including a default gap weight of 3.00, a default gap length weight of 0.10, and weighted end gaps.

The percent sequence identity between a reference sequence and a test sequence of interest may be readily determined by one skilled in the art. The percent identity shared by polynucleotide or polypeptide sequences is determined by direct comparison of the sequence information between the molecules by aligning the sequences and determining the identity by methods known in the art. An example of an algorithm that is suitable for determining sequence similarity is the BLAST algorithm, (See, Altschul, et al., J. Mol. Biol., 215:403-410 [1990]). Software for performing BLAST analyses is publicly available through the National Center for Biotechnology Information. This algorithm involves first identifying high scoring sequence pairs (HSPs) by identifying short words of length W in the query sequence that either match or satisfy some positive-valued threshold score T when aligned with a word of the same length in a database sequence. These initial neighborhood word hits act as starting points to find longer HSPs containing them. The word hits are expanded in both directions along each of the two sequences being compared for as far as the cumulative alignment score can be increased. Extension of the word hits is stopped when: the cumulative alignment score falls off by the quantity X from a maximum achieved value; the cumulative score goes to zero or below; or the end of either sequence is reached. The BLAST algorithm parameters W, T, and X determine the sensitivity and speed of the alignment. The BLAST program uses as defaults a wordlength (W) of 11, the BLOSUM62 scoring matrix (See, Henikoff and Henikoff, Proc. Natl. Acad. Sci. USA 89:10915 [1992]) alignments (B) of 50, expectation (E) of 10, M'S, N'-4, and a comparison of both strands.

The BLAST algorithm then performs a statistical analysis of the similarity between two sequences (See e.g., Karlin and Altschul, supra). One measure of similarity provided by the BLAST algorithm is the smallest sum probability (P(N)), which provides an indication of the probability by which a match between two nucleotide or amino acid sequences would occur by chance. For example, a nucleic acid is considered similar to a serine protease nucleic acid of this invention if the smallest sum probability in a comparison of the test nucleic acid to a serine protease nucleic acid is less than about 0.1, more preferably less than about 0.01, and most preferably less than about 0.001. Where the test nucleic acid encodes a serine protease polypeptide, it is considered similar to a specified serine protease nucleic acid if the comparison results in a smallest sum probability of less than about 0.5, and more preferably less than about 0.2.

Percent "identical" or "identity" in the context of two or more nucleic acid or polypeptide sequences refers to two or more sequences that are the same or have a specified percentage of nucleic acid residues or amino acid residues, respectively, that are the same, when compared and aligned for maximum similarity, as determined using a sequence comparison algorithm or by visual inspection. "Percent sequence identity" or "% identity" or "% sequence identity or "% amino acid sequence identity" of a subject amino acid sequence to a reference (i.e., query) amino acid sequence means that the subject amino acid sequence is identical (i.e., on an amino acid-by-amino acid basis) by a specified percentage to the query amino acid sequence over a comparison length when the sequences are optimally aligned. Thus, 80% amino acid sequence identity or 80% identity with respect to two amino acid sequences means that 80% of the amino acid residues in two optimally aligned amino acid sequences are identical.

"Percent sequence identity" or "% identity" or "% sequence identity or "% nucleotide sequence identity" of a subject nucleic acid sequence to a reference (i.e. query) nucleic acid sequence means that the subject nucleic acid sequence is identical (i.e., on a nucleotide-by-nucleotide basis for a polynucleotide sequence) by a specified percentage to the query sequence over a comparison length when the sequences are optimally aligned. Thus, 80% nucleotide sequence identity or 80% identity with respect to two nucleic acid sequences means that 80% of the nucleotide residues in two optimally aligned nucleic acid sequences are identical.

"Percent sequence identity" or "% identity" or "% sequence identity or "% protein sequence identity" of a subject protein sequence to a reference (i.e. query) protein sequence means that the subject protein sequence is identical (i.e., on a residue by residue basis for a polypeptide sequence) by a specified percentage to the query sequence over a comparison length when the sequences are optimally aligned. Thus, 80% protein sequence identity or 80% identity with respect to two polypeptide sequences means that 80% of the residues in two optimally aligned protein sequences are identical.

In some embodiments, the "percent sequence identity" or "% sequence identity" or "% identity" of a subject sequence to a query sequence can be calculated by optimally aligning the two sequences and comparing the two optimally aligned sequences over the comparison length. The number of positions in the optimal alignment at which identical residues occur in both sequences is determined, thereby providing the number of matched positions, and the number of matched positions is then divided by the total number of positions of the comparison length (which, unless otherwise specified, is the length of the query sequence). The resulting number is multiplied by 100 to yield the percent sequence identity of the subject sequence to the query sequence.

"Optimal alignment" or "optimally aligned" refers to the alignment of two (or more) sequences giving the highest percent identity score. For example, optimal alignment of two protein sequences can be achieved by manually aligning the sequences such that the maximum number of identical amino acid residues in each sequence are aligned together or by using software programs or procedures described herein or known in the art. Optimal alignment of two nucleic acid sequences can be achieved by manually aligning the sequences such that the maximum number of identical nucleotide residues in each sequence are aligned together or by using software programs or procedures described herein or known in the art.

In some embodiments, two polypeptide sequences are deemed "optimally aligned" when they are aligned using defined parameters, such as a defined amino acid substitution matrix, gap existence penalty (also termed gap open penalty), and gap extension penalty, so as to achieve the highest similarity score possible for that pair of sequences. The BLOSUM62 scoring matrix (See, Henikoff and Henikoff, supra) is often used as a default scoring substitution matrix in polypeptide sequence alignment algorithms (e.g., BLASTP). The gap existence penalty is imposed for the introduction of a single amino acid gap in one of the aligned sequences, and the gap extension penalty is imposed for each residue position in the gap. Exemplary alignment parameters employed are: BLOSUM62 scoring matrix, gap existence penalty=11, and gap extension penalty=1. The alignment score is defined by the amino acid positions of each sequence at which the alignment begins and ends (e.g., the alignment window), and optionally by the insertion of a gap or multiple gaps into one or both sequences, so as to achieve the highest possible similarity score.

Optimal alignment between two or more sequences can be determined manually by visual inspection or by using a computer, such as, but not limited to for example, the BLASTP program for amino acid sequences and the BLASTN program for nucleic acid sequences (See e.g., Altschul et al., Nucleic Acids Res. 25(17):3389-3402 (1997); See also, the National Center for Biotechnology Information (NCBI) website).

A polypeptide of interest may be said to be "substantially similar" to a reference polypeptide if the polypeptide of interest comprises an amino acid sequence having at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or at least about 99.5% sequence identity to the amino acid sequence of the reference polypeptide. The percent identity between two such polypeptides can be determined manually by inspection of the two optimally aligned polypeptide sequences or by using software programs or algorithms (e.g., BLAST, ALIGN, CLUSTAL, and MUSCLE) using standard parameters. One indication that two polypeptides are substantially identical is that the first polypeptide is immunologically cross-reactive with the second polypeptide. Typically, polypeptides that differ by conservative amino acid substitutions are immunologically cross-reactive. Thus, a polypeptide is substantially identical to a second polypeptide, for example, where the two peptides differ only by a conservative amino acid substitution or one or more conservative amino acid substitutions.

A nucleic acid of interest may be said to be "substantially similar" to a reference nucleic acid if the nucleic acid of interest comprises a nucleotide sequence having at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or at least about 99.5% sequence identity to the nucleotide sequence of the reference nucleic acid. The percent identity between two such nucleic acids can be determined manually by inspection of the two optimally aligned nucleic acid sequences or by using software programs or algorithms (e.g., BLAST, ALIGN, CLUSTAL, and MUSCLE) using standard parameters. One indication that two nucleic acid sequences are substantially identical is that the two nucleic acid molecules hybridize to each other under stringent conditions (e.g., within a range of medium to high stringency).

A nucleic acid or polynucleotide is "isolated" when it is at least partially or completely separated from other components, including but not limited to for example, other proteins, nucleic acids, cells, etc. Similarly, a polypeptide, protein or peptide is "isolated" when it is at least partially or completely separated from other components, including but not limited to for example, other proteins, nucleic acids, cells, etc. On a molar basis, an isolated species is more abundant than are other species in a composition. For example, an isolated species may comprise at least about 60%, about 65%, about 70%, about 75%, about 80%, about 85%, about 90%, about 91%, about 92%, about 93%, about 94%, about 95%, about 96%, about 97%, about 98%, about 99%, or about 100% (on a molar basis) of all macromolecular species present. Preferably, the species of interest is purified to essential homogeneity (i.e., contaminant species cannot be detected in the composition by conventional detection methods). Purity and homogeneity can be determined using a number of techniques well known in the art, such as agarose or polyacrylamide gel electrophoresis of a nucleic acid or a protein sample, respectively, followed by visualization upon staining. If desired, a high-resolution technique, such as high performance liquid chromatography (HPLC) or a similar means can be utilized for purification of the material.

The term "purified" as applied to nucleic acids or polypeptides generally denotes a nucleic acid or polypeptide that is essentially free from other components as determined by analytical techniques well known in the art (e.g., a purified polypeptide or polynucleotide forms a discrete band in an electrophoretic gel, chromatographic eluate, and/or a media subjected to density gradient centrifugation). For example, a nucleic acid or polypeptide that gives rise to essentially one band in an electrophoretic gel is "purified." A purified nucleic acid or polypeptide is at least about 50% pure, usually at least least about 60%, about 65%, about 70%, about 75%, about 80%, about 85%, about 90%, about 91%, about 92%, about 93%, about 94%, about 95%, about 96%, about 97%, about 98%, about 99%, about 99.5%, about 99.6%, about 99.7%, about 99.8% or more pure (e.g., percent by weight on a molar basis). In a related sense, the invention provides methods of enriching compositions for one or more molecules of the invention, such as one or more polypeptides or polynucleotides of the invention. A composition is enriched for a molecule when there is a substantial increase in the concentration of the molecule after application of a purification or enrichment technique. A substantially pure polypeptide or polynucleotide of the invention (e.g., substantially pure variant protease or polynucleotide encoding a variant protease of the invention, respectively) will typically comprise at least about 55%, about 60%, about 70%, about 80%, about 85%, about 90%, about 91%, about 92%, about 93%, about 94%, about 95%, about 96%, about 97%, about 98, about 99%, about 99.5% or more by weight (on a molar basis) of all macromolecular species in a particular composition.

In a related sense, the invention provides methods of enriching compositions for one or more molecules of the invention, such as one or more polypeptides of the invention (e.g., one or more variant proteases of the invention) or one or more nucleic acids of the invention (e.g., one or more nucleic acids encoding one or more variant proteases of the invention). A composition is enriched for a molecule when there is a substantial increase in the concentration of the molecule after application of a purification or enrichment technique. A substantially pure polypeptide or polynucleotide will typically comprise at least about 55%, about 60%, about 70%, about 80%, about 85%, about 90%, about 91%, about 92%, about 93%, about 94%, about 95%, about 96%, about 97%, about 98, about 99%, about 99.5% or more by weight (on a molar basis) of all macromolecular species in a particular composition.

As used herein, the term "combinatorial mutagenesis" or "combinatorial" refers to methods in which libraries of nucleic acid variants of a reference nucleic acid sequence are generated. In these libraries, the variants contain one or several mutations chosen from a predefined set of mutations. The methods also provide means to introduce random mutations which were not members of the predefined set of mutations. Some such methods include those set forth in U.S. Pat. No. 6,582,914, hereby incorporated by reference. Some such combinatorial mutagenesis methods include and/or encompass methods embodied in commercially available kits (e.g., QUIKCHANGE® Multi Site-Directed Mutagenesis Kit (Stratagene), PCR fusion/extension PCR).

As used herein, "having improved properties" used in connection with a variant protease refers to a variant protease with improved or enhanced wash or cleaning performance, and/or improved or enhanced stability optionally with retained wash or cleaning performance, relative to the corresponding reference protease (e.g., wild-type or naturally-occurring protease). The improved properties of a variant protease may comprise improved wash or cleaning performance and/or improved stability. In some embodiments, the invention provides variant proteases of the invention that exhibit one of more of the following properties: improved hand wash performance, improved hand or manual dishwashing performance, improved automatic dishwashing performance, improved laundry performance, and/or improved stability relative to a reference protease (e.g., wild-type protease, such as a wild-type AprL).

As used herein, the term "functional assay" refers to an assay that provides an indication of a protein's activity. In some embodiments, the term refers to assay systems in which a protein is analyzed for its ability to function in its usual capacity. For example, in the case of enzymes, a functional assay involves determining the effectiveness of the enzyme in catalyzing a reaction.

As used herein, the term "target property" refers to the property of the starting gene that is to be altered. It is not intended that the present invention be limited to any particular target property. However, in some embodiments, the target property is the stability of a gene product (e.g., resistance to denaturation, proteolysis or other degradative factors), while in other embodiments, the level of production in a production host is altered.

The term "property" or grammatical equivalents thereof in the context of a nucleic acid, as used herein, refer to any characteristic or attribute of a nucleic acid that can be selected or detected. These properties include, but are not limited to, a property affecting binding to a polypeptide, a property conferred on a cell comprising a particular nucleic acid, a property affecting gene transcription (e.g., promoter strength, promoter recognition, promoter regulation, enhancer function), a property affecting RNA processing (e.g., RNA splicing, RNA stability, RNA conformation, and post-transcriptional modification), a property affecting translation (e.g., level, regulation, binding of mRNA to ribosomal proteins, post-translational modification). For example, a binding site for a transcription factor, polymerase, regulatory factor, etc., of a nucleic acid may be altered to produce desired characteristics or to identify undesirable characteristics.

The term "property" or grammatical equivalents thereof in the context of a polypeptide (including proteins), as used herein, refer to any characteristic or attribute of a polypeptide that can be selected or detected. These properties include, but are not limited to oxidative stability, substrate specificity, catalytic activity, enzymatic activity, thermal stability, alkaline stability, pH activity profile, resistance to proteolytic degradation, $K_M$, $k_{cat}$, $k_{cat}/k_M$ ratio, protein folding, inducing an immune response, ability to bind to a ligand, ability to bind to a receptor, ability to be secreted, ability to be displayed on the surface of a cell, ability to oligomerize, ability to signal, ability to stimulate cell proliferation, ability to inhibit cell proliferation, ability to induce apoptosis, ability to be modified by phosphorylation or glycosylation, and/or ability to treat disease, etc.

As used herein, the term "screening" has its usual meaning in the art. In one exemplary screening process, a mutant nucleic acid or variant polypeptide encoded therefrom is provided and a property of the mutant nucleic acid or variant polypeptide, respectively, is assessed or determined. The determined property of the mutant nucleic acid or variant polypeptide may be compared to a property of the corresponding precursor (parent) nucleic acid or to the property of the corresponding parent polypeptide, respectively.

It will be apparent to the skilled artisan that the screening procedure for obtaining a nucleic acid or protein with an altered property depends upon the property of the starting material the modification of which the generation of the mutant nucleic acid is intended to facilitate. The skilled artisan will therefore appreciate that the invention is not limited to any specific property to be screened for and that the following description of properties lists illustrative examples only. Methods for screening for any particular property are generally described in the art. For example, one can measure binding, pH, specificity, etc., before and after mutation, wherein a change indicates an alteration. Preferably, the screens are performed in a high-throughput manner, including multiple samples being screened simultaneously, including, but not limited to assays utilizing chips, phage display, and multiple substrates and/or indicators.

As used herein, in some embodiments, a screening process encompasses one or more selection steps in which variants of interest are enriched from a population of variants. Examples of these embodiments include the selection of variants that confer a growth advantage to the host organism, as well as phage display or any other method of display, where variants can be captured from a population of variants based on their binding or catalytic properties. In some embodiments, a library of variants is exposed to stress (e.g., heat, denaturation, etc.) and subsequently variants that are still intact are identified in a screen or enriched by selection. It is intended that the term encompass any suitable means for selection. Indeed, it is not intended that the present invention be limited to any particular method of screening.

The terms "modified nucleic acid sequence" and "modified gene" are used interchangeably herein to refer to a nucleic acid sequence that includes a deletion, insertion or interruption of naturally occurring (i.e., wild-type) nucleic acid sequence. In some embodiments, the expression product of the modified nucleic acid sequence is a truncated protein (e.g., if the modification is a deletion or interruption of the sequence). In some embodiments, the truncated protein retains biological activity. In alternative embodiments, the expression product of the modified nucleic acid sequence is an elongated protein (e.g., modifications comprising an insertion into the nucleic acid sequence). In some embodiments, a nucleotide insertion in the nucleic acid sequence leads to a truncated protein (e.g., when the insertion results in the formation of a stop codon). Thus, an insertion may result in either a truncated protein or an elongated protein as an expression product.

A "mutant" nucleic acid sequence typically refers to a nucleic acid sequence that has an alteration in at least one codon occurring in a host cell's wild-type sequence such that the expression product of the mutant nucleic acid sequence is a protein with an altered amino acid sequence relative to the wild-type protein. The expression product may have an altered functional capacity (e.g., enhanced enzymatic activity).

As used herein, the phrase "alteration in substrate specificity" refers to changes in the substrate specificity of an enzyme. In some embodiments, a change in substrate specificity is defined as a change in $k_{cat}$ and/or $K_m$ for a particular substrate, resulting from mutations of the enzyme or alteration of reaction conditions. The substrate specificity of an enzyme is determined by comparing the catalytic efficiencies it exhibits with different substrates. These determinations find particular use in assessing the efficiency of mutant enzymes, as it is generally desired to produce variant enzymes that exhibit greater ratios of $k_{cat}/K_m$ for substrates of interest. However, it is not intended that the present invention be limited to any particular substrate composition or substrate specificity.

As used herein, "surface property" is used in reference to electrostatic charge, as well as properties such as the hydrophobicity and hydrophilicity exhibited by the surface of a protein.

As used herein, the term "net charge" is defined as the sum of all charges present in a molecule. "Net charge changes" are made to a parent protein molecule to provide a variant that has a net charge that differs from that of the parent molecule (i.e., the variant has a net charge that is not the same as that of the parent molecule). For example, substitution of a neutral amino acid with a negatively charged amino acid or a positively charged amino acid with a neutral amino acid results in net charge of −1 with respect to the parent molecule. Substitution of a positively charged amino acid with a negatively charged amino acid results in a net charge of −2 with respect to the parent. Substitution of a neutral amino acid with a positively charged amino acid or a negatively charged amino acid with a neutral amino acid results in net charge of +1 with respect to the parent. Substitution of a negatively charged amino acid with a positively charged amino acid results in a net charge of +2 with respect to the parent. The net charge of a parent protein can also be altered by deletion and/or insertion of charged amino acids The terms "thermally stable" and "thermostable" and "thermostability" refer to proteases that retain a specified amount of enzymatic activity after exposure to identified temperatures over a given period of time under conditions prevailing during the proteolytic, hydrolyzing, cleaning or other process of the invention, while being exposed to altered temperatures. "Altered temperatures" encompass increased or decreased temperatures. In some embodiments, the proteases retain at least about 50%, about 60%, about 70%, about 75%, about 80%, about 85%, about 90%, about 92%, about 95%, about 96%, about 97%, about 98%, or about 99% proteolytic activity after exposure to altered temperatures over a given time period, for example, at least about 60 minutes, about 120 minutes, about 180 minutes, about 240 minutes, about 300 minutes, etc.

The term "enhanced stability" in the context of an oxidation, chelator, thermal and/or pH stable protease refers to a higher retained proteolytic activity over time as compared to other proteases (e.g., AprL proteases) and/or wild-type enzymes.

The term "diminished stability" in the context of an oxidation, chelator, thermal and/or pH stable protease refers to a lower retained proteolytic activity over time as compared to other proteases (e.g., AprL proteases) and/or wild-type enzymes.

The term "cleaning activity" refers to a cleaning performance achieved by a variant protease or reference protease under conditions prevailing during the proteolytic, hydrolyzing, cleaning, soil/stain removal, or other process of the invention. In some embodiments, cleaning performance of a variant protease or reference protease may be determined by using various assays for cleaning one or more various enzyme sensitive stains on an item or surface (e.g., a stain resulting from food, grass, blood, ink, milk, oil, and/or egg protein). Cleaning performance of a variant or reference protease can be determined by subjecting the stain on the item or surface to standard wash condition(s) and assessing the degree to which the stain is removed by using various chromatographic, spectrophotometric, or other quantitative methodologies. Exemplary cleaning assays and methods are known in the art and include, but are not limited to those described in WO 99/34011 and U.S. Pat. No. 6,605,458, as well as those cleaning assays and methods included in the Examples provided below.

The term "cleaning effective amount" of a variant protease or reference protease refers to the amount of protease that achieves a desired level of enzymatic activity in a specific cleaning composition. Such effective amounts are readily ascertained by one of ordinary skill in the art and are based on many factors, such as the particular protease used, the cleaning application, the specific composition of the cleaning composition, and whether a liquid or dry (e.g., granular, tablet, bar) composition is required, etc. The term "soil removal index" (SRI) of a variant protease or reference protease refers to the degree of soil removal achieved by a certain quantity of enzyme or enzymatic activity.

The term "cleaning adjunct material" refers to any liquid, solid, or gaseous material included in cleaning composition other than a variant protease of the invention. In some embodiments, the cleaning compositions of the present invention include one or more cleaning adjunct materials. Each cleaning adjunct material is typically selected depending on the particular type and form of cleaning composition (e.g., liquid, granule, powder, bar, paste, spray, tablet, gel, foam, or other composition). Preferably, each cleaning adjunct material is compatible with the protease enzyme used in the composition.

The term "enhanced performance" in the context of cleaning activity refers to an increased or greater cleaning activity by an enzyme on certain enzyme sensitive stains such as egg, milk, grass, ink, oil, and/or blood, as determined by usual evaluation after a standard wash cycle and/or multiple wash cycles.

The term "diminished performance" in the context of cleaning activity refers to a decreased or lesser cleaning activity by an enzyme on certain enzyme sensitive stains such as egg, milk, grass or blood, as determined by usual evaluation after a standard wash cycle.

Cleaning performance can be determined by comparing the variant proteases of the present invention with reference proteases in various cleaning assays concerning enzyme sensitive stains such as grass, blood, ink, oil, and/or milk as determined by usual spectrophotometric or analytical methodologies after standard wash cycle conditions.

As used herein, the term "consumer product" means fabric and home care product. As used herein, the term "fabric and home care product" or "fabric and household care product" includes products generally intended to be used or consumed in the form in which they are sold and that are for treating fabrics, hard surfaces and any other surfaces, and cleaning systems all for the care and cleaning of inanimate surfaces, as well as fabric conditioner products and other products designed specifically for the care and maintenance of fabrics, and air care products, including: air care including air fresheners and scent delivery systems, car care, pet care, livestock care, personal care, jewelry care, dishwashing, fabric conditioning (including softening and/or freshening), laundry detergency, laundry and rinse additive and/or care, pre-treatment cleaning compositions, hard surface cleaning and/or treatment including floor and toilet bowl cleaners, glass cleaners and/or treatments, tile cleaners and/or treatments, ceramic cleaners and/or treatments, and other cleaning for consumer or institutional use. In some embodiments, the fabric and home care products are suitable for use on wounds and/or skin. "Fabric and home care product" includes consumer and institutional products.

As used herein, the term "non-fabric and home care products" refers to compositions that are added to other compositions to produce an end product that may be a fabric and home care product.

As used herein, the term "institutional cleaning composition" refers to products suitable for use in institutions including but not limited to schools, hospitals, factories, stores, corporations, buildings, restaurants, office complexes and buildings, processing and/or manufacturing plants, veterinary hospitals, factory farms, factory ranches, etc.

As used herein, the term "cleaning and/or treatment composition" is a subset of fabric and home care products that includes, unless otherwise indicated, compositions suitable for cleaning and/or treating items. Such products include, but are not limited to, products for treating fabrics, hard surfaces and any other surfaces in the area of fabric and home care, including: air care including air fresheners and scent delivery systems, car care, dishwashing, fabric conditioning (including softening and/or freshening), laundry detergency, laundry and rinse additive and/or care, hard surface cleaning and/or treatment including floor and toilet bowl cleaners, granular or powder-form all-purpose or "heavy-duty" washing agents, especially cleaning detergents; liquid, gel or paste-form all-purpose washing agents, especially the so-called heavy-duty liquid types; liquid fine-fabric detergents; hand dishwashing agents or light duty dishwashing agents, especially those of the high-foaming type; machine dishwashing agents, including the various tablet, granular, liquid and rinse-aid types for household and institutional use: car or carpet shampoos, bathroom cleaners including toilet bowl cleaners; as well as cleaning auxiliaries such as bleach additives and "stain-stick" or pre-treat types, substrate-laden products such as dryer added sheets.

Indeed, as used herein, "cleaning composition" or "cleaning formulation" of the invention refers to any composition of the invention useful for removing or eliminating a compound (e.g., undesired compound) from an object, item or surface to be cleaned, including, but not limited to for example, a fabric, fabric item, dishware item, tableware item, glassware item, contact lens, other solid substrate, hair (shampoo) (including human or animal hair), skin (soap or and cream), teeth (mouthwashes, toothpastes), surface of an item or object (e.g., hard surfaces, such as the hard surface of a table, table top, wall, furniture item, floor, ceiling, non-dishware item, non-tableware item, etc.), filters, membranes (e.g., filtration membranes, including but not limited to ultrafiltration membranes), etc. The term encompasses any material and/or added compound selected for the particular type of cleaning composition desired and the form of the product (e.g., liquid, gel, granule, spray, or other composition), as long as the composition is compatible with the protease and other enzyme(s) used in the composition. The specific selection of cleaning composition materials are readily made by considering the surface, object, item, or fabric to be cleaned, and the desired form of the composition for the cleaning conditions during use.

Cleaning compositions and cleaning formulations include any composition that is suited for cleaning, bleaching, disinfecting, and/or sterilizing any object, item, and/or surface. Such compositions and formulations include, but are not limited to for example, liquid and/or solid compositions, including cleaning or detergent compositions (e.g., liquid, tablet, gel, bar, granule, and/or solid laundry cleaning or detergent compositions and fine fabric detergent compositions; hard surface cleaning compositions and formulations, such as for glass, wood, ceramic and metal counter tops and windows; carpet cleaners; oven cleaners; fabric fresheners; fabric softeners; and textile, laundry booster cleaning or detergent compositions, laundry additive cleaning compositions, and laundry pre-spotter cleaning compositions; dishwashing compositions, including hand or manual dishwashing compositions (e.g., "hand" or "manual" dishwashing detergents) and automatic dishwashing compositions (e.g., "automatic dishwashing detergents"). Single dosage unit forms also find use with the present invention, including but not limited to pills, tablets, gelcaps, or other single dosage units such as pre-measured powders, suspensions, or liquids.

Cleaning composition or cleaning formulations, as used herein, include, unless otherwise indicated, granular or powder-form all-purpose or heavy-duty washing agents, especially cleaning detergents; liquid, granular, gel, solid, tablet, paste, or unit dosage-form all-purpose washing agents, especially the so-called heavy-duty liquid (HDL) detergent or heavy-duty dry detergent (HDD) types; liquid fine-fabric detergents; water-soluble single or multi-chamber container pouch, hand or manual dishwashing agents, including those of the high-foaming type; hand or manual dishwashing, automatic dishwashing, or dishware or tableware washing agents, including the various tablet, powder, solid, granular, liquid, gel, and rinse-aid types for household and institutional use; liquid cleaning and disinfecting agents, including antibacterial hand-wash types, cleaning bars, mouthwashes, denture cleaners, car shampoos, carpet shampoos, bathroom cleaners; hair shampoos and/or hair-rinses for humans and other animals; shower gels and foam baths and metal cleaners; as well as cleaning auxiliaries, such as bleach additives and "stain-stick" or pre-treat types. In some embodiments, granular compositions are in "compact" form; in some embodiments, liquid compositions are in a "concentrated" form.

As used herein, "fabric cleaning compositions" include hand and machine laundry detergent compositions including laundry additive compositions and compositions suitable for use in the soaking and/or pretreatment of stained fabrics (e.g., clothes, linens, and other textile materials).

As used herein, "non-fabric cleaning compositions" include non-textile (i.e., non-fabric) surface cleaning compositions, including, but not limited to for example, hand or manual or automatic dishwashing detergent compositions, oral cleaning compositions, denture cleaning compositions, contact lens cleaning compositions, wound debridement compositions, and personal cleansing compositions.

As used herein, the term "fabric and/or hard surface cleaning and/or treatment composition" is a subset of cleaning and treatment compositions that includes, unless otherwise indicated, granular or powder-form all-purpose or "heavy-duty" washing agents, especially cleaning detergents; liquid, gel or paste-form all-purpose washing agents, especially the so-called heavy-duty liquid types; liquid fine-fabric detergents; hand dishwashing agents or light duty dishwashing agents, especially those of the high-foaming type; machine dishwashing agents, including the various tablet, granular, liquid and rinse-aid types for household and institutional use; liquid cleaning and disinfecting agents, car or carpet shampoos, bathroom cleaners including toilet bowl cleaners; fabric conditioning products including softening and/or freshening that may be in liquid, solid and/or dryer sheet form; as well as cleaning auxiliaries such as bleach additives and "stain-stick" or pre-treat types, substrate-laden products such as dryer added sheets. All of such products which are applicable may be in standard, concentrated or even highly concentrated form even to the extent that such products may in certain aspect be non-aqueous.

As used herein, the term "detergent composition" or "detergent formulation" is used in reference to a composition intended for use in a wash medium for the cleaning of soiled or dirty objects, including particular fabric and/or non-fabric objects or items. Such compositions of the present invention are not limited to any particular detergent composition or formulation. Indeed, in some embodiments, the detergents of the invention comprise at least one variant protease of the invention and, in addition, one or more surfactants, transferase(s), hydrolytic enzymes, oxido reductases, builders (e.g., a builder salt), bleaching agents, bleach activators, bluing agents, fluorescent dyes, caking inhibitors, masking agents, enzyme activators, antioxidants, and/or solubilizers. In some instances, a builder salt is a mixture of a silicate salt and a phosphate salt, preferably with more silicate (e.g., sodium metasilicate) than phosphate (e.g., sodium tripolyphosphate). Some compositions of the invention, such as, but not limited to, cleaning compositions or detergent compositions, do not contain any phosphate (e.g., phosphate salt or phosphate builder).

As used herein, the term "bleaching" refers to the treatment of a material (e.g., fabric, laundry, pulp, etc.) or surface for a sufficient length of time and/or under appropriate pH and/or temperature conditions to effect a brightening (i.e., whitening) and/or cleaning of the material. Examples of chemicals suitable for bleaching include, but are not limited to, e.g., $ClO_2$, $H_2O_2$, peracids, $NO_2$, etc.

As used herein, "wash performance" of a protease (e.g., a variant protease of the invention) refers to the contribution of a variant protease to washing that provides additional cleaning performance to the detergent as compared to the detergent without the addition of the variant protease to the composition. Wash performance is compared under relevant washing conditions. In some test systems, other relevant factors, such as detergent composition, sud concentration, water hardness, washing mechanics, time, pH, and/or temperature, can be controlled in such a way that condition(s) typical for household application in a certain market segment (e.g., hand or manual dishwashing, automatic dishwashing, dishware cleaning, tableware cleaning, fabric cleaning, etc.) are imitated.

The term "relevant washing conditions" is used herein to indicate the conditions, particularly washing temperature, time, washing mechanics, sud concentration, type of detergent and water hardness, actually used in households in a hand dishwashing, automatic dishwashing, or laundry detergent market segment.

The term "improved wash performance" is used to indicate that a better end result is obtained in stain removal under relevant washing conditions, or that less variant protease, on weight basis, is needed to obtain the same end result relative to the corresponding wild-type or starting parent protease.

As used herein, the term "disinfecting" refers to the removal of contaminants from the surfaces, as well as the inhibition or killing of microbes on the surfaces of items. It is not intended that the present invention be limited to any particular surface, item, or contaminant(s) or microbes to be removed.

The "compact" form of the cleaning compositions herein is best reflected by density and, in terms of composition, by the amount of inorganic filler salt. Inorganic filler salts are conventional ingredients of detergent compositions in powder form. In conventional detergent compositions, the filler salts are present in substantial amounts, typically about 17 to about 35% by weight of the total composition. In contrast, in compact compositions, the filler salt is present in amounts not exceeding about 15% of the total composition. In some embodiments, the filler salt is present in amounts that do not exceed about 10%, or more preferably, about 5%, by weight of the composition. In some embodiments, the inorganic filler salts are selected from the alkali and alkaline-earth-metal salts of sulfates and chlorides. In some embodiments, the filler salt is sodium sulfate.

The position of an amino acid residue in a given amino acid sequence is typically numbered herein using the numbering of the position of the corresponding amino acid residue of the AprL amino acid sequence shown in SEQ ID NO:2. The AprL amino acid sequence shown in SEQ ID NO:2, thus serves as a reference sequence. A given amino acid sequence, such as a variant protease amino acid sequence described herein, can be aligned with the AprL sequence (SEQ ID NO:2) using an alignment algorithm as described herein, and an amino acid residue in the given amino acid sequence that aligns (preferably optimally aligns) with an amino acid residue in the AprL sequence can be conveniently numbered by reference to the corresponding amino acid residue in the AprL sequence.

Generally, the nomenclature used herein and many of the laboratory procedures in cell culture, molecular genetics, molecular biology, nucleic acid chemistry, and protein chemistry described below are well known and commonly employed by those of ordinary skill in the art. Methods for production and manipulation of recombinant nucleic acid methods, nucleic acid synthesis, cell culture methods, and transgene incorporation (e.g., transfection, electroporation) are known to those skilled in the art and are described in numerous standard texts. Oligonucleotide synthesis and purification steps are typically performed according to specifications. Techniques and procedures are generally performed according to conventional methods well known in the art and various general references that are provided throughout this document. Procedures therein are believed to be well known to those of ordinary skill in the art and are provided for the convenience of the reader.

AprL-Clade Enzymes of the Invention

As used herein, an AprL-clade enzyme includes an enzyme, polypeptide, or protein, or an active fragment thereof, exhibiting a proteolytic activity. This includes members of the AprL-clade, as described in Example 4, alignments shown in FIG. 2 and FIG. 3, and the phylogenetic tree of FIG. 9. Members of the AprL-clade were identified by selecting subtilisin molecules with close homology to AprL, generating a structure-based alignment of these sequences to other subtilisins, and identifying regions of unique sequences conserved for all the AprL-clade enzymes.

In some embodiments, the AprL-clade enzymes comprises subtilisin proteases comprising a YNT (SEQ ID NO:46) motif. In yet other embodiments, the AprL-clade enzymes comprise subtilisin proteases comprising a Y56N57T58 (SEQ ID NO:45) motif, wherein the amino acid positions are numbered by correspondence with the amino acid sequence of the AprL protease set forth in SEQ ID NO:2. In still other embodiments, the AprL-clade enzymes comprise subtilisin proteases comprising a YNT (SEQ ID NO:46) motif between Asp32 and His63, wherein the amino acid positions are numbered by correspondence with the amino acid sequence of the AprL protease set forth in SEQ ID NO:2. In some embodiments, the AprL-clade enzymes comprise subtilisin proteases comprising a loop region between residues 52-60, wherein the amino acid positions are numbered by correspondence with the amino acid sequence of the AprL protease set forth in SEQ ID NO:2.

In further embodiments, the AprL-clade enzymes comprise subtilisin proteases comprising an $FVX_1GEX_2X_3YNT$ (SEQ ID NO:47) motif, wherein $X_1$ is A or S, $X_2$ is absent or any amino acid, and $X_3$ is A or S. In a still further embodiment, the AprL-clade enzymes comprise subtilisin proteases comprising an $F50V51X_152$ $G53E54X_355$ $Y56N57T58$ (SEQ ID NO:48) motif, wherein $X_1$ is an A or S and $X_3$ is an A or S; and further wherein the amino acid positions are numbered by correspondence with the amino acid sequence of the AprL protease set forth in SEQ ID NO:2.

In other embodiments, the AprL-clade enzymes comprise subtilisin proteases comprising an $LSX_4S$ (SEQ ID NO:55) motif, wherein $X_4$ is A or G. In still other embodiments, the AprL-clade enzymes comprise subtilisin proteases comprising an LSAS (SEQ ID NO:49) motif. In another embodiment, the AprL-clade enzymes comprise subtilisin proteases comprising an LSGS (SEQ ID NO:58) motif. In even still other embodiments, the AprL-clade enzymes comprise subtilisin proteases comprising SEQ ID NO:49 or SEQ ID NO:58 between Lys236 and Arg246, wherein the amino acid positions are numbered by correspondence with the amino acid sequence of the AprL protease set forth in SEQ ID NO:2. In some embodiments, the AprL-clade enzymes comprise subtilisin proteases comprising a L240S241A242S243 (SEQ ID NO:50) motif, wherein the amino acid positions are numbered by correspondence with the amino acid sequence of the AprL protease set forth in SEQ ID NO:2. In further embodiments, the AprL-clade enzymes comprise subtilisin proteases comprising a L240S241G242S243 (SEQ ID NO:56) motif, wherein the amino acid positions are numbered by correspondence with the amino acid sequence of the AprL protease set forth in SEQ ID NO:2. In still further embodiments, the AprL-clade enzymes comprise subtilisin proteases comprising a $KXXXLSX_4SQX_5R$ (SEQ ID NO:57) motif, wherein X is any amino acid, $X_4$ is A or G, and $X_5$ is an I or V. In yet further embodiments, the AprL-clade enzymes comprise subtilisin proteases comprising a $KXXXLSASQX_5R$ (SEQ ID NO:51) motif, wherein X is any amino acid and $X_5$ is an I or V. In an even yet further embodiment, the AprL-clade enzymes comprise subtilisin proteases comprising a $KXXXLSGSQX_5R$ (SEQ ID NO:59) motif, wherein X is any amino acid and $X_5$ is an I or V. In still further embodiments, the AprL-clade enzymes comprise subtilisin proteases comprising a $K236XXXLSASQX_5R246$ (SEQ ID NO:52) motif, wherein X is any amino acid and $X_5$ is an I or V; and further wherein the amino acid positions are numbered by correspondence with the amino acid sequence of the AprL protease set forth in SEQ ID NO:2. In an even yet still further embodiment, the AprL-clade enzymes comprise subtilisin proteases comprising a $K236XXXLSGSQX_5R246$ (SEQ ID NO:60) motif, wherein X is any amino acid and $X_5$ is an I or V; and further wherein the amino acid positions are numbered by correspondence with the amino acid sequence of the AprL protease set forth in SEQ ID NO:2.

In even further embodiments, the AprL-clade enzymes comprise subtilisin proteases comprising SEQ ID NO:45, 46, 47, or 48 and SEQ ID NO:49, 50, 51, or 52. In another embodiment, the AprL-clade enzymes comprise subtilisin proteases comprising SEQ ID NO:45, 46, 47, or 48 and SEQ ID NO: 49, 50, 51, 52, 55, 56, 57, 58, 59, or 60. In a still even further embodiment, the AprL-clade enzymes comprise subtilisin proteases comprising SEQ ID NO:45, 46, 47, or 48 and SEQ ID NO: 49 or 50. In yet another embodiment, the AprL-clade enzymes comprise subtilisin proteases comprising SEQ ID NO:58 between Lys236 and Arg246 and SEQ ID NO:46 between Asp32 and His63, wherein the amino acid positions are numbered by correspondence with the amino acid sequence of the AprL protease set forth in SEQ ID NO:2. In still yet another embodiment, the AprL-clade enzymes comprise subtilisin proteases comprising SEQ ID NO:49 between Lys236 and Arg246 and SEQ ID NO:46 between Asp32 and His63, wherein the amino acid positions are numbered by correspondence with the amino acid sequence of the AprL protease set forth in SEQ ID NO:2. In even yet other embodiments, the AprL-clade enzymes comprise subtilisin proteases comprising SEQ ID NO: 47 or 48 and SEQ ID NO: 50, 52, 55, 56, or 60.

In some embodiments, the AprL-clade enzymes comprise subtilisin proteases comprising an Arg248 residue. In some embodiments, the AprL-clade enzymes comprise subtilisin proteases comprising an Asn96 residue. In some embodiments, the AprL-clade enzymes comprise subtilisin proteases comprising a hydrogen bond between residues 96 and 98. In each instance, the residue numbers are numbered by correspondence with the amino acid sequence of AprL protease set forth in SEQ ID NO:2.

In some embodiments, any of the wildtype AprL-clade enzyme sequences can be used as a parent sequence for generation of AprL-clade variant subtilisin enzymes of the present invention. In further embodiments, the parent of one or more AprL-Clade protease variants described herein is a wild-type AprL-clade enzyme. In some embodiments, an AprL enzyme clade subtilisin protease can have one or more signature motif, as shown above. Members of the AprL-clade enzymes were confirmed to cluster to the same branching points in a phylogentic tree created using the Neighbor Joining method (Saitou, N. and Nei, M. (1987) MolBiol. Evol. 4:406-425). The sequence identity for the AprL-clade enzymes includes enzymes that are at least 60%, 65%, 70%, 75%, 80%, 85%, 90%, 91%, 92%, 93%, 94%, 95%, 96%, 97%, 98%, 99% or 100% identical to the AprL sequence (SEQ ID NO:2). Members of the AprL-clade include: AprL (SEQ ID NO:2), *B. licheniformis* subtilisin enzyme CAA62667 (SEQ ID NO:12), *B. licheniformis* subtilisin enzyme YP_006712489 (SEQ ID NO:14), *B. licheniformis* subtilisin enzyme BliD02339 (SEQ ID NO:9), *B. licheniformis* subtilisin enzyme AEU12640 (SEQ ID NO:13), B_licheniformis_DY_P00781 subtilisin enzyme (SEQ ID NO:15), and B_sonorensis_WP_006636716 subtilisin enzyme (SEQ ID NO:16). In other embodiments, the parent of an Aprl-Clade protease variant is an Aprl-clade enzyme selected from AprL (SEQ ID NO:2), *B. licheniformis* subtilisin enzyme CAA62667 (SEQ ID NO:12), *B. licheniformis* subtilisin enzyme YP_006712489 (SEQ ID NO:14), *B. licheniformis* subtilisin enzyme BliD02339 (SEQ ID NO:9), *B. licheniformis* subtilisin enzyme AEU12640 (SEQ ID NO:13), B_licheniformis_DY_P00781 subtilisin enzyme (SEQ ID NO:15), and B_sonorensis_WP_006636716 subtilisin enzyme (SEQ ID NO:16). In yet other embodiments, the parent of an Aprl-Clade protease variant is AprL (SEQ ID NO:2) or *B. licheniformis* subtilisin enzyme BliD02339 (SEQ ID NO:9). In yet even still other embodiments, the parent of an Aprl-Clade protease variant is an AprL-clade enzyme having at least 60%, 65%, 70%, 75%, 80%, 85%, 90%, 91%, 92%, 93%, 94%, 95%, 96%, 97%, 98%, 99% or 100% identity to the AprL sequence of SEQ ID NO:2. In still other embodiments, the parent of an Aprl-Clade protease variant is an AprL-clade enzyme having at least 85%, 90%, 91%, 92%, 93%, 94%, 95%, 96%, 97%, 98%, 99% or 100% identity to the AprL sequence of SEQ ID NO:2. In still yet other embodiments, the parent of an Aprl-Clade protease variant is an AprL-clade enzyme having at least 90%, 91%, 92%, 93%, 94%, 95%, 96%, 97%, 98%, 99% or 100% identity to the AprL sequence of SEQ ID NO:2. In still yet other embodiments, the parent of an Aprl-Clade protease variant is an AprL-clade enzyme having at least 95%, 96%, 97%, 98%, 99% or 100% identity to the AprL sequence of SEQ ID NO:2.

In some embodiments, the invention includes novel enzymes and variants of the AprL-clade. In some embodiments, the invention includes variant enzymes of AprL, wherein the variant has at least 60%, 65%, 70%, 75%, 80%, 85%, 90%, 91%, 92%, 93%, 94%, 95%, 96%, 97%, 98%, 99% or 100% identity to the AprL sequence of SEQ ID NO:2. In some embodiments, the invention includes variant enzymes of *Bacillus licheniformis* subtilisin enzyme CAA62667, wherein the variant has at least 60%, 65%, 70%, 75%, 80%, 85%, 90%, 91%, 92%, 93%, 94%, 95%, 96%, 97%, 98%, 99% or 100% identity to the *Bacillus licheniformis* subtilisin enzyme CAA62667 sequence of SEQ ID NO:12. In some embodiments, the invention includes variant enzymes of *Bacillus licheniformis* subtilisin enzyme YP_006712489, wherein the variant has at least 60%, 65%, 70%, 75%, 80%, 85%, 90%, 91%, 92%, 93%, 94%, 95%, 96%, 97%, 98%, 99% or 100% identity to the *Bacillus licheniformis* subtilisin enzyme YP_006712489 sequence of SEQ ID NO:14. In some embodiments, the invention includes variant enzymes of *Bacillus licheniformis* subtilisin enzyme BliD02339, wherein the variant has at least 60%, 65%, 70%, 75%, 80%, 85%, 90%, 91%, 92%, 93%, 94%, 95%, 96%, 97%, 98%, 99% or 100% identity to the *Bacillus licheniformis* subtilisin enzyme BliD02339 sequence of SEQ ID NO:9. In some embodiments, the invention includes variant enzymes of *Bacillus licheniformis* subtilisin enzyme AEU12640, wherein the variant has at least 60%, 65%, 70%, 75%, 80%, 85%, 90%, 91%, 92%, 93%, 94%, 95%, 96%, 97%, 98%, 99% or 100% identity to the *Bacillus licheniformis* subtilisin enzyme AEU12640 sequence of SEQ ID NO:13. In some embodiments, the invention includes variant enzymes of *Bacillus licheniformis* subtilisin enzyme DY_P00781, wherein the variant has at least 60%, 65%, 70%, 75%, 80%, 85%, 90%, 91%, 92%, 93%, 94%, 95%, 96%, 97%, 98%, 99% or 100% identity to the *Bacillus licheniformis* subtilisin enzyme DY_P00781 sequence of SEQ ID NO:15. In some embodiments, the invention includes variant enzymes of *Bacillus sorensis* subtilisin enzyme WP_006636716, wherein the variant has at least 60%, 65%, 70%, 75%, 80%, 85%, 90%, 91%, 92%, 93%, 94%, 95%, 96%, 97%, 98%, 99% or 100% identity to the *Bacillus sorensis* subtilisin enzyme WP_006636716 sequence of SEQ ID NO:16.

Productive Positions of AprL-Clade Enzymes

The invention provides amino acid positions in an AprL-clade enzyme, for example the AprL serine protease, which can be useful in a detergent composition where favorable modifications result in a minimum performing index for cleaning performance, stability of the enzyme in detergent compositions and thermostability of the enzyme, while having at least one of these characteristics improved from its parent AprL-clade enzyme, such as AprL of SEQ ID NO:2 in the above description. These modifications are considered suitable modifications of the invention.

The terms "thermal stability" and "thermostability" refer to AprL-clade serine proteases of the present invention that retain a specified amount of enzymatic activity after exposure to an identified temperature, often over a given period of time under conditions prevailing during the proteolytic, hydrolyzing, cleaning or other process disclosed herein, for example while exposed to altered temperatures. Altered temperatures include increased or decreased temperatures. In some embodiments, the AprL-clade protease retains at least about 50%, about 60%, about 70%, about 75%, about 80%, about 85%, about 90%, about 92%, about 95%, about 96%, about 97%, about 98%, or about 99% protease activity after exposure to altered temperatures over a given time period, e.g., at least about 60, 120, 180, 240, and 300 min.

As used herein, improved properties of an AprL-clade protease enzyme includes a variant AprL-clade protease variant enzyme with improved or enhanced wash or cleaning performance, and/or improved or enhanced stability optionally with retained wash or cleaning performance, relative to the corresponding parent AprL-clade enzyme (e.g., wild-type or naturally-occurring AprL-clade enzyme). The improved properties of a variant AprL-clade enzyme may comprise improved wash or cleaning performance and/or improved stability. In some embodiments, the invention provides variant AprL-clade enzymes of the invention that exhibit one of more of the following properties: improved hand wash performance, improved hand or manual dishwashing performance, improved automatic dishwashing performance, improved laundry performance, and/or improved stability relative to a reference parent AprL-clade enzyme (e.g., wild-type AprL enzyme, such as a wild-type AprL protease having the mature sequence of SEQ ID NO:2).

Productive positions are described as those positions within a molecule that are most useful for making combinatorial variants exhibiting an improved characteristic, where the position itself allows for at least one combinable mutation. Combinable mutations can be described as those substitutions in a molecule that can be used to make combinatorial variants. Combinable mutations are ones that improve at least one desired property of the molecule, while not significantly decreasing either: expression, activity, or stability.

Combinable mutations are ones that improve at least one desired property of the molecule, while not significantly decreasing either: expression, activity, or stability. For example, Combinable mutations in AprL-clade proteases can be determined using performance index (PI) values resulting from the assays described in Example 1: N-suc-AAPF-pNA or dimethylcasein (DMC) protease assay (activity), EMPA-116, PAS-38 microswatch assays (activity), detergent stability and thermostability assays, and protein determination (expression).

AprL-clade protease enzyme amino acid positions found to be useful positions can have different modifications that are suitable for use in a detergent composition. Modifications can include an insertion, deletion or substitution at the particular position. In one embodiment, a modification is a substitution. In other embodiments, a naturally occurring amino acid is substituted to a non-naturally occurring amino acid, wherein the parent of the AprL-Clade protease variant is a wild-type AprL-clade enzyme. In some still other embodiments, an AprL-clade variant subtilisin enzyme or an active fragment thereof comprises an amino acid modification to a parent AprL-clade subtilisin enzyme, wherein the AprL-clade variant subtilisin enzyme has improved cleaning properties compared to the parent AprL-clade subtilisin enzyme.

For each position, greater numbers of possible suitable modifications results in a higher productivity score for the position. For example, amino acid positions can have at least 60%, 40% or 15% of the modifications tested at a productive position as suitable modifications, wherein the modification meets at least one of the following suitability criteria:

a) a position wherein the minimum PI relative to the parent AprL-clade subtilisin enzyme for: 1) expression; 2) at least one protease activity assay selected from hydrolysis of N-suc-AAPF-pNA, hydrolysis of DMC, PAS-38 microswatch cleaning at pH 9 or 10, and EMPA-116 microswatch cleaning at pH 6, 8, or 10; and 3) detergent stability under stress conditions, are ≥0.9, and in addition have a PI for any one of these tests that is ≥1.0;

b) a position wherein the minimum PI relative to the parent AprL-clade subtilisin enzyme for: 1) expression; 2) at least one protease activity assay selected from hydrolysis of N-suc-AAPF-pNA, hydrolysis of DMC, PAS-38 microswatch cleaning at pH 9 or 10, and EMPA-116 microswatch cleaning at pH 6, 8, or 10; and 3) detergent stability under stress conditions, are ≥ to 0.8, and in addition have a PI for any one of these tests that is ≥1.2; or c) a position wherein the minimum PI relative to the parent AprL-clade subtilisin enzyme for: 1) expression; 2) at least one protease activity assay selected from hydrolysis of N-suc-AAPF-pNA, hydrolysis of DMC, PAS-38 microswatch cleaning at pH 9 or 10, and EMPA-116 microswatch cleaning at pH 6, 8, or 10; and 3) detergent stability under stress conditions, are ≥ to 0.5, and in addition have a PI for any one of these tests that is ≥ to 1.5.

AprL-clade enzymes positions of the present invention that have at least 60% of the modifications tested as suitable modifications include positions 12, 15, 26, 27, 43, 45, 48, 52, 55, 57, 58, 60, 77, 78, 88, 96, 97, 98, 99, 102, 116, 117, 126, 127, 129, 132, 136, 143, 144, 160, 161, 165, 171, 210, 238, 239, 241, 247, and 274, wherein the amino acid positions of the AprL-clade variant are numbered by correspondence with the amino acid sequence of AprL protease set forth in SEQ ID NO:2. Suitable modifications include 12 (K,A,C,F, G,H,L,M,N,Q,S,Y); 15 (K,A,C,E,F,H,I,M,N,R,S,T,V); 26 (V,A,C,E, H,I,M,N,Q,R,S,T); 27 (K,A,C,D,E,L,M,N,P,Q,R, T); 43 (N,A,C,F,G,H,I,K,L,M,Q,R,S,W,Y); 45 (V,A,C, D,E, F,G,I,K,M,N,P,Q,R,S,T,Y); 48 (A,C,D,E,F,H,I,K,M,N,Q,R, W,Y); 52 (A,C,D,E,F,G,H,K,L,M, N,P, Q,R,S,T,V,Y); 55 (A,C,D,E,F,G,H,I,M,N,P,Q,R,S,T,V); 57 (N,A,C,D,E,G,H,P, R,S,V,Y); 58 (T,C,D,F, H,I,K,L,M,P,R,S,V,W,Y); 60 (G,C, E,F,H,I,K,L,M,Q,R,T,Y); 77 (T,C,D,F,H,K,L,M,N,P,Q,R,S, W); 78 (T,C,D,G,I,L,N,Q,S,V,W,Y); 88 (S,A,E,F,G,L,M,N, Q,R,T,V,W,Y); 96 (N,A,C,D,E,G,H,I,K,L,M,Q,S,V, Y); 97 (S,A,C,D,F,G,H,I,K,M,N,P,Q,R,T,W,Y); 98 (S,A,D,E,F,H, K,L,N,P,R,T,V,Y); 99 (G,A,C,D,E,L, M,Q,S,T,V,W); 102 (S,A,D,E,F,G,K,L,N,P,Q,R,T); 116 (N,A,C,D,E,F,G,H,K,L, M,Q,R,S,T,V,Y); 117 (G,C,D,E,H,K,M,N,Q,R,T,V); 126 (G,A,C,E,H,I,K,M,N,Q,R,S,T,V,W,Y); 127 (G,A,D,E,F,I,L, M,Q,S,T, V,W,Y); 129 (S,C,E,F,H,I,M,N,Q,R,T,V,W,Y); 132 (T,A,C,D,E,F,H,I,K,L,M,N,P,Q,S,V,W,Y); 136 (Q,A,C, D,F,G,H,K,L,N,R,S,T,W); 143 (A,C,D,E,F,G,H,I,K,M,N,S, T,Y); 144 (R,A,C,D,E,F,G,H,I,L,M, N,Q,V,Y); 160 (N,A,C, D,G,I,K,M,P,R); 161 (T,A,C,D,E,I,K,L,M,Q,R,W); 165 (G,A,E,I,K,L,P,Q,R, S, T,Y); 171 (D,A,C,G,H,I,K,N,P,Q,S, T,V); 210 (T,C,D,E,F,H,I,M,N,P,V,Y); 238 (P,A,C,D,E,F,G, I,L,M, N,Q,R, S,T,W); 239 (N,A,C,D,E,H,I,K,L,M,S,T,V, Y); 241 (S,C,D,E,H,L,N,P,Q,T,V); 247 (N,A,D,E,F, H,I,L, M,Q,S,V,W,Y); and 274 (Q,A,C,D,E,F,G,H,I,L,N,S,T,V,W), wherein the amino acid positions of the AprL-clade variant are numbered by correspondence with the amino acid sequence of the AprL protease set forth in SEQ ID NO:2.

AprL-clade enzymes positions of the present invention that have at least 40% but <60% of the modifications tested as suitable modifications include positions 1, 9, 22, 24, 25, 53, 86, 89, 95, 100, 105, 108, 114, 115, 119, 125, 128, 140, 146, 155, 158, 187, 202, 203, 234, 237, 240, 243, 244, and 264, wherein the amino acid positions of the AprL-clade variant are numbered by correspondence with the amino acid sequence of the AprL protease set forth in SEQ ID NO:2. Suitable modifications include 1 (A,D,E,F,G,N,Q,S, T,V); 9 (P,A,C,D,E,G,N,Q,S,T); 22 (K,A,F,M,Q,R,S,T,VY); 24 (A,C,D,E,G,N,Q,S, W); 25 (N,D,E,F,G,H,L,M,P,Q,R,S); 53 (G,C,D,E,H,K,N,Q,R); 86 (S,C,E,H,K, L,N,R); 89 (L,A, C,F,G,I, M,N,S,V); 95 (L,A,F,G,I,M,Q,S,V); 100 (S,C,F,G, M,N,R,T,Y); 105 (G,A,C, D,I,M,N,R,S,T); 108 (S,E, F,G, H,K,L,N,Q,R,Y); 114 (T,A,C,D,F,I,K,L,N,Q,S,V); 115 (T,D,E,F,H,I,K, Q,S,W); 119 (D,A,E,F,G,H, M,Q,S); 125 (L,A,E,F,I,N,S,V,Y); 128 (A,C,D,E,H,K,N,P,Q,R,S,T); 140 (N,C,D,F,G,H,M,R,T,V); 146 (V,A,E,H,I,K,L,N,Q,S,T); 155 (S,A,D,E,F,G,H,K,N,Q,R,W); 158 (S,A,D, E,I,K,N,Q, R); 187 (S,A,C, D, E,H,K,P,Q,W); 202 (A,C,D,E,I,K,L,M, Q,S,T,V); 203 (G,A,C,E,H,K,M,N, Q,R,S); 234 (L,E,F,H,Q, S, W,Y); 237 (H,A,C,D,G,I,M,N,Q,S); 240 (L,A,D,E,F,I,M, N,Q,T); 243 (S,C,E, F,I,N,Q,T,V,W); 244 (Q, A,C,D,E,G,H, I,N,R,S,V); and 264 (K,A,C,D,H,M,Q,R,S,Y), wherein the amino acid positions of the AprL-clade variant are numbered by correspondence with the amino acid sequence of the AprL protease set forth in SEQ ID NO:2.

AprL-clade enzymes positions of the present invention that have at least 15% but <40% of the modifications tested as suitable modifications include positions 2, 3, 10, 18, 19, 28, 29, 31, 35, 37, 38, 40, 44, 46, 50, 54, 56, 61, 67, 68, 71, 87, 90, 91, 92, 101, 103, 104, 113, 118, 120, 123, 130, 131, 133, 139, 145, 147, 148, 181, 182, 184, 193, 205, 211, 212, 214, 216, 217, 221, 235, 242, 245, 248, 251, 258, 259, and 268, wherein the amino acid positions of the AprL-clade variant are numbered by correspondence with the amino acid sequence of the AprL protease set forth in SEQ ID NO:2. Suitable modifications include 2 (Q,A,I,N); 3 (T,E,I, Q,V); 10 (L,F,M,Q); 18 (A,C,D,E,S); 19 (Q,A,D,E,G,M); 28 (V,A,C,S); 29 (A,C,S,T,V); 31 (L,C,I,V); 35 (I,A,C,G,M,S, T,V); 37 (A,E,G,S); 38 (S,A,C,E,G,N,T); 40 (P,A,C,D,E,M, V); 44 (V,C,E,P,S,T); 46 (G,A,C,D,W); 50 (F,H,K,M,Q,R, V,Y); 54 (E,Q,R,T); 56 (Y,C,E, F,H,P); 61 (N, A,D,F,H,K, Q); 67 (V,M,N,Q); 68 (A,C,G,N,S,T); 71 (V,A,G,L,S); 87 (V,C,G,S,T); 90 (Y,A,C,F,H,N, V); 91 (A,G,M,P,V); 92 (V,A,C,I,T); 101 (G,A,C,N,S,T); 103 (Y,A,F,I,L,M,V,W); 104 (S,A, D,E); 113 (A,C,G,S); 118 (M,F,H,P,Q); 120 (V,A, C,I,S,T); 123 (M,C,I,L,N,Q,S); 130 (G,D,E,H,S); 131 (S,D, R,T); 133 (A,G,M,P,S,T,V); 139 (D,G,K,N,S,T); 145 (G,D, N,S); 147 (V,A,L,M,N); 148 (V,A,C,F, M,Q,S); 181 (S,A, C,D,H,Q); 182 (N,C,D,E,Q); 184 (N,C,E,H,M,Q); 193 (A,D,P,Q,R); 205 (Y,C,E,F,I, M,V); 211 (N,C,E,S); 212 (T,A,D,S); 214 (A,E,H,L,T); 216 (L,A,C,H,K,M); 217 (N,C, E,S); 221 (M,C, H,K); 235 (S,C,D,E,G); 242 (A,E,G,N,S); 245 (V,A,C,I,T); 248 (R,A,N,Q,S); 251 (S,A,C,E,G,N); 258 (S,C,D,E,H, P); 259 (S,E,P,Q); and 268 (N,D,E,Q), wherein the amino acid positions of the AprL-clade variant are numbered by correspondence with the amino acid sequence of the AprL protease set forth in SEQ ID NO:2. For each of the above sets of mutations, the first listed substitution represents the native amino acid for AprL (SEQ ID NO:2). In some embodiments of the invention, the variant is an AprL-clade variant, wherein the mutation is any of those in the above listed sets, exclusive of the first listed substitution.

AprL-clade enzymes positions of the present invention that have at least one modification but <15% of the modifications tested as suitable modifications include positions 4, 17, 21, 30, 33, 36, 47, 49, 51, 62, 66, 72, 74, 75, 76, 93, 106, 107, 110, 111, 112, 121, 134, 135, 137, 138, 141, 149, 151, 156, 157, 159, 163, 169, 175, 183, 186, 188, 191, 204, 207, 208, 209, 215, 223, 224, 227, 229, 230, 231, 232, 233, 236, 249, 250, 254, 255, 260, 267, 269, 271, and 273, wherein the amino acid positions of the AprL-clade variant are numbered by correspondence with the amino acid sequence of the AprL protease set forth in SEQ ID NO:2. Suitable modifications include 4 (V,I); 17 (Q,H,M); 21 (F,Y); 30 (V,C,T); 33 (T,C,M); 36 (Q,E,H); 47 (G,A,M); 49 (S,I,T); 51 (V,C,I); 62 (G,S); 66 (H,R); 72 (A,G,S); 74 (L,G); 75 (D,C,E); 76 (N,K); 93 (K,D); 106 (I,G,M); 107 (V,F,I); 110 (I,F); 111 (E,D,Q); 112 (W,A); 121 (I,L,M); 134 (M, L); 135 (K,E,H); 137 (A,S); 138 (V,C,S); 141 (A,S); 149 (V,C); 151 (A,G,P); 156 (G,E); 157 (S,D, R); 159 (G,A,F); 163 (T,E); 169 (K,R); 175 (A,C); 183 (S,A,G); 186 (A,C); 188 (F,W); 191 (V,C); 204 (V,I); 207 (T,C); 208 (Y,F); 209 (P,S); 215 (T,C,V); 223 (S,A,C); 224 (P,A); 227 (A,S); 229 (A,G, S); 230 (A, G); 231 (A,C); 232 (L,Q); 233 (I,V); 236 (K,A); 249 (L,I,M); 250 (S,A,G); 254 (T, D); 255 (Y,C,E); 260 (F,C,W); 267 (I,C); 269 (V,A,C); 271 (A,D,E); and 273 (A,S), wherein the amino acid positions of the AprL-clade variant are numbered by correspondence with the amino acid sequence of the AprL protease set forth in SEQ ID NO:2.

In some embodiments, an AprL-clade variant subtilisin enzyme or an active fragment thereof has one or more amino acid modifications to a parent AprL-clade subtilisin enzyme, wherein the modification is at a productive position of the AprL-clade variant subtilisin enzyme selected from the group consisting of A001C, A001D, A024E, A024G, A048C, A048D, A048K, A048N, A052F, A052M, A052V, A052Y, A055C, A072G, A091G, A113C, A128P, A128Q, A133G, A133S, A133T, A143E, A143F, A143H, A143N, A143S, A143W, A193D, A202C, A202D, A202E, A202Q, A227S, D119F, D119S, D119Y, G053C, G053E, G053N, G053Q, G060L, G060Y, G099A, G099T, G101A, G117D, G117V, G127A, G127S, G127T, G130D, G203A, G203C, G203E, G203M, H237I, I035A, I035C, I035M, I035T, I121L, K012N, K015M, K027C, K027L, K027M, K027R, K264A, K264S, L010M, L095F, L125V, L234Q, L240N, L249I, M123C, M123I, M123L, N025F, N025G, N025L, N025 S, N057C, N061A, N076G, N096D, N096G, N116A, N116C, N116L, N116Y, N140A, N160C, N182C, N182D, N184C, N211S, N247F, N247H, N247I, N247L, N247Q, N247S, N247V, N247W, N247Y, P009E, P009T, P238A, P238C, P238D, P238F, P238I, P238R, Q017H, Q136A, Q136C, Q136F, Q136H, Q136K, Q136L, R144F, R144L, R248K, S086R, S088N, S088Y, S097G, S097H, S097Y, S098H, S098L, S100L, S102D, S102E, S102G, S102K, S129E, S129H, S155A, S155D, S155E, S155H, S157D, S158I, S158Q, S181A, S181Q, S183G, S241R, S241T, S243I, S243N, S243T, S243V, S243Y, S251E, S258C, S258D, S258P, T058C, T058D, T058F, T058I, T077C, T077F, T077L, T077M, T078Q, T132A, T132Q, T132V, T132Y, T161Q, T210I, T215C, V026Q, V026R, V026T, V028A, V028C, V045I, V071A, V071L, V120A, V120C, V120I, V146A, V146H, V146K, V147L, V149C, Y056H, and Y255C, wherein the amino acid positions of the AprL-clade subtilisin variant are numbered by correspondence with the amino acid sequence of the AprL protease set forth in SEQ ID NO:2. In some embodiments, the above list has improved ADW cleaning. In other embodiments, the improved ADW cleaning is (i) an ADW cleaning PI>1.1, or (ii) an ADW cleaning PI>1.1 and one or more of an HDL pH 6 cleaning PI>0.8, an HDL pH 8 cleaning PI>0.8, an HDD cleaning PI>0.8, an expression PI>0.8, or a stability PI>0.8.

In some embodiments, an AprL-clade variant subtilisin enzyme or an active fragment thereof has one or more amino acid modifications to a parent AprL-clade subtilisin enzyme, wherein the modification is at a productive position of the AprL-clade variant subtilisin enzyme selected from the group consisting of A029T, A048K, A048R, A052F, A052R, A068G, A113C, D119H, E111Q, G099A, G099S, G127A, G127T, G165A, K012G, K012H, K027C, K027E, K027M, L095F, L125I, L125V, L240Q, N025F, N025G, N025L, N043R, N116R, N140R, N160C, N184C, N239K, P238C, P238I, P238M, Q136F, Q136H, Q136K, Q136R, Q136W, S098F, S098H, S104A, S158Q, S241R, V045R, and Y103M, wherein the amino acid positions of the AprL-clade subtilisin variant are numbered by correspondence with the amino acid sequence of the AprL protease set forth in SEQ ID NO:2. In some embodiments, the above list has improved HDD cleaning when compared to the parent AprL-clade subtilisin enzyme. In other embodiments, the improved HDD cleaning is (i) an HDD cleaning PI>1.1, or (ii) an HDD cleaning PI>1.1 and one or more of an HDL pH 6 cleaning PI>0.8, an HDL pH 8 cleaning PI>0.8, an ADW cleaning PI>0.8, an expression PI>0.8, or a stability PI>0.8.

In some embodiments, an AprL-clade variant subtilisin enzyme or an active fragment thereof has one or more amino acid modifications to a parent AprL-clade subtilisin enzyme, wherein the modification is at a productive position of the AprL-clade variant subtilisin enzyme selected from the group consisting of A001C, A048R, A052F, G099S, G099T, G101A, G127F, G127I, G127M, G127Q, G127T, G127V, I121M, L010M, L095A, L095F, L095Q, L095S, L125I, L125V, M123C, M123I, N025F, N025S, N116C, N140R, N184C, P238C, P238D, P238I, P238M, P238N, Q136A, S098F, S098H, S102D, S158Q, S241R, T077C, T077F, T215C, V026I, V026Q, V045R, and V149C, wherein the amino acid positions of the AprL-clade subtilisin variant are numbered by correspondence with the amino acid sequence of the AprL protease set forth in SEQ ID NO:2. In some embodiments, the above list has improved HDL cleaning at pH 8 when compared to the parent AprL-clade subtilisin enzyme. In other embodiments, the improved HDL cleaning at pH 8 is (i) an HDL pH 8 cleaning PI>1.1, or (ii) an HDL pH 8 cleaning PI>1.1 and one or more of an HDD cleaning PI>0.8, an HDL pH 6 cleaning PI>0.8, an ADW cleaning PI>0.8, an expression PI>0.8, or a stability PI>0.8.

In some embodiments, an AprL-clade variant subtilisin enzyme or an active fragment thereof has one or more amino acid modifications to a parent AprL-clade subtilisin enzyme, wherein the modification is at a productive position of the AprL-clade variant subtilisin enzyme selected from the group consisting of A001C, A024E, A128D, G053C, G099T, G101A, G101N, G165E, G203C, L095Q, L095 S, L125S, N061E, N116C, N184C, S098D, S102D, S102E, S104D, S129E, S155D, S158E, and V026T, wherein the amino acid positions of the AprL-clade subtilisin variant are numbered by correspondence with the amino acid sequence of the AprL protease set forth in SEQ ID NO:2. In some embodiments, the above list has improved HDL cleaning at pH 6 when compared to the parent AprL-clade subtilisin enzyme. In other embodiments, the improved HDL cleaning at pH 6 is (i) an HDL pH 6 cleaning PI>1.1, or (ii) an HDL pH 6 cleaning PI>1.1 and one or more of an HDD Cleaning PI>0.8, an HDL pH 8 cleaning PI>0.8, an ADW cleaning PI>0.8, an expression PI>0.8, or a stability PI>0.8.

In some embodiments, an AprL-clade variant subtilisin enzyme or an active fragment thereof has one or more amino acid modifications to a parent AprL-clade subtilisin enzyme, wherein the modification is at a productive position of the AprL-clade variant subtilisin enzyme selected from the group consisting of A001C, A001D, A001E, A001Q, A001S, L010M, L010Q, S100G, S102K, S102R, Y103F, Y103M, S104D, G105M, G105R, S108F, S108H, S108K, S108R, E111Q, T114D, T115D, T115E, T115F, T115K, T115Q, N116E, K012C, K012F, K012H, K012M, K012N, K012Q, K012Y, V120S, M123C, M123I, L125I, G127A, G127D, G127I, G127M, G127S, G127T, G127V, A128E, A128H, A128K, A128P, A128R, A128S, A128T, S129H, S129Q, S129R, S129T, S129V, T132C, T132D, T132E, T132K, T132N, T132P, Q136A, Q136C, Q136K, Q136R, V138C, A143D, A143N, G145S, V147L, V148A, V148C, V148M, V148Q, K015A, K015C, K015E, K015I, K015M, K015S, K015T, K015V, S155D, S155F, S155K, S155N, S155R, S157D, S158D, S158I, S158K, S158R, N160C, N160D, N160I, N160M, N160R, T161C, T161D, T161E, T161K, T161Q, T161R, G165A, G165E, G165Q, G165R, G165S, Q017H, A018D, A018E, S181Q, N182D, S183A, S183G, N184C, N184E, N184Q, A186C, S187D, S187E, S187P, Q019D, Q019E, A193D, A193R, A202D, A202E, A202K, A202Q, A202V, G203A, G203C, G203E, G203N, G203Q, Y205E, T210C, T210E, T210I, T210P, T210V, A214E, T215C, L216C, L216H, L216K, L216M, N217S, L234E, L234F, L234Q, L234S, S235D, S235E, P238T, N239A, N239D, N239H, N239M, N239S, N239T, A024E, A024Q, L240D, S241E, S241N, S241Q, S241V, A242G, A242N, S243E, S243Q, S243V, Q244C, Q244E, V245A, V245C, V245T, N247D, N247W, N025D, N025G, N025Q, S250G, S251E, S258C, S258D, S258E, S258H, S258P, S259E, S259P, S259Q, V026A, V026C, V026E, V026H, V026Q, V026R, F260W, K264A, K264C, K264D, K264H, K264M, K264Q, K264S, K264Y, I267C, N268D, N268E, N268Q, V269C, K027C, K027D, K027E, K027M, K027P, A271E, Q274A, Q274C, Q274D, Q274E, Q274G, A029S, T003E, T003I, T003Q, T003V, V030C, I035A, I035S, I035T, I035V, S038T, N043A, N043C, N043F, N043H, N043Q, V044P, V045A, V045C, V045D, V045E, V045F, V045G, V045M, V045N, V045Q, V045R, V045S, V045T, G046D, A048N, A048W, F050H, V051I, A052F, A052G, A052K, A052N, A052P, A052R, A052V, G053N, G053R, A055C, A055D, A055E, A055G, A055H, A055N, A055S, A055V, N057C, N057E, N057G, N057V, T058C, T058I, T058K, T058W, A068C, A068N, A068S, V071A, L074G, D075E, N076K, T077C, T077D, T077H, T077M, T077N, T077P, T077Q, T077S, T078D, T078I, T078V, S086E, S086H, S086R, V087C, V087G, V087S, V087T, S088E, S088N, S088R, L089N, P009C, P009D, P009E, P009N, P009T, L095A, L095V, N096S, S098K, S098R, and G099Q, wherein the amino acid positions of the AprL-clade subtilisin variant are numbered by correspondence with the amino acid sequence of the AprL protease set forth in SEQ ID NO:2. In some embodiments, the above list has improved stability when compared to the parent AprL-clade subtilisin enzyme. In other embodiments, the improved stability is (i) a stability PI>1.2, or (ii) a stability PI>1.2 and one or more of an HDD cleaning PI>0.8, an HDL pH 6 or pH 8 cleaning PI>0.8, an ADW cleaning PI>0.8, or an expression PI>0.8.

In still further embodiments, the stability PI is measured in accordance with a stability assay of Example 1, HDD Cleaning PI is measured in accordance with an HDD cleaning assay of Example 1, HDL cleaning PI is measured in accordance with an HDL cleaning assay of Example 1, ADW Cleaning PI is measured in accordance with an ADW cleaning assay of Example 1, and/or expression PI is measured in accordance with a protein determination assay of Example 1.

In some embodiments, an AprL-clade variant subtilisin enzyme or an active fragment thereof has one or more amino acid modifications to a parent AprL-clade subtilisin enzyme, wherein the modification is at a productive position of the AprL-clade variant subtilisin enzyme selected from the group consisting of P009E, S038G, V045R, A052V, T077Q, A091G, S098R, M123I, T132N, T132S, A133S, Q136A, Q136S, G145S, N160R, G165Q, P238R, N239K, A242N, S243Q, S243T, S258E, and Q274F, wherein the amino acid positions of the AprL-clade subtilisin variant are numbered by correspondence with the amino acid sequence of the AprL protease set forth in SEQ ID NO:2. In some embodiments, the above list has improved soil removal compared to the parent AprL-clade subtilisin enzyme. In other embodiments, an AprL-clade variant subtilisin enzyme or an active fragment thereof has one or more amino acid modifications to a parent AprL-clade subtilisin enzyme, wherein the modification is at a productive position of the AprL-clade variant subtilisin enzyme selected from the group consisting of P009E, V045R, A052V, T077Q, S098R, M123I, T132N, Q136A, G145S, N160R, G165Q, A242N, S243Q, and S258E, wherein the amino acid positions of the AprL-clade subtilisin variant are numbered by correspondence with the amino acid sequence of the AprL protease set forth in SEQ ID NO:2. In some embodiments, the above list has improved soil removal compared to the parent AprL-clade subtilisin enzyme.

Polypeptides of the Invention

The present invention provides novel polypeptides, which may be collectively referred to as "polypeptides of the invention." Polypeptides of the invention include isolated, recombinant, substantially pure, or non-naturally occurring variant and newly discovered AprL-clade enzyme polypeptides, including for example, variant AprL-clade enzyme polypeptides having enzymatic activity (e.g., protease activity). In some embodiments, polypeptides of the invention are useful in cleaning applications and can be incorporated into cleaning compositions that are useful in methods of cleaning an item or a surface (e.g. surface of an item) in need of cleaning.

In some embodiments, the AprL-clade enzyme variant can be a variant of a parent AprL-clade enzyme from the Genus *Bacillus*. Various AprL-clade enzymes have been found in the genus *Bacillus* that have a high identity to each other and to the AprL mature enzyme from AprL as shown in SEQ ID NO:2. See, for example, Tables 8 and 9, and FIG. 2 in Example 4, FIG. 3 in Example 6, and FIG. 9 in Example 12. In various embodiments, the AprL-clade enzyme variant can be a variant of a parent AprL-clade enzyme from any of the species described in Table 8 or 9, or FIG. 2, 3, or 9.

Figure 9:
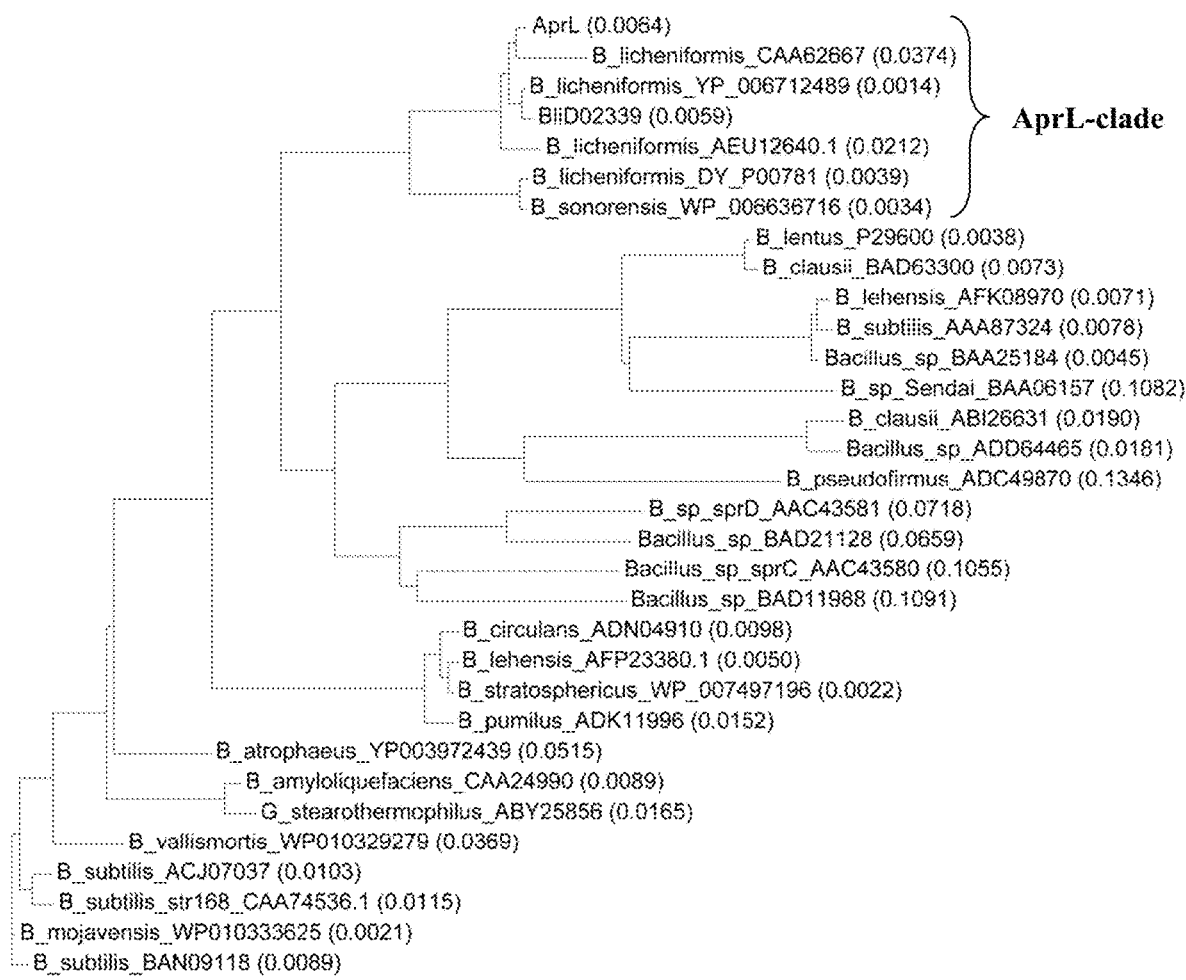
FIG. 9 shows the phylogenetic tree of subtilisins uncluding AprL, BliD02339 and other members of the AprL-clade.

In some embodiments, the AprL-clade enzyme variant can be a variant having 50, 60, 70, 80, 90, 95, 96, 97, 98, 99 or 100% identity to an AprL-clade enzyme described in Table 8 or 9, or FIG. 2, 3, or 9; for example, the AprL protease of SEQ ID NO:2 or SEQ ID NO:9.

Described are compositions and methods relating to AprL-clade enzymes. The compositions and methods are based, in part, on the observation that cloned and expressed AprL has proteolytic activity in the presence of a detergent composition. AprL also demonstrates excellent stability in detergent compositions. These features of AprL makes it well suited for use in a variety of cleaning applications, where the enzyme can hydrolyze proteins in the presence of surfactants and other components found in detergent compositions.

In one aspect, the present compositions and methods provide a variant AprL-clade polypeptide. The mature AprL-clade polypeptide has the amino acid sequence of SEQ ID NO:2. Similar, substantially identical AprL-clade polypeptides may occur in nature, e.g., in other strains or isolates. These and other recombinant AprL-clade polypeptides are encompassed by the present compositions and methods.

In some embodiments, the invention includes an isolated, recombinant, substantially pure, or non-naturally occurring variant AprL-clade enzyme having protease activity, which polypeptide comprises a polypeptide sequence having at least about 60%, at least about 65%, at least about 70%, at least about 75%, at least about 80%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, at least about 99.5%, or 100% sequence identity to a parent AprL-clade enzyme as provided herein.

In some embodiments, the variant polypeptide is a variant having a specified degree of amino acid sequence homology to the exemplified AprL-clade polypeptide, e.g., at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or even at least 99% sequence homology to the amino acid sequence of SEQ ID NO:2. Homology can be determined by amino acid sequence alignment, e.g., using a program such as BLAST, ALIGN, or CLUSTAL, as described herein.

Also provided is an isolated, recombinant, substantially pure, or non-naturally occurring sequence which encodes a variant AprL-clade enzyme having protease activity, said variant AprL-clade enzyme (e.g., variant AprL) comprising an amino acid sequence which differs from the amino acid sequence of SEQ ID NO:2 by no more than 50, no more than 40, no more than 30, no more than 35, no more than 25, no more than 20, no more than 19, no more than 18, no more than 17, no more than 16, no more than 15, no more than 14, no more than 13, no more than 12, no more than 11, no more than 10, no more than 9, no more than 8, no more than 7, no more than 6, no more than 5, no more than 4, no more than 3, no more than 2, or no more than 1 amino acid residue(s), wherein amino acid positions of the variant AprL-clade enzyme are numbered according to the numbering of corresponding amino acid positions in the amino acid sequence of AprL shown in SEQ ID NO:2 as determined by alignment of the variant AprL-clade enzyme amino acid sequence with the AprL amino acid sequence.

As noted above, the variant AprL-clade enzyme polypeptides of the invention have enzymatic activities (e.g., proteolytic activities) and thus are useful in cleaning applications, including but not limited to, methods for cleaning dishware items, tableware items, fabrics, and items having hard surfaces (e.g., the hard surface of a table, table top, wall, furniture item, floor, ceiling, etc.). Exemplary cleaning compositions comprising one or more variant AprL-clade enzyme polypeptides of the invention are described infra. The enzymatic activity (e.g., AprL-clade enzyme activity) of a variant AprL-clade enzyme polypeptide of the invention can be determined readily using procedures well known to those of ordinary skill in the art. The Examples presented infra describe methods for evaluating the enzymatic activity, cleaning performance, detergent stability and/or thermostability. The performance of variant AprL-clade enzymes of the invention in removing stains (e.g., a protein stain), cleaning hard surfaces, or cleaning laundry, dishware or tableware item(s) can be readily determined using procedures well known in the art and/or by using procedures set forth in the Examples.

A polypeptide of the invention can be subject to various changes, such as one or more amino acid insertions, deletions, and/or substitutions, either conservative or non-conservative, including where such changes do not substantially alter the enzymatic activity of the polypeptide. Similarly, a nucleic acid of the invention can also be subject to various changes, such as one or more substitutions of one or more nucleic acids in one or more codons such that a particular codon encodes the same or a different amino acid, resulting in either a silent variation (e.g., mutation in a nucleotide sequence results in a silent mutation in the amino acid sequence, for example when the encoded amino acid is not altered by the nucleic acid mutation) or non-silent variation, one or more deletions of one or more nucleic acids (or codons) in the sequence, one or more additions or insertions of one or more nucleic acids (or codons) in the sequence, and/or cleavage of or one or more truncations of one or more nucleic acids (or codons) in the sequence. Many such changes in the nucleic acid sequence may not substantially alter the enzymatic activity of the resulting encoded variant AprL-clade enzyme compared to the variant AprL-clade enzyme encoded by the original nucleic acid sequence. A nucleic acid of the invention can also be modified to include one or more codons that provide for optimum expression in an expression system (e.g., bacterial expression system), while, if desired, said one or more codons still encode the same amino acid(s).

In some embodiments, the present invention provides a genus of polypeptides comprising variant AprL-clade enzyme polypeptides having the desired enzymatic activity (e.g., AprL-clade enzyme activity or cleaning performance activity) which comprise sequences having the amino acid substitutions described herein and also which comprise one or more additional amino acid substitutions, such as conservative and non-conservative substitutions, wherein the polypeptide exhibits, maintains, or approximately maintains the desired enzymatic activity (e.g., AprL-clade enzyme activity or proteolytic activity, as reflected in the cleaning activity or performance of the variant AprL-clade enzyme). Amino acid substitutions in accordance with the invention may include, but are not limited to, one or more non-conservative substitutions and/or one or more conservative amino acid substitutions. A conservative amino acid residue substitution typically involves exchanging a member within one functional class of amino acid residues for a residue that belongs to the same functional class (identical amino acid residues are considered functionally homologous or conserved in calculating percent functional homology). A conservative amino acid substitution typically involves the substitution of an amino acid in an amino acid sequence with a functionally similar amino acid. For example, alanine, glycine, serine, and threonine are functionally similar and thus may serve as conservative amino acid substitutions for one another. Aspartic acid and glutamic acid may serve as conservative substitutions for one another. Asparagine and glutamine may serve as conservative substitutions for one another. Arginine, lysine, and histidine may serve as conservative substitutions for one another. Isoleucine, leucine, methionine, and valine may serve as conservative substitutions for one another. Phenylalanine, tyrosine, and tryptophan may serve as conservative substitutions for one another.

Other conservative amino acid substitution groups can be envisioned. For example, amino acids can be grouped by similar function or chemical structure or composition (e.g., acidic, basic, aliphatic, aromatic, sulfur-containing). For instance, an aliphatic grouping may comprise: Glycine (G), Alanine (A), Valine (V), Leucine (L), Isoleucine (I). Other groups containing amino acids that are considered conservative substitutions for one another include: aromatic: Phenylalanine (F), Tyrosine (Y), Tryptophan (W); sulfur-containing: Methionine (M), Cysteine (C); Basic: Arginine (R), Lysine (K), Histidine (H); Acidic: Aspartic acid (D), Glutamic acid (E); non-polar uncharged residues, Cysteine (C), Methionine (M), and Proline (P); hydrophilic uncharged residues: Serine (S), Threonine (T), Asparagine (N), and Glutamine (Q). Additional groupings of amino acids are well-known to those of skill in the art and described in various standard textbooks. Listing of a polypeptide sequence herein, in conjunction with the above substitution groups, provides an express listing of all conservatively substituted polypeptide sequences.

More conservative substitutions exist within the amino acid residue classes described above, which also or alternatively can be suitable. Conservation groups for substitutions that are more conservative include: valine-leucine-isoleucine, phenylalanine-tyrosine, lysine-arginine, alanine-valine, and asparagine-glutamine.

Conservatively substituted variations of a polypeptide sequence of the invention (e.g., variant proteases of the invention) include substitutions of a small percentage, sometimes less than 25%, 20%, 15%, 14%, 13%, 12%, 11%, 10%, 9%, 8%, 7%, or 6% of the amino acids of the polypeptide sequence, or less than 5%, 4%, 3%, 2%, or 1%, or less than 10, 9, 8, 7, 6, 5, 4, 3, 2, or 1 amino acid substitution of the amino acids of the polypeptide sequence, with a conservatively selected amino acid of the same conservative substitution group.

As described elsewhere herein in greater detail and in the Examples provided herein, polypeptides of the invention may have cleaning abilities that may be compared to known proteases, including known serine proteases. In some embodiments, the protease variant comprises one or more mutations, and having a total net charge of −5, −4, −3, −2, −1, 0, 1, 2, 3, 4, or 5 relative to AprL (SEQ ID NO:2). In some embodiments, the invention provides an isolated, recombinant, substantially pure, or non-naturally occurring variant protease (e.g., variant AprL) having proteolytic activity, said variant protease comprising an amino acid sequence which differs from the amino acid sequence shown in SEQ ID NO:2, 9, 12, 13, 14, 15, or 16 by no more than 50, no more than 45, no more than 40, no more than 35, no more than 30, no more than 25, no more than 20, no more than 19, no more than 18, no more than 17, no more than 16, no more than 15, no more than 14, no more than 13, no more than 12, no more than 11, no more than 10, no more than 9, or no more than 8 amino acid residues, wherein amino acid positions are numbered according to the numbering of corresponding amino acid positions in the amino acid sequence of the AprL protease shown in SEQ ID NO:2, as determined by alignment of the variant protease amino acid sequence with the AprL amino acid sequence.

Nucleic Acids of the Invention

The invention provides isolated, non-naturally occurring, or recombinant nucleic acids (also referred to herein as "polynucleotides"), which may be collectively referred to as "nucleic acids of the invention" or "polynucleotides of the invention", which encode polypeptides of the invention. Nucleic acids of the invention, including all described below, are useful in recombinant production (e.g., expression) of polypeptides of the invention, typically through expression of a plasmid expression vector comprising a sequence encoding the polypeptide of interest or fragment thereof. As discussed above, polypeptides include variant protease polypeptides, including variant AprL-clade polypeptides having enzymatic activity (e.g., proteolytic activity) which are useful in cleaning applications and cleaning compositions for cleaning an item or a surface (e.g., surface of an item) in need of cleaning.

In some embodiments, the invention provides an isolated, recombinant, substantially pure, or non-naturally occurring nucleic acid comprising a nucleotide sequence encoding any polypeptide (including any fusion protein, etc.) of the invention described above in the section entitled "Polypeptides of the Invention" and elsewhere herein. The invention also provides an isolated, recombinant, substantially pure, or non-naturally-occurring nucleic acid comprising a nucleotide sequence encoding a combination of two or more of any polypeptides of the invention described above and elsewhere herein.

In some embodiments, the invention includes a polynucleotide encoding an isolated, recombinant, substantially pure, or non-naturally occurring variant AprL-clade enzyme having protease activity, which polynucleotide comprises a polynucleotide sequence having at least about 60%, at least about 65%, at least about 70%, at least about 75%, at least about 80%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, at least about 99.5%, or 100% sequence identity to a parent AprL-clade enzyme nucleotide sequence as provided herein.

Other embodiments are directed to a polynucleotide comprising a nucleic acid sequence: (i) encoding an amino acid sequence having at least 99% identity to SEQ ID NO:9; (ii) encoding an amino acid sequence of SEQ ID NO:9; (iii) encoding an amino acid sequence of SEQ ID NO: 45, 46, 47, 48, 49, 50, 51, or 52 and further encoding an amino acid sequence having at least 99% identity to SEQ ID NO:9; (iv) encoding an amino acid sequence of SEQ ID NO: 45, 46, 47, 48, 49, 50, 51, or 52 and further encoding an amino acid sequence of SEQ ID NO:9; (v) having at least 99% identity to SEQ ID NO:1 or SEQ ID NO:7; and (vi) having complementarity to SEQ ID NO:1 or SEQ ID NO:7.

In some embodiments, the invention includes a polynucleotide encoding an isolated, recombinant, substantially pure, or non-naturally occurring variant AprL-clade enzyme having protease activity, which polypeptide comprises a polypeptide sequence having at least about 60%, at least about 65%, at least about 70%, at least about 75%, at least about 80%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, at least about 99.5%, or 100% sequence identity to a parent AprL-clade enzyme polypeptide sequence as provided herein.

In some embodiments, the variant polypeptide is a variant having a specified degree of amino acid sequence homology to the exemplified AprL-clade polypeptide, e.g., at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or even at least 99% sequence homology to the amino acid sequence of SEQ ID NO: 2, 9, 12, 13, 14, 15, or 16. Homology can be determined by amino acid sequence alignment, e.g., using a program such as BLAST, ALIGN, or CLUSTAL, as described herein.

Also provided is an isolated, recombinant, substantially pure, or non-naturally occurring nucleic acid comprising a polynucleotide sequence which encodes a variant protease having proteolytic activity, said variant protease (e.g., variant AprL) comprising an amino acid sequence which differs from the amino acid sequence of SEQ ID NO:2, 9, 12, 13, 14, 15, or 16 by no more than 50, no more than 40, no more than 30, no more than 35, no more than 25, no more than 20, no more than 19, no more than 18, no more than 17, no more than 16, no more than 15, no more than 14, no more than 13, no more than 12, no more than 11, no more than 10, no more than 9, no more than 8, no more than 7, no more than 6, no more than 5, no more than 4, no more than 3, no more than 2, or no more than 1 amino acid residue(s), wherein amino acid positions of the variant AprL-clade enzyme are numbered according to the numbering of corresponding amino acid positions in the amino acid sequence of AprL shown in SEQ ID NO:2 as determined by alignment of the variant protease amino acid sequence with the AprL amino acid sequence.

The present invention provides nucleic acids encoding an AprL-clade variant, such as the AprL protease set forth in the amino acid sequence off SEQ ID NO:2, wherein the AprL-clade variant is a mature form having proteolytic activity and comprises an amino acid sequence comprising a combination of amino acid substitutions as listed throughout the specification, wherein the amino acid positions of the AprL-clade variant are numbered by correspondence with the amino acid sequence of the AprL protease set forth in SEQ ID NO:2.

Nucleic acids of the invention can be generated by using any suitable synthesis, manipulation, and/or isolation techniques, or combinations thereof. For example, a polynucleotide of the invention may be produced using standard nucleic acid synthesis techniques, such as solid-phase synthesis techniques that are well-known to those skilled in the art. In such techniques, fragments of up to 50 or more nucleotide bases are typically synthesized, then joined (e.g., by enzymatic or chemical ligation methods, or polymerase mediated recombination methods) to form essentially any desired continuous nucleic acid sequence. The synthesis of the nucleic acids of the invention can be also facilitated (or alternatively accomplished) by any suitable method known in the art, including but not limited to chemical synthesis using the classical phosphoramidite method (See e.g., Beaucage et al. Tetrahedron Letters 22:1859-69 [1981]); or the method described by Matthes et al. (See, Matthes et al., EMBO J. 3:801-805 [1984], as is typically practiced in automated synthetic methods. Nucleic acids of the invention also can be produced by using an automatic DNA synthesizer. Customized nucleic acids can be ordered from a variety of commercial sources (e.g., The Midland Certified Reagent Company, the Great American Gene Company, Operon Technologies Inc., and DNA2.0). Other techniques for synthesizing nucleic acids and related principles are known in the art (See e.g., Itakura et al., Ann. Rev. Biochem. 53:323 [1984]; and Itakura et al., Science 198:1056 [1984]).

As indicated above, recombinant DNA techniques useful in modification of nucleic acids are well known in the art. For example, techniques such as restriction endonuclease digestion, ligation, reverse transcription and cDNA production, and polymerase chain reaction (e.g., PCR) are known and readily employed by those of skill in the art. Nucleotides of the invention may also be obtained by screening cDNA libraries (e.g., cDNA libraries generated using mutagenesis techniques commonly used in the art, including those described herein) using one or more oligonucleotide probes that can hybridize to or PCR-amplify polynucleotides which encode a variant protease polypeptide(s) of the invention. Procedures for screening and isolating cDNA clones and PCR amplification procedures are well known to those of skill in the art and described in standard references known to those skilled in the art. Some nucleic acids of the invention can be obtained by altering a naturally occurring polynucleotide backbone (e.g., that encodes an enzyme or parent protease) by, for example, a known mutagenesis procedure (e.g., site-directed mutagenesis, site saturation mutagenesis, and in vitro recombination).

Methods for Making Modified Variant Proteases of the Invention

A variety of methods are known in the art that are suitable for generating modified polynucleotides of the invention that encode variant proteases of the invention, including, but not limited to, for example, site-saturation mutagenesis, scanning mutagenesis, insertional mutagenesis, deletion mutagenesis, random mutagenesis, site-directed mutagenesis, synthetic gene construction by oligonucleotide synthesis and ligation, and directed-evolution, as well as various other recombinatorial approaches. Methods for making modified polynucleotides and proteins (e.g., variant proteases) include DNA shuffling methodologies, methods based on non-homologous recombination of genes, such as ITCHY (See, Ostermeier et al., 7:2139-44 [1999]), SCRACHY (See, Lutz et al. 98:11248-53 [2001]), SHIPREC (See, Sieber et al., 19:456-60 [2001]), and NRR (See, Bittker et al., 20:1024-9 [2001]; Bittker et al., 101:7011-6 [2004]), and methods that rely on the use of oligonucleotides to insert random and targeted mutations, deletions and/or insertions (See, Ness et al., 20:1251-5 [2002]; Coco et al., 20:1246-50 [2002]; Zha et al., 4:34-9 [2003]; Glaser et al., 149:3903-13 [1992]).

Vectors, Cells, and Methods for Producing Variant Proteases of the Invention

The present invention provides isolated or recombinant vectors comprising at least one polynucleotide of the invention described herein (e.g., a polynucleotide encoding a variant protease of the invention described herein), isolated or recombinant expression vectors or expression cassettes comprising at least one nucleic acid or polynucleotide of the invention, isolated, substantially pure, or recombinant DNA constructs comprising at least one nucleic acid or polynucleotide of the invention, isolated or recombinant cells comprising at least one polynucleotide of the invention, cell cultures comprising cells comprising at least one polynucleotide of the invention, cell cultures comprising at least one nucleic acid or polynucleotide of the invention, and compositions comprising one or more such vectors, nucleic acids, expression vectors, expression cassettes, DNA constructs, cells, cell cultures, or any combination or mixtures thereof.

In some embodiments, the invention provides recombinant cells comprising at least one vector (e.g., expression vector or DNA construct) of the invention which comprises at least one nucleic acid or polynucleotide of the invention. Some such recombinant cells are transformed or transfected with such at least one vector. Such cells are typically referred to as host cells. Some such cells comprise bacterial cells, including, but are not limited to *Bacillus* sp. cells, such as *B. subtilis* cells. The invention also provides recombinant cells (e.g., recombinant host cells) comprising at least one variant protease of the invention.

In some embodiments, the invention provides a vector comprising a nucleic acid or polynucleotide of the invention. In some embodiments, the vector is an expression vector or expression cassette in which a polynucleotide sequence of the invention which encodes a variant protease of the invention is operably linked to one or additional nucleic acid segments required for efficient gene expression (e.g., a promoter operably linked to the polynucleotide of the invention which encodes a variant protease of the invention). A vector may include a transcription terminator and/or a selection gene, such as an antibiotic resistance gene that enables continuous cultural maintenance of plasmid-infected host cells by growth in antimicrobial-containing media.

An expression vector may be derived from plasmid or viral DNA, or in alternative embodiments, contains elements of both. Exemplary vectors include, but are not limited to pXX, pC194, pJH101, pE194, pHP13 (See, Harwood and Cutting [eds.], Chapter 3, "Molecular Biological Methods for *Bacillus*", John Wiley & Sons [1990]; suitable replicating plasmids for *B. subtilis* include those listed on p. 92; See also, Perego, Integrational Vectors for Genetic Manipulations in *B. subtilis*, in Sonenshein et al., [eds.]"*B. subtilis* and Other Gram-Positive Bacteria: Biochemistry, Physiology and Molecular Genetics", American Society for Microbiology, Washington, D.C. [1993], pp. 615-624).

For expression and production of a protein of interest (e.g., variant protease) in a cell, at least one expression vector comprising at least one copy of a polynucleotide encoding the modified protease, and preferably comprising multiple copies, is transformed into the cell under conditions suitable for expression of the protease. In some embodiments of the present invention, a polynucleotide sequence encoding the variant protease (as well as other sequences included in the vector) is integrated into the genome of the host cell, while in other embodiments, a plasmid vector comprising a polynucleotide sequence encoding the variant protease remains as autonomous extra-chromosomal element within the cell. The invention provides both extrachromosomal nucleic acid elements as well as incoming nucleotide sequences that are integrated into the host cell genome. The vectors described herein are useful for production of the variant proteases of the invention. In some embodiments, a polynucleotide construct encoding the variant protease is present on an integrating vector that enables the integration and optionally the amplification of the polynucleotide encoding the variant protease into the bacterial chromosome. Examples of sites for integration are well known to those skilled in the art. In some embodiments, transcription of a polynucleotide encoding a variant protease of the invention is effectuated by a promoter that is the wild-type promoter for the selected precursor protease. In some other embodiments, the promoter is heterologous to the precursor protease, but is functional in the host cell. Specifically, examples of suitable promoters for use in bacterial host cells include, but are not limited to, for example, the AprE, amyE, amyQ, amyL, pstS, sacB, pSPAC, pVeg, pHpaII promoters, the promoter of the *B. stearothermophilus* maltogenic amylase gene, the *B. amyloliquefaciens* (BAN) amylase gene, the *B. subtilis* alkaline protease gene, the *B. clausii* alkaline protease gene the *B. pumilis* xylosidase gene, the *B. thuringiensis* cryIIIA, and the *B. licheniformis* alpha-amylase gene. Additional promoters include, but are not limited to the A4 promoter, as well as phage Lambda $P_R$ or $P_L$ promoters, and the *E. coli* lac, trp or tac promoters.

Variant proteases of the present invention can be produced in host cells of any suitable microorganism, including bacteria and fungi. For example, in some embodiments, the variant protease is produced in host cells of fungal and/or bacterial origin. In some embodiments, the host cells are *Bacillus* spp., *Streptomyces* spp., *Escherichia* spp., *Aspergillus* spp., *Trichoderma* spp., *Pseudomonas* spp., *Corynebacterium* spp., *Saccharomyces* spp., or *Pichia* spp. In some embodiments, the variant proteases are produced by *Bacillus* sp. host cells. Examples of *Bacillus* sp. host cells that find use in the production of the variant proteases of the invention include, but are not limited to *B. licheniformis*, *B. lentus*, *B. subtilis*, *B. amyloliquefaciens*, *B. lentus*, *B. sonorensis*, *B. brevis*, *B. stearothermophilus*, *B. alkalophilus*, *B. coagulans*, *B. circulars*, *B. pumilis*, *B. thuringiensis*, *B. clausii*, and *B. megaterium*, as well as other organisms within the genus *Bacillus*. In some embodiments, *B. subtilis* host cells are used for production of variant proteases. U.S. Pat. No. 5,264,366 and RE 34,606 describe various *Bacillus* host strains that can be used for producing variant proteases of the invention, although other suitable strains can be used.

Several industrial bacterial strains that can be used to produce variant proteases of the invention include non-recombinant (i.e., wild-type) *Bacillus* sp. strains, as well as variants of naturally-occurring strains and/or recombinant strains. In some embodiments, the host strain is a recombinant strain, wherein a polynucleotide encoding a polypeptide of interest has been introduced into the host. In some embodiments, the host strain is a *B. subtilis* host strain and particularly a recombinant *B. subtilis* host strain. Numerous *B. subtilis* strains are known, including, but not limited to for example, 1A6 (ATCC 39085), 168 (1A01), SB19, W23, Ts85, B637, PB1753 through PB1758, PB3360, JH642, 1A243 (ATCC 39,087), ATCC 21332, ATCC 6051, MI113, DE100 (ATCC 39,094), GX4931, PBT 110, and PEP 211 strain (See e.g., Hoch et al., Genetics 73:215-228 [1973]; See also, U.S. Pat. Nos. 4,450,235 and 4,302,544, and EP 0134048, each of which is incorporated by reference in its entirety). The use of *B. subtilis* as an expression host cells is well known in the art (See e.g., Palva et al., Gene 19:81-87 [1982]; Fahnestock and Fischer, J. Bacteriol., 165:796-804 [1986]; and Wang et al., Gene 69:39-47 [1988]).

In some embodiments, the *Bacillus* host cell is a *Bacillus* sp. that includes a mutation or deletion in at least one of the following genes, degU, degS, degR and degQ. Preferably the mutation is in a degU gene, and more preferably the mutation is degU(Hy)32 (See e.g., Msadek et al., J. Bacteriol. 172:824-834 [1990]; and Olmos et al., Mol. Gen. Genet. 253:562-567 [1997]). One suitable host strain is a *B. subtilis* carrying a degU32(Hy) mutation. In some embodiments, the *Bacillus* host comprises a mutation or deletion in scoC4 (See e.g., Caldwell et al., J. Bacteriol. 183:7329-7340 [2001]); spoIIE (See e.g., Arigoni et al., Mol. Microbiol. 31:1407-1415 [1999]); and/or oppA or other genes of the opp operon (See e.g., Perego et al., Mol. Microbiol. 5:173-185 [1991]). Indeed, it is contemplated that any mutation in the opp operon that causes the same phenotype as a mutation in the oppA gene will find use in some embodiments of the altered *Bacillus* strain of the invention. In some embodiments, these mutations occur alone, while in other embodiments, combinations of mutations are present. In some embodiments, an altered *Bacillus* host cell strain that can be used to produce a variant protease of the invention is a *Bacillus* host strain that already includes a mutation in one or more of the above-mentioned genes. In addition, *Bacillus* sp. host cells that comprise mutation(s) and/or deletions of endogenous protease genes find use. In some embodiments, the *Bacillus* host cell comprises a deletion of the aprE and the nprE genes. In other embodiments, the *Bacillus* sp. host cell comprises a deletion of 5 protease genes, while in other embodiments, the *Bacillus* sp. host cell comprises a deletion of 9 protease genes (See e.g., U.S. Pat. Appln. Pub. No. 2005/0202535, incorporated herein by reference).

Host cells are transformed with at least one nucleic acid encoding at least one variant protease of the invention using any suitable method known in the art. Whether the nucleic acid is incorporated into a vector or is used without the presence of plasmid DNA, it is typically introduced into a microorganism, in some embodiments, preferably an *E. coli* cell or a competent *Bacillus* cell. Methods for introducing a nucleic acid (e.g., DNA) into *Bacillus* cells or *E. coli* cells utilizing plasmid DNA constructs or vectors and transforming such plasmid DNA constructs or vectors into such cells are well known. In some embodiments, the plasmids are subsequently isolated from *E. coli* cells and transformed into *Bacillus* cells. However, it is not essential to use intervening microorganisms such as *E. coli*, and in some embodiments, a DNA construct or vector is directly introduced into a *Bacillus* host.

Those of skill in the art are well aware of suitable methods for introducing nucleic acid or polynucleotide sequences of the invention into *Bacillus* cells (See e.g., Ferrari et al., "Genetics," in Harwood et al. [eds.], *Bacillus*, Plenum Publishing Corp. [1989], pp. 57-72; Saunders et al., J. Bacteriol. 157:718-726 [1984]; Hoch et al., J. Bacteriol. 93:1925-1937 [1967]; Mann et al., Current Microbiol. 13:131-135 [1986]; Holubova, Folia Microbiol. 30:97 [1985]; Chang et al., Mol. Gen. Genet. 168:11-115 [1979]; Vorobjeva et al., FEMS Microbiol. Lett. 7:261-263 [1980]; Smith et al., Appl. Env. Microbiol. 51:634 [1986]; Fisher et al., Arch. Microbiol. 139:213-217 [1981]; and McDonald, J. Gen. Microbiol. 130:203 [1984]). Indeed, such methods as transformation, including protoplast transformation and congression, transduction, and protoplast fusion are well known and suited for use in the present invention. Methods of transformation are used to introduce a DNA construct or vector comprising a nucleic acid encoding a variant protease of the present invention into a host cell. Methods known in the art to transform *Bacillus* cells include such methods as plasmid marker rescue transformation, which involves the uptake of a donor plasmid by competent cells carrying a partially homologous resident plasmid (See, Contente et al., Plasmid 2:555-571 [1979]; Haima et al., Mol. Gen. Genet. 223:185-191 [1990]; Weinrauch et al., J. Bacteriol. 154: 1077-1087 [1983]; and Weinrauch et al., J. Bacteriol. 169: 1205-1211 [1987]). In this method, the incoming donor plasmid recombines with the homologous region of the resident "helper" plasmid in a process that mimics chromosomal transformation.

In addition to commonly used methods, in some embodiments, host cells are directly transformed with a DNA construct or vector comprising a nucleic acid encoding a variant protease of the invention (i.e., an intermediate cell is not used to amplify, or otherwise process, the DNA construct or vector prior to introduction into the host cell). Introduction of the DNA construct or vector of the invention into the host cell includes those physical and chemical methods known in the art to introduce a nucleic acid sequence (e.g., DNA sequence) into a host cell without insertion into a plasmid or vector. Such methods include, but are not limited to calcium chloride precipitation, electroporation, naked DNA, liposomes and the like. In additional embodiments, DNA constructs or vector are co-transformed with a plasmid, without being inserted into the plasmid. In further embodiments, a selective marker is deleted from the altered *Bacillus* strain by methods known in the art (See, Stahl et al., J. Bacteriol. 158:411-418 [1984]; and Palmeros et al., Gene 247:255-264 [2000]).

In some embodiments, the transformed cells of the present invention are cultured in conventional nutrient media. The suitable specific culture conditions, such as temperature, pH and the like are known to those skilled in the art and are well described in the scientific literature. In some embodiments, the invention provides a culture (e.g., cell culture) comprising at least one variant protease or at least one nucleic acid of the invention. Also provided are compositions comprising at least one nucleic acid, vector, or DNA construct of the invention.

In some embodiments, host cells transformed with at least one polynucleotide sequence encoding at least one variant protease of the invention are cultured in a suitable nutrient medium under conditions permitting the expression of the present protease, after which the resulting protease is recovered from the culture. The medium used to culture the cells comprises any conventional medium suitable for growing the host cells, such as minimal or complex media containing appropriate supplements. Suitable media are available from commercial suppliers or may be prepared according to published recipes (See e.g., the catalogues of the American Type Culture Collection). In some embodiments, the protease produced by the cells is recovered from the culture medium by conventional procedures, including, but not limited to for example, separating the host cells from the medium by centrifugation or filtration, precipitating the proteinaceous components of the supernatant or filtrate by means of a salt (e.g., ammonium sulfate), chromatographic purification (e.g., ion exchange, gel filtration, affinity, etc.). Any method suitable for recovering or purifying a variant protease finds use in the present invention.

In some embodiments, a variant protease produced by a recombinant host cell is secreted into the culture medium. A nucleic acid sequence that encodes a purification facilitating domain may be used to facilitate purification of soluble proteins. A vector or DNA construct comprising a polynucleotide sequence encoding a variant protease may further comprise a nucleic acid sequence encoding a purification facilitating domain to facilitate purification of the variant protease (See e.g., Kroll et al., DNA Cell Biol. 12:441-53 [1993]). Such purification facilitating domains include, but are not limited to, for example, metal chelating peptides such as histidine-tryptophan modules that allow purification on immobilized metals (See, Porath, Protein Expr. Purif. 3:263-281 [1992]), protein A domains that allow purification on immobilized immunoglobulin, and the domain utilized in the FLAGS extension/affinity purification system (e.g., protein A domains available from Immunex Corp., Seattle, Wash.). The inclusion of a cleavable linker sequence such as Factor XA or enterokinase (e.g., sequences available from Invitrogen, San Diego, Calif.) between the purification domain and the heterologous protein also find use to facilitate purification.

Assays for detecting and measuring the enzymatic activity of an enzyme, such as a variant protease of the invention, are well known. Various assays for detecting and measuring activity of proteases (e.g., variant proteases of the invention), are also known to those of ordinary skill in the art. In particular, assays are available for measuring protease activity that are based on the release of acid-soluble peptides from casein or hemoglobin, measured as absorbance at 280 nm or colorimetrically using the Folin method, well known to those skilled in the art. Other exemplary assays involve the solubilization of chromogenic substrates (See e.g., Ward, "Proteinases," in Fogarty (ed.), "Microbial Enzymes and Biotechnology", Applied Science, London, [1983], pp. 251-317). Other exemplary assays include, but are not limited to succinyl-Ala-Ala-Pro-Phe-para nitroanilide assay (suc-AAPF-pNA) and the 2,4,6-trinitrobenzene sulfonate sodium salt assay (TNBS assay). Numerous additional references known to those in the art provide suitable methods (See e.g., Wells et al., Nucleic Acids Res. 11:7911-7925 [1983]; Christianson et al., Anal. Biochem. 223:119-129 [1994]; and Hsia et al., Anal Biochem. 242:221-227 [1999]).

A variety of methods can be used to determine the level of production of a mature protease (e.g., mature variant proteases of the present invention) in a host cell. Such methods include, but are not limited to, for example, methods that utilize either polyclonal or monoclonal antibodies specific for the protease. Exemplary methods include, but are not limited to enzyme-linked immunosorbent assays (ELISA), radioimmunoassays (RIA), fluorescent immunoassays (FIA), and fluorescent activated cell sorting (FACS). These and other assays are well known in the art (See e.g., Maddox et al., J. Exp. Med. 158:1211 [1983]).

In some other embodiments, the invention provides methods for making or producing a mature variant protease of the invention. A mature variant protease does not include a signal peptide or a propeptide sequence. Some methods comprise making or producing a variant protease of the invention in a recombinant bacterial host cell, such as for example, a *Bacillus* sp. cell (e.g., a *B. subtilis* cell). In some embodiments, the invention provides a method of producing a variant protease of the invention, the method comprising cultivating a recombinant host cell comprising a recombinant expression vector comprising a nucleic acid encoding a variant protease of the invention under conditions conducive to the production of the variant protease. Some such methods further comprise recovering the variant protease from the culture.

In some embodiments the invention provides methods of producing a variant protease of the invention, the methods comprising: (a) introducing a recombinant expression vector comprising a nucleic acid encoding a variant protease of the invention into a population of cells (e.g., bacterial cells, such as *B. subtilis* cells); and (b) culturing the cells in a culture medium under conditions conducive to produce the variant protease encoded by the expression vector. Some such methods further comprise: (c) isolating the variant protease from the cells or from the culture medium.

Cleaning Compositions

Unless otherwise noted, all component or composition levels provided herein are made in reference to the active level of that component or composition, and are exclusive of impurities, for example, residual solvents or by-products, which may be present in commercially available sources. Enzyme components weights are based on total active protein. All percentages and ratios are calculated by weight unless otherwise indicated. All percentages and ratios are calculated based on the total composition unless otherwise indicated. Compositions of the invention include cleaning compositions, such as detergent compositions. In the exemplified detergent compositions, the enzymes levels are expressed by pure enzyme by weight of the total composition and unless otherwise specified, the detergent ingredients are expressed by weight of the total compositions.

An even further embodiment is directed to a composition comprising one or more AprL-clade variants described herein, or recombinant polypeptide or an active fragment thereof. In yet still an even further embodiment, the composition described herein contains phosphate, is phosphate-free, contains borate, is boron-free, or combinations thereof. In other embodiments, the composition is a boron-free composition. In some embodiments, a boron-free composition is a composition to which a borate stabilizer has not been added. In another embodiment, a boron-free composition is a composition that contains less than 5.5% boron. In a still further embodiment, a boron-free composition is a composition that contains less than 4.5% boron. In yet still another embodiment, a boron-free composition is a composition that contains less than 3.5% boron. In yet still further embodiments, a boron-free composition is a composition that contains less than 2.5% boron. In even further embodiments, a boron-free composition is a composition that contains less than 1.5% boron. In another embodiment, a boron-free composition is a composition that contains less than 1.0% boron. In still further embodiments, a boron-free composition is a composition that contains less than 0.5% boron. In still further embodiments, a boron-free composition is a composition substantially-free of boron.

While not essential for the purposes of the present invention, the non-limiting list of adjuncts illustrated hereinafter are suitable for use in the instant cleaning compositions. In some embodiments, these adjuncts are incorporated for example, to assist or enhance cleaning performance, for treatment of the substrate to be cleaned, or to modify the aesthetics of the cleaning composition as is the case with perfumes, colorants, dyes or the like. It is understood that such adjuncts are in addition to the serine protease polypeptides of the present invention. The precise nature of these additional components, and levels of incorporation thereof, will depend on the physical form of the composition and the nature of the cleaning operation for which it is to be used. Suitable adjunct materials include, but are not limited to, bleach catalysts, other enzymes, enzyme stabilizing systems, chelants, optical brighteners, soil release polymers, dye transfer agents, dispersants, suds suppressors, dyes, perfumes, colorants, filler salts, photoactivators, fluorescers, fabric conditioners, hydrolyzable surfactants, preservatives, anti-oxidants, anti-shrinkage agents, anti-wrinkle agents, germicides, fungicides, color speckles, silvercare, anti-tarnish and/or anti-corrosion agents, alkalinity sources, solubilizing agents, carriers, processing aids, pigments, and pH control agents, surfactants, builders, chelating agents, dye transfer inhibiting agents, deposition aids, dispersants, additional enzymes, and enzyme stabilizers, catalytic materials, bleach activators, bleach boosters, hydrogen peroxide, sources of hydrogen peroxide, preformed peracids, polymeric dispersing agents, clay soil removal/anti-redeposition agents, brighteners, suds suppressors, dyes, perfumes, structure elasticizing agents, fabric softeners, carriers, hydrotropes, processing aids and/or pigments. In addition to the disclosure below, suitable examples of such other adjuncts and levels of use are found in U.S. Pat. Nos. 5,576,282; 6,306,812; 6,326,348; 6,610,642; 6,605,458; 5,705,464; 5,710,115; 5,698,504; 5,695,679; 5,686,014; and 5,646,101. In embodiments in which the cleaning adjunct materials are not compatible with the serine protease polypeptides of the present invention in the cleaning compositions, then suitable methods of keeping the cleaning adjunct materials and the protease(s) separated (i.e., not in contact with each other) until combination of the two components is appropriate are used. Such separation methods include any suitable method known in the art (e.g., gelcaps, encapsulation, tablets, physical separation, etc.). The aforementioned adjunct ingredients may constitute the balance of the cleaning compositions of the present invention.

The cleaning compositions of the present invention are advantageously employed for example, in laundry applications, hard surface cleaning applications, dishwashing applications, including automatic dishwashing and hand dishwashing, as well as cosmetic applications such as dentures, teeth, hair and skin cleaning. The enzymes of the present invention are also suited for use in contact lens cleaning and wound debridement applications.

The variant proteases of the present invention also find use in cleaning additive products. In some embodiments, low temperature solution cleaning applications find use. In some embodiments, the present invention provides cleaning additive products including at least one enzyme of the present invention is ideally suited for inclusion in a wash process when additional bleaching effectiveness is desired. Such instances include, but are not limited to low temperature solution cleaning applications. In some embodiments, the additive product is in its simplest form, one or more proteases. In some embodiments, the additive is packaged in dosage form for addition to a cleaning process. In some embodiments, the additive is packaged in dosage form for addition to a cleaning process where a source of peroxygen is employed and increased bleaching effectiveness is desired. Any suitable single dosage unit form finds use with the present invention, including but not limited to pills, tablets, gelcaps, or other single dosage units such as pre-measured powders or liquids. In some embodiments, filler(s) or carrier material(s) are included to increase the volume of such compositions. Suitable filler or carrier materials include, but are not limited to, various salts of sulfate, carbonate and silicate as well as talc, clay and the like. Suitable filler or carrier materials for liquid compositions include, but are not limited to water or low molecular weight primary and secondary alcohols including polyols and diols. Examples of such alcohols include, but are not limited to, methanol, ethanol, propanol and isopropanol. In some embodiments, the compositions contain from about 5% to about 90% of such materials. Acidic fillers find use to reduce pH. Alternatively, in some embodiments, the cleaning additive includes adjunct ingredients, as more fully described below.

The present cleaning compositions and cleaning additives require an effective amount of at least one of the protease variants provided herein, alone or in combination with other proteases and/or additional enzymes. The required level of enzyme is achieved by the addition of one or more protease variants of the present invention. Typically the present cleaning compositions comprise at least about 0.0001 weight percent, from about 0.0001 to about 10, from about 0.001 to about 1, or even from about 0.01 to about 0.1 weight percent of at least one of the variant proteases of the present invention.

The cleaning compositions herein are typically formulated such that, during use in aqueous cleaning operations, the wash water will have a pH of from about 4.0 to about 11.5, or even from about 5.0 to about 11.5, or even from about 5.0 to about 8.0, or even from about 7.5 to about 10.5. Liquid product formulations are typically formulated to have a pH from about 3.0 to about 9.0 or even from about 3 to about 5. Granular laundry products are typically formulated to have a pH from about 9 to about 11. In some embodiments, the cleaning compositions of the present invention can be formulated to have an alkaline pH under wash conditions, such as a pH of from about 8.0 to about 12.0, or from about 8.5 to about 11.0, or from about 9.0 to about 11.0. In some embodiments, the cleaning compositions of the present invention can be formulated to have a neutral pH under wash conditions, such as a pH of from about 5.0 to about 8.0, or from about 5.5 to about 8.0, or from about 6.0 to about 8.0, or from about 6.0 to about 7.5. In some embodiments, the neutral pH conditions can be measured when the cleaning composition is dissolved 1:100 (wt:wt) in de-ionised water at 20° C., measured using a conventional pH meter. Techniques for controlling pH at recommended usage levels include the use of buffers, alkalis, acids, etc., and are well known to those skilled in the art.

In some embodiments, when the variant protease(s) is/are employed in a granular composition or liquid, it is desirable for the variant protease to be in the form of an encapsulated particle to protect the variant protease from other components of the granular composition during storage. In addition, encapsulation is also a means of controlling the availability of the variant protease during the cleaning process. In some embodiments, encapsulation enhances the performance of the variant protease(s) and/or additional enzymes. In this regard, the variant proteases of the present invention are encapsulated with any suitable encapsulating material known in the art. In some embodiments, the encapsulating material typically encapsulates at least part of the catalyst for the variant protease(s) of the present invention. Typically, the encapsulating material is water-soluble and/or water-dispersible. In some embodiments, the encapsulating material has a glass transition temperature (Tg) of 0° C. or higher. Glass transition temperature is described in more detail in WO 97/11151. The encapsulating material is typically selected from consisting of carbohydrates, natural or synthetic gums, chitin, chitosan, cellulose and cellulose derivatives, silicates, phosphates, borates, polyvinyl alcohol, polyethylene glycol, paraffin waxes, and combinations thereof. When the encapsulating material is a carbohydrate, it is typically selected from monosaccharides, oligosaccharides, polysaccharides, and combinations thereof. In some typical embodiments, the encapsulating material is a starch (See e.g., EP 0922499; U.S. Pat. Nos. 4,977,252; 5,354,559, and 5,935,826). In some embodiments, the encapsulating material is a microsphere made from plastic such as thermoplastics, acrylonitrile, methacrylonitrile, polyacrylonitrile, polymethacrylonitrile and mixtures thereof; commercially available microspheres that find use include, but are not limited to those supplied by EXPANCEL® (Stockviksverken, Sweden), and PM 6545, PM 6550, PM 7220, PM 7228, EXTENDOSPHERES®, LUXSIL®, Q-CEL®, and SPHERICEL® (PQ Corp., Valley Forge, Pa.).

As described herein, the variant proteases of the present invention find particular use in the cleaning industry, including, but not limited to laundry and dish detergents. These applications place enzymes under various environmental stresses. The variant proteases of the present invention provide advantages over many currently used enzymes, due to their stability under various conditions.

Indeed, there are a variety of wash conditions including varying detergent formulations, wash water volumes, wash water temperatures, and lengths of wash time, to which proteases involved in washing are exposed. In addition, detergent formulations used in different geographical areas have different concentrations of their relevant components present in the wash water. For example, European detergents typically have about 4500-5000 ppm of detergent components in the wash water, while Japanese detergents typically have approximately 667 ppm of detergent components in the wash water. In North America, particularly the United States, detergents typically have about 975 ppm of detergent components present in the wash water.

A low detergent concentration system includes detergents where less than about 800 ppm of the detergent components are present in the wash water. Japanese detergents are typically considered low detergent concentration system as they have approximately 667 ppm of detergent components present in the wash water.

A medium detergent concentration includes detergents where between about 800 ppm and about 2000 ppm of the detergent components are present in the wash water. North American detergents are generally considered to be medium detergent concentration systems as they have approximately 975 ppm of detergent components present in the wash water. Brazil typically has approximately 1500 ppm of detergent components present in the wash water.

A high detergent concentration system includes detergents where greater than about 2000 ppm of the detergent components are present in the wash water. European detergents are generally considered to be high detergent concentration systems as they have approximately 4500-5000 ppm of detergent components in the wash water.

Latin American detergents are generally high suds phosphate builder detergents and the range of detergents used in Latin America can fall in both the medium and high detergent concentrations as they range from 1500 ppm to 6000 ppm of detergent components in the wash water. As mentioned above, Brazil typically has approximately 1500 ppm of detergent components present in the wash water. However, other high suds phosphate builder detergent geographies, not limited to other Latin American countries, may have high detergent concentration systems up to about 6000 ppm of detergent components present in the wash water.

In light of the foregoing, it is evident that concentrations of detergent compositions in typical wash solutions throughout the world varies from less than about 800 ppm of detergent composition ("low detergent concentration geographies"), for example about 667 ppm in Japan, to between about 800 ppm to about 2000 ppm ("medium detergent concentration geographies"), for example about 975 ppm in U.S. and about 1500 ppm in Brazil, to greater than about 2000 ppm ("high detergent concentration geographies"), for example about 4500 ppm to about 5000 ppm in Europe and about 6000 ppm in high suds phosphate builder geographies.

The concentrations of the typical wash solutions are determined empirically. For example, in the U.S., a typical washing machine holds a volume of about 64.4 L of wash solution. Accordingly, in order to obtain a concentration of about 975 ppm of detergent within the wash solution about 62.79 g of detergent composition must be added to the 64.4 L of wash solution. This amount is the typical amount measured into the wash water by the consumer using the measuring cup provided with the detergent.

As a further example, different geographies use different wash temperatures. The temperature of the wash water in Japan is typically less than that used in Europe. For example, the temperature of the wash water in North America and Japan is typically between about 10 and about 30° C. (e.g., about 20° C.), whereas the temperature of wash water in Europe is typically between about 30 and about 60° C. (e.g., about 40° C.). However, in the interest of saving energy, many consumers are switching to using cold water washing. In addition, in some further regions, cold water is typically used for laundry, as well as dish washing applications. In some embodiments, the "cold water washing" of the present invention utilizes "cold water detergent" suitable for washing at temperatures from about 10° C. to about 40° C., or from about 20° C. to about 30° C., or from about 15° C. to about 25° C., as well as all other combinations within the range of about 15° C. to about 35° C., and all ranges within 10° C. to 40° C.

As a further example, different geographies typically have different water hardness. Water hardness is usually described in terms of the grains per gallon mixed $Ca^{2+}/Mg^{2+}$. Hardness is a measure of the amount of calcium ($Ca^{2+}$) and magnesium ($Mg^{2+}$) in the water. Most water in the United States is hard, but the degree of hardness varies. Moderately hard (60-120 ppm) to hard (121-181 ppm) water has 60 to 181 parts per million (parts per million converted to grains per U.S. gallon is ppm # divided by 17.1 equals grains Der gallon) of hardness minerals.

| Water | Grains per gallon | Parts per million |
|---|---|---|
| Soft | less than 1.0 | less than 17 |
| Slightly hard | 1.0 to 3.5 | 17 to 60 |
| Moderately hard | 3.5 to 7.0 | 60 to 120 |
| Hard | 7.0 to 10.5 | 120 to 180 |
| Very hard | greater than 10.5 | greater than 180 |

European water hardness is typically greater than about 10.5 (for example about 10.5 to about 20.0) grains per gallon mixed $Ca^{2+}/Mg^{2+}$ (e.g., about 15 grains per gallon mixed $Ca^{2+}/Mg^{2+}$). North American water hardness is typically greater than Japanese water hardness, but less than European water hardness. For example, North American water hardness can be between about 3 to about 10 grains, about 3 to about 8 grains or about 6 grains. Japanese water hardness is typically lower than North American water hardness, usually less than about 4, for example about 3 grains per gallon mixed $Ca^{2+}/Mg^{2+}$.

Accordingly, in some embodiments, the present invention provides variant proteases that show surprising wash performance in at least one set of wash conditions (e.g., water temperature, water hardness, and/or detergent concentration). In some embodiments, the variant proteases of the present invention are comparable in wash performance to other AprL proteases. In some embodiments of the present invention, the variant proteases provided herein exhibit enhanced oxidative stability, enhanced thermal stability, enhanced cleaning capabilities under various conditions, and/or enhanced chelator stability. In addition, the variant proteases of the present invention find use in cleaning compositions that do not include detergents, again either alone or in combination with builders and stabilizers.

In some embodiments of the present invention, the cleaning compositions comprise at least one variant protease of the present invention at a level from about 0.00001% to about 10% by weight of the composition and the balance (e.g., about 99.999% to about 90.0%) comprising cleaning adjunct materials by weight of composition. In some other embodiments of the present invention, the cleaning compositions of the present invention comprises at least one variant protease at a level of about 0.0001% to about 10%, about 0.001% to about 5%, about 0.001% to about 2%, about 0.005% to about 0.5% by weight of the composition and the balance of the cleaning composition (e.g., about 99.9999% to about 90.0%, about 99.999% to about 98%, about 99.995% to about 99.5% by weight) comprising cleaning adjunct materials.

In some embodiments, the cleaning compositions of the present invention comprise one or more additional detergent enzymes, which provide cleaning performance and/or fabric care and/or dishwashing benefits. Examples of suitable enzymes include, but are not limited to, additional serine proteases, acyl transferases, alpha-amylases, beta-amylases, alpha-galactosidases, arabinosidases, aryl esterases, beta-galactosidases, carrageenases, catalases, cellobiohydrolases, cellulases, chondroitinases, cutinases, endo-beta-1, 4-glucanases, endo-beta-mannanases, esterases, exo-mannanases, galactanases, glucoamylases, hemicellulases, hyaluronidases, keratinases, laccases, lactases, ligninases, lipases, lipoxygenases, mannanases, metalloproteases, non-serine proteases, oxidases, pectate lyases, pectin acetyl esterases, pectinases, pentosanases, perhydrolases, peroxidases, phenoloxidases, phosphatases, phospholipases, phytases, polygalacturonases, proteases, pullulanases, reductases, rhamnogalacturonases, beta-glucanases, tannases, transglutaminases, xylan acetyl-esterases, xylanases, xyloglucanases, and xylosidases, or any combinations or mixtures thereof. In some embodiments, a combination of enzymes is used (i.e., a "cocktail") comprising conventional applicable enzymes like amylase, lipase, cutinase and/or cellulase in conjunction with protease is used.

In addition to the protease variants provided herein, any other suitable protease finds use in the compositions of the present invention. Suitable proteases include those of animal, vegetable or microbial origin. In some embodiments, microbial proteases are used. In some embodiments, chemically or genetically modified mutants are included. In some embodiments, the protease is a serine protease, preferably an alkaline microbial protease or a trypsin-like protease. Examples of alkaline proteases include subtilisins, especially those derived from *Bacillus* (e.g., subtilisin, *lentus*, *amyloliquefaciens*, subtilisin Carlsberg, subtilisin 309, subtilisin 147 and subtilisin 168). Additional examples include those mutant proteases described in U.S. Pat. Nos. RE 34,606: 5,955,340; 5,700,676; 6,312,936; and 6,482,628. Additional protease examples include, but are not limited to trypsin (e.g., of porcine or bovine origin), and the *Fusarium* protease described in WO 89/06270. In some embodiments, commercially available protease enzymes that find use in the present invention include, but are not limited to MAX-ATASE®, MAXACAL™, MAXAPEM™, OPTICLEAN®, OPTIMASE®, PROPERASE®, PURAFECT®, PURAFECT® OXP, PURAMAX™, EXCELLASE™, PREFERENZ™ proteases (e.g. P100, P110, P280), EFFECTENZ™ proteases (e.g. P1000, P1050, P2000), EXCELLENZ™ proteases (e.g. P1000), ULTIMASE®, and PURAFAST™ (DuPont); ALCALASE®, BLAZE®, CORONASE®, SAVNASE®, PRIMASE®, DURAZYM™, POLARZYME®, OVOZYME®, KANNASE®, LIQUANASE®, NEUTRASE®, RELASE® and ESPERASE® (Novozymes); BLAP™ and BLAP™ variants (Henkel), and KAP (*B. alkalophilus* subtilisin; Kao). Various proteases are described in WO 92/21760, WO95/23221, WO 2008/010925, WO 09/149200, WO 09/149144, WO 09/149145, WO 10/056640, WO 10/056653, WO 2010/0566356, WO 11/072099, WO 2011/13022, WO 11/140364, WO 12/151534, WO 2015/038792, WO 2015/089447, WO 2015/089441, US Publ. No. 2008/0090747, U.S. Pat. Nos. 5,801,039 5,340,735 5,500,364, 5,855,625, RE 34,606, 5,955,340, 5,700,676 6,312,936, 6,482,628, 8,530,219, U.S. Provisional Appl Nos. 62/180,673 and 62/161,077, and PCT Appl Nos. PCT/US2015/021813, PCT/US2015/055900, PCT/US2015/057497, PCT/US2015/057492, PCT/US2015/057512, PCT/US2015/057526, PCT/US2015/057520, PCT/US2015/057502, and PCT/US2016/022282. In some further embodiments, metalloproteases find use in the present invention, including but not limited to the metalloproteases described in WO 1999014341, WO 1999033960, WO1999014342, WO1999034003, WO2007044993, WO2009058303, WO2009058661, WO 2014071410, WO2014194032, WO2014194034, WO 2014194054, and WO 2014/194117. Exemplary metalloproteases include nprE, the recombinant form of neutral metalloprotease expressed in *B. subtilis* (See e.g., WO 07/044993), and PMN, the purified neutral metalloprotease from B. amyloliquefacients.

In addition, any suitable lipase finds use in the present invention. Suitable lipases include, but are not limited to those of bacterial or fungal origin. Chemically or genetically modified mutants are encompassed by the present invention. Examples of useful lipases include *H. lanuginosa* lipase (See e.g., EP 258068, and EP 305216), *Rhizomucor miehei* lipase (See e.g., EP 238023), *Candida* lipase, such as *C. antarctica* lipase (e.g., *C. antarctica* lipase A or B; See e.g., EP 214761), *Pseudomonas* lipases such as *P. alcaligenes* and *P. pseudoalcaligenes* lipases (See e.g., EP 218 272), *P. cepacia* lipase (See e.g., EP 331 376), *P. stutzeri* lipase (See e.g., GB 1,372,034), *P. fluorescens* lipase, *B.* lipase (e.g., *B. subtilis* lipase [Dartois et al., Biochem. Biophys. Acta 1131: 253-260 [1993]); *B. stearothermophilus* lipase [See e.g., JP 64/744992]; and *B. pumilus* lipase [See e.g., WO 91/16422]).

Furthermore, a number of cloned lipases find use in some embodiments of the present invention, including but not limited to *Penicillium camembertii* lipase (See, Yamaguchi et al., Gene 103:61-67 [1991]), *Geotricum candidum* lipase (See, Schimada et al., J. Biochem., 106:383-388 [1989]), and various *Rhizopus* lipases such as *R. delemar* lipase (See, Hass et al., Gene 109:117-113 [1991]), a *R. niveus* lipase (Kugimiya et al., Biosci. Biotech. Biochem. 56:716-719 [1992]) and *R. oryzae* lipase.

Other types of lipase polypeptide enzymes such as cutinases also find use in some embodiments of the present invention, including but not limited to the cutinase derived from *Pseudomonas mendocina* (See, WO 88/09367), and the cutinase derived from *Fusarium solani pisi* (See, WO 90/09446).

Additional suitable lipases include lipases such as M1 LIPASE™, LUMA FAST™, and LIPOMAX™ (DuPont); LIPEX®, LIPOLASE® and LIPOLASE® ULTRA (Novozymes); and LIPASE P™ "Amano" (Amano Pharmaceutical Co. Ltd).

In some embodiments of the present invention, the cleaning compositions of the present invention further comprise lipases at a level from about 0.00001% to about 10% of additional lipase by weight of the composition and the balance of cleaning adjunct materials by weight of composition. In some other embodiments of the present invention, the cleaning compositions of the present invention also comprise lipases at a level of about 0.0001% to about 10%, about 0.001% to about 5%, about 0.001% to about 2%, about 0.005% to about 0.5% lipase by weight of the composition.

In some embodiments of the present invention, any suitable amylase finds use in the present invention. In some embodiments, any amylase (e.g., alpha and/or beta) suitable for use in alkaline solutions also find use. Suitable amylases include, but are not limited to those of bacterial or fungal origin. Chemically or genetically modified mutants are included in some embodiments. Amylases that find use in the present invention, include, but are not limited to α-amylases obtained from *B. licheniformis* (See e.g., GB 1,296, 839). Additional suitable amylases include those found in WO9100353, WO9402597, WO94183314, WO9510603, WO9526397, WO9535382, WO9605295, WO9623873, WO9623874, WO9630481, WO9710342, WO9741213, WO9743424, WO9813481, WO 9826078, WO9902702, WO9909183, WO9919467, WO9923211, WO9929876, WO9942567, WO 9943793, WO9943794, WO9946399, WO0029560, WO0060058, WO0060059, WO0060060, WO 0114532, WO0134784, WO0164852, WO0166712, WO0188107, WO0196537, WO02092797, WO 0210355, WO0231124, WO2004055178, WO2004113551, WO2005001064, WO2005003311, WO 2005018336, WO2005019443, WO2005066338, WO2006002643, WO2006012899, WO2006012902, WO2006031554, WO2006063594, WO2006066594, WO2006066596, WO2006136161, WO 2008000825, WO2008088493, WO2008092919, WO2008101894, WO2008/112459, WO2009061380, WO2009061381, WO2009100102, WO2009140504, WO2009149419, WO 2010/059413, WO 2010088447, WO2010091221, WO2010104675, WO2010115021, WO10115028, WO2010117511, WO 2011076123, WO2011076897, WO2011080352, WO2011080353, WO 2011080354, WO2011082425, WO2011082429, WO2011087836, WO2011098531, WO2013063460, WO2013184577, WO 2014099523, WO2014164777, and WO2015077126. Commercially available amylases that find use in the present invention include, but are not limited to DURAMYL®, TERMAMYL®, FIJNGAMYL®, STAINZYME®, STAINZYME PLUS®, STAINZYME ULTRA®, and BAN™ (Novozymes), as well as EFFECTENZ™ S1000, POWERASE™, PREFERENZ™ S 100, PREFERENZ™ S 110, EXCELLENZ™ S 2000, RAPIDASE® and MAXAMYL® P (DuPont).

In some embodiments of the present invention, the cleaning compositions of the present invention further comprise amylases at a level from about 0.00001% to about 10% of additional amylase by weight of the composition and the balance of cleaning adjunct materials by weight of composition. In some other embodiments of the present invention, the cleaning compositions of the present invention also comprise amylases at a level of about 0.0001% to about 10%, about 0.001% to about 5%, about 0.001% to about 2%, about 0.005% to about 0.5% amylase by weight of the composition.

In some further embodiments, any suitable cellulase finds used in the cleaning compositions of the present invention. Suitable cellulases include, but are not limited to those of bacterial or fungal origin. Chemically or genetically modified mutants are included in some embodiments. Suitable cellulases include, but are not limited to *H. insolens* cellulases (See e.g., U.S. Pat. No. 4,435,307). Especially suitable cellulases are the cellulases having color care benefits (See e.g., EP 0495257). Commercially available cellulases that find use in the present include, but are not limited to CELLUZYME®, CAREZYME®, and CAREZYME® PREMIUM (Novozymes), REVITALENZ™ 100 and REVITALENZ® 2000 (DuPont), and KAC-500(B)™ (Kao). In some embodiments, cellulases are incorporated as portions or fragments of mature wild-type or variant cellulases, wherein a portion of the N-terminus is deleted (See e.g., U.S. Pat. No. 5,874,276). Additional suitable cellulases include those found in WO2005054475, WO2005056787, U.S. Pat. Nos. 7,449,318, 7,833,773, 4,435,307, EP 0495257, and U.S. Provisional Appl. No. 62/296,678. In some embodiments, the cleaning compositions of the present invention further comprise cellulases at a level from about 0.00001% to about 10% of additional cellulase by weight of the composition and the balance of cleaning adjunct materials by weight of composition. In some other embodiments of the present invention, the cleaning compositions of the present invention also comprise cellulases at a level of about 0.0001% to about 10%, about 0.001% to about 5%, about 0.001% to about 2%, about 0.005% to about 0.5% cellulase by weight of the composition.

Any mannanase suitable for use in detergent compositions also finds use in the present invention. Suitable mannanases include, but are not limited to those of bacterial or fungal origin. Chemically or genetically modified mutants are included in some embodiments. Various mannanases are known which find use in the present invention (See e.g., U.S. Pat. Nos. 6,566,114; 6,602,842; 6,440,991; and U.S. Provisional Appl. Nos. 62/251,516, 62/278,383, and 62/278,387). Commercially available mannanases that find use in the present invention include, but are not limited to EFFECTENZ™ M 1000, PREFERENZ® M 100, MANNASTAR®, and PURABRITE™ (DuPont), as well as MANNAWAY® (Novozymes). In some embodiments, the cleaning compositions of the present invention further comprise mannanases at a level from about 0.00001% to about 10% of additional mannanase by weight of the composition and the balance of cleaning adjunct materials by weight of composition. In some embodiments of the present invention, the cleaning compositions of the present invention also comprise mannanases at a level of about 0.0001% to about 10%, about 0.001% to about 5%, about 0.001% to about 2%, about 0.005% to about 0.5% mannanase by weight of the composition.

In some embodiments, peroxidases are used in combination with hydrogen peroxide or a source thereof (e.g., a percarbonate, perborate or persulfate) in the compositions of the present invention. In some alternative embodiments, oxidases are used in combination with oxygen. Both types of enzymes are used for "solution bleaching" (i.e., to prevent transfer of a textile dye from a dyed fabric to another fabric when the fabrics are washed together in a wash liquor), preferably together with an enhancing agent (See e.g., WO 9412621 and WO 9501426). Suitable peroxidases/oxidases include, but are not limited to those of plant, bacterial or fungal origin. Chemically or genetically modified mutants are included in some embodiments. In some embodiments, the cleaning compositions of the present invention further comprise peroxidase and/or oxidase enzymes at a level from about 0.00001% to about 10% of additional peroxidase and/or oxidase by weight of the composition and the balance of cleaning adjunct materials by weight of composition. In some other embodiments of the present invention, the cleaning compositions of the present invention also comprise, peroxidase and/or oxidase enzymes at a level of about 0.0001% to about 10%, about 0.001% to about 5%, about 0.001% to about 2%, about 0.005% to about 0.5% peroxidase and/or oxidase enzymes by weight of the composition.

In some embodiments, additional enzymes find use, including but not limited to perhydrolases (See e.g., WO2005056782, WO2007106293, WO2008063400, WO2008106214, and WO2008106215). In addition, in some embodiments, mixtures of the above mentioned enzymes are encompassed herein, in particular one or more additional protease, amylase, lipase, mannanase, and/or at least one cellulase. Indeed, it is contemplated that various mixtures of these enzymes will find use in the present invention. It is also contemplated that the varying levels of the variant protease(s) and one or more additional enzymes may both independently range to about 10%, the balance of the cleaning composition being cleaning adjunct materials. The specific selection of cleaning adjunct materials are readily made by considering the surface, item, or fabric to be cleaned, and the desired form of the composition for the cleaning conditions during use (e.g., through the wash detergent use).

Examples of suitable cleaning adjunct materials include, but are not limited to, surfactants, builders, bleaches, bleach activators, bleach catalysts, other enzymes, enzyme stabilizing systems, chelants, optical brighteners, soil release polymers, dye transfer agents, dye transfer inhibiting agents, catalytic materials, hydrogen peroxide, sources of hydrogen peroxide, preformed peracids, polymeric dispersing agents, clay soil removal agents, structure elasticizing agents, dispersants, suds suppressors, dyes, perfumes, colorants, filler salts, hydrotropes, photoactivators, fluorescers, fabric conditioners, fabric softeners, carriers, hydrotropes, processing aids, solvents, pigments, hydrolyzable surfactants, preservatives, anti-oxidants, anti-shrinkage agents, anti-wrinkle agents, germicides, fungicides, color speckles, silvercare, anti-tarnish and/or anti-corrosion agents, alkalinity sources, solubilizing agents, carriers, processing aids, pigments, and pH control agents (See e.g., U.S. Pat. Nos. 6,610,642; 6,605,458; 5,705,464; 5,710,115; 5,698,504; 5,695,679; 5,686,014 and 5,646,101). Embodiments of specific cleaning composition materials are exemplified in detail below. In embodiments in which the cleaning adjunct materials are not compatible with the variant proteases of the present invention in the cleaning compositions, then suitable methods of keeping the cleaning adjunct materials and the protease(s) separated (i.e., not in contact with each other) until combination of the two components is appropriate are used. Such separation methods include any suitable method known in the art (e.g., gelcaps, encapsulation, tablets, physical separation, etc.).

In some embodiments, an effective amount of one or more variant protease(s) provided herein is included in compositions useful for cleaning a variety of surfaces in need of proteinaceous stain removal. Such cleaning compositions include cleaning compositions for such applications as cleaning hard surfaces, fabrics, and dishes. Indeed, in some embodiments, the present invention provides fabric cleaning compositions, while in other embodiments, the present invention provides non-fabric cleaning compositions. Notably, the present invention also provides cleaning compositions suitable for personal care, including oral care (including dentifrices, toothpastes, mouthwashes, etc., as well as denture cleaning compositions), skin, and hair cleaning compositions. It is intended that the present invention encompass detergent compositions in any form (i.e., liquid, granular, bar, semi-solid, gels, emulsions, tablets, capsules, etc.).

By way of example, several cleaning compositions wherein the variant proteases of the present invention find use are described in greater detail below. In some embodiments in which the cleaning compositions of the present invention are formulated as compositions suitable for use in laundry machine washing method(s), the compositions of the present invention preferably contain at least one surfactant and at least one builder compound, as well as one or more cleaning adjunct materials preferably selected from organic polymeric compounds, bleaching agents, additional enzymes, suds suppressors, dispersants, lime-soap dispersants, soil suspension and anti-redeposition agents and corrosion inhibitors. In some embodiments, laundry compositions also contain softening agents (i.e., as additional cleaning adjunct materials). The compositions of the present invention also find use detergent additive products in solid or liquid form. Such additive products are intended to supplement and/or boost the performance of conventional detergent compositions and can be added at any stage of the cleaning process. In some embodiments, the density of the laundry detergent compositions herein ranges from about 400 to about 1200 g/liter, while in other embodiments, it ranges from about 500 to about 950 g/liter of composition measured at 20° C.

In embodiments formulated as compositions for use in manual dishwashing methods, the compositions of the invention preferably contain at least one surfactant and preferably at least one additional cleaning adjunct material selected from organic polymeric compounds, suds enhancing agents, group II metal ions, solvents, hydrotropes and additional enzymes.

In some embodiments, various cleaning compositions such as those provided in U.S. Pat. No. 6,605,458, find use with the variant proteases of the present invention. Thus, in some embodiments, the compositions comprising at least one variant protease of the present invention is a compact granular fabric cleaning composition, while in other embodiments, the composition is a granular fabric cleaning composition useful in the laundering of colored fabrics, in further embodiments, the composition is a granular fabric cleaning composition which provides softening through the wash capacity, in additional embodiments, the composition is a heavy duty liquid fabric cleaning composition. In some embodiments, the compositions comprising at least one variant protease of the present invention are fabric cleaning compositions such as those described in U.S. Pat. Nos. 6,610,642 and 6,376,450. In addition, the variant proteases of the present invention find use in granular laundry detergent compositions of particular utility under European or Japanese washing conditions (See e.g., U.S. Pat. No. 6,610,642).

In some alternative embodiments, the present invention provides hard surface cleaning compositions comprising at least one variant protease provided herein. Thus, in some embodiments, the compositions comprising at least one variant protease of the present invention is a hard surface cleaning composition such as those described in U.S. Pat. Nos. 6,610,642; 6,376,450; and 6,376,450.

In yet further embodiments, the present invention provides dishwashing compositions comprising at least one variant protease provided herein. Thus, in some embodiments, the compositions comprising at least one variant protease of the present invention is a hard surface cleaning composition such as those in U.S. Pat. Nos. 6,610,642 and 6,376,450. In some still further embodiments, the present invention provides dishwashing compositions comprising at least one variant protease provided herein. In some further embodiments, the compositions comprising at least one variant protease of the present invention comprise oral care compositions such as those in U.S. Pat. Nos. 6,376,450, and 6,376,450. The formulations and descriptions of the compounds and cleaning adjunct materials contained in the aforementioned U.S. Pat. Nos. 6,376,450, 6,605,458, 6,605, 458, and 6,610,642, find use with the variant proteases provided herein.

The cleaning compositions of the present invention are formulated into any suitable form and prepared by any process chosen by the formulator (See e.g., U.S. Pat. Nos. 5,879,584; 5,691,297; 5,574,005; 5,569,645; 5,565,422; 5,516,448; 5,489,392; and 5,486,303. When a low pH cleaning composition is desired, the pH of such composition is adjusted via the addition of a material such as monoethanolamine or an acidic material such as HCl.

In some embodiments, the cleaning compositions according to the present invention comprise an acidifying particle or an amino carboxylic builder. Examples of an amino carboxylic builder include aminocarboxylic acids, salts and derivatives thereof. In some embodiment, the amino carboxylic builder is an aminopolycarboxylic builder, such as glycine-N,N-diacetic acid or derivative of general formula MOOC—CHR—N(CH$_2$COOM)$_2$ where R is C$_{1-12}$ alkyl and M is alkali metal. In some embodiments, the amino carboxylic builder can be methylglycine diacetic acid (MGDA), GLDA (glutamic-N,N-diacetic acid), iminodisuccinic acid (IDS), carboxymethyl inulin and salts and derivatives thereof, aspartic acid-N-monoacetic acid (ASMA), aspartic acid-N,N-diacetic acid (ASDA), aspartic acid-N-monopropionic acid (ASMP), iminodisuccinic acid (IDA), N-(2-sulfomethyl) aspartic acid (SMAS), N-(2-sulfoethyl) aspartic acid (SEAS), N-(2-sulfomethyl)glutamic acid (SMGL), N-(2-sulfoethyl) glutamic acid (SEGL), IDS (iminodiacetic acid) and salts and derivatives thereof such as N-methyliminodiacetic acid (MIDA), alpha-alanine-N,N-diacetic acid (alpha-ALDA), serine-N,N-diacetic acid (SEDA), isoserine-N,Ndiacetic acid (ISDA), phenylalanine-N,N-diacetic acid (PHDA), anthranilic acid-N,N-diacetic acid (ANDA), sulfanilic acid-N,N-diacetic acid (SLDA), taurine-N,N-diacetic acid (TUDA) and sulfomethyl-N,N-diacetic acid (SMDA) and alkali metal salts and derivative thereof. In some embodiments, the acidifying particle has a weight geometric mean particle size of from about 400μ to about 1200μ and a bulk density of at least 550 g/L. In some embodiments, the acidifying particle comprises at least about 5% of the builder.

In some embodiments, the acidifying particle can comprise any acid, including organic acids and mineral acids. Organic acids can have one or two carboxyls and in some instances up to 15 carbons, especially up to 10 carbons, such as formic, acetic, propionic, capric, oxalic, succinic, adipic, maleic, fumaric, sebacic, malic, lactic, glycolic, tartaric and glyoxylic acids. In some embodiments, the acid is citric acid. Mineral acids include hydrochloric and sulphuric acid. In some instances, the acidifying particle of the invention is a highly active particle comprising a high level of amino carboxylic builder. Sulphuric acid has been found to further contribute to the stability of the final particle.

While not essential for the purposes of the present invention, the non-limiting list of adjuncts illustrated hereinafter are suitable for use in the instant cleaning compositions. In some embodiments, these adjuncts are incorporated for example, to assist or enhance cleaning performance, for treatment of the substrate to be cleaned, or to modify the aesthetics of the cleaning composition as is the case with perfumes, colorants, dyes or the like. It is understood that such adjuncts are in addition to the variant proteases of the present invention. The precise nature of these additional components, and levels of incorporation thereof, will depend on the physical form of the composition and the nature of the cleaning operation for which it is to be used. Suitable adjunct materials include, but are not limited to, surfactants, builders, chelating agents, dye transfer inhibiting agents, deposition aids, dispersants, additional enzymes, and enzyme stabilizers, catalytic materials, bleach activators, bleach boosters, hydrogen peroxide, sources of hydrogen peroxide, preformed peracids, polymeric dispersing agents, clay soil removal/anti-redeposition agents, brighteners, suds suppressors, dyes, perfumes, structure elasticizing agents, fabric softeners, carriers, hydrotropes, processing aids and/or pigments. In addition to the disclosure below, suitable examples of such other adjuncts and levels of use are found in U.S. Pat. Nos. 5,576,282, 6,306,812, and 6,326,348. The aforementioned adjunct ingredients may constitute the balance of the cleaning compositions of the present invention.

In some embodiments, the cleaning compositions according to the present invention comprise at least one surfactant and/or a surfactant system wherein the surfactant is selected from nonionic surfactants, anionic surfactants, cationic surfactants, ampholytic surfactants, zwitterionic surfactants, semi-polar nonionic surfactants and mixtures thereof. In some low pH cleaning composition embodiments (e.g., compositions having a neat pH of from about 3 to about 5), the composition typically does not contain alkyl ethoxylated sulfate, as it is believed that such surfactant may be hydrolyzed by such compositions the acidic contents. In some embodiments, the surfactant is present at a level of from about 0.1% to about 60%, while in alternative embodiments the level is from about 1% to about 50%, while in still further embodiments the level is from about 5% to about 40%, by weight of the cleaning composition.

In some embodiments, the cleaning compositions of the present invention comprise one or more detergent builders or builder systems. In some embodiments incorporating at least one builder, the cleaning compositions comprise at least about 1%, from about 3% to about 60% or even from about 5% to about 40% builder by weight of the cleaning composition. Builders include, but are not limited to, the alkali metal, ammonium and alkanolammonium salts of polyphosphates, alkali metal silicates, alkaline earth and alkali metal carbonates, aluminosilicates, polycarboxylate compounds, ether hydroxypolycarboxylates, copolymers of maleic anhydride with ethylene or vinyl methyl ether, 1, 3, 5-trihydroxy benzene-2, 4, 6-trisulphonic acid, and carboxymethyloxysuccinic acid, the various alkali metal, ammonium and substituted ammonium salts of polyacetic acids such as ethylenediamine tetraacetic acid and nitrilotriacetic acid, as well as polycarboxylates such as mellitic acid, succinic acid, citric acid, oxydisuccinic acid, polymaleic acid, benzene 1,3,5-tricarboxylic acid, carboxymethyloxysuccinic acid, and soluble salts thereof. Indeed, it is contemplated that any suitable builder will find use in various embodiments of the present invention.

In some embodiments, the builders form water-soluble hardness ion complexes (e.g., sequestering builders), such as citrates and polyphosphates (e.g., sodium tripolyphosphate and sodium tripolyphospate hexahydrate, potassium tripolyphosphate, and mixed sodium and potassium tripolyphosphate, etc.). It is contemplated that any suitable builder will find use in the present invention, including those known in the art (See e.g., EP 2100949).

In some embodiments, builders for use herein include phosphate builders and non-phosphate builders. In some embodiments, the builder is a phosphate builder. In some embodiments, the builder is a non-phosphate builder. If present, builders are used in a level of from 0.1% to 80%, or from 5 to 60%, or from 10 to 50% by weight of the composition. In some embodiments the product comprises a mixture of phosphate and non-phosphate builders. Suitable phosphate builders include mono-phosphates, di-phosphates, tri-polyphosphates or oligomeric-poylphosphates, including the alkali metal salts of these compounds, including the sodium salts. In some embodiments, a builder can be sodium tripolyphosphate (STPP). Additionally, the composition can comprise carbonate and/or citrate, preferably citrate that helps to achieve a neutral pH composition of the invention. Other suitable non-phosphate builders include homopolymers and copolymers of polycarboxylic acids and their partially or completely neutralized salts, monomeric polycarboxylic acids and hydroxycarboxylic acids and their salts. In some embodiments, salts of the above mentioned compounds include the ammonium and/or alkali metal salts, i.e. the lithium, sodium, and potassium salts, including sodium salts. Suitable polycarboxylic acids include acyclic, alicyclic, hetero-cyclic and aromatic carboxylic acids, wherein in some embodiments, they can contain at least two carboxyl groups which are in each case separated from one another by, in some instances, no more than two carbon atoms.

In some embodiments, the cleaning compositions of the present invention contain at least one chelating agent. Suitable chelating agents include, but are not limited to copper, iron and/or manganese chelating agents and mixtures thereof. In embodiments in which at least one chelating agent is used, the cleaning compositions of the present invention comprise from about 0.1% to about 15% or even from about 3.0% to about 10% chelating agent by weight of the subject cleaning composition.

In some still further embodiments, the cleaning compositions provided herein contain at least one deposition aid. Suitable deposition aids include, but are not limited to, polyethylene glycol, polypropylene glycol, polycarboxylate, soil release polymers such as polytelephthalic acid, clays such as kaolinite, montmorillonite, atapulgite, illite, bentonite, halloysite, and mixtures thereof.

As indicated herein, in some embodiments, anti-redeposition agents find use in some embodiments of the present invention. In some embodiments, non-ionic surfactants find use. For example, in automatic dishwashing embodiments, non-ionic surfactants find use for surface modification purposes, in particular for sheeting, to avoid filming and spotting and to improve shine. These non-ionic surfactants also find use in preventing the re-deposition of soils. In some embodiments, the anti-redeposition agent is a non-ionic surfactant as known in the art (See e.g., EP 2100949). In some embodiments, the non-ionic surfactant can be ethoxylated nonionic surfactants, epoxy-capped poly(oxyalkylated) alcohols and amine oxides surfactants.

In some embodiments, the cleaning compositions of the present invention include one or more dye transfer inhibiting agents. Suitable polymeric dye transfer inhibiting agents include, but are not limited to, polyvinylpyrrolidone polymers, polyamine N-oxide polymers, copolymers of N-vinylpyrrolidone and N-vinylimidazole, polyvinyloxazolidones and polyvinylimidazoles or mixtures thereof. In embodiments in which at least one dye transfer inhibiting agent is used, the cleaning compositions of the present invention comprise from about 0.0001% to about 10%, from about 0.01% to about 5%, or even from about 0.1% to about 3% by weight of the cleaning composition.

In some embodiments, silicates are included within the compositions of the present invention. In some such embodiments, sodium silicates (e.g., sodium disilicate, sodium metasilicate, and crystalline phyllosilicates) find use. In some embodiments, silicates are present at a level of from about 1% to about 20%. In some embodiments, silicates are present at a level of from about 5% to about 15% by weight of the composition.

In some still additional embodiments, the cleaning compositions of the present invention also contain dispersants. Suitable water-soluble organic materials include, but are not limited to the homo- or co-polymeric acids or their salts, in which the polycarboxylic acid comprises at least two carboxyl radicals separated from each other by not more than two carbon atoms.

In some further embodiments, the enzymes used in the cleaning compositions are stabilized by any suitable technique. In some embodiments, the enzymes employed herein are stabilized by the presence of water-soluble sources of calcium and/or magnesium ions in the finished compositions that provide such ions to the enzymes. In some embodiments, the enzyme stabilizers include oligosaccharides, polysaccharides, and inorganic divalent metal salts, including alkaline earth metals, such as calcium salts, such as calcium formate. It is contemplated that various techniques for enzyme stabilization will find use in the present invention. For example, in some embodiments, the enzymes employed herein are stabilized by the presence of water-soluble sources of zinc (II), calcium (II) and/or magnesium (II) ions in the finished compositions that provide such ions to the enzymes, as well as other metal ions (e.g., barium (II), scandium (II), iron (II), manganese (II), aluminum (III), Tin (II), cobalt (II), copper (II), nickel (II), and oxovanadium (IV). Chlorides and sulfates also find use in some embodiments of the present invention. Examples of suitable oligosaccharides and polysaccharides (e.g., dextrins) are known in the art (See e.g., WO 07145964). In some embodiments, reversible protease inhibitors also find use, such as boron-containing compounds (e.g., borate, 4-formyl phenyl boronic acid) and/or a tripeptide aldehyde find use to further improve stability, as desired.

In some embodiments, bleaches, bleach activators and/or bleach catalysts are present in the compositions of the present invention. In some embodiments, the cleaning compositions of the present invention comprise inorganic and/or organic bleaching compound(s). Inorganic bleaches include, but are not limited to perhydrate salts (e.g., perborate, percarbonate, perphosphate, persulfate, and persilicate salts). In some embodiments, inorganic perhydrate salts are alkali metal salts. In some embodiments, inorganic perhydrate salts are included as the crystalline solid, without additional protection, although in some other embodiments, the salt is coated. Any suitable salt known in the art finds use in the present invention (See e.g., EP 2100949).

In some embodiments, bleach activators are used in the compositions of the present invention. Bleach activators are typically organic peracid precursors that enhance the bleaching action in the course of cleaning at temperatures of 60° C. and below. Bleach activators suitable for use herein include compounds which, under perhydrolysis conditions, give aliphatic peroxoycarboxylic acids having preferably from about 1 to about 10 carbon atoms, in particular from about 2 to about 4 carbon atoms, and/or optionally substituted perbenzoic acid. Additional bleach activators are known in the art and find use in the present invention (See e.g., EP 2100949).

In addition, in some embodiments and as further described herein, the cleaning compositions of the present invention further comprise at least one bleach catalyst. In some embodiments, the manganese triazacyclononane and related complexes find use, as well as cobalt, copper, manganese, and iron complexes. Additional bleach catalysts find use in the present invention (See e.g., U.S. Pat. Nos. 4,246,612, 5,227,084, 4,810,410, WO9906521, and EP 2100949).

In some embodiments, the cleaning compositions of the present invention contain one or more catalytic metal complexes. In some embodiments, a metal-containing bleach catalyst finds use. In some embodiments, the metal bleach catalyst comprises a catalyst system comprising a transition metal cation of defined bleach catalytic activity, (e.g., copper, iron, titanium, ruthenium, tungsten, molybdenum, or manganese cations), an auxiliary metal cation having little or no bleach catalytic activity (e.g., zinc or aluminum cations), and a sequestrate having defined stability constants for the catalytic and auxiliary metal cations, particularly ethylenediaminetetraacetic acid, ethylenediaminetetra (methylenephosphonic acid) and water-soluble salts thereof are used (See e.g., U.S. Pat. No. 4,430,243). In some embodiments, the cleaning compositions of the present invention are catalyzed by means of a manganese compound. Such compounds and levels of use are well known in the art (See e.g., U.S. Pat. No. 5,576,282). In additional embodiments, cobalt bleach catalysts find use in the cleaning compositions of the present invention. Various cobalt bleach catalysts are known in the art (See e.g., U.S. Pat. Nos. 5,597,936 and 5,595,967) and are readily prepared by known procedures.

In some additional embodiments, the cleaning compositions of the present invention include a transition metal complex of a macropolycyclic rigid ligand (MRL). As a practical matter, and not by way of limitation, in some embodiments, the compositions and cleaning processes provided by the present invention are adjusted to provide on the order of at least one part per hundred million of the active MRL species in the aqueous washing medium, and in some embodiments, provide from about 0.005 ppm to about 25 ppm, more preferably from about 0.05 ppm to about 10 ppm, and most preferably from about 0.1 ppm to about 5 ppm, of the MRL in the wash liquor.

In some embodiments, transition-metals in the instant transition-metal bleach catalyst include, but are not limited to manganese, iron and chromium. MRLs also include, but are not limited to special ultra-rigid ligands that are cross-bridged (e.g., 5,12-diethyl-1,5,8,12-tetraazabicyclo[6.6.2] hexadecane). Suitable transition metal MRLs are readily prepared by known procedures (See e.g., WO 200032601 and U.S. Pat. No. 6,225,464).

In some embodiments, the cleaning compositions of the present invention comprise metal care agents. Metal care agents find use in preventing and/or reducing the tarnishing, corrosion, and/or oxidation of metals, including aluminum, stainless steel, and non-ferrous metals (e.g., silver and copper). Suitable metal care agents include those described in EP 2 100 949, WO 9426860 and WO 94/26859). In some embodiments, the metal care agent is a zinc salt. In some further embodiments, the cleaning compositions of the present invention comprise from about 0.1% to about 5% by weight of one or more metal care agent.

In some embodiments, the cleaning composition is a high density liquid (HDL) composition having a variant AprL-clade protease. The HDL liquid laundry detergent can comprise a detersive surfactant (10%-40% wt/wt), including an anionic detersive surfactant (selected from a group of linear or branched or random chain, substituted or unsubstituted alkyl sulphates, alkyl sulphonates, alkyl alkoxylated sulphate, alkyl phosphates, alkyl phosphonates, alkyl carboxylates, and/or mixtures thereof); and optionally non-ionic surfactant (selected from a group of linear or branched or random chain, substituted or unsubstituted alkyl alkoxylated alcohol, for example a $C_8$-$C_{18}$ alkyl ethoxylated alcohol and/or $C_6$-$C_{12}$ alkyl phenol alkoxylates), optionally wherein the weight ratio of anionic detersive surfactant (with a hydrophilic index (HIc) of from 6.0 to 9) to non-ionic detersive surfactant is greater than 1:1. Suitable detersive surfactants also include cationic detersive surfactants (selected from a group of alkyl pyridinium compounds, alkyl quarternary ammonium compounds, alkyl quarternary phosphonium compounds, alkyl ternary sulphonium compounds, and/or mixtures thereof); zwitterionic and/or amphoteric detersive surfactants (selected from a group of alkanolamine sulpho-betaines); ampholytic surfactants; semi-polar non-ionic surfactants and mixtures thereof.

The composition can comprise optionally, a surfactancy boosting polymer consisting of amphiphilic alkoxylated grease cleaning polymers (selected from a group of alkoxylated polymers having branched hydrophilic and hydrophobic properties, such as alkoxylated polyalkylenimines in the range of 0.05 wt %-10 wt %) and/or random graft polymers (typically comprising of hydrophilic backbone comprising monomers selected from the group consisting of: unsaturated $C_1$-$C_6$ carboxylic acids, ethers, alcohols, aldehydes, ketones, esters, sugar units, alkoxy units, maleic anhydride, saturated polyalcohols such as glycerol, and mixtures thereof; and hydrophobic side chain(s) selected from the group consisting of: $C_4$-$C_{25}$ alkyl group, polypropylene, polybutylene, vinyl ester of a saturated $C_1$-$C_6$ mono-carboxylic acid, $C_1$-$C_6$ alkyl ester of acrylic or methacrylic acid, and mixtures thereof.

The composition can comprise additional polymers such as soil release polymers (include anionically end-capped polyesters, for example SRP1, polymers comprising at least one monomer unit selected from saccharide, dicarboxylic acid, polyol and combinations thereof, in random or block configuration, ethylene terephthalate-based polymers and co-polymers thereof in random or block configuration, for example Repel-o-tex SF, SF-2 and SRP6, Texcare SRA100, SRA300, SRN100, SRN170, SRN240, SRN300 and SRN325, Marloquest SL), anti-redeposition polymers (0.1 wt % to 10 wt %, include carboxylate polymers, such as polymers comprising at least one monomer selected from acrylic acid, maleic acid (or maleic anhydride), fumaric acid, itaconic acid, aconitic acid, mesaconic acid, citraconic acid, methylenemalonic acid, and any mixture thereof, vinylpyrrolidone homopolymer, and/or polyethylene glycol, molecular weight in the range of from 500 to 100,000 Da); cellulosic polymer (including those selected from alkyl cellulose, alkyl alkoxyalkyl cellulose, carboxyalkyl cellulose, alkyl carboxyalkyl cellulose examples of which include carboxymethyl cellulose, methyl cellulose, methyl hydroxyethyl cellulose, methyl carboxymethyl cellulose, and mixtures thereof) and polymeric carboxylate (such as maleate/acrylate random copolymer or polyacrylate homopolymer).

The composition can further comprise saturated or unsaturated fatty acid, preferably saturated or unsaturated $C_{12}$-$C_{24}$ fatty acid (0 wt % to 10 wt %); deposition aids (examples for which include polysaccharides, preferably cellulosic polymers, poly diallyl dimethyl ammonium halides (DADMAC), and co-polymers of DAD MAC with vinyl pyrrolidone, acrylamides, imidazoles, imidazolinium halides, and mixtures thereof, in random or block configuration, cationic guar gum, cationic cellulose such as cationic hydoxyethyl cellulose, cationic starch, cationic polyacylamides, and mixtures thereof.

The composition can further comprise dye transfer inhibiting agents examples of which include manganese phthalocyanine, peroxidases, polyvinylpyrrolidone polymers, polyamine N-oxide polymers, copolymers of N-vinylpyrrolidone and N-vinylimidazole, polyvinyloxazolidones and polyvinylimidazoles and/or mixtures thereof; chelating agents examples of which include ethylene-diamine-tetraacetic acid (EDTA); diethylene triamine penta methylene phosphonic acid (DTPMP); hydroxy-ethane diphosphonic acid (HEDP); ethylenediamine N,N'-disuccinic acid (EDDS); methyl glycine diacetic acid (MGDA); diethylene triamine penta acetic acid (DTPA); propylene diamine tetracetic acid (PDT A); 2-hydroxypyridine-N-oxide (HPNO);

or methyl glycine diacetic acid (MGDA); glutamic acid N,N-diacetic acid (N,N-dicarboxymethyl glutamic acid tetrasodium salt (GLDA); nitrilotriacetic acid (NTA); 4,5-dihydroxy-m-benzenedisulfonic acid; citric acid and any salts thereof; N-hydroxyethylethylenediaminetri-acetic acid (HEDTA), triethylenetetraaminehexaacetic acid (TTHA), N-hydroxyethyliminodiacetic acid (HEIDA), dihydroxyethylglycine (DHEG), ethylenediaminetetrapropionic acid (EDTP) and derivatives thereof.

The composition can further comprise enzymes (generally about 0.01 wt % active enzyme to 0.5 wt % active enzyme) selected from proteases; amylases; lipases; cellulases; choline oxidases; peroxidases/oxidases; pectate lyases; mannanases; cutinases; laccases; phospholipases; lysophospholipases; acyltransferase; perhydrolase; arylesterase and any mixture thereof. The composition may comprise an enzyme stabilizer (examples of which include polyols such as propylene glycol or glycerol, sugar or sugar alcohol, lactic acid, reversible protease inhibitor, boric acid, or a boric acid derivative, e.g., an aromatic borate ester, or a phenyl boronic acid derivative such as 4-formylphenyl boronic acid).

The composition can further comprise silicone or fatty-acid based suds suppressors; hueing dyes, calcium and magnesium cations, visual signaling ingredients, anti-foam (0.001 wt % to about 4.0 wt %), and/or structurant/thickener (0.01 wt % to 5 wt %, selected from the group consisting of diglycerides and triglycerides, ethylene glycol distearate, microcrystalline cellulose, cellulose based materials, microfiber cellulose, biopolymers, xanthan gum, gellan gum, and mixtures thereof).

The composition can be any liquid form, for example a liquid or gel form, or any combination thereof.

In some embodiments, the cleaning compositions of the present invention are provided in unit dose form, including tablets, capsules, sachets, pouches, and multi-compartment pouches. In some embodiments, the unit dose format is designed to provide controlled release of the ingredients within a multi-compartment pouch (or other unit dose format). Suitable unit dose and controlled release formats are known in the art (See e.g., EP 2100949, WO02102955, U.S. Pat. Nos. 4,765,916, 4,972,017, and WO04111178 for materials suitable for use in unit dose and controlled release formats). In some embodiments, the unit dose form is provided by tablets wrapped with a water-soluble film or water-soluble pouches. Examples of various unit dose formats are provided in EP 2100947 and WO 2013165725.

In some embodiments, the cleaning composition is a high density powder (HDD) composition having a variant AprL-clade protease. The HDD powder laundry detergent can comprise a detersive surfactant including anionic detersive surfactants (e.g., linear or branched or random chain, substituted or unsubstituted alkyl sulphates, alkyl sulphonates, alkyl alkoxylated sulphate, alkyl phosphates, alkyl phosphonates, alkyl carboxylates and/or mixtures thereof), non-ionic detersive surfactant (e.g., linear or branched or random chain, substituted or unsubstituted $C_8$-$C_{18}$ alkyl ethoxylates, and/or $C_6$-$C_{12}$ alkyl phenol alkoxylates), cationic detersive surfactants (e.g., alkyl pyridinium compounds, alkyl quaternary ammonium compounds, alkyl quaternary phosphonium compounds, alkyl ternary sulphonium compounds, and mixtures thereof), zwitterionic and/or amphoteric detersive surfactants (e.g., alkanolamine sulpho-betaines); ampholytic surfactants; semi-polar non-ionic surfactants and mixtures thereof; builders (phosphate free builders (e.g., zeolite builders examples of which include zeolite A, zeolite X, zeolite P and zeolite MAP in the range of 0 wt % to less than 10 wt %); phosphate builders (e.g., sodium tri-polyphosphate in the range of 0 wt % to less than 10 wt %); citric acid, citrate salts and nitrilotriacetic acid or salt thereof in the range of less than 15 wt %); silicate salt (e.g., sodium or potassium silicate or sodium meta-silicate in the range of 0 wt % to less than 10 wt %, or layered silicate (SKS-6)); carbonate salt (e.g., sodium carbonate and/or sodium bicarbonate in the range of 0 wt % to less than 10 wt %); and bleaching agents (including photobleaches, (e.g., sulfonated zinc phthalocyanines, sulfonated aluminum phthalocyanines, xanthenes dyes, and mixtures thereof); hydrophobic or hydrophilic bleach activators (e.g., dodecanoyl oxybenzene sulfonate, decanoyl oxybenzene sulfonate, decanoyl oxybenzoic acid or salts thereof, 3,5,5-trimethy hexanoyl oxybenzene sulfonate, tetraacetyl ethylene diamine-TAED, nonanoyloxybenzene sulfonate-NOBS, nitrile quats, and mixtures thereof); sources of hydrogen peroxide (e.g., inorganic perhydrate salts examples of which include mono or tetra hydrate sodium salt of perborate, percarbonate, persulfate, perphosphate, or persilicate); preformed hydrophilic and/or hydrophobic peracids (e.g.,percarboxylic acids and salts, percarbonic acids and salts, perimidic acids and salts, and peroxymonosulfuric acids and salts) and mixtures thereof and/or bleach catalysts (e.g., imine bleach boosters (e.g., iminium cations and polyions); iminium zwitterions; modified amines; modified amine oxides; N-sulphonyl imines; N-phosphonyl imines; N-acyl imines; thiadiazole dioxides; perfluoroimines; cyclic sugar ketones and mixtures thereof; and metal-containing bleach catalyst (e.g., copper, iron, titanium, ruthenium, tungsten, molybdenum, or manganese cations along with an auxiliary metal cations such as zinc or aluminum and a sequestrate such as ethylenediaminetetraacetic acid, ethylenediaminetetra (methylenephosphonic acid) and water-soluble salts thereof).

The composition can further comprise enzymes selected from proteases; amylases; lipases; cellulases; choline oxidases; peroxidases/oxidases; pectate lyases; mannanases; cutinases; laccases; phospholipases; lysophospholipases; acyltransferase; perhydrolase; arylesterase and any mixture thereof.

The composition can further comprise additional detergent ingredients including perfume microcapsules, starch encapsulated perfume accord, hueing agents, additional polymers including fabric integrity and cationic polymers, dye lock ingredients, fabric-softening agents, brighteners (for example C.I. Fluorescent brighteners), flocculating agents, chelating agents, alkoxylated polyamines, fabric deposition aids, and/or cyclodextrin.

In some embodiments, the cleaning composition is an automatic dishwashing (ADW) detergent composition having a variant AprL-clade protease. The ADW detergent composition can comprise two or more non-ionic surfactants selected from a group of ethoxylated non-ionic surfactants, alcohol alkoxylated surfactants, epoxy-capped poly(oxyalkylated) alcohols, or amine oxide surfactants present in amounts from 0 to 10% by weight; builders in the range of 5-60% comprising either phosphate (mono-phosphates, di-phosphates, tri-polyphosphates or oligomeric-poylphosphates, preferred sodium tripolyphosphate-STPP or phosphate-free builders [amino acid based compounds, examples of which include MGDA (methyl-glycine-diacetic acid), and salts and derivatives thereof, GLDA (glutamic-N,Ndiacetic acid) and salts and derivatives thereof, IDS (iminodisuccinic acid) and salts and derivatives thereof, carboxy methyl inulin and salts and derivatives thereof and mixtures thereof, nitrilotriacetic acid (NTA), diethylene triamine penta acetic acid (DTPA), B-alaninediacetic acid (B-ADA) and their salts], homopolymers and copolymers of poly-carboxylic acids and their partially or completely neutralized salts, monomeric polycarboxylic acids and hydroxycarboxylic acids and their salts in the range of 0.5% to 50% by weight; sulfonated/carboxylated polymers (provide dimensional stability to the product) in the range of about 0.1% to about 50% by weight; drying aids in the range of about 0.1% to about 10% by weight (selected from polyesters, especially anionic polyesters optionally together with further monomers with 3 to 6 functionalities which are conducive to polycondensation, specifically acid, alcohol or ester functionalities, polycarbonate-, polyurethane- and/or polyurea-polyorganosiloxane compounds or precursor compounds thereof of the reactive cyclic carbonate and urea type); silicates in the range from about 1% to about 20% by weight (sodium or potassium silicates for example sodium disilicate, sodium meta-silicate and crystalline phyllosilicates); bleach-inorganic (for example perhydrate salts such as perborate, percarbonate, perphosphate, persulfate and persilicate salts) and organic (for example organic peroxyacids including diacyl and tetraacylperoxides, especially diperoxydodecanedioc acid, diperoxytetradecanedioc acid, and diperoxyhexadecanedioc acid); bleach activators-organic peracid precursors in the range from about 0.1% to about 10% by weight; bleach catalysts (selected from manganese triazacyclononane and related complexes, Co, Cu, Mn and Fe bispyridylamine and related complexes, and pentamine acetate cobalt(III) and related complexes); metal care agents in the range from about 0.1% to 5% by weight (selected from benzatriazoles, metal salts and complexes, and/or silicates); enzymes in the range from about 0.01 to 5.0 mg of active enzyme per gram of automatic dishwashing detergent composition (acyl transferases, alpha-amylases, beta-amylases, alpha-galactosidases, arabinosidases, aryl esterases, beta-galactosidases, carrageenases, catalases, cellobiohydrolases, cellulases, chondroitinases, cutinases, endo-beta-1, 4-glucanases, endo-beta-mannanases, esterases, exo-mannanases, galactanases, glucoamylases, hemicellulases, hyaluronidases, keratinases, laccases, lactases, ligninases, lipases, lipoxygenases, mannanases, oxidases, pectate lyases, pectin acetyl esterases, pectinases, pentosanases, peroxidases, phenoloxidases, phosphatases, phospholipases, phytases, polygalacturonases, proteases, pullulanases, reductases, rhamnogalacturonases, beta-glucanases, tannases, transglutaminases, xylan acetyl-esterases, xylanases, xyloglucanases, and xylosidases, and any mixture thereof); and enzyme stabilizer components (selected from oligosaccharides, polysaccharides and inorganic divalent metal salts).

As indicated above, the cleaning compositions of the present invention are formulated into any suitable form and prepared by any process chosen by the formulator, non-limiting examples of which are described in U.S. Pat. Nos. 5,879,584; 5,691,297; 5,574,005; 5,569,645; 5,516,448; 5,489,392; and 5,486,303. In some embodiments in which a low pH cleaning composition is desired, the pH of such composition is adjusted via the addition of an acidic material such as HCl.

The cleaning compositions disclosed herein of find use in cleaning a situs (e.g., a surface, item, dishware, or fabric). Typically, at least a portion of the situs is contacted with an embodiment of the present cleaning composition, in neat form or diluted in wash liquor, and then the situs is optionally washed and/or rinsed. For purposes of the present invention, "washing" includes but is not limited to, scrubbing, and mechanical agitation. In some embodiments, the cleaning compositions are typically employed at concentrations of from about 500 ppm to about 15,000 ppm in solution. When the wash solvent is water, the water temperature typically ranges from about 5° C. to about 90° C. and, when the situs comprises a fabric, the water to fabric mass ratio is typically from about 1:1 to about 30:1.

Processes of Making and Using Cleaning Compositions

The cleaning compositions of the present invention are formulated into any suitable form and prepared by any suitable process chosen by the formulator, (See e.g., U.S. Pat. Nos. 5,879,584; 5,691,297; 5,574,005; 5,569,645; 5,565,422; 5,516,448; 5,489,392; 5,486,303; 4,515,705; 4,537,706; 4,515,707; 4,550,862; 4,561,998; 4,597,898; 4,968,451; 5,565,145; 5,929,022; 6,294,514 and 6,376,445).

Methods of Use

In some embodiments, the cleaning compositions of the present invention find use in cleaning surfaces (e.g., dishware), laundry, hard surfaces, contact lenses, etc. In some embodiments, at least a portion of the surface is contacted with at least one embodiment of the cleaning compositions of the present invention, in neat form or diluted in a wash liquor, and then the surface is optionally washed and/or rinsed. For purposes of the present invention, "washing" includes, but is not limited to, scrubbing, and mechanical washing. In some embodiments, the cleaning compositions of the present invention are used at concentrations of from about 500 ppm to about 15,000 ppm in solution. In some embodiments in which the wash solvent is water, the water temperature typically ranges from about 5° C. to about 90° C.

The present invention provides methods for cleaning or washing an item or surface (e.g., hard surface) in need of cleaning, including, but not limited to methods for cleaning or washing a dishware item, a tableware item, a fabric item, a laundry item, personal care item, etc., or the like, and methods for cleaning or washing a hard or soft surface (e.g., a hard surface of an item).

In some embodiments, the present invention provides a method for cleaning an item, object, or surface in need of cleaning, the method comprising contacting the item or surface (or a portion of the item or surface desired to be cleaned) with at least one variant AprL-clade protease of the present invention or a composition of the present invention for a sufficient time and/or under conditions suitable and/or effective to clean the item, object, or surface to a desired degree. Some such methods further comprise rinsing the item, object, or surface with water. For some such methods, the cleaning composition is a dishwashing detergent composition and the item or object to be cleaned is a dishware item or tableware item. As used herein, a "dishware item" is an item generally used in serving or eating food. A dishware item can be, but is not limited to for example, a dish, plate, cup, bowl, etc., and the like. As used herein, "tableware" is a broader term that includes, but is not limited to for example, dishes, cutlery, knives, forks, spoons, chopsticks, glassware, pitchers, sauce boats, drinking vessels, serving items, etc. It is intended that "tableware item" includes any of these or similar items for serving or eating food. For some such methods, the cleaning composition is an automatic dishwashing detergent composition or a hand dishwashing detergent composition and the item or object to be cleaned is a dishware or tableware item. For some such methods, the cleaning composition is a laundry detergent composition (e.g., a power laundry detergent composition or a liquid laundry detergent composition), and the item to be cleaned is a fabric item. In some other embodiments, the cleaning composition is a laundry pre-treatment composition.

In some embodiments, the present invention provides methods for cleaning or washing a fabric item optionally in need of cleaning or washing, respectively. In some embodiments, the methods comprise providing a composition comprising the variant protease, including but not limited to fabric or laundry cleaning composition, and a fabric item or laundry item in need of cleaning, and contacting the fabric item or laundry item (or a portion of the item desired to be cleaned) with the composition under conditions sufficient or effective to clean or wash the fabric or laundry item to a desired degree.

In some embodiments, the present invention provides a method for cleaning or washing an item or surface (e.g., hard surface) optionally in need of cleaning, the method comprising providing an item or surface to be cleaned or washed and contacting the item or surface (or a portion of the item or surface desired to be cleaned or washed) with at least one AprL-clade variant of the invention or a composition of the invention comprising at least one such AprL-clade variant for a sufficient time and/or under conditions sufficient or effective to clean or wash the item or surface to a desired degree. Such compositions include, but are not limited to for example, a cleaning composition or detergent composition of the invention (e.g., a hand dishwashing detergent composition, hand dishwashing cleaning composition, laundry detergent or fabric detergent or laundry or fabric cleaning composition, liquid laundry detergent, liquid laundry cleaning composition, powder laundry detergent composition, powder laundry cleaning composition, automatic dishwashing detergent composition, laundry booster cleaning or detergent composition, laundry cleaning additive, and laundry pre-spotter composition, etc.). In some embodiments, the method is repeated one or more times, particularly if additional cleaning or washing is desired. For example, in some instance, the method optionally further comprises allowing the item or surface to remain in contact with the at least one variant protease or composition for a period of time sufficient or effective to clean or wash the item or surface to the desired degree. In some embodiments, the methods further comprise rinsing the item or surface with water and/or another liquid. In some embodiments, the methods further comprise contacting the item or surface with at least one variant protease of the invention or a composition of the invention again and allowing the item or surface to remain in contact with the at least one variant protease or composition for a period of time sufficient to clean or wash the item or surface to the desired degree. In some embodiments, the cleaning composition is a dishwashing detergent composition and the item to be cleaned is a dishware or tableware item. In some embodiments of the present methods, the cleaning composition is an automatic dishwashing detergent composition or a hand dishwashing detergent composition and the item to be cleaned is a dishware or tableware item. In some embodiments of the methods, the cleaning composition is a laundry detergent composition and the item to be cleaned is a fabric item.

The present invention also provides methods of cleaning a tableware or dishware item in an automatic dishwashing machine, the method comprising providing an automatic dishwashing machine, placing an amount of an automatic dishwashing composition comprising at least one AprL-clade variant of the present invention or a composition of the invention sufficient to clean the tableware or dishware item in the machine (e.g., by placing the composition in an appropriate or provided detergent compartment or dispenser in the machine), putting a dishware or tableware item in the machine, and operating the machine so as to clean the tableware or dishware item (e.g., as per the manufacturer's instructions). In some embodiments, the methods include any automatic dishwashing composition described herein, which comprises, but is not limited to at least one AprL-clade variant provided herein. The amount of automatic dishwashing composition to be used can be readily determined according to the manufacturer's instructions or suggestions and any form of automatic dishwashing composition comprising at least one variant protease of the invention (e.g., liquid, powder, solid, gel, tablet, etc.), including any described herein, may be employed.

The present invention also provides methods for cleaning a surface, item or object optionally in need of cleaning, the method comprises contacting the item or surface (or a portion of the item or surface desired to be cleaned) with at least one AprL-clade variant of the present invention or a cleaning composition of the invention in neat form or diluted in a wash liquor for a sufficient time and/or under conditions sufficient or effective to clean or wash the item or surface to a desired degree. The surface, item, or object may then be (optionally) washed and/or rinsed if desired. For purposes of the present invention, "washing" includes, but is not limited to for example, scrubbing and mechanical agitation. In some embodiments, the cleaning compositions are employed at concentrations of from about 500 ppm to about 15,000 ppm in solution (e.g., aqueous solution). When the wash solvent is water, the water temperature typically ranges from about 5° C. to about 90° C.

The present invention also provides methods of cleaning a laundry or fabric item in an washing machine, the method comprising providing an washing machine, placing an amount of a laundry detergent composition comprising at least one variant AprL-clade enzyme of the invention sufficient to clean the laundry or fabric item in the machine (e.g., by placing the composition in an appropriate or provided detergent compartment or dispenser in the machine), placing the laundry or fabric item in the machine, and operating the machine so as to clean the laundry or fabric item (e.g., as per the manufacturer's instructions). The methods of the present invention include any laundry washing detergent composition described herein, comprising but not limited to at least one of any variant AprL-clade enzyme provided herein. The amount of laundry detergent composition to be used can be readily determined according to manufacturer's instructions or suggestions and any form of laundry detergent composition comprising at least one variant protease of the invention (e.g., solid, powder, liquid, tablet, gel, etc.), including any described herein, may be employed.

Representative detergent formulations that beneficially include a serine protease polypeptide of the present invention include the detergent formulations found in WO2013063460, pages 78-152, and in particular the tables of pages 94 to 152 are hereby incorporated by reference. The serine proteases are normally incorporated into the detergent composition at a level of from 0.00001% to 10% of enzyme protein by weight of the composition. In some embodiments, the detergent composition comprises more than 0.0001%, 0.001%, 0.01%, or 0.1% of the serine protease by weight of the composition. In some embodiments, the detergent composition comprises less than 1%, 0.1%, 0.01%, or 0.001% of the serine protease by weight of the composition.

AprL-Clade Protease Polypeptides of the Present Invention for Use in Animal Feed In a further aspect of the invention, the AprL-clade protease polypeptides of the present invention can be used as a componetnt of an animal feed composition, animal feed additive and/or pet food comprising an AprL-clade protease and variants thereof. The present invention further relates to a method for preparing such an animal feed composition, animal feed additive composition and/or pet food comprising mixing the AprL-clade protease polypeptide with one or more animal feed ingredients and/or animal feed additive ingredients and/or pet food ingredients. Furthermore, the present invention relates to the use of the AprL-clade protease polypeptide in the preparation of an animal feed composition and/or animal feed additive composition and/or pet food.

The term "animal" includes all non-ruminant and ruminant animals. In a particular embodiment, the animal is a non-ruminant animal, such as a horse and a mono-gastric animal. Examples of mono-gastric animals include, but are not limited to, pigs and swine, such as piglets, growing pigs, sows; poultry such as turkeys, ducks, chicken, broiler chicks, layers; fish such as salmon, trout, tilapia, catfish and carps; and crustaceans such as shrimps and prawns. In a further embodiment the animal is a ruminant animal including, but not limited to, cattle, young calves, goats, sheep, giraffes, bison, moose, elk, yaks, water buffalo, deer, camels, alpacas, llamas, antelope, pronghorn and nilgai.

In the present context, it is intended that the term "pet food" is understood to mean a food for a household animal such as, but not limited to, dogs, cats, gerbils, hamsters, chinchillas, fancy rats, guinea pigs; avian pets, such as canaries, parakeets, and parrots; reptile pets, such as turtles, lizards and snakes; and aquatic pets, such as tropical fish and frogs.

The terms "animal feed composition," "feedstuff" and "fodder" are used interchangeably and can comprise one or more feed materials selected from the group comprising a) cereals, such as small grains (e.g., wheat, barley, rye, oats and combinations thereof) and/or large grains such as maize or sorghum; b) by products from cereals, such as corn gluten meal, Distillers Dried Grain Solubles (DDGS) (particularly corn based Distillers Dried Grain Solubles (cDDGS), wheat bran, wheat middlings, wheat shorts, rice bran, rice hulls, oat hulls, palm kernel, and citrus pulp; c) protein obtained from sources such as soya, sunflower, peanut, lupin, peas, fava beans, cotton, canola, fish meal, dried plasma protein, meat and bone meal, potato protein, whey, copra, sesame; d) oils and fats obtained from vegetable and animal sources; e) minerals and vitamins.

AprL-Clade Protease Polypeptides of the Present Invention for Use in Textile Desizing Also contemplated are compositions and methods of treating fabrics (e.g., to desize a textile) using an AprL-clade protease polypeptide of the present invention. Fabric-treating methods are well known in the art (see, e.g., U.S. Pat. No. 6,077,316). For example, the feel and appearance of a fabric can be improved by a method comprising contacting the fabric with an AprL-clade protease in a solution. The fabric can be treated with the solution under pressure.

An AprL-clade protease of the present invention can be applied during or after the weaving of a textile, or during the desizing stage, or one or more additional fabric processing steps. During the weaving of textiles, the threads are exposed to considerable mechanical strain. Prior to weaving on mechanical looms, warp yarns are often coated with sizing starch or starch derivatives to increase their tensile strength and to prevent breaking. An AprL-clade protease of the present invention can be applied during or after the weaving to remove the sizing starch or starch derivatives. After weaving, the AprL-clade protease can be used to remove the size coating before further processing the fabric to ensure a homogeneous and wash-proof result.

An AprL-clade protease of the present invention can be used alone or with other desizing chemical reagents and/or desizing enzymes to desize fabrics, including cotton-containing fabrics, as detergent additives, e.g., in aqueous compositions. An amylase also can be used in compositions and methods for producing a stonewashed look on indigo-dyed denim fabric and garments. For the manufacture of clothes, the fabric can be cut and sewn into clothes or garments, which are afterwards finished. In particular, for the manufacture of denim jeans, different enzymatic finishing methods have been developed. The finishing of denim garment normally is initiated with an enzymatic desizing step, during which garments are subjected to the action of proteolytic enzymes to provide softness to the fabric and make the cotton more accessible to the subsequent enzymatic finishing steps. The AprL-clade protease can be used in methods of finishing denim garments (e.g., a "bio-stoning process"), enzymatic desizing and providing softness to fabrics, and/or finishing process.

AprL-Clade Protease Polypeptides of the Present Invention for Use in Paper Pulp Bleaching The AprL-clade protease polypeptides described herein find further use in the enzyme aided bleaching of paper pulps such as chemical pulps, semi-chemical pulps, kraft pulps, mechanical pulps or pulps prepared by the sulfite method. In general terms, paper pulps are incubated with an AprL-clade protease polypeptide of the present invention under conditions suitable for bleaching the paper pulp.

In some embodiments, the pulps are chlorine free pulps bleached with oxygen, ozone, peroxide or peroxyacids. In some embodiments, the AprL-clade protease polypeptides are used in enzyme aided bleaching of pulps produced by modified or continuous pulping methods that exhibit low lignin contents. In some other embodiments, the AprL-clade protease polypeptides are applied alone or preferably in combination with xylanase and/or endoglucanase and/or alpha-galactosidase and/or cellobiohydrolase enzymes.

AprL-Clade Protease Polypeptides of the Present Invention for Use in Protein Degradation The AprL-clade protease polypeptides described herein find further use in the enzyme aided removal of proteins from animals and their subsequent degradation or disposal, such as feathers, skin, hair, hide, and the like. In some instances, immersion of the animal carcass in a solution comprising an AprL-clade protease polypeptide of the present invention can act to protect the skin from damage in comparison to the traditional immersion in scalding water or the defeathering process. In one embodiment, feathers can be sprayed with an isolated metalloprotase polypeptide of the present invention under conditions suitable for digesting or initiating degradation of the plumage. In some embodiments, an AprL-clade protease of the present invention can be used, as above, in combination with an oxidizing agent.

In some embodiments, removal of the oil or fat associated with raw feathers is assisted by using an AprL-clade protease polypeptide of the present invention. In some embodiments, the AprL-clade protease polypeptides are used in compositions for cleaning the feathers as well as to sanitize and partially dehydrate the fibers. In some other embodiments, the AprL-clade protease polypeptides are applied in a wash solution in combination with 95% ethanol or other polar organic solvent with or without a surfactant at about 0.5% (v/v).

In yet other embodiments, the disclosed AprL-clade protease polypeptides find use in recovering protein from plumage. The disclosed AprL-clade protease polypeptides may be used alone or in combination with other enzymes or pre-treatments such as heat and pressure, in suitable feather processing and proteolytic methods, such as those disclosed in PCT/EP2013/065362, PCT/EP2013/065363, and PCT/EP2013/065364, which are hereby incorporated by reference. In some embodiments, the recovered protein can be subsequently used in animal or fish feed.

AprL-Clade Protease Polypeptides of the Present Invention for Use in Tissue Debridement The AprL-clade protease polypeptides described herein find further use in the enzyme aided debridement of tissue. This involves the removal of dead or damaged tissue, for example, removal from wounds to aid in healing.

AprL-Clade Protease Polypeptides of the Present Invention for Use in Tissue Culture The AprL-clade protease polypeptides described herein find further use in tissue culture. In particular, AprL-clade proteases of the present invention can be used to suspend or resuspend cells adherent to a cell culture wall, such as during the process of harvesting cells. AprL-clade proteases of the present invention can be used to cleave protein bonds between cultured cells and the dish, allowing cells to become suspended in solution.

AprL-Clade Protease Polypeptides of the Present Invention in Food Applications

The AprL-clade protease polypeptides described herein find further use as a food additive, a digestive aide or a food processing aid.

AprL-Clade Protease Polypeptides of the Present Invention for Use in Leather Processing The AprL-clade protease polypeptides described herein find further use in leather processing by removing hair from animal hides, soaking, degreasing, or bating, which is a process involving degradation of non-structural proteins during leather making.

EXAMPLE 1

Assays

The following assays are standard assays used in the examples described below. Occasionally specific protocols call for deviations from these standard assays. In those cases, deviations from these standard assay protocols below are identified in the examples.

Performance Index

The performance index (PI) of an enzyme compares the performance of the variant (measured value) with the parent enzyme (theoretical value or measured value) at the same protein concentration. Theoretical concentrations for the parent enzyme can be calculated using the parameters extracted from a Langmuir fit of a standard curve of the parent enzyme. A PI that is greater than 1 (PI>1) indicates improved performance by a variant as compared to the parent (e.g. AprL mature protein, SEQ ID NO: 2), while a PI of 1 (PI=1) identifies a variant that performs the same as the parent, and a PI that is less than 1 (PI<1) identifies a variant that performs worse than the parent.

Protein Determination Assay

Protein concentration was performed using a high performance liquid chromatography (HPLC) method to measure the integrated peak area of supernatants derived from cultures grown in 96-well microtiter plates (MTPs). An Agilent 1200 or 1260 HPLC equipped with an Acquity UPLC BEH 125 SEC (Waters) size exclusion column was used. Sample was eluted from the column using 25 mM sodium phosphate buffer pH 6.8 containing 250 mM sodium chloride. Absorbance was measured at 220 nm, and peaks were integrated using ChemStation software (Agilent Technologies). The protein concentration of the samples was calculated based on a standard curve of the purified parent enzyme.

Protease Activity

The protease activity of AprL protease and variants thereof was tested by measuring the hydrolysis of N-suc-AAPF-pNA or dimethylcasein (DMC) substrates. For the AAPF assay, the reagent solutions used were: 100 mM Tris pH 8.6, 10 mM CalC12, 0.005% Tween®-80 (Tris/Ca buffer) and 160 mM suc-AAPF-pNA in DMSO (suc-AAPF-pNA stock solution) (Sigma: S-7388). To prepare a working solution, 1 mL suc-AAPF-pNA stock solution was added to 100 mL Tris/Ca buffer and mixed. An enzyme sample was added to a MTP (Greiner 781101) containing 1 mg/mL suc-AAPF-pNA working solution and assayed for activity at 405 nm over 3 min using a SpectraMax plate reader in kinetic mode at RT. The protease activity was expressed as $mOD*min^{-1}$.

For the DMC assay, the reagent solutions used were: 2.5% Dimethylcasein (DMC, Sigma) in 100 mM Sodium Carbonate pH 9.5, 0.075% TNBSA (2,4,6-trinitrobenzene sulfonic acid, Thermo Scientific) in Reagent A. Reagent A: 45.4 g $Na_2B_4O_7.10H_2O$ (Merck) in 15 mL 4N NaOH to reach a final volume of 1000 mL in MQ water, Dilution Solution: 10 mM NaCl, 0.1 mM $CaCl_2$, 0.005% Tween-80, 0.02% Na-azide. MTPs (Greiner PS-microwell 384) were filled with 47.5 uL DMC substrate following the addition of 2.5 uL of 20 ppm protease supernatant. 50 uL of TNBSA in reagent A was then added with slow mixing. Activity was measured at 405 nm over 5 min using a SpectraMax plate reader in kinetic mode at RT. As stated above for the AAPF assay, activity was expressed as mOD/min.

General Sample Set-Up for Stability Assays

Variants were tested for stability under various stress conditions (buffers and detergents as indicated on the Table below) by measuring the residual activity following incubation at elevated temperature. The elevated temperature was set to obtain approximately 30% residual activity of the stressed sample compared to the unstressed sample. Diluted enzyme sample was mixed in stressor and unstressed protease activity was measured. The diluted sample in stressor was incubated at elevated temperature followed by measurement of the stressed protease activity either by AAPF or DMC hydrolysis.

The stability assay conditions are described in the Table 1 below, detergents were inactivated prior to use in stability assays:

TABLE 1

Conditions used for protease stability assays

| Condition | Stress temperature (° C.) |
| --- | --- |
| 0.02% LAS, 2.1 mM EDTA in 50 mM Hepes pH 8, 0.005% Tween | 53.5 |
| 10% Kirkland Ultra | 56 |
| 10% OMO Klein & Krachtig | 51 |

For the unstressed condition, enzyme was assayed immediately for activity on AAPF or DMC (see above). For the stressed condition, the PCR plate was sealed and incubated at elevated temperature for 5 min using an Eppendorf 385 MasterCycler Pro Thermocycler, then assayed for activity. Stressed and unstressed activity was measured by either the hydrolysis of the synthetic substrate or by the DMC method, as described above. % residual activities were calculated by taking a ratio of the stressed to unstressed activity and multiplying it by 100. Stability PIs were obtained by dividing the residual activity of a variant by that of the wild type.

Cleaning Performance in Laundry and Automatic Dish Detergents

Variants were tested for cleaning performance relative to wild type AprL on BMI (blood/milk/ink on cotton) microswatches (EMPA-116) for laundry-based applications, and on egg yolk (egg yolk on polyacryl fabric, aged and colored with carbon black dye) microswatches (PAS-38) for dish-based applications. Pre-punched (to fit on MPT), rinsed, and filled swatch-containing plates (Corning 3641) were prepared by Center for Testmaterials BV. Vlaardingen, Netherlands. The microswatch plates were filled with detergent prior to enzyme addition. Commercial detergents were heat-inactivated to remove enzyme activity and dosed as described on Table 2.

Detergent treatments for enzyme inactivation were as follows. HDL laundry detergents were inactivated by heating the neat liquid to 95° C. for 16 hours in a water bath. Protease activity was assayed following inactivation using the AAPF substrate to ensure complete inactivation. HDD laundry detergents were inactivated by preparing a 10× concentrated solution relative to what is used in the final cleaning assay and heating for 16 hours at 95° C. Protease activity was assayed following inactivation using the AAPF substrate. After 16 hours of heating both HDD and HDL detergents, protease activity was non-existent. Table 3 shows the composition of the GSM-B pH10.5 ADW detergent (purchased from WFK Testgewebe GmbH, Brüggen, Deutschland, www.testgewebe.de)

TABLE 2

List of detergent conditions used for performance assays

| Detergent | Type | Final Wash Conc, (g/L) | Hardness Conc. (ppm) | Buffer | *Set pH |
|---|---|---|---|---|---|
| Kirkland Ultra | HDD | 1.09 | 150 | 2 mM NaCO$_3$ | 10.6 |
| OMO Color | HDD | 5.3 | 250 | 2 mM NaCO$_3$ | 10.6 |
| Surf Excel | HDD | 4 | 400 | 2 mM NaCO$_3$ | 10.6 |
| Kirkland Ultraclean | HDL | 0.71 | 150 | 5 mM sodium HEPES | 8.2 |
| OMO Klein & Krachtig | HDL | 2.8 | 250 | 5 mM sodium HEPES | 8.2 |
| Blue Moon | HDL | 13 | 250 | 5 mM sodium HEPES | 6.5 |
| GSM-B 10.5 | ADW | 3 | 374 ppm | 1M citrate added | 10.5 |
| GSM-B 9 | ADW | 3 | 374 ppm | 1M citrate added | 9 |

*pH was set for those detergents where value is provided and not for those marked ND. Detergent sources: Kirkland Ultra and Kirkland Ultraclean (Sun Products), OMO Color, and OMO Klein & Krachtig, Surf Excel (Unilever), and Blue Moon (Guangzhou Blue Moon) were purchased from local supermarkets in 2012.

TABLE 3

Composition of GSM-B pH 10.5 ADW
GSM-B Phosphate-Free Detergent

| Component | Wt % |
|---|---|
| Sodium citrate dehydrate | 30.0 |
| Maleic acid/acrylic acid copolymer sodium Salt (SOKALAN ® CP5; BASF) | 12.0 |
| Sodium perborate monohydrate | 5.0 |
| TAED | 2.0 |
| Sodium disilicate: Protil A (Cognis) | 25.0 |
| Linear fatty alcohol ethoxylate | 2.0 |
| Sodium carbonate anhydrous | add to 100 |

Aliquots of enzyme were added to a detergent-filled microswatch plate to reach a final volume of 200 uL for laundry assays with a final enzyme concentration between 5-0.5 ppm. Laundry cleaning assays with HDL or HDD formulas were carried out at 25° C. for 15-20 min while automatic dish (ADW) assays were carried out at 40° C. for 30 min. Following incubation, 100 uL of supernatant was transferred to a fresh MTP (Costar 9017) and absorbance was read at 600 nm for EMPA-116 swatches or at 405 nm for PAS-38 swatches using the SpectraMax plate reader. Absorbance results were obtained by subtracting the value for a blank control (no enzyme) from each sample value. The cleaning PI for each assay condition was obtained by dividing the absorbance values for a given variant by that of the predicted wild-type at the same concentration. The wild-type value was determined by fitting the standard curve of the purified parent to a Langmuir fit.

EXAMPLE 2

Generation of Site Evaluation Library (SEL) of AprL Protease

Figure 1:
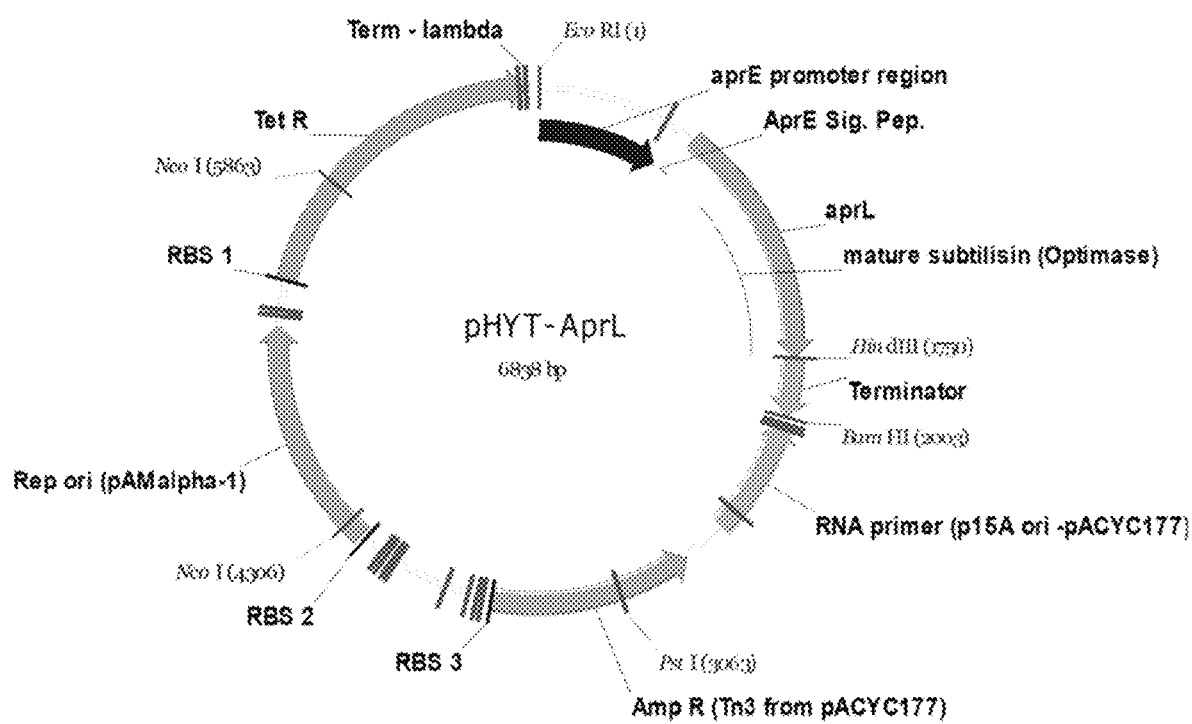

A synthetic gene encoding the AprL sequence was synthesized by GeneArt, Life Technologies and cloned into the expression vector "pHYT" (derived from pHY300PLK (Takara)). The pHYT expression vector contains the aprE promoter and leader sequences. A map of the pHYT vector containing the AprL gene (pHYT-AprL) is shown in FIG. 1. The nucleotide sequence of the AprL gene is set forth in SEQ ID NO:1. The amino acid sequence of the mature form of AprL protein is set forth in SEQ ID NO:2. The nucleotide sequence of the aprE promoter is set forth in SEQ ID NO:3. The nucleotide sequence of the signal peptide is set forth in SEQ ID NO:4. The nucleotide sequence of the propeptide is set forth in SEQ ID NO:5. The nucleotide sequence of the terminator is set forth below as SEQ ID NO:6.

Using molecular biology techniques known in the art, positional libraries at each of the sites in the AprL mature protein were generated. The corresponding codon for each site was substituted with codons for at least 10 (out of a possible 19) different amino acids. A suitable B. subtilis host strain was transformed with expression plasmids containing the variants. The variants were provided in 96-well MTPs. The variants were grown in cultivation medium (enriched semi-defined media based on MOPs buffer, with urea as major nitrogen source, glucose as the main carbon source, and supplemented with 1% soytone for robust cell growth) containing 25 ppm tetracycline in square enzyscreen plates for 2 days at 32° C., 300 rpm, with 80% humidity in Shaking Incubator.

EXAMPLE 3

Productive Positions and Combinable Mutations

Productive positions are positions within a molecule that are most useful for making combinatorial variants exhibiting an improved characteristic, where the position itself allows for at least one combinable mutation. Combinable mutations are substitutions that can be used to make combinatorial variants.

Combinable mutations are ones that improve at least one desired property of the molecule, while not significantly decreasing either: expression, activity, or stability. Combinable mutations in AprL were determined using PI values resulting from the following assays described in Example 1:

Expression (Protein Determination); Protease activity (AAPF assay and DMC assay); Cleaning activity in the following detergents: Kirkland Ultra HDD pH 10.6, OMO Color HDD pH 10.6, Surf Excel HDD pH 10.6, Kirkland Ultraclean, HDL pH 8.2,OMO Klein & Krachtig HDL pH 8.2, Blue Moon HDL pH6.5, GSM-B pH 10, GSM-B pH 9; Stability assays in the following detergent and buffers: LAS-EDTA buffer at 53.5° C., 10% Kirkland Ultra at 56° C., and 10% OMO Klein & Krachtig at 51° C.

Combinable mutations have been grouped according to the following criteria: (i) a variant where the minimum PI relative to AprL parent for expression, protease activity including activity in one or more of the cleaning activity assays, and one or more of the stability assays are ≥0.9, and in addition have a PI for any one of these tests that is ≥1.0 (Group A); (ii) a variant where the minimum PI relative to AprL parent for expression, protease activity including activity in one or more of the cleaning activity assays, and one or more of the stability assays are ≥0.8, and in addition have a PI for any one of these tests that ≥1.2 (Group B); or (iii) a variant where the minimum PI relative to AprL parent for expression, protease activity including activity in one or more of the cleaning activity assays, and one or more of the stability assays ≥0.5, and in addition have a PI for any one of these tests that is ≥1.5 (Group C). The properties of combinable mutations are summarized in Table 4

TABLE 4

Properties For Each Group Of Combinable Mutations

| | | Performance Index (PI) | | | |
|---|---|---|---|---|---|
| Group | Expression | Cleaning (pH 6, 8, 9, 10) | Stability (detergent or buffer) | Protease activity assay | Minimum PI in one or more tests |
| A | ≥0.9 | ≥0.9 | ≥0.9 | ≥0.9 | X ≥ 1.0 |
| B | ≥0.8 | ≥0.8 | ≥0.8 | ≥0.8 | X ≥ 1.2 |
| C | ≥0.5 | ≥0.5 | ≥0.5 | ≥0.5 | X ≥ 1.5 |

Groups A, B, and C further contain amino acid positions that have differing degrees of tolerance for multiple substitutions. To identify productive positions, we measure the degree of substitutions tolerated at each position and assign a Productivity Score to each position. The Productivity Score was assigned according to the percentage of substitutions within each position that fall within groups A, B, or C, using the criteria set forth below.

Productive positions are defined as the positions which have shown a certain degree of tolerance for multiple substitutions, while at the same time meeting a set of criteria for combinability as set forth below. The criteria to determine the Productivity Score for productive positions are set forth as follows: (i) positions where <15% of the substitutions at a given position fall within groups A, B, or C are given a Productivity Score of "1"; (ii) positions where <40%, but ≥ to 15% of the substitutions at a given position fall within groups A, B, or C are given a Productivity Score of "2"; (iii) positions where <60%, but ≥40% of the substitutions at a given position fall within groups A, B, or C are given a Productivity Score of "3"; and (iv) positions where 60% or more of the substitutions at a given position fall within groups A, B, or C are given a Productivity Score of "4".

Positions with Productivity Score of "1" are:
4, 17, 21, 30, 33, 36, 47, 49, 51, 62, 66, 72, 74, 75, 76, 93, 106, 107, 110, 111, 112, 121, 134, 135, 137, 138, 141, 149, 151, 156, 157, 159, 163, 169, 175, 183, 186, 188, 191, 204, 207, 208, 209, 215, 223, 224, 227, 229, 230, 231, 232, 233, 236, 249, 250, 254, 255, 260, 267, 269, 271, and 273.

Positions and Corresponding Mutations with Productivity Score of "1" are:
4 (V,I); 17 (Q,H, M); 21 (F,Y); 30 (V,C,T); 33 (T,C,M); 36 (Q,E,H); 47 (G,A,M); 49 (S,I,T); 51 (V,C,I); 62 (G,S); 66 (H, R); 72 (A,G,S); 74 (L,G); 75 (D,C,E); 76 (N,K); 93 (K,D); 106 (I,G,M); 107 (V,F,I); 110 (I,F); 111 (E,D, Q); 112 (W,A); 121 (I,L,M); 134 (M,L); 135 (K,E,H); 137 (A,S); 138 (V,C,S); 141 (A,S); 149 (V,C); 151 (A,G,P); 156 (G,E); 157 (S,D,R); 159 (G,A,F); 163 (T,E); 169 (K,R); 175 (A,C); 183 (S,A,G); 186 (A, C); 188 (F,W); 191 (V,C); 204 (V,I); 207 (T,C); 208 (Y,F); 209 (P,S); 215 (T,C,V); 223 (S,A,C); 224 (P, A); 227 (A,S); 229 (A,G,S); 230 (A,\G); 231 (A,C); 232 (L,Q); 233 (I,V); 236 (K,A); 249 (L,I,M); 250 (S,A,G); 254 (T,D); 255 (Y,C,E); 260 (F,C,W); 267 (I,C); 269 (V,A,C); 271 (A,D,E); and 273 (A,S).

Positions with Productivity Score of "2" are:
2, 3, 10, 18, 19, 28, 29, 31, 35, 37, 38, 40, 44, 46, 50, 54, 56, 61, 67, 68, 71, 87, 90, 91, 92, 101, 103, 104, 113, 118, 120, 123, 130, 131, 133, 139, 145, 147, 148, 181, 182, 184, 193, 205, 211, 212, 214, 216, 217, 221, 235, 242, 245, 248, 251, 258, 259, and 268.

Positions and Corresponding Mutations with Productivity Score of "2" are:
2 (Q,A,I,N); 3 (T,E,I,Q, V); 10 (L,F,M,Q); 18 (A,C,D,E, S); 19 (Q,A,D,E,G,M); 28 (V,A,C,S); 29 (A,C,S,T,V); 31 (L,C, I,V); 35 (I,A,C,G,M,S,T,V); 37 (A,E,G,S); 38 (S,A, C,E,G,N,T); 40 (P,A,C,D,E,M,V); 44 (V,C,E,P,S,T); 46 (G,A,C,D,W); 50 (F,H,K,M,Q,R,V,Y); 54 (E,Q,R,T); 56 (Y,C,E,F,H,P); 61 (N,A,D,F,H,K,Q); 67 (V, M,N,Q); 68 (A,C,G,N,S,T); 71 (V,A,G,L,S); 87 (V,C,G,S,T); 90 (Y,A, C,F,H,N,V); 91 (A,G,M,P,V); 92 (V,A,C,I,T); 101 (G,A,C, N,S,T); 103 (Y,A,F,I,L,M,V,W); 104 (S,A,D,E); 113 (A,C, G,S); 118 (M,F,H,P, Q); 120 (V,A,C,I,S,T); 123 (M,C,I,L, N,Q,S); 130 (G,D,E,H,S); 131 (S,D,R,T); 133 (A,G,M,P, S,T,V); 139 (D,G,K,N,S,T); 145 (G,D,N,S); 147 (V,A,L,M, N); 148 (V,A,C,F,M,Q,S); 181 (S,A,C,D,H, Q); 182 (N,C, D,E,Q); 184 (N,C,E,H,M,Q); 193 (A,D,P,Q,R); 205 (Y,C,E, F,I,M,V); 211 (N,C,E,S); 212 (T,A,D, S); 214 (A,E,H,L,T); 216 (L,A,C,H,K,M); 217 (N,C,E,S); 221 (M,C,H,K); 235 (S,C,D,E,G); 242 (A,E,G, N,S); 245 (V,A,C,I,T); 248 (R,A, N,Q,S); 251 (S,A,C,E,G,N); 258 (S,C,D,E,H,P); 259 (S,E, P,Q); and 268 (N,D,E,Q).

Positions with Productivity Score of "3" are:
1, 9, 22, 24, 25, 53, 86, 89, 95, 100, 105, 108, 114, 115, 119, 125, 128, 140, 146, 155, 158, 187, 202, 203, 234, 237, 240, 243, 244, and 264.

Positions and Corresponding Mutations with Productivity Score of "3" are:
1 (A,D,E,F,G,N, Q,S,T,V); 9 (P,A,C,D,E,G,N,Q,S,T); 22 (K,A,F,M,Q,R,S,T,VY); 24 (A,C,D,E,G,N,Q,S,W); 25 (N,D,E, F,G,H,L,M,P,Q,R,S); 53 (G,C,D,E,H,K,N,Q,R); 86 (S,C,E,H,K,L,N,R); 89 (L,A,C,F,G,I,M,N,S,V); 95 (L,A,F, G,I,M,Q,S,V); 100 (S,C,F,G,M,N,R,T,Y); 105 (G,A,C,D,I, M,N,R,S,T); 108 (S,E,F,G,H,K,L,N,Q, R,Y); 114 (T,A,C,D, F,I,K,L,N,Q,S,V); 115 (T,D,E,F,H,I,K,Q,S,W); 119 (D,A,E, F,G,H,M,Q,S); 125 (L, A, E, F, I,N,S,V,Y); 128 (A,C,D,E, H,K,N,P,Q,R,S,T); 140 (N,C,D,F,G,H,M,R,T,V); 146 (V,A, E, H,I,K, L,N,Q,S, T); 155 (S,A,D,E,F,G,H,K,N,Q,R,W); 158 (S,A,D,E,I,K,N,Q,R); 187 (S,A,C,D,E,H,K,P,Q,W); 202 (A, C,D,E,I,K,L,M,Q,S,T,V); 203 (G,A,C,E,H,K,M,N, Q,R,S); 234 (L,E,F,H,Q,S,W,Y); 237 (H,A,C, D, G,I, M,N, Q,S); 240 (L,A,D,E,F,I,M,N,Q,T); 243 (S,C,E,F,I,N,Q,T,V, W); 244 (Q,A,C,D,E,G,H,I, N, R,S,V); and 264 (K,A,C,D, H,M,Q,R,S,Y).

Positions with Productivity Score of "4" are:
12, 15, 26, 27, 43, 45, 48, 52, 55, 57, 58, 60, 77, 78, 88, 96, 97, 98, 99, 102, 116, 117, 126, 127, 129, 132, 136, 143, 144, 160, 161, 165, 171, 210, 238, 239, 241, 247, and 274.

Positions and Corresponding Mutations with Productivity Score of "4" are:

12 (K,A,C,F,G, H, L,M, N,Q,S,Y); 15 (K,A,C,E,F,H,I,M, N,R,S,T,V); 26 (V,A,C,E,H,I,M,N,Q,R,S,T); 27 (K,A,C,D, E,L, M,N,P, Q,R,T); 43 (N,A,C,F,G,H,I,K,L,M,Q,R,S,W,Y); 45 (V,A,C,D,E,F,G,I,K,M,N,P,Q, R,S,T,Y); 48 (A,C, D,E,F, H,I,K,M,N,Q,R,W,Y); 52 (A,C,D,E,F,G,H,K,L,M,N,P,Q,R, S,T,V,Y); 55 (A,C,D,E,F,G, H,I, M,N, P,Q,R,S,T,V); 57 (N,A,C,D,E,G,H,P,R,S,V,Y); 58 (T,C,D,F,H,I,K,L,M,P,R,S, V,W,Y); 60 (G,C,E, F, H,I, K,L,M,Q,R,T,Y); 77 (T,C,D,F, H,K,L,M,N,P,Q,R,S,W); 78 (T,C,D,G,I,L,N,Q,S,V,W, Y); 88 (S, A, E, F,G, L,M,N,Q,R,T,V,W,Y); 96 (N,A,C,D,E,G, H,I,K,L,M,Q,S,V,Y); 97 (S,A,C,D,F,G,H, I,K,M,N, P,Q,R, T,W, Y); 98 (S,A,D,E,F,H,K,L,N,P,R,T,V,Y); 99 (G,A,C,D, E,L,M,Q,S,T,V,W); 102 (S,A,D,E,F, G,K, L,N,P, Q,R,T); 116 (N,A,C,D,E,F,G,H,K,L,M,Q,R,S,T,V,Y); 117 (G,C,D,E, H,K,M,N,Q,R,T, V); 126 (G,A,C, E,H,I,K,M,N,Q,R,S,T,V, W,Y); 127 (G,A,D,E,F,I,L,M,Q,S,T,V,W,Y); 129 (S,C,E,F, H,I, M, N, Q,R,T,V, W,Y); 132 (T,A,C,D,E,F,H,I,K,L,M,N, P,Q,S,V,W,Y); 136 (Q,A,C,D,F,G,H,K,L,N,R,S,T, W); 143 (A,C, D,E,F,G,H,I,K,M,N,S,T,Y); 144 (R,A,C,D,E,F,G,H,L, M,N,Q,V,Y); 160 (N,A,C,D,G,I,K, M,P,R); 161 (T,A,C,D, E,I,K,L,M,Q,R,W); 165 (G,A,E,I,K,L,P,Q,R,S,T,Y); 171 (D,A,C,G,H,I,K,N,P,Q, S,T,V); 210 (T,C,D,E,F,H,I,M,N,P, V,Y); 238 (P,A,C,D,E,F,G,I,L,M,N,Q,R,S,T,W); 239 (N,A, C,D,E,H, I,K,L,M,S, T,V,Y); 241 (S,C,D,E,H,L,N,P,Q,T,V); 247 (N,A,D,E,F,H,I,L,M,Q,S,V,W,Y); and 274 (Q,A, C, D,E,F,G, H,I,L,N,S,T,V,W).

Combinable mutations in AprL were determined using PI values resulting from the assays described in Example 1: Protein Determination (expression), Protease activity assays (AAPF, DMC), Cleaning activity in the following detergents (Kirkland Ultra HDD pH 10.6, OMO Color HDD pH 10.6, Surf Excel HDD pH 10.6, Kirkland Ultraclean, HDL pH 8.2, OMO Klein & Krachtig HDL pH 8.2, Blue Moon HDL pH6.5, GSM-B pH 10, and GSM-B pH 9) and stability assays in the following detergent and buffers (LAS-EDTA buffer at 53.5° C., 10% Kirkland Ultra at 56° C., and 10% OMO Klein & Krachtig at 51° C.). Combinable mutations were assigned to groups A, B or C according to criteria set forth in Example 4. These substitutions are further assigned a Suitability Score based on the group(s) (A, B, C) where the substitution appears, and where a higher suitability score represents a substitution more suitable for use in making combinatorial variants. Suitability scores are defined in Table 5. Suitability scores for individual substitutions of AprL that fit the above criteria are reported in Table 6.

TABLE 5

Definitions of suitability scores

| Substitutions Occur in Group(s): | Suitability Score |
|---|---|
| A, B and C | +++++ |
| A and B | ++++ |
| A or (B and C) | +++ |
| B | ++ |
| C | + |

TABLE 6

Suitability scores of individual substitutions in AprL

| Position AprL numbering | VARIANTS SUITABILITY SCORE | | | | |
|---|---|---|---|---|---|
| | (+) | (++) | (+++) WT AA 1ST | (++++) | (+++++) |
| 1 | | | AFGTV | NQS | DE |
| 2 | AIN | | Q | | |
| 3 | | | TE | IQV | |
| 4 | | | VI | | |
| 9 | | | P | ADGNQT | CES |
| 10 | F | | L | Q | M |
| 12 | | | KS | FGLMQ | ACHNY |
| 15 | | | KFHNR | | ACEIMSTV |
| 17 | | | Q | H | M |
| 18 | | | ACS | D | E |
| 19 | | AG | QM | DE | |
| 21 | | | F | Y | |
| 22 | | V | KAFMRST | QY | |
| 24 | | CGW | A | DENS | Q |
| 25 | | L | N | DEFGHMPQRS | |
| 26 | | | VST | CEHIMNQ | AR |
| 27 | | L | KQR | ACDEMPT | N |
| 28 | | | VS | AC | |
| 29 | | | ACTV | S | |
| 30 | | | V | CT | |
| 31 | | | LCIV | | |
| 33 | | | TCM | | |
| 35 | | G | I | CSTV | AM |
| 36 | | | QEH | | |
| 37 | | E | AGS | | |
| 38 | | | SAGN | CET | |
| 40 | AM | V | P | DE | C |
| 43 | | H | NIKMRSW | AFGLQY | C |
| 44 | | | VT | CES | P |
| 45 | | K | VP | ACDEFGIMNQRSTY | |
| 46 | | | GACW | D | |
| 47 | AM | | G | | |
| 48 | | | ADEFHIMQY | CKNRW | |
| 49 | | | ST | | I |

TABLE 6-continued

Suitability scores of individual substitutions in AprL

| Position AprL numbering | (+) | (++) | (+++) WT AA 1ST | (++++) | (+++++) |
|---|---|---|---|---|---|
| 50 |  | R | FKMQVY | H |  |
| 51 |  |  | VC | I |  |
| 52 |  | D | ACEHLQSTY | FGKMNPRV |  |
| 53 |  |  | GDEHQ | KNR | C |
| 54 |  | R | EQT |  |  |
| 55 |  |  | AFIMPQ | CDEGHNRSTV |  |
| 56 |  |  | YCEFP | H |  |
| 57 |  |  | NAHPRSY | CDEGV |  |
| 58 |  |  | TFHLMSV | CDIPRWY | K |
| 60 |  | MRT | GEFQ | CHIKLY |  |
| 61 |  |  | NFHKQ | A | D |
| 62 |  | S | G |  |  |
| 66 |  | R | H |  |  |
| 67 | NQ | M | V |  |  |
| 68 |  |  | AGT | CN | S |
| 71 |  | G | VS | L | A |
| 72 |  |  | AS | G |  |
| 74 |  |  | L | G |  |
| 75 |  |  | DC | E |  |
| 76 |  |  | N | K |  |
| 77 |  | KR | TFW | HLMPQS | CDN |
| 78 |  |  | TCDGLQSWY | INV |  |
| 86 |  | C | SKLN | H | ER |
| 87 |  |  | V | GT | CS |
| 88 |  |  | SFGLMQTVWY | AENR |  |
| 89 |  |  | LACFGIMSV | N |  |
| 90 |  |  | YACFHNV |  |  |
| 91 |  |  | AGPV | M |  |
| 92 |  |  | VACIT |  |  |
| 93 |  |  | KD |  |  |
| 95 | G |  | LI | FMSV | AQ |
| 96 | LY |  | NCDEMQV | AGHKS | I |
| 97 |  | DI | SCFGHPQRTY | AKMNW |  |
| 98 | P | F | SADENTVY | HLR | K |
| 99 | CL | W | GV | ADEQST | M |
| 100 |  |  | SMNT | FG | CRY |
| 101 |  |  | GNST |  | AC |
| 102 |  |  | SDGNPQT | AEFKL | R |
| 103 |  |  | YAILVW | FM |  |
| 104 |  |  | SA | E | D |
| 105 |  | I | GACNST | DMR |  |
| 106 | G |  | I | M |  |
| 107 | F |  | VI |  |  |
| 108 |  |  | SEGNQY | FHLR | K |
| 110 | F |  | I |  |  |
| 111 |  |  | ED | Q |  |
| 112 | A |  | W |  |  |
| 113 |  |  | ACGS |  |  |
| 114 |  | A | TCFIKLNQSV | D |  |
| 115 |  |  | THIQSW | EK | DF |
| 116 |  |  | NADFGHKLQRSTV | CEMY |  |
| 117 |  | V | GEHKNQRT | CDM |  |
| 118 |  |  | MFHPQ |  |  |
| 119 |  | GM | DEFHQ | AS |  |
| 120 |  | S | VCIT | A |  |
| 121 |  |  | ILM |  |  |
| 123 | NQS |  | ML | I | C |
| 125 |  | I | LAENS | VY | F |
| 126 | HW |  | GY | R | ACEIKMNQSTV |
| 127 |  |  | G | QSV | ADEFILMTWY |
| 128 |  |  | AC | DEHNQST | KPR |
| 129 | F |  | SIMNWY | CEHQTV | R |
| 130 | S |  | G | DEH |  |
| 131 |  |  | SRT | D |  |
| 132 |  |  | TFHILSVW | ACEKMNPQY | D |
| 133 |  | MV | AT | GPS |  |
| 134 |  |  | M | L |  |
| 135 |  |  | KH | E |  |
| 136 |  |  | QDGHNSTW | AFKLR | C |
| 137 |  |  | AS |  |  |

TABLE 6-continued

Suitability scores of individual substitutions in AprL

| Position AprL numbering | (+) | (++) | (+++) WT AA 1ST | (++++) | (+++++) |
|---|---|---|---|---|---|
| 138 | | | VS | | C |
| 139 | | K | DGNT | S | |
| 140 | | | NCDFGHMRTV | | |
| 141 | | | A | S | |
| 143 | C | | AGHNT | DEFKSY | IM |
| 144 | | | RAEFGMNQV | CDHLY | |
| 145 | | | GDN | S | |
| 146 | | KL | VEINQST | AH | |
| 147 | N | A | VM | L | |
| 148 | F | | VS | AM | CQ |
| 149 | | | V | C | |
| 151 | | G | A | | P |
| 155 | | | SHQ | AFNW | DEGKR |
| 156 | | | GE | | |
| 157 | | | SR | | D |
| 158 | | | SA | DEIKNQR | |
| 159 | AF | | G | | |
| 160 | | | NAGKP | DIMR | C |
| 161 | | | TAILMW | CDEKQ | R |
| 163 | | | TE | | |
| 165 | | | GILT | P | AEKQRSY |
| 169 | | | KR | | |
| 171 | | IP | DGHS | ACKNQTV | |
| 175 | C | | A | | |
| 181 | | | SD | AH | CQ |
| 182 | | | NQ | C | DE |
| 183 | | | S | AG | |
| 184 | | H | NC | M | EQ |
| 186 | | | A | | C |
| 187 | | | SHKQW | AP | CDE |
| 188 | | | FW | | |
| 191 | | | V | C | |
| 193 | | | APQ | R | D |
| 202 | | M | ALST | IKQ | CDEV |
| 203 | | | GHKRS | AMQ | CEN |
| 204 | | | VI | | |
| 205 | C | | Yl | EFMV | |
| 207 | | | TC | | |
| 208 | | | YF | | |
| 209 | S | | P | | |
| 210 | | | TDN | CEFHIMVY | P |
| 211 | | CE | N | S | |
| 212 | | | TADS | | |
| 214 | L | | A | T | EH |
| 215 | | | TV | | C |
| 216 | | | L | ARM | CK |
| 217 | | | NE | C | S |
| 221 | HK | | MC | | |
| 223 | | A | SC | | |
| 224 | | | P | | A |
| 227 | | | AS | | |
| 229 | | | AS | | G |
| 230 | | | AG | | |
| 231 | | | A | C | |
| 232 | | | LQ | | |
| 233 | | | IV | | |
| 234 | | W | LHY | S | EFQ |
| 235 | | | SCG | D | E |
| 236 | | | KA | | |
| 237 | | A | HDGIMNQS | C | |
| 238 | | CL | PAEIMNQSW | DFGRT | |
| 239 | C | | NEIKVY | ADHLMST | |
| 240 | | T | LFIM | ADENQ | |
| 241 | | Q | SCHLPT | DENV | |
| 242 | | | AES | GN | |
| 243 | | | SCFINTW | EQV | |
| 244 | | | QAGHINRSV | CDE | |
| 245 | | | VI | ACT | |
| 247 | | | NAFHLQSY | DEIMVW | |
| 248 | | | RAQS | N | |

TABLE 6-continued

Suitability scores of individual substitutions in AprL

| Position AprL numbering | (+) | (++) | (+++) WT AA 1ST | (++++) | (+++++) |
|---|---|---|---|---|---|
| 249 | | | LI | | M |
| 250 | | | S | AG | |
| 251 | | N | SAG | CE | |
| 254 | | | TD | | |
| 255 | E | | Y | C | |
| 258 | | | S | H | CDEP |
| 259 | | | S | PQ | E |
| 260 | | | F | C | W |
| 264 | | R | KC | DM | AHQSY |
| 267 | | | I | | C |
| 268 | | | N | Q | DE |
| 269 | | | VA | C | |
| 271 | | | A | E | D |
| 273 | | | AS | | |
| 274 | | LN | QFHISTVW | ACG | DE |

Evaluation of Beneficial AprL Mutations for Certain Cleaning Applications

The SEL variants were further grouped in various categories based on their performance in different assay conditions as described below. For this analysis, the SEL variants for which the HPLC PI values were either 0 or 0.1 were excluded. In addition, for each assay, PI values were made blank where the corresponding CV value were less than 0 or larger than 100.

To obtain the best mutations for each category of performance, in addition to HPLC PI values and HDL pH 6 PI values, 4 surrogate PI values were calculated: 1) HDD PI value that is the larger of the BMI-OMO-HDD PI or BMI-Kirkland-HDD PI; 2) HDL PI value that is larger of the BMI-OMO-HDL PI or BMI-Kirkland-HDL PI; 3) ADW PI value that is larger of the EGG-GSM9 PI or EGG GSM10 PI; and 4) Stability PI that is the maximum of LAS/EDTA stability PI, HDL Kirkland stability PI or HDL OMO stability PI.

To group most beneficial mutations in the HDL pH8 application, the surrogate HDL pH8 PI value was set to be larger than 1.1 and all other PI value cutoffs were set for larger than 0.8. For most beneficial mutations in HDD application, the HDD surrogate PI was set to be larger than 1.1 and all other PI value cutoffs were set for larger than 0.8. For most beneficial mutations in ADW application, the surrogate ADW PI was set to be larger than 1.1 and all other PI value cutoffs were set for larger than 0.8. For most beneficial mutations in HDL pH6 application, the surrogate HDL pH6 PI value was set to be larger than 1.1 and all other PI value cutoffs were set larger than 0.8. For most beneficial stability mutations, stability PI values were set to be larger than 1.2 and all other PI value cutoffs were set larger than 0.8. The number of mutations obtained for each category is shown in Table 7 below and the specific mutations in each category are listed below.

Criteria for grouping in each category: PI>1.1 for the specific category, i.e. ADW, HDL pH6, HDL pH 8, or HDD, and PI>0.8 for ALL properties tested including expression; or PI>1.2 for stability and PI>0.8 for ALL properties tested including expression.

TABLE 7

Summary of number of mutations in each category

| Category | Number of mutations |
|---|---|
| ADW | 194 |
| HDL pH 6 | 22 |
| HDL pH 8 | 44 |
| HDD | 46 |
| Stability | 326 |

List of Most Beneficial Mutations for ADW Application: A001C, A001D, A024E, A024G, A048C, A048D, A048K, A048N, A052F, A052M, A052V, A052Y, A055C, A072G, A091G, A113C, A128P, A128Q, A133G, A133S, A133T, A143E, A143F, A143H, A143N, A143S, A143W, A193D, A202C, A202D, A202E, A202Q, A227S, D119F, D119S, D119Y, G053C, G053E, G053N, G053Q, G060L, G060Y, G099A, G099T, G101A, G117D, G117V, G127A, G127S, G127T, G130D, G130H, G203A, G203C, G203E, G203M, H237I, I035A, I035C, I035M, I035T, I121L, K012N, K015M, K027C, K027L, K027M, K027R, K264A, K264S, L010M, L095F, L125V, L234Q, L240N, L249I, M123C, M123I, M123L, N025F, N025G, N025L, N025S, N057C, N061A, N076G, N096D, N096G, N116A, N116C, N116L, N116Y, N140A, N160C, N182C, N182D, N184C, N211S, N247F, N247H, N247I, N247L, N247Q, N247S, N247V, N247W, N247Y, P009E, P009T, P238A, P238C, P238D, P238F, P238I, P238R, Q017H, Q136A, Q136C, Q136F, Q136H, Q136K, Q136L, R144F, R144L, R248K, S086R, S088N, S088Y, S097G, S097H, S097Y, S098H, S098L, S100L, S102D, S102E, S102G, S102K, S129E, S129H, S155A, S155D, S155E, S155H, S157D, S158I, S158Q, S181A, S181Q, S183G, S241R, S241T, S243I, S243N, S243T, S243V, S243Y, S251E, S258C, S258D, S258P, T058C, T058D, T058F, T058I, T077C, T077F, T077L, T077M, T078Q, T132A, T132Q, T132V, T132Y, T161Q, T210I, T215C, V026Q, V026R, V026T, V028A, V028C, V045I, V071A, V071L, V120A, V120C, V120I, V146A, V146H, V146K, V147L, V149C, Y056H, and Y255C.

List of Most Beneficial Mutations for HDD Application: A029T, A048K, A048R, A052F, A052R, A068G, A113C, D119H, E111Q, G099A, G099S, G127A, G127T, G165A, K012G, K012H, K027C, K027E, K027M, L095F, L125I, L125V, L240Q, N025F, N025G, N025L, N043R, N116R, N140R, N160C, N184C, N239K, P238C, P238I, P238M, Q136F, Q136H, Q136K, Q136R, Q136W, S098F, S098H, S104A, S158Q, S241R, V045R, and Y103M.

List of Most Beneficial Mutations for HDL (pH 8) Application:

A001C, A048R, A052F, G099S, G099T, G101A, G127F, G127I, G127M, G127Q, G127T, G127V, I121M, L010M, L095A, L095F, L095Q, L095S, L125I, L125V, M123C, M123I, N025F, N025 S, N116C, N140R, N184C, P238C,

P238D, P238I, P238M, P238N, Q136A, S098F, S098H, S102D, S158Q, S241R, T077C, T077F, T215C, V026I, V026Q, V045R, and V149C.

List of Most Beneficial Mutations in HDL (pH 6) Application:

A001C, A024E, A128D, G053C, G099T, G101A, G101N, G165E, G203C, L095Q, L095S, L125S, N061E, N116C, N184C, S098D, S102D, S102E, S104D, S129E, S155D, S158E, and V026T.

List of Most Beneficial Mutations for Stability:

A001C; A001D; A001E; A001Q; A001S; L010M; L010Q; S100G; S102K; S102R; Y103F; Y103M; S104D; G105M; G105R; S108F; S108H; S108K; S108R; E111Q; T114D; T115D; T115E; T115F; T115K; T115Q; N116E; K012C; K012F; K012H; K012M; K012N; K012Q; K012Y; V120S; M123C; M123I; L125I; G127A; G127D; G127I; G127M; G127S; G127T; G127V; A128E; A128H; A128K; A128P; A128R; A128S; A128T; S129H; S129Q; S129R; S129T; S129V; T132C; T132D; T132E; T132K; T132N; T132P; Q136A; Q136C; Q136K; Q136R; V138C; A143D; A143N; G145S; V147L; V148A; V148C; V148M; V148Q; K015A; K015C; K015E; K015I; K015M; K015S; K015T; K015V; S155D; S155F; S155K; S155N; S155R; S157D; S158D; S158I; S158K; S158R; N160C; N160D; N160I; N160M; N160R; T161C; T161D; T161E; T161K; T161Q; T161R; G165A; G165E; G165Q; G165R; G165S; Q017H; A018D; A018E; S181Q; N182D; S183A; S183G; N184C; N184E; N184Q; A186C; S187D; S187E; S187P; Q019D; Q019E; A193D; A193R; A202D; A202E; A202K; A202Q; A202V; G203A; G203C; G203E; G203N; G203Q; Y205E; T210C; T210E; T210I; T210P; T210V; A214E; T215C; L216C; L216H; L216K; L216M; N217S; L234E; L234F; L234Q; L234S; S235D; S235E; P238T; N239A; N239D; N239H; N239M; N239S; N239T; A024E; A024Q; L240D; S241E; S241N; S241Q; S241V; A242G; A242N; S243E; S243Q; S243V; Q244C; Q244E; V245A; V245C; V245T; N247D; N247W; N025D; N025G; N025Q; S250G; S251E; S258C; S258D; S258E; S258H; S258P; S259E; S259P; S259Q; V026A; V026C; V026E; V026H; V026Q; V026R; F260W; K264A; K264C; K264D; K264H; K264M; K264Q; K264S; K264Y; I267C; N268D; N268E; N268Q; V269C; K027C; K027D; K027E; K027M; K027P; A271E; Q274A; Q274C; Q274D; Q274E; Q274G; A029S; T003E; T003I; T003Q; T003V; V030C; I035A; I035S; I035T; I035V; S038T; N043A; N043C; N043F; N043H; N043Q; V044P; V045A; V045C; V045D; V045E; V045F; V045G; V045M; V045N; V045Q; V045R; V045S; V045T; G046D; A048N; A048W; F050H; V051I; A052F; A052G; A052K; A052N; A052P; A052R; A052V; G053N; G053R; A055C; A055D; A055E; A055G; A055H; A055N; A055S; A055V; N057C; N057E; N057G; N057V; T058C; T058I; T058K; T058W; A068C; A068N; A068S; V071A; L074G; D075E; N076K; T077C; T077D; T077H; T077M; T077N; T077P; T077Q; T077S; T078D; T078I; T078V; S086E; S086H; S086R; V087C; V087G; V087S; V087T; S088E; S088N; S088R; L089N; P009C; P009D; P009E; P009N; P009T; L095A; L095V; N096S; S098K; S098R; and G099Q.

EXAMPLE 4

Comparison of AprL Protease to Related Molecules

Identification of Homologous Proteases

Related proteins were identified by a BLAST search (Altschul et al., Nucleic Acids Res, 25:3389-402, 1997) against the NCBI non-redundant protein database and a subset are shown on Table 8. A similar search was run against the Genome Quest Patent database with search parameters set to default values using the mature protein amino acid sequences for AprL protease (SEQ ID NO:2) as the query sequence, and a subset are shown in Table 9. Percent identity (PID) for both search sets is defined as the number of identical residues divided by the number of aligned residues in the pairwise alignment. Value labeled "Sequence length" on tables corresponds to the length (in amino acids) for the proteins referenced with the listed Accession numbers, while "Aligned length" refers to sequence used for alignment and PID calculation.

TABLE 8

List of Sequences With % Identity to AprL Protein Identified In NCBI Non-redundant Protein Database

| Accession No. | PID | Organism | Sequence Length | Alignment Length |
|---|---|---|---|---|
| CAJ70731.1 | 100 | B. licheniformis | 379 | 274 |
| AEQ38580 | 99.6 | B. licheniformis | 370 | 275 |
| WP_025811752 | 99.6 | Bacillus | 378 | 274 |
| AAG10033/AF283295 | 99.6 | B. licheniformis | 310 | 274 |
| AKI30031 | 99.6 | B. licheniformis | 379 | 274 |
| WP_043054574 | 99.6 | Bacillus licheniformis | 378 | 274 |
| AID16241 | 99.3 | B. licheniformis | 379 | 274 |
| WP_031314535 | 99.3 | B. licheniformis | 378 | 274 |
| AAG00493 | 98.9 | B. licheniformis | 310 | 274 |
| AEU17777 | 98.9 | B. licheniformis | 349 | 274 |
| ADK11044 | 98.5 | B. licheniformis | 379 | 274 |
| EWH21773 | 98.2 | B. licheniformis S 16 | 378 | 274 |
| YP_006712489 | 98 | B. licheniformis DSM13 | 379 | 274 |
| AEU12640 | 97 | B. licheniformis | 379 | 274 |
| CAA62667 | 95 | B. licheniformis | 379 | 273 |
| CAA62666 | 95.6 | Bacillus licheniformis | 379 | 273 |
| WP_026586291 | 89.1 | Bacillus sp. NSP9.1 | 379 | 275 |
| P00781 | 88 | B. subtilis DY | 274 | 274 |
| WP_006636716 | 87 | B. sonorensis | 378 | 274 |
| WP_048353666 | 85.4 | Bacillus sp. GO-13 | 378 | 274 |
| WP_046128901 | 85.0 | Bacillus sp. TH008 | 378 | 274 |
| WP_008359041 | 74 | Bacillus sp. HYC-10 | 381 | 274 |
| WP_007497196 | 73 | B. stratosphericus | 383 | 274 |
| ADK11996 | 72 | B. pumilus | 383 | 274 |

TABLE 8-continued

List of Sequences With % Identity to AprL Protein
Identified In NCBI Non-redundant Protein Database

| Accession No. | PID | Organism | Sequence Length | Alignment Length |
|---|---|---|---|---|
| ADN04910 | 72 | B. circulans | 275 | 274 |
| AFP23380 | 72 | B. lehensis | 276 | 274 |
| WP_017360299 | 72 | B. cereus | 383 | 274 |
| YP_003972439 | 72 | B. atrophaeus 1942 | 382 | 275 |
| BAN09118 | 71 | B. subtilis | 381 | 274 |
| WP_010192405 | 71 | Bacillus sp. m3-13 | 379 | 276 |
| WP_010333625 | 71 | B. mojavensis | 381 | 274 |
| AAC43580 | 70 | Bacillus sp. SprC | 378 | 274 |
| ACJ07037 | 70 | B. subtilis | 381 | 274 |
| WP_010329279 | 70 | B. vallismortis | 381 | 274 |
| BAD11988 | 69 | Bacillus sp. KSM-LD1 | 376 | 274 |
| BAD21128 | 69 | Bacillus sp. KSM-LD1 | 377 | 276 |
| AAC43581 | 69 | Bacillus sp. SprD | 379 | 276 |
| CAA74536 | 69 | B. subtilis str. 168 | 379 | 275 |
| CAA24990 | 69 | B. amyloliquefaciens | 376 | 275 |
| AGC81872 | 69 | B. methylotrophicus | 382 | 275 |
| ABY25856 | 68 | Geobacillus stearothermophilus | 382 | 275 |
| ADC49870 | 62 | B pseudofirmus | 374 | 274 |
| AAA22212 | 60 | B alcalophilus | 380 | 274 |
| BAD63300 | 60 | B clausii KSM-K16 | 380 | 274 |
| P29600 | 60 | B. lentus | 269 | 274 |
| BAA25184 | 58 | Bacillus sp AprN | 379 | 273 |
| AFK08970 | 58 | B. lehensis | 378 | 273 |
| AAA87324 | 58 | B. subtilis | 378 | 273 |
| ADD64465 | 55 | Bacillus sp. JB99 | 361 | 274 |
| BAA06157.1 | 54.9 | Prepro-subtilisin Sendai, Bacillus sp. G-825-6 | 382 | 273 |
| BAB04574.1 | 54.7 | B. halodurans C-125 | 361 | 274 |
| ABI26631 | 54 | B. clausii | 361 | 274 |
| BAA05540 | 54 | Bacillus sp. | 361 | 274 |

TABLE 9

List Of Sequences With % Identity To AprL Protein
Identified In Genome Quest Patent Database

| Patent/Patent Appl Pub No-SEQ ID NO | PID | Organism | Sequence Length | Alignment Length |
|---|---|---|---|---|
| JP2013500714-0115 | 100.0 | B. licheniformis | 269 | 269 |
| CN101215534-0002 | 99.6 | B. licheniformis YP1A | 379 | 274 |
| WO9739130-0002 | 99.6 | B. licheniformis; strain PWD-1 | 379 | 274 |
| US8110391-0009 | 99.3 | B. licheniformis | 274 | 274 |
| JP2013500714-0110 | 98.9 | B. licheniformis | 274 | 274 |
| WO2006122655-0031 | 98.5 | B. licheniformis | 379 | 274 |
| US7087415-0014 | 98.2 | B. licheniformis | 379 | 274 |
| US20110171718-0120 | 97.8 | B. licheniformis | 274 | 273 |
| US20030049619-0014 | 97.4 | B. licheniformis | 378 | 273 |
| JP2013500714-0121 | 96.0 | B. licheniformis | 274 | 273 |
| US7569226-0012 | 88.3 | B. subtilis DY | 274 | 274 |
| US20050009167-0017 | 88.0 | B. subtilis DY | 274 | 274 |
| US20110171718-0098 | 87.6 | B. licheniformis | 274 | 274 |
| WO2008066931-6106 | 83.6 | B. licheniformis; SJ1904 (ATCC PTA-7992) | 333 | 274 |
| JP2013500714-0406 | 73.0 | B. pumilus | 275 | 274 |
| JP2004313043-0022 | 72.7 | Bacillus sp. KSM-9865 | 275 | 275 |
| JP2004313043-0021 | 72.7 | Bacillus sp. KSM-KP43 | 275 | 275 |
| JP2013500714-0419 | 72.6 | B. pumilus | 275 | 274 |
| WO2011014278 | 72.3 | B. pumilus SAFR-032 | 275 | 274 |
| WO2011014278-0084 | 70.6 | B. subtilis | 275 | 275 |
| US5719021-0003 | 70.6 | B. amylosacchariticus | 352 | 275 |
| EP0405901-0004 | 70.2 | Bacillus sp. | 275 | 275 |
| US20130196415-0003 | 70.2 | B. Subtilis | 381 | 275 |

Alignment of Subtilisin Sequences with AprL

The amino acid sequence of mature AprL (SEQ ID NO: 2) protein was aligned with multiple subtilisin sequences using CLUSTALW software (Thompson et al., Nucleic Acids Research, 22:4673-4680, 1994) with the default parameters. FIG. 2 shows the alignment of AprL protein with a subset of these protease sequences.

EXAMPLE 5

Discovery and Identification of Subtilisin BliD02339

Sequencing of the genome of B. licheniformis strain Bra7 (Culture Collection Dupont) revealed that this strain produces a subtilisin that is different from subtilisin Carlsberg (NCBI Database Accession No. CAJ70731.1), and other subtilisins from *B. licheniformis* species. The sequence of the gene, BliD02339.n, encoding the subtilisin (precursor) of *B. licheniformis* Bra7 is depicted in SEQ ID NO:7.

The pre-proenzyme encoded by the BliD02339.n gene is depicted in SEQ ID NO:8. At the N-terminus, the protein has a signal peptide with a length of 29 amino acids as predicted by SignalP-NN (Emanuelsson et al., Nature Protocols (2007) 2: 953-971). This signal peptide sequence is underlined and in bold in SEQ ID NO:8. The presence of a signal peptide indicates that this serine protease is a secreted enzyme. Like other serine proteases, the enzyme has a pro sequence which is predicted to be 76 amino acids (in italics in SEQ ID NO: 8). This prediction is based on pro-mature junction in homologous serine proteases like subtilisin Carlsberg (Waldeck et al., Appl. Environ. Microbiol. (2006) 72:7879-7885). The sequence of the predicted, fully processed mature chain (BliD02339, 274 amino acids) is depicted in SEQ ID NO: 9. The amino acid sequence of the BliD02339 pre-proenzyme is set forth as SEQ ID NO:8:

MMRKKSFWLGMLTALMLVFTMAFSDSASAAQPAKNVEKDYIVGFKSGVKT

ASVKKDIIKESGGKVDKQFRIINAAKAKLDKEALKEVKNDPDVAYVEEDH

VAHALAQTVPYGIPLIKADKVQAQGFKGANVKVAVLDTGIQASHPDLNVV

GGASFVAGEAYNTDGNGHGTHVAGTVAALDNTTGVLGVAPNVSLYAVKVL

NSSGSGSYSGIVSGIEWATTNGMDVINMSLGGPSGSTAMKQAVDNAYARG

VVVVAAAGNSGSSGNTNTIGYPAKYDSVIAVGAVDSNSNRASFSSVGAKL

EVMAPGAGVYSTYPTSTYATLNGTSMASPHVAGAAALILSKHPNLSASQV

RNRLSSTATYLGSSFYYGKGLINVEAAAQ.

EXAMPLE 6

Comparison of BliD02339 Protease to Subtilisin Carlsberg

A sequence alignment of BliD02339 protease with subtilisin AprL is shown in FIG. 3. BliD02339 differs from subtilisin Carlsberg at 4 positions: positions 86, 128, 194 and 211. Most striking is the lysine residue at position 194 in BliD02339 (subtilisin Carlsberg has an aspartic acid residue at this position) as this results in a significant difference in charge between BliD02339 and subtilisin Carlsberg and other *B. licheniformis* subtilisins known in the art. The calculated charge at pH 7 for BliD02339 is 1.19, for subtilisin Carlsberg −0.80. This difference in charge may impact properties of the enzyme like cleaning performance, stability and/or productivity.

EXAMPLE 7

Heterologous Expression of BliD02339

Figure 4:
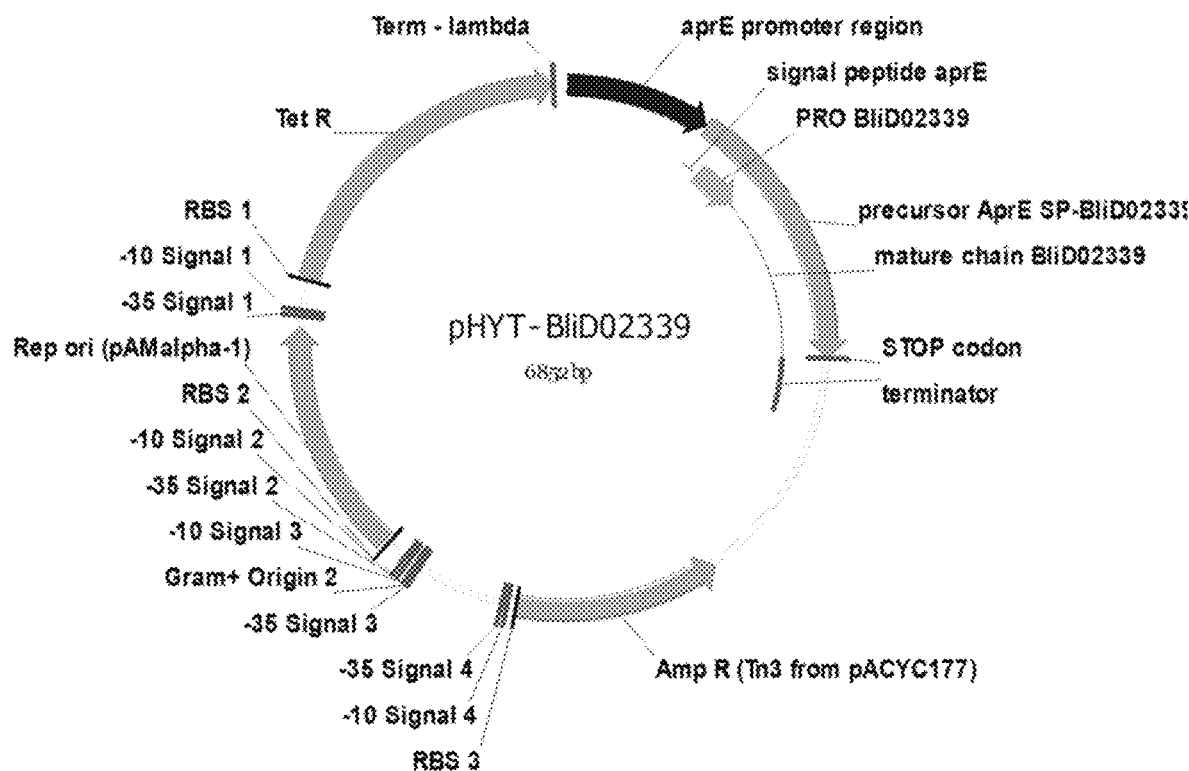

BliD02339 protease was produced in *B. subtilis* using an expression cassette consisting of the *B. subtilis* aprE promoter, the *B. subtilis* aprE signal peptide sequence, the native BliD02339 protease pro-peptide, the mature BliD02339 protease and a BPN' terminator. This cassette was cloned into the pHYT replicating shuttle vector and transformed into a suitable *B. subtilis* strain. The pHYT vector was derived from pHY300PLK (Takara) by adding a terminator after the tetracycline resistance gene using the BstEII and EcoRI sites (terminator sequence (SEQ ID NO:10)). The HindIII site in pHY300PLK was also removed using a linker cloned into the BamHI and HindIII sites (new linker sequence, (SEQ ID NO:11)). A map of the pHYT vector containing the BliD02339 gene (pHYT-BliD02339) is shown in FIG. 4.

To produce BliD02339, a suitable *B. subtilis* strain containing pHYT-BliD02339 was cultivated in an enriched semi-defined media based on MOPs buffer, with urea as major nitrogen source, glucose as the main carbon source, and supplemented with 1% soytone for robust cell growth. The media was supplemented with 25 ppm tetracycline. After incubation (2 days at 32° C.), BliD02339 protease was detected in the growth medium. After centrifugation and filtration, culture supernatants with BliD02339 protease were used for assays.

Protein was quantified by the stain-free Imager Criterion method. The method is based on utilizing of stain-free precast PAGE gels, where the intensity of each band will depend on amount of tryptophan residues presented in the protein of interest. The Criterion™ TGX (Tris-Glycine extended) Stain-Free™ precast gels for PAGE include unique trihalo compounds. This allows rapid fluorescent detection of proteins with the Gel Doc™ EZ imaging system. The trihalo compounds react with tryptophan residues in a UV-induced reaction to produce fluorescence, which can be easily detected by the Gel Doc EZ imager within gels. Reagents used in the assay: Concentrated (10×) Laemmli Sample Buffer (Kem-En-Tec, Catalogue #42556); either 18 or 26-well Criterion TGX Strain-Free Precast gels (Bio-Rad, Catalogue #567-8124 and 567-8125, respectively); and protein markers "Precision Plus Protein Standards" (Bio-Rad, Catalogue #161-0363). The assay was carried out as follow: 250 protein sample and 25 μl 10.5M HCL was added to a 96 well-PCR plate on ice to inactivate the protease and prevent self-hydrolysis. To 500 of the acid protein mix was added 50 μL sample buffer containing 0.385 mg DTT in the 96 well-PCR plate. After that, the chamber was filled by running buffer, gel cassette was set. Then, 10 μL of each sample together with markers was load in each pocket. After that the electrophoresis was started at 200 V for 35 min. Following electrophoresis, the gel was transferred to Imager. Image Lab software was used for calculation of intensity of each band. By knowing the protein amount and the tryptophan content of the standard sample, the calibration curve can be made. The amount of experimental sample can be determined by extrapolation of the band intensity and tryptophan numbers to protein concentration. This protein quantification method was employed to prepare samples of BliD02339 protease used for assays shown in subsequent Examples.

A sample of isolated BliD02339 protease was analyzed by LC-MS/MS as described subsequently. In preparation for sequence confirmation, including N- and C-terminal determination, a sample of BliD02339 protease was subjected to a series of chemical treatments in a 10 kDa spinfilter. The sample was denatured and reduced/alkylated by urea and DTT/Iodoacetamide treatment. A guanidination step was performed to convert lysines to homoarginines to protect lysine side chains from acetylation. The acetylation reaction using Sulfo-NHS-Acetate (Sulfosuccinimidyl Acetate) only modifies the protein N-terminal residue. The sample is then mixed with a buffer containing 40v/v % $^{18}O$ water: 60v/v % $^{16}O$ water and the proteolytic enzymes used for protein digestion. The resulting peptides will contain mixtures of $^{18}O$ and $^{16}O$, except for the Carboxyl terminus which will retain the native $^{16}$O, as will be apparent from the isotopic pattern of the peptides. The peptide, originating from the protein N-terminus, will appear as the only acetylated peptide. The resulting peptides were separated and analyzed using a nano-LC system followed by LTQ Orbitrap (Thermo Fisher) high resolution mass spectrometer. The amino acid sequence was deduced from the MS/MS fragment spectra of the peptides. Based on this analysis, the N-terminus of the isolated protein was confirmed to begin with A at position 1 from the predicted mature sequence. The sequence of the mature protein was determined to correspond to the sequence listed in SEQ ID:9, consisting of 274 amino acids.

EXAMPLE 8

Protease Activity of BliD02339

Figure 5:
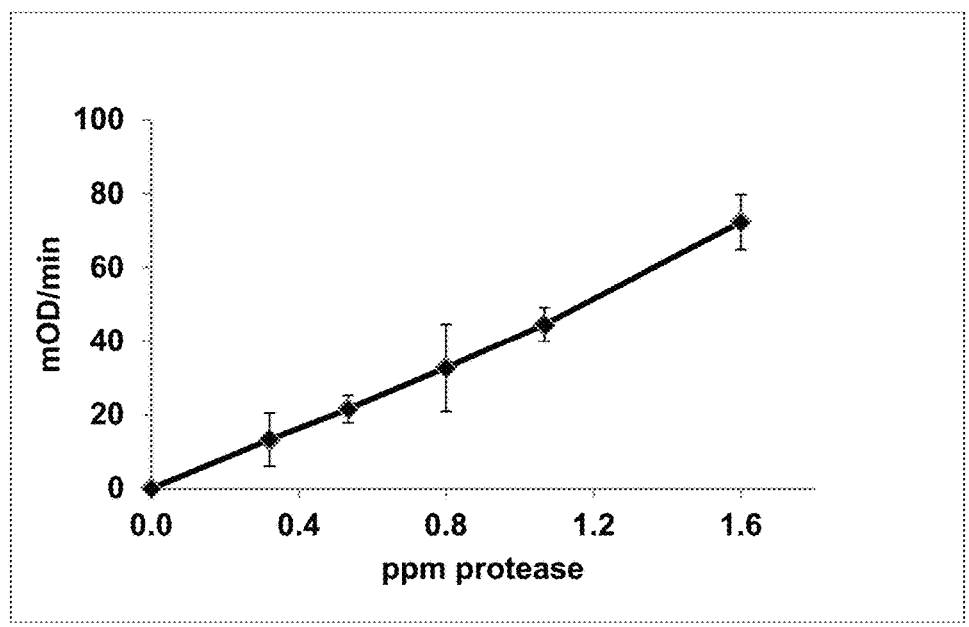
FIG. 5 shows the protease activity of BliD02339 protease on DMC substrate.

The protease activity of BliD02339 protease was tested by measuring the hydrolysis of DMC substrate. The reagent solutions used for the DMC assay were: 2.5% w/v Dimethylcasein (DMC, Sigma C-9801) in 100 mM Sodium Carbonate buffer pH 9.5, 0.075% TNBSA (2,4,6-trinitrobenzene sulfonic acid, Thermo Scientific) in Reagent A. Reagent A: 45.4 g $Na_2B_4O_7.10H_2O$ (Merck) in 15 mL 4N NaOH to reach a final volume of 1000 mL in deionised water. Protease supernatants were diluted in dilution Solution: 10 mM NaCl, 0.1 mM $CaCl_2$, 0.005% Tween-80 to appropriate concentration to achieve linear response during hydrolysis over 5 min. A 96-well MTP plate was filled with 95 µl DMC substrate followed by the addition of 5 µl diluted protease supernatant. 100 uL of TNBSA in Reagent A was then added with slow mixing. Activity was measured at 405 nm over 5 min using a SpectraMax plate reader in kinetic mode at RT. The absorbance of a blank containing no protease was subtracted from values. The activity was expressed as mOD/min. The protease activity curve for BliD02339 is shown in FIG. 5. The specific activity of BliD02339 protease in the DMC assay was found to be 26 mOD/min/ppm (where ppm is the final concentration of protease in the assay). The specific activities of GG36 and BPN' proteases were found to be 54 and 23 mOD/min/ppm, respectively, under the same assay conditions.

EXAMPLE 9 pH Profile of BliD02339

The pH dependence of proteolytic activity of BliD02339 protease was studied using an azo-casein substrate in a 50 mM Acetate/Bis-Tris/HEPES/CHES buffer including 50 mM $CaCl_2$. The effect of pH between 4 to 12 was measured in 1 pH unit increments. One Protaxyme AK tablet (Megazyme, Ireland) was added to a glass test tube together with 1.9 mL of appropriate buffer and a magnet stirrer, followed by gentle hydration at 40° C. for 5 min in a temperature controlled water bath fitted with magnetic stirrer. A 100 µl sample of freshly prepared protease (diluted in deionised water to appropriate concentration for the assay) was added to the prehydrated substrate and reaction was carried out at 40° C. for 10 min. To stop the reaction, 10 mL of a 2% w/v Tris buffer pH 12 was added and solution was stirred and immediately filtered through a Whatman No. 1 filter. The supernatant was collected and the absorbance at 590 nm was measured for this supernatant to quantify the product of the reaction. The absorbance from a buffer-only control was subtracted from each sample reading, and the resulting values were converted to percentages of relative activity, by defining the activity at the optimal pH as 100%. BliD02339 was determined to maintain ≥50% activity over the pH range of 6-12, under the conditions of this assay.

EXAMPLE 10

Temperature Profile of BliD02339

The temperature dependence of proteolytic activity of BliD02339 protease was measured using an azo-casein substrate in a 50 mM Acetate/Bis-Tris/HEPES/CHES buffer including 50 mM $CaCl_2$ at pH 9. The activity was measured at temperatures between 30° C. and 80° C. with 10° C. increments. One Protaxyme AK tablet (Megazyme, Ireland) was added to a glass test tube together with 1.9 mL of appropriate buffer and a magnet stirrer, followed by gentle hydration at set temperatures for 5 min in a temperature controlled water bath fitted with magnetic stirrer. A 100 µl sample of freshly prepared protease (diluted in deionised water to appropriate concentration for the assay) was added to the prehydrated substrate and reaction was carried out at temperatures between 30° C. and 80° C. for 10 min. To terminate the reaction, 10 mL of a 2% w/Tris buffer pH 12 was added and solution was stirred and filtered immediately through a Whatman No. 1 filter. The supernatant was collected and the absorbance at 590 nm was measured for this supernatant to quantify the product of the reaction. The absorbance from a buffer-only control was subtracted from each sample reading, and the resulting values were converted to percentages of relative activity, by defining the activity at the optimal temperature at 100%. BliD02339 was determined to retain ≥50% activity over a range of 55-75° C., under the conditions of this assay.

EXAMPLE 11

Cleaning Performance of BliD02339

The cleaning performance of BliD02339 was tested on BMI (blood/milk/ink on cotton) microswatches (EMPA-116, Center for Testmaterials, The Netherlands) for laundry based applications, and on egg yolk (egg yolk on polyacryl fabric, aged and colored with carbon black dye) microswatches (PAS-38, Center for Testmaterials, The Netherlands) for dish based applications. MTPs (Corning 3641) containing pre-punched (to fit on MTP) swatches, were rinsed, and filled with detergent prior to enzyme addition. Detergents OMO color HDD, Kirkland Ultra HDD, OMO Klein & Krachtig HDL, Kirkland Ultraclean HDL, GSM-B 10.5 ADW, and GSM-B 9 ADW, were dosed as described in Tables 2 or 3 above.

The commercial HDL laundry detergents were inactivated by heating to 95° C. for 4 hours in a water bath. The commercial HDD laundry detergents were inactivated by preparing a 10% w/v solution and heating for 4 hours at 95° C. Protease activity was assayed following inactivation using the AAPF substrate. After 4 hour heating of both HDD and HDL detergents, protease activity was non-existent.

Aliquots of enzyme were added to a detergent-filled microswatch plate to reach a final volume of 200 uL for laundry assays, to 0.04 to 10 ppm final enzyme concentration. Laundry cleaning assays with HDL or HDD formulas was carried out at 25° C. for 15 min, while ADW assays were carried out at 40° C. for 30 min.

Figure 6:
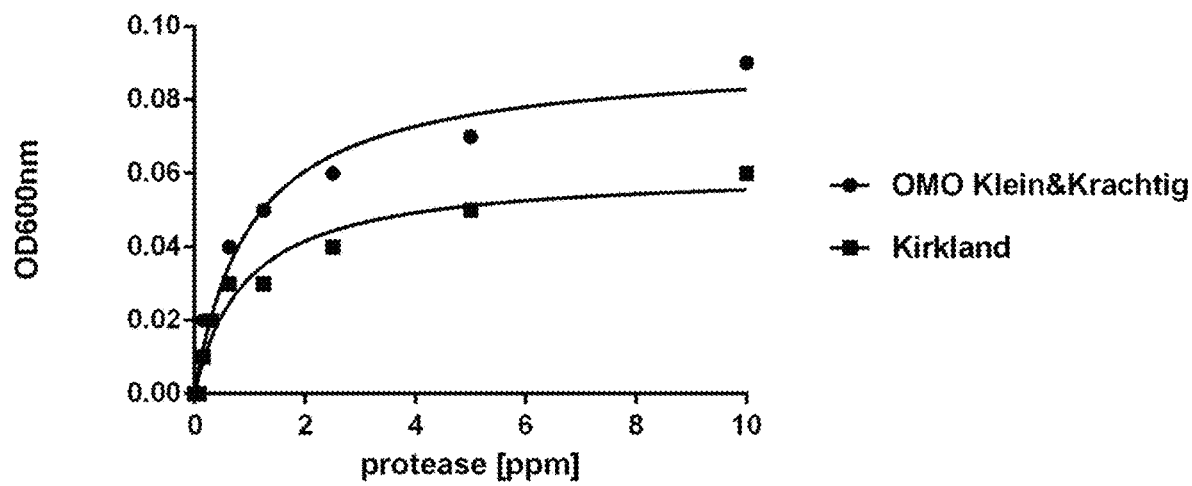
FIG. 6 shows the cleaning performance of BliD02339 in HDL detergents.
Figure 7:
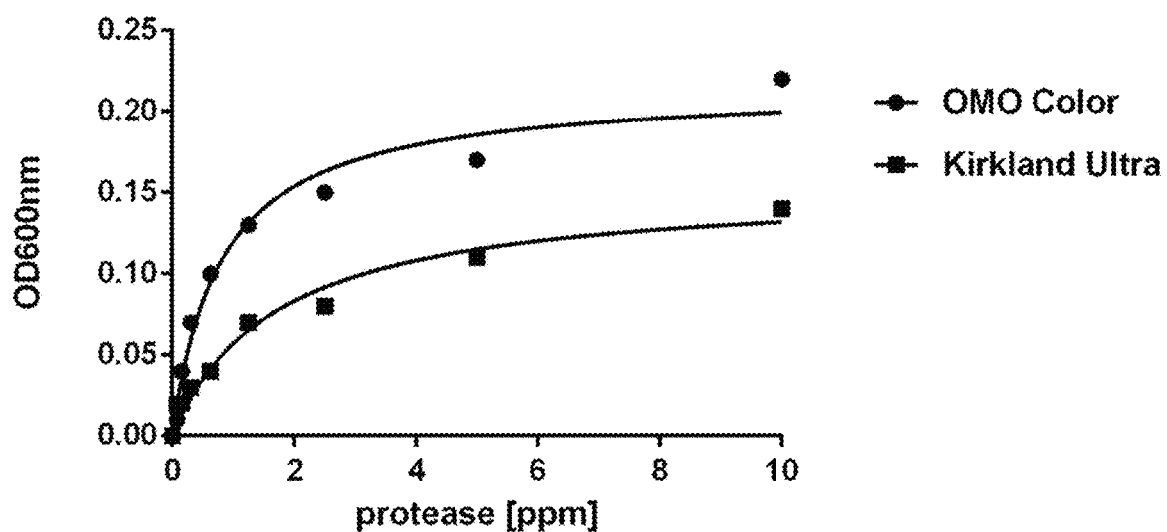
FIG. 7 shows the cleaning performance of BliD02339 in HDD detergents.
Figure 8:
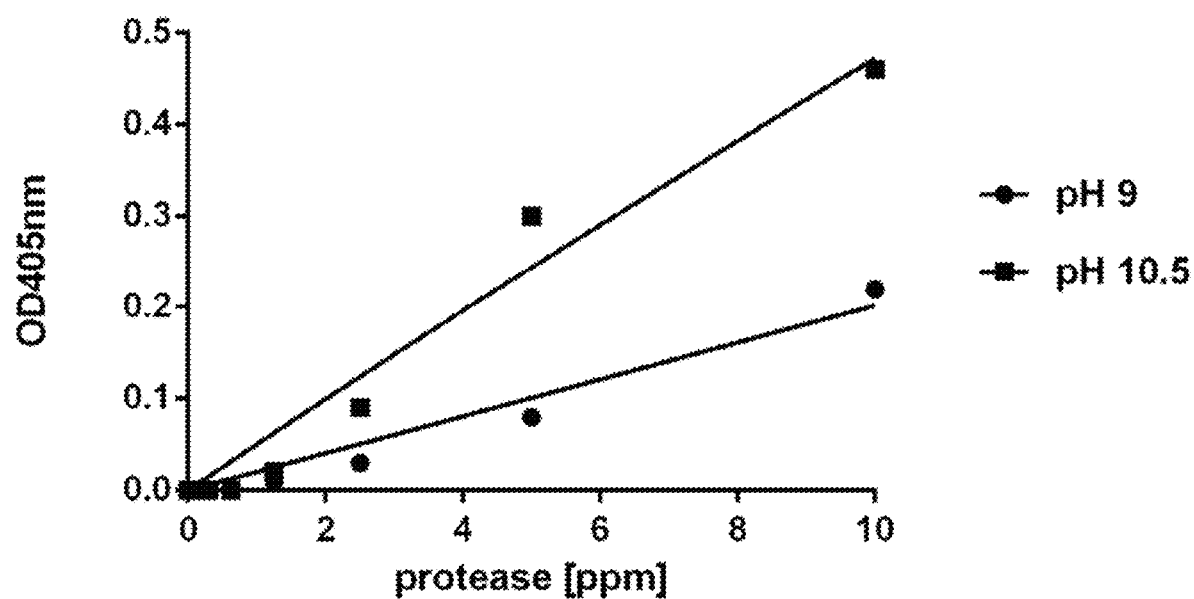
FIG. 8 shows the cleaning performance of BliD02339 in ADW detergents.

Following incubation, 100 uL of supernatant was transferred to a fresh MTP (Costar 9017) and absorbance was read at 600 nm for EMPA-116 swatches, or at 405 nm for PAS-38 swatches, using the SpectraMax plate reader. The absorbance from a buffer-only control was subtracted and the resulting OD values at 600 nm (for HDL and HDD detergents) and 405 nm (for ADW detergents) were plotted as a function of protease concentration. The data was fitted to Langmuir equation. The cleaning performances of BliD02339 are shown graphically in FIGS. 6-8.

EXAMPLE 12

Phylogenetic Tree for Subtilisins Including AprL and BliD02339

A phylogenetic tree for mature sequences of AprL protein (SEQ ID NO:2) and BliD02339 (SEQ ID NO: 9) was built using a subset of the sequences of subtilisins shown in Table 8. The sequences were entered in the Vector NTI Advance suite and a Guide Tree was created using the Neighbor Joining method (NJ) (Saitou, N.; and Nei, M. (1987) Mol Biol Evol 4, 406-425). The NJ method works on a matrix of distances between all pairs of sequences to be analyzed. These distances are related to the degree of divergence between the sequences. The Guide Tree is calculated after the sequences are aligned. The tree construction was calculated using the following parameters: Kimura's correction for sequence distance and ignoring positions with gaps. AlignX displays the calculated distance values in parenthesis following the molecule name displayed on the phylogenetic tree shown in FIG. 9. Based on the phylogenetic tree distribution, certain subtilisins have been grouped as shown in FIG. 9 to form the AprL-clade.

EXAMPLE 13

Unique Features of AprL-Clade Subtilisins

As shown in FIG. 9, subtilisin AprL (*B. licheniformis* Carlsberg), its close homolog BliD02339, and all other *B. licheniformis* subtilisins plus *B. sonorenisis* subtilisins share sufficient features to create a clade, subsequently termed the AprL-Clade. A high resolution structure of AprL (pdb 3UNX) was used to evaluate the position of invariate residues shared by the enzymes in the AprL-Clade. High resolution structures of other subtilisins were used as comparison (BPN' pdb 2ST1 and *B. lentus* subtilisin pdb 1JEA). Comparison of these structures served to identify a series of sequence/structure motifs with significant differences between the AprL-Clade enzymes and other subtilisins. Some of these invariate regions of significance are described below.

Figure 10:
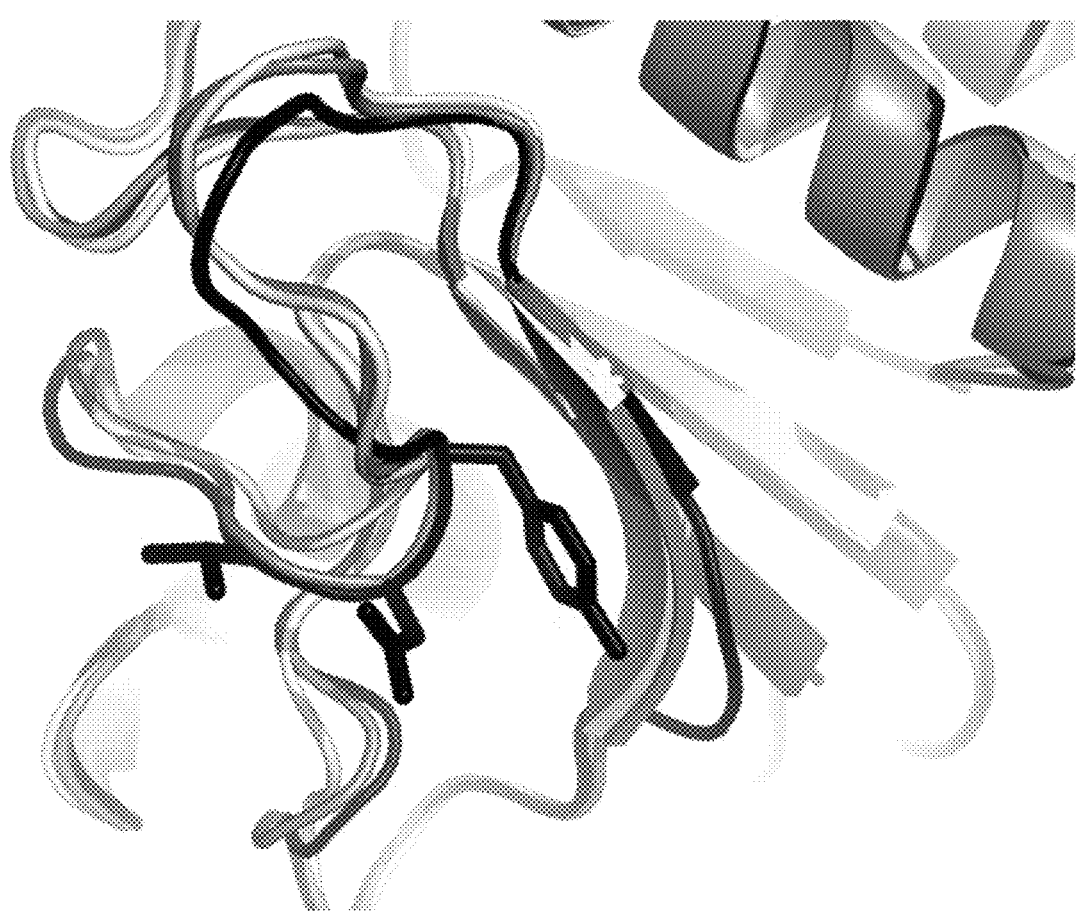
FIG. 10 shows a structural representation of the loop region encompassing Y56N57T58 (side chains shown as sticks) of AprL (black), in comparison to cognate region in BPN' (gray) and *B. lentus* (light gray) subtilisins.

The 52-60 loop differs wildly between AprL-Clade subtilisins and other subtilins, exemplified by BPN' and *B. lentus* subtilisin. One feature in the AprL-Clade subtilisins sequence is Tyr-Asn-Thr ("YNT") residues at positions 56-58, which will determine the end course of this loop in AprL-Clade subtilisins, see FIG. 10. In FIG. 10 we find that the unique YNT sequence occurs at the tip of a loop. The conformation of this loop 52-60 is heterologous in the different subtilisin structures shown. We attribute this difference in part to this unique sequence. This loop is sometimes the site of autolytic cleavage and thus the conformation of the AprL loop which is not clipped is crucial to its function.

Residues 240-243 in AprL-Clade subtilisins have the common sequence Leu-Ser-Ala-Ser ("LSAS"). In this region, Leu240 is smaller than the larger hydrophobic residues found in other subtilisins such as BPN' and *B. lentus* where a tryptophan side chain is found, see FIG. 11. The smaller Leu in AprL-Clade can accommodate the Arg 248 side chain allowing a conservation of the turn and introduction of a positive charge on the surface at this position in AprL-Clade subtilisins.

In addition, the Asn 96 in AprL-Clade subtilisins can form a hydrogen bond with the main chain amide of residue Ser 98 to stabilize a turn leading to the strand 101-104 which is one part of the substrate binding site, see FIG. 12.

---

SEQUENCE LISTING

<160> NUMBER OF SEQ ID NOS: 60

<210> SEQ ID NO 1
<211> LENGTH: 822
<212> TYPE: DNA
<213> ORGANISM: Artificial Sequence
<220> FEATURE:
<223> OTHER INFORMATION: Synthetic nucleotide sequence of the AprL gene

<400> SEQUENCE: 1

```
gcgcaaaccg ttccttacgg cattcctctc attaaagcgg acaaagtgca ggctcaaggc      60
tttaagggag cgaatgtaaa agtagccgtc ctggatacag gaatccaagc atctcatccg     120
gacttgaacg tagtcggcgg agcgagcttt gtggctggcg aagcatataa caccgacggc     180
aacggacacg gcacacatgt tgccggtaca gtagctgcgc ttgacaatac aacgggtgta     240
ttaggcgttg cgccaagcgt atccttgtac gcggttaaag tactgaactc aagcggaagc     300
ggatcataca gcggcattgt aagcggaatc gagtgggcga caacaaacgg catggatgtt     360
atcaatatga gccttggggg agcatcaggc tcgacagcga tgaaacaggc agtcgacaat     420
gcatacgcaa gagggggttgt cgttgtagca gcagctggga acagcggatc ttcaggaaac     480
acgaatacaa ttggctatcc tgcgaaatac gattctgtca tcgctgttgg cgcggtagac     540
tctaacagca acagagcttc attttccagt gtgggagcag agcttgaagt catggctcct     600
```

```
ggcgcaggcg tatacagcac ttacccaacg aacacttatg caacattgaa cggaacgtca      660
atggcttctc ctcatgtagc gggagcagca gctttgatct tgtcaaaaca tccgaacctt      720
tcagcttcac aagtccgcaa ccgtctctcc agcacggcga cttatttggg aagctccttc      780
tactatggga aaggtctgat caatgtcgaa gctgccgctc aa                         822
```

<210> SEQ ID NO 2
<211> LENGTH: 274
<212> TYPE: PRT
<213> ORGANISM: unknown
<220> FEATURE:
<223> OTHER INFORMATION: Bacillus sp.
<220> FEATURE:
<221> NAME/KEY: misc_feature
<223> OTHER INFORMATION: AprL subtilisin from Bacillus sp.

<400> SEQUENCE: 2

```
Ala Gln Thr Val Pro Tyr Gly Ile Pro Leu Ile Lys Ala Asp Lys Val
1               5                   10                  15

Gln Ala Gln Gly Phe Lys Gly Ala Asn Val Lys Val Ala Val Leu Asp
            20                  25                  30

Thr Gly Ile Gln Ala Ser His Pro Asp Leu Asn Val Val Gly Gly Ala
        35                  40                  45

Ser Phe Val Ala Gly Glu Ala Tyr Asn Thr Asp Gly Asn Gly His Gly
    50                  55                  60

Thr His Val Ala Gly Thr Val Ala Ala Leu Asp Asn Thr Thr Gly Val
65                  70                  75                  80

Leu Gly Val Ala Pro Ser Val Ser Leu Tyr Ala Val Lys Val Leu Asn
                85                  90                  95

Ser Ser Gly Ser Gly Ser Tyr Ser Gly Ile Val Ser Gly Ile Glu Trp
            100                 105                 110

Ala Thr Thr Asn Gly Met Asp Val Ile Asn Met Ser Leu Gly Gly Ala
        115                 120                 125

Ser Gly Ser Thr Ala Met Lys Gln Ala Val Asp Asn Ala Tyr Ala Arg
    130                 135                 140

Gly Val Val Val Ala Ala Ala Gly Asn Ser Gly Ser Ser Gly Asn
145                 150                 155                 160

Thr Asn Thr Ile Gly Tyr Pro Ala Lys Tyr Asp Ser Val Ile Ala Val
                165                 170                 175

Gly Ala Val Asp Ser Asn Ser Asn Arg Ala Ser Phe Ser Ser Val Gly
            180                 185                 190

Ala Glu Leu Glu Val Met Ala Pro Gly Ala Gly Val Tyr Ser Thr Tyr
        195                 200                 205

Pro Thr Asn Thr Tyr Ala Thr Leu Asn Gly Thr Ser Met Ala Ser Pro
    210                 215                 220

His Val Ala Gly Ala Ala Ala Leu Ile Leu Ser Lys His Pro Asn Leu
225                 230                 235                 240

Ser Ala Ser Gln Val Arg Asn Arg Leu Ser Ser Thr Ala Thr Tyr Leu
                245                 250                 255

Gly Ser Ser Phe Tyr Tyr Gly Lys Gly Leu Ile Asn Val Glu Ala Ala
            260                 265                 270

Ala Gln
```

<210> SEQ ID NO 3
<211> LENGTH: 607
<212> TYPE: DNA

<213> ORGANISM: Artificial Sequence
<220> FEATURE:
<223> OTHER INFORMATION: Synthetic nucleotide sequence of the aprE
    promoter

<400> SEQUENCE: 3

| | | | | | |
|---|---|---|---|---|---|
| attcctccat | tttcttctgc | tatcaaaata | acagactcgt | gattttccaa | acgagctttc | 60 |
| aaaaaagcct | ctgccccttg | caaatcggat | gcctgtctat | aaaattcccg | atattggtta | 120 |
| aacagcggcg | caatggcggc | cgcatctgat | gtctttgctt | ggcgaatgtt | catcttattt | 180 |
| cttcctccct | ctcaataatt | ttttcattct | atcccttttc | tgtaaagttt | attttcaga | 240 |
| atacttttat | catcatgctt | tgaaaaaata | tcacgataat | atccattgtt | ctcacggaag | 300 |
| cacacgcagg | tcatttgaac | gaattttttc | gacaggaatt | tgccgggact | caggagcatt | 360 |
| taacctaaaa | aagcatgaca | tttcagcata | atgaacattt | actcatgtct | attttcgttc | 420 |
| ttttctgtat | gaaaatagtt | atttcgagtc | tctacggaaa | tagcgagaga | tgatatacct | 480 |
| aaatagagat | aaaatcatct | caaaaaaatg | ggtctactaa | aatattattc | catctattac | 540 |
| aataaattca | cagaatagtc | ttttaagtaa | gtctactctg | aattttttta | aaaggagagg | 600 |
| gtaacta | | | | | | 607 |

<210> SEQ ID NO 4
<211> LENGTH: 87
<212> TYPE: DNA
<213> ORGANISM: Artificial Sequence
<220> FEATURE:
<223> OTHER INFORMATION: Synthetic nucleotide sequence of the signal
    peptide

<400> SEQUENCE: 4

| | | | | | |
|---|---|---|---|---|---|
| gtgagaagca | aaaaattgtg | gatcagcttg | ttgtttgcgt | taacgttaat | ctttacgatg | 60 |
| gcgttcagca | acatgtctgc | tagcgca | | | | 87 |

<210> SEQ ID NO 5
<211> LENGTH: 228
<212> TYPE: DNA
<213> ORGANISM: Artificial Sequence
<220> FEATURE:
<223> OTHER INFORMATION: Synthetic nucleotide sequence of the propeptide

<400> SEQUENCE: 5

| | | | | | |
|---|---|---|---|---|---|
| gctcaaccgg | cgaaaaatgt | tgaaaaggat | tatattgtcg | gatttaagtc | aggagtgaaa | 60 |
| accgcatctg | tcaaaaagga | catcatcaaa | gagagcggcg | gaaaagtgga | caagcagttt | 120 |
| agaatcatca | acgcggcaaa | agcgaagcta | gacaaagaag | cgcttaagga | agtcaaaaat | 180 |
| gatccggatg | tcgcttatgt | ggaagaggat | catgtggccc | atgccttg | | 228 |

<210> SEQ ID NO 6
<211> LENGTH: 247
<212> TYPE: DNA
<213> ORGANISM: Artificial Sequence
<220> FEATURE:
<223> OTHER INFORMATION: Synthetic nucleotide sequence of the terminator

<400> SEQUENCE: 6

| | | | | | |
|---|---|---|---|---|---|
| acataaaaaa | ccggccttgg | ccccgccggt | tttttattat | ttttcttcct | ccgcatgttc | 60 |
| aatccgctcc | ataatcgacg | gatggctccc | tctgaaaatt | ttaacgagaa | acggcgggtt | 120 |
| gacccggctc | agtcccgtaa | cggccaagtc | ctgaaacgtc | tcaatcgccg | cttcccggtt | 180 |
| tccggtcagc | tcaatgccgt | aacggtcggc | ggcgttttcc | tgataccggg | agacggcatt | 240 | cgtaatc                                                                        247

<210> SEQ ID NO 7
<211> LENGTH: 1137
<212> TYPE: DNA
<213> ORGANISM: Bacillus licheniformis
<220> FEATURE:
<221> NAME/KEY: misc_feature
<222> LOCATION: (1)..(1137)
<223> OTHER INFORMATION: nucleotide sequence of the BliD02339.n gene

<400> SEQUENCE: 7

```
atgatgagga aaaagagttt ttggcttggg atgctgacgg ccttaatgct cgtgttcacg      60
atggcattca gcgattccgc ttctgctgct caaccggcga aaatgttga aaaggattat     120
attgtcggat ttaagtcagg agtgaaaacc gcatctgtca aaaggacat catcaaagag     180
agcggcggaa aagtggacaa gcagtttaga atcatcaacg cggcaaaagc gaagctagac     240
aaagaagcgc ttaaggaagt caaaaatgat ccggatgtcg cttatgtgga agaggatcat     300
gtggcccatg ccttggcgca aaccgttcct tacggcattc ctctcattaa agcggacaaa     360
gtgcaggctc aaggctttaa gggagcgaat gtaaaagtag ccgtcctgga tacaggaatc     420
caagcttctc atccggactt gaacgtagtc ggcggagcaa gctttgtggc tggcgaagct     480
tataacaccg acggcaacgg acacggcacg catgttgccg gtacagtagc tgcgcttgac     540
aatacaacgg gtgtattagg cgttgcgccg aacgtatcct tgtacgcggt taaagtgctg     600
aattcaagcg gaagcggatc ttacagcggc attgtaagcg gaatcgagtg ggcgacgaca     660
aacggcatgg atgttatcaa catgagcctt ggaggaccat caggctcaac agcgatgaaa     720
caggcggttg acaatgcata tgcaagaggg gttgtcgttg tggcggctgc tgggaacagc     780
ggatcttcag gaaacacgaa tacaatcggc tatcctgcga aatacgactc tgtcatcgca     840
gttggcgcgg tagactctaa cagcaacaga gcttcatttt ccagcgtcgg agcaaagctt     900
gaagtcatgg ctcctggcgc aggcgtgtac agcacttacc caaccagcac ttatgcaaca     960
ttgaacggaa cgtcaatggc ttctcctcat gtagcgggag cagcagcttt gatcttgtca    1020
aaacatccga acctttcagc ttcacaagtc cgcaaccgtc tctccagtac ggcgactyat    1080
ttgggaagct ccttctacta tggaaaaggt ctgatcaatg tcgaagctgc cgctcaa      1137
```

<210> SEQ ID NO 8
<211> LENGTH: 379
<212> TYPE: PRT
<213> ORGANISM: Bacillus licheniformis
<220> FEATURE:
<221> NAME/KEY: misc_feature
<222> LOCATION: (1)..(379)
<223> OTHER INFORMATION: amino acid sequence of the BliD02339
     pre-proenzyme

<400> SEQUENCE: 8

Met Met Arg Lys Lys Ser Phe Trp Leu Gly Met Leu Thr Ala Leu Met
1               5                   10                  15

Leu Val Phe Thr Met Ala Phe Ser Asp Ser Ala Ser Ala Ala Gln Pro
            20                  25                  30

Ala Lys Asn Val Glu Lys Asp Tyr Ile Val Gly Phe Lys Ser Gly Val
        35                  40                  45

Lys Thr Ala Ser Val Lys Lys Asp Ile Ile Lys Glu Ser Gly Gly Lys
    50                  55                  60

Val Asp Lys Gln Phe Arg Ile Ile Asn Ala Ala Lys Ala Lys Leu Asp

```
                65                  70                  75                  80
Lys Glu Ala Leu Lys Glu Val Lys Asn Asp Pro Asp Val Ala Tyr Val
                    85                  90                  95

Glu Glu Asp His Val Ala His Ala Leu Ala Gln Thr Val Pro Tyr Gly
                100                 105                 110

Ile Pro Leu Ile Lys Ala Asp Lys Val Gln Ala Gln Gly Phe Lys Gly
                115                 120                 125

Ala Asn Val Lys Val Ala Val Leu Asp Thr Gly Ile Gln Ala Ser His
                130                 135                 140

Pro Asp Leu Asn Val Val Gly Gly Ala Ser Phe Val Ala Gly Glu Ala
145                 150                 155                 160

Tyr Asn Thr Asp Gly Asn Gly His Gly Thr His Val Ala Gly Thr Val
                165                 170                 175

Ala Ala Leu Asp Asn Thr Thr Gly Val Leu Gly Val Ala Pro Asn Val
                180                 185                 190

Ser Leu Tyr Ala Val Lys Val Leu Asn Ser Ser Gly Ser Gly Ser Tyr
                195                 200                 205

Ser Gly Ile Val Ser Gly Ile Glu Trp Ala Thr Thr Asn Gly Met Asp
                210                 215                 220

Val Ile Asn Met Ser Leu Gly Gly Pro Ser Gly Ser Thr Ala Met Lys
225                 230                 235                 240

Gln Ala Val Asp Asn Ala Tyr Ala Arg Gly Val Val Val Val Ala Ala
                245                 250                 255

Ala Gly Asn Ser Gly Ser Ser Gly Asn Thr Asn Thr Ile Gly Tyr Pro
                260                 265                 270

Ala Lys Tyr Asp Ser Val Ile Ala Val Gly Ala Val Asp Ser Asn Ser
                275                 280                 285

Asn Arg Ala Ser Phe Ser Ser Val Gly Ala Lys Leu Glu Val Met Ala
                290                 295                 300

Pro Gly Ala Gly Val Tyr Ser Thr Tyr Pro Thr Ser Thr Tyr Ala Thr
305                 310                 315                 320

Leu Asn Gly Thr Ser Met Ala Ser Pro His Val Ala Gly Ala Ala Ala
                325                 330                 335

Leu Ile Leu Ser Lys His Pro Asn Leu Ser Ala Ser Gln Val Arg Asn
                340                 345                 350

Arg Leu Ser Ser Thr Ala Thr Tyr Leu Gly Ser Ser Phe Tyr Tyr Gly
                355                 360                 365

Lys Gly Leu Ile Asn Val Glu Ala Ala Ala Gln
                370                 375

<210> SEQ ID NO 9
<211> LENGTH: 274
<212> TYPE: PRT
<213> ORGANISM: Bacillus licheniformis
<220> FEATURE:
<221> NAME/KEY: misc_feature
<222> LOCATION: (1)..(274)
<223> OTHER INFORMATION: BliD02339

<400> SEQUENCE: 9

Ala Gln Thr Val Pro Tyr Gly Ile Pro Leu Ile Lys Ala Asp Lys Val
1               5                   10                  15

Gln Ala Gln Gly Phe Lys Gly Ala Asn Val Lys Val Ala Val Leu Asp
                20                  25                  30

Thr Gly Ile Gln Ala Ser His Pro Asp Leu Asn Val Val Gly Gly Ala
                35                  40                  45
```

```
Ser Phe Val Ala Gly Glu Ala Tyr Asn Thr Asp Gly Asn Gly His Gly
 50                  55                  60

Thr His Val Ala Gly Thr Val Ala Ala Leu Asp Asn Thr Thr Gly Val
 65                  70                  75                  80

Leu Gly Val Ala Pro Asn Val Ser Leu Tyr Ala Val Lys Val Leu Asn
                 85                  90                  95

Ser Ser Gly Ser Gly Ser Tyr Ser Gly Ile Val Ser Gly Ile Glu Trp
            100                 105                 110

Ala Thr Thr Asn Gly Met Asp Val Ile Asn Met Ser Leu Gly Gly Pro
        115                 120                 125

Ser Gly Ser Thr Ala Met Lys Gln Ala Val Asp Asn Ala Tyr Ala Arg
130                 135                 140

Gly Val Val Val Ala Ala Ala Gly Asn Ser Gly Ser Ser Gly Asn
145                 150                 155                 160

Thr Asn Thr Ile Gly Tyr Pro Ala Lys Tyr Asp Ser Val Ile Ala Val
                165                 170                 175

Gly Ala Val Asp Ser Asn Ser Asn Arg Ala Ser Phe Ser Ser Val Gly
            180                 185                 190

Ala Lys Leu Glu Val Met Ala Pro Gly Ala Gly Val Tyr Ser Thr Tyr
        195                 200                 205

Pro Thr Ser Thr Tyr Ala Thr Leu Asn Gly Thr Ser Met Ala Ser Pro
210                 215                 220

His Val Ala Gly Ala Ala Ala Leu Ile Leu Ser Lys His Pro Asn Leu
225                 230                 235                 240

Ser Ala Ser Gln Val Arg Asn Arg Leu Ser Ser Thr Ala Thr Tyr Leu
                245                 250                 255

Gly Ser Ser Phe Tyr Tyr Gly Lys Gly Leu Ile Asn Val Glu Ala Ala
            260                 265                 270

Ala Gln

<210> SEQ ID NO 10
<211> LENGTH: 93
<212> TYPE: DNA
<213> ORGANISM: Artificial Sequence
<220> FEATURE:
<223> OTHER INFORMATION: Synthetic terminator sequence

<400> SEQUENCE: 10
ggttaccttg aatgtatata aacattctca aagggatttc taataaaaaa cgctcggttg    60
ccgccgggcg ttttttatgc atcgatggaa ttc                                 93

<210> SEQ ID NO 11
<211> LENGTH: 21
<212> TYPE: DNA
<213> ORGANISM: Artificial Sequence
<220> FEATURE:
<223> OTHER INFORMATION: Synthetic new linker sequence

<400> SEQUENCE: 11
ggatcctgac tgcctgagct t                                              21

<210> SEQ ID NO 12
<211> LENGTH: 274
<212> TYPE: PRT
<213> ORGANISM: Bacillus licheniformis
<220> FEATURE:
<221> NAME/KEY: misc_feature
<222> LOCATION: (1)..(274)
```

<223> OTHER INFORMATION: B_licheniformis_CAA62667

<400> SEQUENCE: 12

```
Gly Gln Thr Val Pro Tyr Gly Ile Pro Leu Ile Lys Ala Asp Lys Val
1               5                   10                  15

Gln Ala Gln Gly Phe Lys Gly Ala Asn Val Lys Val Ala Val Leu Asp
            20                  25                  30

Thr Gly Ile Gln Ala Ser His Pro Asp Leu Asn Val Val Gly Gly Ala
        35                  40                  45

Ser Phe Val Ala Gly Glu Ala Tyr Asn Thr Asp Gly Asn Gly His Gly
    50                  55                  60

Thr His Val Ala Gly Thr Val Ala Ala Leu Asp Asn Thr Thr Gly Val
65                  70                  75                  80

Leu Gly Val Ala Pro Ser Val Ser Leu Tyr Ala Val Lys Val Leu Asn
                85                  90                  95

Ser Ser Gly Ser Gly Ser Tyr Ser Ala Ile Val Ser Gly Ile Glu Trp
            100                 105                 110

Ala Thr Thr Thr Gly Met Asp Val Ile Asn Met Ser Leu Gly Gly Ala
        115                 120                 125

Ser Val Ser Thr Ala Met Lys Gln Ala Val Asp His Ala Tyr Ala Arg
    130                 135                 140

Gly Ala Val Val Ser Ser Ala Gly Asn Ser Gly Ser Ser Gly Asn
145                 150                 155                 160

Thr Asn Thr Ile Gly Tyr Pro Ala Lys Tyr Asp Ser Val Ile Ala Val
                165                 170                 175

Gly Ala Val Asp Ser Asn Ser Asn Arg Ala Ser Phe Ser Ser Val Gly
            180                 185                 190

Ala Glu Leu Glu Val Met Ala Pro Gly Ala Gly Val Tyr Ser Thr Tyr
        195                 200                 205

Pro Thr Asn Thr Tyr Ala Thr Leu Asn Gly Thr Ser Met Ala Ser Pro
    210                 215                 220

His Val Ala Gly Ala Ala Ala Leu Ile Leu Ser Lys His Pro Asn Leu
225                 230                 235                 240

Ser Ala Ser Gln Val Arg Thr Arg Leu Ser Arg Thr Ala Thr Tyr Leu
                245                 250                 255

Gly Ser Ser Phe Ser Tyr Gly Arg Gly Leu Ile Asn Val Glu Ala Ala
            260                 265                 270

Ala Gln
```

<210> SEQ ID NO 13
<211> LENGTH: 274
<212> TYPE: PRT
<213> ORGANISM: Bacillus licheniformis
<220> FEATURE:
<221> NAME/KEY: misc_feature
<222> LOCATION: (1)..(274)
<223> OTHER INFORMATION: B_licheniformis_AEU12640.1

<400> SEQUENCE: 13

```
Ala Gln Thr Val Pro Tyr Gly Ile Pro Leu Ile Lys Ala Asp Lys Leu
1               5                   10                  15

His Ala Gln Gly Phe Lys Gly Ala Asn Val Lys Gly Ala Val Leu Ala
            20                  25                  30

Thr Gly Ile Pro Thr Ser His Pro Asp Leu Asn Val Val Gly Gly Ala
        35                  40                  45

Ser Phe Val Ala Gly Glu Ala Tyr Asn Thr Asp Gly Asn Gly His Gly
```

```
                50                  55                  60
Thr His Val Ala Gly Thr Val Ala Ala Leu Asp Asn Thr Thr Gly Val
 65                  70                  75                  80

Leu Gly Val Ala Pro Ser Val Ser Leu Tyr Ala Val Lys Val Leu Asn
                 85                  90                  95

Ser Ser Gly Ser Gly Ser Tyr Ser Gly Ile Val Ser Gly Ile Glu Trp
                100                 105                 110

Ala Thr Thr Asn Gly Met Asp Val Ile Asn Met Ser Leu Gly Gly Ala
                115                 120                 125

Ser Gly Ser Thr Ala Met Lys Gln Ala Val Asp Asn Ala Tyr Ala Lys
                130                 135                 140

Gly Val Val Val Ala Ala Gly Asn Ser Gly Ser Ser Gly Asn
145                 150                 155                 160

Thr Asn Thr Ile Gly Tyr Pro Ala Lys Tyr Asp Ser Val Ile Ala Val
                165                 170                 175

Gly Ala Val Asp Ser Asn Ser Asn Arg Ala Ser Phe Ser Ser Val Gly
                180                 185                 190

Ala Glu Leu Glu Val Met Ala Pro Gly Ala Gly Val Tyr Ser Thr Tyr
                195                 200                 205

Pro Thr Asn Thr Tyr Ala Thr Leu Asn Gly Thr Ser Met Ala Ser Pro
                210                 215                 220

His Val Ala Gly Ala Ala Ala Leu Ile Leu Ser Lys His Pro Asn Leu
225                 230                 235                 240

Ser Ala Ser Gln Val Arg Asn Arg Leu Ser Ser Thr Ala Thr Tyr Leu
                245                 250                 255

Gly Ser Ser Phe Tyr Tyr Gly Lys Gly Leu Ile Asn Val Glu Ala Ala
                260                 265                 270

Ala Gln

<210> SEQ ID NO 14
<211> LENGTH: 274
<212> TYPE: PRT
<213> ORGANISM: Bacillus licheniformis
<220> FEATURE:
<221> NAME/KEY: misc_feature
<222> LOCATION: (1)..(274)
<223> OTHER INFORMATION: B_licheniformis_YP_006712489

<400> SEQUENCE: 14

Ala Gln Thr Val Pro Tyr Gly Ile Pro Leu Ile Lys Ala Asp Lys Val
 1               5                  10                  15

Gln Ala Gln Gly Tyr Lys Gly Ala Asn Val Lys Val Ala Val Leu Asp
                 20                  25                  30

Thr Gly Ile Gln Ala Ser His Pro Asp Leu Asn Val Val Gly Gly Ala
                 35                  40                  45

Ser Phe Val Ala Gly Glu Ala Tyr Asn Thr Asp Gly Asn Gly His Gly
                 50                  55                  60

Thr His Val Ala Gly Thr Val Ala Ala Leu Asp Asn Thr Thr Gly Val
 65                  70                  75                  80

Leu Gly Val Ala Pro Asn Val Ser Leu Tyr Ala Val Lys Val Leu Asn
                 85                  90                  95

Ser Ser Gly Ser Gly Ser Tyr Ser Gly Ile Val Ser Gly Ile Glu Trp
                100                 105                 110

Ala Thr Thr Asn Gly Met Asp Val Ile Asn Met Ser Leu Gly Gly Pro
                115                 120                 125
```

```
Ser Gly Ser Thr Ala Met Lys Gln Ala Val Asp Asn Ala Tyr Ala Arg
    130                 135                 140

Gly Val Val Val Ala Ala Gly Asn Ser Gly Ser Ser Gly Asn
145                 150                 155                 160

Thr Asn Thr Ile Gly Tyr Pro Ala Lys Tyr Asp Ser Val Ile Ala Val
                165                 170                 175

Gly Ala Val Asp Ser Asn Ser Asn Arg Ala Ser Phe Ser Ser Val Gly
                180                 185                 190

Ala Glu Leu Glu Val Met Ala Pro Gly Ala Gly Val Tyr Ser Thr Tyr
            195                 200                 205

Pro Thr Ser Thr Tyr Ala Thr Leu Asn Gly Thr Ser Met Ala Ser Pro
    210                 215                 220

His Val Ala Gly Ala Ala Ala Leu Ile Leu Ser Lys His Pro Asn Leu
225                 230                 235                 240

Ser Ala Ser Gln Val Arg Asn Arg Leu Ser Ser Thr Ala Thr Tyr Leu
                245                 250                 255

Gly Ser Ser Phe Tyr Tyr Gly Lys Gly Leu Ile Asn Val Glu Ala Ala
                260                 265                 270

Ala Gln

<210> SEQ ID NO 15
<211> LENGTH: 274
<212> TYPE: PRT
<213> ORGANISM: Bacillus licheniformis
<220> FEATURE:
<221> NAME/KEY: misc_feature
<222> LOCATION: (1)..(274)
<223> OTHER INFORMATION: B_licheniformis_DY_P00781

<400> SEQUENCE: 15

Ala Gln Thr Val Pro Tyr Gly Ile Pro Leu Ile Lys Ala Asp Lys Val
1               5                   10                  15

Gln Ala Gln Gly Tyr Lys Gly Ala Asn Val Lys Val Gly Ile Ile Asp
            20                  25                  30

Thr Gly Ile Ala Ala Ser His Thr Asp Leu Lys Val Val Gly Gly Ala
        35                  40                  45

Ser Phe Val Ser Gly Glu Ser Tyr Asn Thr Asp Gly Asn Gly His Gly
    50                  55                  60

Thr His Val Ala Gly Thr Val Ala Ala Leu Asp Asn Thr Thr Gly Val
65                  70                  75                  80

Leu Gly Val Ala Pro Asn Val Ser Leu Tyr Ala Ile Lys Val Leu Asn
                85                  90                  95

Ser Ser Gly Ser Gly Thr Tyr Ser Ala Ile Val Ser Gly Ile Glu Trp
            100                 105                 110

Ala Thr Gln Asn Gly Leu Asp Val Ile Asn Met Ser Leu Gly Gly Pro
        115                 120                 125

Ser Gly Ser Thr Ala Leu Lys Gln Ala Val Asp Lys Ala Tyr Ala Ser
    130                 135                 140

Gly Ile Val Val Val Ala Ala Gly Asn Ser Gly Ser Ser Gly Ser
145                 150                 155                 160

Gln Asn Thr Ile Gly Tyr Pro Ala Lys Tyr Asp Ser Val Ile Ala Val
                165                 170                 175

Gly Ala Val Asp Ser Asn Lys Asn Arg Ala Ser Phe Ser Ser Val Gly
                180                 185                 190

Ala Glu Leu Glu Val Met Ala Pro Gly Val Ser Val Tyr Ser Thr Tyr
            195                 200                 205
```

Pro Ser Asn Thr Tyr Thr Ser Leu Asn Gly Thr Ser Met Ala Ser Pro
     210                 215                 220

His Val Ala Gly Ala Ala Leu Ile Leu Ser Lys Tyr Pro Thr Leu
225                 230                 235                 240

Ser Ala Ser Gln Val Arg Asn Arg Leu Ser Ser Thr Ala Thr Asn Leu
             245                 250                 255

Gly Asp Ser Phe Tyr Tyr Gly Lys Gly Leu Ile Asn Val Glu Ala Ala
             260                 265                 270

Ala Gln

<210> SEQ ID NO 16
<211> LENGTH: 274
<212> TYPE: PRT
<213> ORGANISM: Bacillus sonorensis
<220> FEATURE:
<221> NAME/KEY: misc_feature
<222> LOCATION: (1)..(274)
<223> OTHER INFORMATION: B_sonorensis_WP_006636716

<400> SEQUENCE: 16

Ala Gln Thr Val Pro Tyr Gly Ile Pro Leu Ile Lys Ala Asp Lys Val
1               5                   10                  15

Gln Ala Gln Gly Tyr Lys Gly Ala Asn Val Lys Val Gly Ile Ile Asp
             20                  25                  30

Thr Gly Ile Ala Ser Ser His Thr Asp Leu Lys Val Val Gly Gly Ala
         35                  40                  45

Ser Phe Val Ser Gly Glu Ser Tyr Asn Thr Asp Gly Asn Gly His Gly
 50                  55                  60

Thr His Val Ala Gly Thr Val Ala Ala Leu Asp Asn Thr Thr Gly Val
65                  70                  75                  80

Leu Gly Val Ala Pro Asn Val Ser Leu Tyr Ala Ile Lys Val Leu Asn
                 85                  90                  95

Ser Ser Gly Ser Gly Thr Tyr Ser Ala Ile Val Ser Gly Ile Glu Trp
            100                 105                 110

Ala Thr Gln Asn Gly Leu Asp Val Ile Asn Met Ser Leu Gly Gly Pro
        115                 120                 125

Ser Gly Ser Thr Ala Leu Lys Gln Ala Val Asp Lys Ala Tyr Ala Ser
130                 135                 140

Gly Ile Val Val Val Ala Ala Ala Gly Asn Ser Gly Ser Ser Gly Ser
145                 150                 155                 160

Gln Asn Thr Ile Gly Tyr Pro Ala Lys Tyr Asp Ser Val Ile Ala Val
                165                 170                 175

Gly Ala Val Asp Ser Asn Lys Asn Arg Ala Ser Phe Ser Ser Val Gly
            180                 185                 190

Ser Glu Leu Glu Val Met Ala Pro Gly Val Ser Val Tyr Ser Thr Tyr
        195                 200                 205

Pro Ser Asn Thr Tyr Thr Ser Leu Asn Gly Thr Ser Met Ala Ser Pro
     210                 215                 220

His Val Ala Gly Ala Ala Leu Ile Leu Ser Lys Tyr Pro Thr Leu
225                 230                 235                 240

Ser Ala Ser Gln Val Arg Asn Arg Leu Ser Ser Thr Ala Thr Asn Leu
             245                 250                 255

Gly Asp Ser Phe Tyr Tyr Gly Lys Gly Leu Ile Asn Val Glu Ala Ala
             260                 265                 270

Ala Gln

<210> SEQ ID NO 17
<211> LENGTH: 269
<212> TYPE: PRT
<213> ORGANISM: Bacillus lentus
<220> FEATURE:
<221> NAME/KEY: misc_feature
<222> LOCATION: (1)..(269)
<223> OTHER INFORMATION: B_lentus_P29600

<400> SEQUENCE: 17

Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
        35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Ser Gly Ser Gly Ser Val Ser Ser Ile Ala Gln Gly Leu Glu Trp Ala
            100                 105                 110

Gly Asn Asn Gly Met His Val Ala Asn Leu Ser Leu Gly Ser Pro Ser
        115                 120                 125

Pro Ser Ala Thr Leu Glu Gln Ala Val Asn Ser Ala Thr Ser Arg Gly
    130                 135                 140

Val Leu Val Val Ala Ala Ser Gly Asn Ser Gly Ala Gly Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
        195                 200                 205

Ala Ser Leu Asn Gly Thr Ser Met Ala Thr Pro His Val Ala Gly Ala
    210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265

<210> SEQ ID NO 18
<211> LENGTH: 269
<212> TYPE: PRT
<213> ORGANISM: Bacillus clausii
<220> FEATURE:
<221> NAME/KEY: misc_feature
<222> LOCATION: (1)..(269)
<223> OTHER INFORMATION: B_clausii_BAD63300

<400> SEQUENCE: 18

Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
                20                  25                  30

Thr Gly Ile Ser Thr His Pro Asp Leu Asn Ile Arg Gly Gly Ala Ser
            35                  40                  45

Phe Val Pro Gly Glu Pro Ser Thr Gln Asp Gly Asn Gly His Gly Thr
50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Ser Gly Ser Gly Ser Val Ser Ser Ile Ala Gln Gly Leu Glu Trp Ala
            100                 105                 110

Gly Asn Asn Gly Met His Val Ala Asn Leu Ser Leu Gly Ser Pro Ser
        115                 120                 125

Pro Ser Ala Thr Leu Glu Gln Ala Val Asn Ser Ala Thr Ser Arg Gly
130                 135                 140

Val Leu Val Val Ala Ala Ser Gly Asn Ser Gly Ala Gly Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
        195                 200                 205

Ala Ser Leu Asn Gly Thr Ser Met Ala Thr Pro His Val Ala Gly Val
210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Gly Leu Gly Asn Thr Asn Leu
                245                 250                 255

Tyr Gly Ser Gly Leu Val Asn Ala Glu Ala Ala Thr Arg
            260                 265

<210> SEQ ID NO 19
<211> LENGTH: 269
<212> TYPE: PRT
<213> ORGANISM: Bacillus lehensis
<220> FEATURE:
<221> NAME/KEY: misc_feature
<222> LOCATION: (1)..(269)
<223> OTHER INFORMATION: B_lehensis_AFK08970

<400> SEQUENCE: 19

Met Gln Thr Val Pro Trp Gly Ile Asn Arg Val Gln Ala Pro Ile Ala
1               5                   10                  15

Gln Ser Arg Gly Phe Thr Gly Thr Gly Val Arg Val Ala Val Leu Asp
                20                  25                  30

Thr Gly Ile Ser Asn His Ala Asp Leu Arg Ile Arg Gly Gly Ala Ser
            35                  40                  45

Phe Val Pro Gly Glu Pro Asn Ile Ser Asp Gly Asn Gly His Gly Thr
50                  55                  60

His Val Ala Gly Thr Ile Ala Ala Leu Asn Asn Ser Ile Gly Val Ile
65                  70                  75                  80

Gly Val Ala Pro Asn Val Asp Leu Tyr Gly Val Lys Val Leu Gly Ala
                85                  90                  95

Ser Gly Cys Gly Ser Ile Ser Gly Ile Ala Gln Gly Leu Gln Trp Ala

```
            100                 105                 110
Ala Asn Asn Gly Met His Ile Ala Asn Met Ser Leu Gly Ser Ser Ala
            115                 120                 125

Gly Ser Ala Thr Met Glu Gln Ala Val Asn Gln Ala Thr Ala Ser Gly
        130                 135                 140

Val Leu Val Val Ala Ala Ser Gly Asn Ser Gly Ala Gly Asn Val Gly
145                 150                 155                 160

Phe Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Gly Val Gln Ser Thr Val Pro Gly Asn Gly Tyr
        195                 200                 205

Ala Ser Phe Asn Gly Thr Ser Met Ala Thr Pro His Val Ala Gly Val
    210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Asn Leu Gly Asn Thr Thr Gln
                245                 250                 255

Phe Gly Ser Gly Leu Val Asn Ala Glu Ala Ala Thr Arg
            260                 265

<210> SEQ ID NO 20
<211> LENGTH: 269
<212> TYPE: PRT
<213> ORGANISM: Bacillus subtilis
<220> FEATURE:
<221> NAME/KEY: misc_feature
<222> LOCATION: (1)..(269)
<223> OTHER INFORMATION: B_subtilis_AAA87324

<400> SEQUENCE: 20

Met Gln Thr Val Pro Trp Gly Ile Asn Arg Val Gln Ala Pro Ile Ala
1               5                   10                  15

Gln Ser Arg Gly Phe Thr Gly Thr Gly Val Arg Val Ala Val Leu Asp
            20                  25                  30

Thr Gly Ile Ser Asn His Ala Asp Leu Arg Ile Arg Gly Gly Ala Ser
        35                  40                  45

Phe Val Pro Gly Glu Pro Asn Ile Ser Asp Gly Asn Gly His Gly Thr
    50                  55                  60

Gln Val Ala Gly Thr Ile Ala Ala Leu Asn Asn Ser Ile Gly Val Leu
65                  70                  75                  80

Gly Val Ala Pro Asn Val Asp Leu Tyr Gly Val Lys Val Leu Gly Ala
                85                  90                  95

Ser Gly Ser Gly Ser Ile Ser Gly Ile Ala Gln Gly Leu Gln Trp Ala
            100                 105                 110

Ala Asn Asn Gly Met His Ile Ala Asn Met Ser Leu Gly Ser Ser Ala
            115                 120                 125

Gly Ser Ala Thr Met Glu Gln Ala Val Asn Gln Ala Thr Ala Ser Gly
        130                 135                 140

Val Leu Val Val Ala Ala Ser Gly Asn Ser Gly Ala Gly Asn Val Gly
145                 150                 155                 160

Phe Pro Ala Arg Tyr Ala Asn Ala Met Ala Val Gly Ala Thr Asp Gln
                165                 170                 175

Asn Asn Asn Arg Ala Thr Phe Ser Gln Tyr Gly Ala Gly Leu Asp Ile
            180                 185                 190
```

Val Ala Pro Gly Val Gly Val Gln Ser Thr Val Pro Gly Asn Gly Tyr
            195                 200                 205

Ala Ser Phe Asn Gly Thr Ser Met Ala Thr Pro His Val Ala Gly Val
            210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Asn Leu Gly Asn Thr Thr Gln
            245                 250                 255

Phe Gly Ser Gly Leu Val Asn Ala Glu Ala Ala Thr Arg
            260                 265

<210> SEQ ID NO 21
<211> LENGTH: 269
<212> TYPE: PRT
<213> ORGANISM: Bacillus sp.
<220> FEATURE:
<221> NAME/KEY: misc_feature
<222> LOCATION: (1)..(269)
<223> OTHER INFORMATION: Bacillus_sp_BAA25184

<400> SEQUENCE: 21

Met Gln Thr Val Pro Trp Gly Ile Asn Arg Val Gln Ala Pro Ile Ala
1               5                   10                  15

Gln Ser Arg Gly Phe Thr Gly Thr Gly Val Arg Val Ala Val Leu Asp
            20                  25                  30

Thr Gly Ile Ser Asn His Ala Asp Leu Arg Ile Arg Gly Gly Ala Ser
            35                  40                  45

Phe Val Pro Gly Glu Pro Asn Ile Ser Asp Gly Asn Gly His Gly Thr
50                  55                  60

His Val Ala Gly Thr Ile Ala Ala Leu Asn Asn Ser Ile Gly Val Leu
65                  70                  75                  80

Gly Val Ala Pro Asn Val Asp Leu Tyr Gly Val Lys Val Leu Gly Ala
            85                  90                  95

Ser Gly Ser Gly Ser Ile Ser Gly Ile Ala Gln Gly Leu Gln Trp Ala
            100                 105                 110

Ala Asn Asn Gly Met His Ile Ala Asn Met Ser Leu Gly Ser Ser Ala
            115                 120                 125

Gly Ser Ala Thr Met Glu Gln Ala Val Asn Gln Ala Thr Ala Ser Gly
            130                 135                 140

Val Leu Val Val Ala Ala Ser Gly Asn Ser Gly Ala Gly Asn Val Gly
145                 150                 155                 160

Phe Pro Ala Arg Tyr Ala Asn Ala Met Ala Val Gly Ala Thr Asp Gln
            165                 170                 175

Asn Asn Asn Arg Ala Ser Phe Ser Gln Tyr Gly Ala Gly Leu Asp Ile
            180                 185                 190

Val Ala Pro Gly Val Gly Val Gln Ser Thr Val Pro Gly Asn Gly Tyr
            195                 200                 205

Ser Ser Phe Asn Gly Thr Ser Met Ala Thr Pro His Val Ala Gly Val
            210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Asn Leu Gly Asn Thr Asn Gln
            245                 250                 255

Phe Gly Ser Gly Leu Val Asn Ala Glu Ala Ala Thr Arg
            260                 265

-continued

```
<210> SEQ ID NO 22
<211> LENGTH: 269
<212> TYPE: PRT
<213> ORGANISM: Bacillus sp.
<220> FEATURE:
<221> NAME/KEY: misc_feature
<222> LOCATION: (1)..(269)
<223> OTHER INFORMATION: B_sp_Sendai_BAA06157

<400> SEQUENCE: 22

Asn Gln Val Thr Pro Trp Gly Ile Thr Arg Val Gln Ala Pro Thr Ala
1               5                   10                  15

Trp Thr Arg Gly Tyr Thr Gly Thr Gly Val Arg Val Ala Val Leu Asp
                20                  25                  30

Thr Gly Ile Ser Thr His Pro Asp Leu Asn Ile Arg Gly Gly Val Ser
            35                  40                  45

Phe Val Pro Gly Glu Pro Ser Tyr Gln Asp Gly Asn Gly His Gly Thr
    50                  55                  60

His Val Ala Gly Thr Ile Ala Ala Leu Asn Asn Ser Ile Gly Val Val
65                  70                  75                  80

Gly Val Ala Pro Asn Ala Glu Leu Tyr Ala Val Lys Val Leu Gly Ala
                85                  90                  95

Asn Gly Ser Gly Ser Val Ser Ser Ile Ala Gln Gly Leu Gln Trp Thr
            100                 105                 110

Ala Gln Asn Asn Ile His Val Ala Asn Leu Ser Leu Gly Ser Pro Val
        115                 120                 125

Gly Ser Gln Thr Leu Glu Leu Ala Val Asn Gln Ala Thr Asn Ala Gly
    130                 135                 140

Val Leu Val Val Ala Ala Thr Gly Asn Asn Gly Ser Gly Thr Val Ser
145                 150                 155                 160

Tyr Pro Ala Arg Tyr Ala Asn Ala Leu Ala Val Gly Ala Thr Asp Gln
                165                 170                 175

Asn Asn Asn Arg Ala Ser Phe Ser Gln Tyr Gly Thr Gly Leu Asn Ile
            180                 185                 190

Val Ala Pro Gly Val Gly Ile Gln Ser Thr Tyr Pro Gly Asn Arg Tyr
        195                 200                 205

Ala Ser Leu Ser Gly Thr Ser Met Ala Thr Pro His Val Ala Gly Val
    210                 215                 220

Ala Ala Leu Val Lys Gln Lys Asn Pro Ser Trp Ser Asn Thr Gln Ile
225                 230                 235                 240

Arg Gln His Leu Thr Ser Thr Ala Thr Ser Leu Gly Asn Ser Asn Gln
                245                 250                 255

Phe Gly Ser Gly Leu Val Asn Ala Glu Ala Ala Thr Arg
            260                 265

<210> SEQ ID NO 23
<211> LENGTH: 269
<212> TYPE: PRT
<213> ORGANISM: Bacillus clausii
<220> FEATURE:
<221> NAME/KEY: misc_feature
<222> LOCATION: (1)..(269)
<223> OTHER INFORMATION: B_clausii_ABI26631

<400> SEQUENCE: 23

Ser Gln Thr Val Pro Trp Gly Ile Ser Phe Ile Asn Thr Gln Gln Ala
1               5                   10                  15

His Asn Arg Gly Ile Phe Gly Asn Gly Ala Arg Val Ala Val Leu Asp
```

```
            20                  25                  30
Thr Gly Ile Ala Ser His Pro Asp Leu Arg Ile Ala Gly Gly Ala Ser
        35                  40                  45

Phe Ile Ser Ser Glu Pro Ser Tyr His Asp Asn Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Ser Ala Asp Leu Tyr Ala Val Lys Val Leu Asp Arg
                85                  90                  95

Asn Gly Ser Gly Ser Leu Ala Ser Val Ala Gln Gly Ile Glu Trp Ala
            100                 105                 110

Ile Asn Asn Asn Met His Ile Ile Asn Met Ser Leu Gly Ser Thr Ser
        115                 120                 125

Gly Ser Ser Thr Leu Glu Leu Ala Val Asn Arg Ala Asn Asn Ala Gly
    130                 135                 140

Ile Leu Leu Val Gly Ala Ala Gly Asn Thr Gly Arg Gln Gly Val Asn
145                 150                 155                 160

Tyr Pro Ala Arg Tyr Ser Gly Val Met Ala Ala Ala Val Asp Gln
                165                 170                 175

Asn Gly Gln Arg Ala Ser Phe Ser Thr Tyr Gly Pro Glu Ile Glu Ile
            180                 185                 190

Ser Ala Pro Gly Val Asn Ile Asn Ser Thr Tyr Thr Gly Asn Arg Tyr
        195                 200                 205

Glu Ser Leu Ser Gly Thr Ser Met Ala Thr Pro His Val Ala Gly Val
    210                 215                 220

Ala Ala Leu Val Lys Ser Arg Tyr Pro Ser Tyr Thr Asn Asn Gln Ile
225                 230                 235                 240

Arg Gln Arg Ile Asn Gln Thr Ala Thr Tyr Leu Gly Ser Pro Ser Leu
                245                 250                 255

Tyr Gly Asn Gly Leu Val His Ala Gly Arg Ala Thr Gln
            260                 265

<210> SEQ ID NO 24
<211> LENGTH: 269
<212> TYPE: PRT
<213> ORGANISM: Bacillus halodurans
<220> FEATURE:
<221> NAME/KEY: misc_feature
<222> LOCATION: (1)..(269)
<223> OTHER INFORMATION: B_halodurans_BAB04574

<400> SEQUENCE: 24

Ser Gln Thr Val Pro Trp Gly Ile Ser Phe Ile Asn Thr Gln Gln Ala
1               5                   10                  15

His Asn Arg Gly Ile Phe Gly Asn Gly Ala Arg Val Ala Val Leu Asp
            20                  25                  30

Thr Gly Ile Ala Ser His Pro Asp Leu Arg Ile Ala Gly Gly Ala Ser
        35                  40                  45

Phe Ile Ser Ser Glu Pro Ser Tyr His Asp Asn Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Ser Ala Asp Leu Tyr Ala Val Lys Val Leu Asp Arg
                85                  90                  95

Asn Gly Ser Gly Ser Leu Ala Ser Val Ala Gln Gly Ile Glu Trp Ala
            100                 105                 110
```

Ile Asn Asn Asn Met His Ile Ile Asn Met Ser Leu Gly Ser Thr Ser
            115                 120                 125

Gly Ser Ser Thr Leu Glu Leu Ala Val Asn Arg Ala Asn Asn Ala Gly
        130                 135                 140

Ile Leu Leu Val Gly Ala Ala Gly Asn Thr Gly Arg Gln Gly Val Asn
145                 150                 155                 160

Tyr Pro Ala Arg Tyr Ser Gly Val Met Ala Val Ala Ala Val Asp Gln
                165                 170                 175

Asn Gly Gln Arg Ala Ser Phe Ser Thr Tyr Gly Pro Glu Ile Glu Ile
                180                 185                 190

Ser Ala Pro Gly Val Asn Val Ser Thr Tyr Thr Gly Asn Arg Tyr
                195                 200                 205

Val Ser Leu Ser Gly Thr Ser Met Ala Thr Pro His Val Ala Gly Val
210                 215                 220

Ala Ala Leu Val Lys Ser Arg Tyr Pro Ser Tyr Thr Asn Asn Gln Ile
225                 230                 235                 240

Arg Gln Arg Ile Asn Gln Thr Ala Thr Tyr Leu Gly Ser Pro Ser Leu
                245                 250                 255

Tyr Gly Asn Gly Leu Val His Ala Gly Arg Ala Thr Gln
                260                 265

<210> SEQ ID NO 25
<211> LENGTH: 269
<212> TYPE: PRT
<213> ORGANISM: Bacillus sp.
<220> FEATURE:
<221> NAME/KEY: misc_feature
<222> LOCATION: (1)..(269)
<223> OTHER INFORMATION: Bacillus_sp_ADD64465

<400> SEQUENCE: 25

Ser Gln Thr Val Pro Trp Gly Ile Ser Phe Ile Ser Thr Gln Gln Ala
1               5                   10                  15

His Asn Arg Gly Ile Phe Gly Asn Gly Ala Arg Val Ala Val Leu Asp
                20                  25                  30

Thr Gly Ile Ala Ser His Pro Asp Leu Arg Ile Ala Gly Gly Ala Ser
            35                  40                  45

Phe Ile Ser Ser Glu Pro Ser Tyr His Asp Asn Gly His Gly Thr
50                  55                  60

His Val Ala Gly Thr Ile Ala Ala Leu Asn Asn Ser Ile Gly Val Leu
65                  70                  75                  80

Gly Val Ala Pro Ser Ala Asp Leu Tyr Ala Val Lys Val Leu Asp Arg
                85                  90                  95

Asn Gly Ser Gly Ser Leu Ala Ser Val Ala Gln Gly Ile Glu Trp Ala
                100                 105                 110

Ile Asn Asn Asn Met His Ile Ile Asn Met Ser Leu Gly Ser Thr Ser
            115                 120                 125

Gly Ser Ser Thr Leu Glu Leu Ala Val Asn Arg Gly Asn Asn Ala Gly
        130                 135                 140

Ile Leu Leu Val Gly Ala Ala Gly Asn Thr Gly Arg Gln Gly Val Asn
145                 150                 155                 160

Tyr Pro Ala Arg Tyr Ser Gly Val Met Ala Val Ala Ala Val Asp Gln
                165                 170                 175

Asn Gly Gln Arg Ala Ser Phe Ser Thr Tyr Gly Pro Glu Ile Glu Ile
                180                 185                 190

```
Ser Ala Pro Gly Val Asn Val Ser Thr Tyr Thr Gly Asn Arg Tyr
        195                 200                 205

Val Ser Leu Ser Gly Thr Ser Met Ala Ala Pro His Val Ala Gly Thr
210                 215                 220

Ala Ala Leu Val Lys Ser Arg Tyr Pro Ser Tyr Thr Asn Asn Gln Ile
225                 230                 235                 240

Arg Gln Arg Ile Asn Gln Thr Ala Thr Tyr Leu Gly Ser Ser Asn Leu
                245                 250                 255

Tyr Gly Asn Gly Leu Val His Ala Gly Arg Ala Thr Gln
                260                 265

<210> SEQ ID NO 26
<211> LENGTH: 273
<212> TYPE: PRT
<213> ORGANISM: Bacillus pseudofirmus
<220> FEATURE:
<221> NAME/KEY: misc_feature
<222> LOCATION: (1)..(273)
<223> OTHER INFORMATION: B_pseudofirmus_ADC49870

<400> SEQUENCE: 26

Ala Gln Thr Val Pro Trp Gly Ile Pro Tyr Ile Tyr Ser Asp Val Val
1               5                   10                  15

His Arg Gln Gly Tyr Phe Gly Asn Gly Val Lys Val Ala Val Leu Asp
                20                  25                  30

Thr Gly Val Ala Pro His Pro Asp Leu His Ile Arg Gly Gly Val Ser
            35                  40                  45

Phe Ile Ser Thr Glu Asn Thr Tyr Val Asp Tyr Asn Gly His Gly Thr
50                  55                  60

His Val Ala Gly Thr Val Ala Ala Leu Asn Asn Ser Tyr Gly Val Leu
65                  70                  75                  80

Gly Val Ala Pro Gly Ala Glu Leu Tyr Ala Val Lys Val Leu Asp Arg
                85                  90                  95

Asn Gly Ser Gly Ser His Ala Ser Ile Ala Gln Gly Ile Glu Trp Ala
            100                 105                 110

Met Asn Asn Gly Met Asp Ile Ala Asn Met Ser Leu Gly Ser Pro Ser
        115                 120                 125

Gly Ser Thr Thr Leu Gln Leu Ala Ala Asp Arg Ala Arg Asn Ala Gly
    130                 135                 140

Val Leu Leu Ile Gly Ala Ala Gly Asn Ser Gly Gln Gln Gly Gly Ser
145                 150                 155                 160

Asn Asn Met Gly Tyr Pro Ala Arg Tyr Ala Ser Val Met Ala Val Gly
                165                 170                 175

Ala Val Asp Gln Asn Gly Asn Arg Ala Asn Phe Ser Ser Tyr Gly Ser
            180                 185                 190

Glu Leu Glu Ile Met Ala Pro Gly Val Asn Ile Asn Ser Thr Tyr Leu
        195                 200                 205

Asn Asn Gly Tyr Arg Ser Leu Asn Gly Thr Ser Met Ala Ser Pro His
    210                 215                 220

Val Ala Gly Val Ala Ala Leu Val Lys Gln Lys His Pro His Leu Thr
225                 230                 235                 240

Ala Ala Gln Ile Arg Asn Arg Met Asn Gln Thr Ala Ile Pro Leu Gly
                245                 250                 255

Asn Ser Thr Tyr Tyr Gly Asn Gly Leu Val Asp Ala Glu Tyr Ala Ala
            260                 265                 270

Gln
```

<210> SEQ ID NO 27
<211> LENGTH: 276
<212> TYPE: PRT
<213> ORGANISM: Bacillus sp.
<220> FEATURE:
<221> NAME/KEY: misc_feature
<222> LOCATION: (1)..(276)
<223> OTHER INFORMATION: B_sp_sprD_AAC43581

<400> SEQUENCE: 27

```
Ala Gln Thr Val Pro Tyr Gly Val Pro His Ile Lys Ala Asp Val Ala
1               5                   10                  15

His Ala Gln Asn Val Thr Gly Ser Gly Val Lys Val Ala Val Leu Asp
            20                  25                  30

Thr Gly Ile Asp Ala Ser His Glu Asp Leu Arg Val Val Gly Gly Ala
        35                  40                  45

Ser Phe Val Ser Glu Glu Pro Asp Ala Leu Thr Asp Gly Asn Gly His
    50                  55                  60

Gly Thr His Val Ala Gly Thr Ile Ala Ala Leu Asn Asn Asn Val Gly
65                  70                  75                  80

Val Leu Gly Val Ser Tyr Asp Val Asp Leu Tyr Ala Val Lys Val Leu
                85                  90                  95

Ser Ala Gly Gly Ser Gly Thr Leu Ala Gly Ile Ala Gln Gly Ile Glu
            100                 105                 110

Trp Ala Ile Asp Asn Asn Met Asp Val Ile Asn Met Ser Leu Gly Gly
        115                 120                 125

Ser Thr Gly Ser Thr Thr Leu Lys Gln Ala Ser Asp Asn Ala Tyr Asn
130                 135                 140

Ser Gly Ile Val Val Ile Ala Ala Ala Gly Asn Ser Gly Ser Val Leu
145                 150                 155                 160

Gly Leu Val Asn Thr Ile Gly Tyr Pro Ala Arg Tyr Asp Ser Val Ile
                165                 170                 175

Ala Val Gly Ala Val Asp Ser Asn Asn Asn Arg Ala Ser Phe Ser Ser
            180                 185                 190

Val Gly Ser Gln Leu Glu Val Met Ala Pro Gly Val Ala Ile Asn Ser
        195                 200                 205

Thr Leu Pro Gly Asn Gln Tyr Gly Glu Leu Asn Gly Thr Ser Met Ala
    210                 215                 220

Ser Pro His Val Ala Gly Ala Ala Leu Leu Leu Ala Gln Asn Pro
225                 230                 235                 240

Asn Leu Thr Asn Val Gln Val Arg Glu Arg Leu Arg Asp Thr Ala Thr
                245                 250                 255

Asn Leu Gly Ser Ala Phe Asn Tyr Gly His Gly Val Ile Asn Leu Glu
            260                 265                 270

Arg Ala Leu Gln
        275
```

<210> SEQ ID NO 28
<211> LENGTH: 276
<212> TYPE: PRT
<213> ORGANISM: Bacillus sp.
<220> FEATURE:
<221> NAME/KEY: misc_feature
<222> LOCATION: (1)..(276)
<223> OTHER INFORMATION: Bacillus_sp_BAD21128

<400> SEQUENCE: 28

-continued

Ser Gln Thr Val Pro Tyr Gly Val Pro His Ile Lys Ala Asp Val Ala
1               5                   10                  15

His Ser Gln Asn Val Thr Gly Asn Gly Val Lys Val Ala Ile Leu Asp
            20                  25                  30

Thr Gly Ile Asp Ala Ala His Glu Asp Leu Arg Val Val Gly Gly Ala
        35                  40                  45

Ser Phe Val Ala Gly Glu Pro Asn Ala Leu Gln Asp Gly Asn Gly His
50                  55                  60

Gly Thr His Val Ala Gly Thr Val Ala Ala Leu Asn Asn Gln Val Gly
65                  70                  75                  80

Val Leu Gly Val Ala Tyr Asp Val Asp Leu Tyr Ala Val Lys Val Leu
                85                  90                  95

Gly Ala Asp Gly Ser Gly Thr Leu Ser Gly Ile Ala Gln Gly Ile Glu
            100                 105                 110

Trp Ser Ile Ala Asn Asn Met Asp Val Ile Asn Met Ser Leu Gly Gly
        115                 120                 125

Ser Thr Gly Ser Thr Thr Leu Lys Gln Ala Ala Asp Asn Ala Tyr Asn
    130                 135                 140

Ser Gly Leu Val Val Ala Ala Ala Gly Asn Ser Gly Asp Phe Phe
145                 150                 155                 160

Gly Leu Ile Asn Thr Ile Gly Tyr Pro Ala Arg Tyr Asp Ser Val Ile
                165                 170                 175

Ala Val Gly Ala Val Asp Ser Asn Asn Arg Arg Ala Ser Phe Ser Ser
            180                 185                 190

Val Gly Ser Gln Leu Glu Val Met Ala Pro Gly Val Asn Ile Leu Ser
        195                 200                 205

Thr Leu Pro Gly Asn Ser Tyr Gly Ser Leu Asn Gly Thr Ser Met Ala
    210                 215                 220

Ser Pro His Val Ala Gly Ala Ala Leu Leu Leu Ala Gln Asp Pro
225                 230                 235                 240

Thr Leu Thr Asn Val Gln Val Arg Glu Ile Leu Arg Asp Thr Ala Thr
                245                 250                 255

Asn Leu Gly Ser Ser Phe Tyr Tyr Gly Asn Gly Val Ile Asp Val Glu
            260                 265                 270

Lys Ala Leu Gln
    275

<210> SEQ ID NO 29
<211> LENGTH: 275
<212> TYPE: PRT
<213> ORGANISM: Bacillus sp.
<220> FEATURE:
<221> NAME/KEY: misc_feature
<222> LOCATION: (1)..(275)
<223> OTHER INFORMATION: Bacillus_sp_sprC_AAC43580

<400> SEQUENCE: 29

Ala Gln Thr Val Pro Trp Gly Ile Pro His Ile Lys Ala Asp Lys Ala
1               5                   10                  15

His Ala Ala Gly Val Thr Gly Ser Gly Val Lys Val Ala Ile Leu Asp
            20                  25                  30

Thr Gly Ile Asp Ala Asn His Ala Asp Leu Asn Val Lys Gly Gly Ala
        35                  40                  45

Ser Phe Val Ser Gly Glu Pro Asn Ala Leu Gln Asp Gly Asn Gly His
50                  55                  60

Gly Thr His Val Ala Gly Thr Val Ala Ala Leu Asn Asn Thr Thr Gly

```
                65                  70                  75                  80
Val Leu Gly Val Ala Tyr Asn Ala Asp Leu Tyr Ala Val Lys Val Leu
                    85                  90                  95

Ser Ala Ser Gly Ser Gly Thr Leu Ser Gly Ile Ala Gln Gly Ile Glu
                100                 105                 110

Trp Ser Ile Ser Asn Gly Met Asn Val Ile Asn Met Ser Leu Gly Gly
                115                 120                 125

Ser Ser Gly Ser Thr Ala Leu Gln Gln Ala Cys Asn Asn Ala Tyr Asn
130                 135                 140

Arg Gly Ile Val Val Ile Ala Ala Gly Asn Ser Gly Ser Ser Gly
145                 150                 155                 160

Asn Arg Asn Thr Met Gly Tyr Pro Ala Arg Tyr Ser Ser Val Ile Ala
                165                 170                 175

Val Gly Ala Val Ser Ser Asn Asn Thr Arg Ala Ser Phe Ser Ser Val
                180                 185                 190

Gly Ser Glu Leu Glu Val Met Ala Pro Gly Val Asn Ile Leu Ser Thr
                195                 200                 205

Thr Pro Gly Asn Asn Tyr Ala Ser Phe Asn Gly Thr Ser Met Ala Ala
210                 215                 220

Pro His Val Ala Gly Ala Ala Leu Ile Lys Ala Lys Tyr Pro Ser
225                 230                 235                 240

Met Thr Asn Val Gln Ile Arg Glu Arg Leu Lys Asn Thr Ala Thr Asn
                245                 250                 255

Leu Gly Asp Pro Phe Phe Tyr Gly Lys Gly Val Ile Asn Val Glu Ser
                260                 265                 270

Ala Leu Gln
        275

<210> SEQ ID NO 30
<211> LENGTH: 275
<212> TYPE: PRT
<213> ORGANISM: Bacillus sp.
<220> FEATURE:
<221> NAME/KEY: misc_feature
<222> LOCATION: (1)..(275)
<223> OTHER INFORMATION: Bacillus_sp_BAD11988

<400> SEQUENCE: 30

Ala Gln Thr Thr Pro Trp Gly Val Thr His Ile Asn Ala His Arg Ala
1               5                   10                  15

His Ser Ser Gly Val Thr Gly Ser Gly Val Lys Val Ala Ile Leu Asp
                20                  25                  30

Thr Gly Ile His Ala Ser His Pro Asp Leu Asn Val Arg Gly Gly Ala
                35                  40                  45

Ser Phe Ile Ser Gly Glu Ser Asn Pro Tyr Ile Asp Ser Asn Gly His
    50                  55                  60

Gly Thr His Val Ala Gly Thr Val Ala Ala Leu Asn Asn Thr Val Gly
65                  70                  75                  80

Val Leu Gly Val Ala Tyr Asn Ala Glu Leu Tyr Ala Val Lys Val Leu
                    85                  90                  95

Ser Ala Ser Gly Ser Gly Thr Leu Ser Gly Ile Ala Gln Gly Val Glu
                100                 105                 110

Trp Ser Ile Ala Asn Lys Met Asp Val Ile Asn Met Ser Leu Gly Gly
                115                 120                 125

Ser Ser Gly Ser Thr Ala Leu Gln Arg Ala Val Asp Asn Ala Tyr Arg
130                 135                 140
```

```
Asn Asn Ile Val Val Ala Ala Gly Asn Ser Gly Ala Gln Gly
145                 150                 155                 160

Asn Arg Asn Thr Ile Gly Tyr Pro Ala Arg Tyr Ser Ser Val Ile Ala
                165                 170                 175

Val Gly Ala Val Asp Ser Asn Asn Arg Ala Ser Phe Ser Ser Val
            180                 185                 190

Gly Ser Glu Leu Glu Val Met Ala Pro Gly Val Ser Ile Leu Ser Thr
            195                 200                 205

Val Pro Gly Ser Ser Tyr Ala Ser Tyr Asn Gly Thr Ser Met Ala Ser
        210                 215                 220

Pro His Val Ala Gly Ala Ala Leu Leu Lys Ala Lys Tyr Pro Asn
225                 230                 235                 240

Trp Ser Ala Ala Gln Ile Arg Asn Lys Leu Asn Ser Thr Thr Thr Tyr
                245                 250                 255

Leu Gly Ser Ser Phe Tyr Tyr Gly Asn Gly Val Ile Asn Val Glu Arg
            260                 265                 270

Ala Leu Gln
        275

<210> SEQ ID NO 31
<211> LENGTH: 275
<212> TYPE: PRT
<213> ORGANISM: Bacillus circulans
<220> FEATURE:
<221> NAME/KEY: misc_feature
<222> LOCATION: (1)..(275)
<223> OTHER INFORMATION: B_circulans_ADN04910

<400> SEQUENCE: 31

Ala Gln Thr Val Pro Tyr Gly Ile Pro Gln Ile Lys Ala Pro Ala Val
1               5                   10                  15

His Ala Gln Gly Tyr Lys Gly Ala Asn Val Lys Val Ala Val Leu Asp
                20                  25                  30

Thr Gly Ile His Ala Ala His Pro Asp Leu Asn Val Ala Gly Gly Ala
            35                  40                  45

Ser Phe Val Pro Ser Glu Pro Asn Ala Thr Gln Asp Phe Gln Ser His
        50                  55                  60

Gly Thr His Val Ala Gly Thr Ile Ala Ala Leu Asp Asn Thr Ile Gly
65                  70                  75                  80

Val Leu Gly Val Ala Pro Ser Ala Ser Leu Tyr Ala Val Lys Val Leu
                85                  90                  95

Asp Arg Asn Gly Asp Gly Gln Tyr Ser Trp Ile Ile Ser Gly Ile Glu
            100                 105                 110

Trp Ala Val Ala Asn Asn Met Asp Val Ile Asn Met Ser Leu Gly Gly
        115                 120                 125

Pro Asn Gly Ser Thr Ala Leu Lys Asn Ala Val Asp Thr Ala Asn Asn
    130                 135                 140

Arg Gly Val Val Val Ala Ala Gly Asn Ser Gly Ser Thr Gly
145                 150                 155                 160

Ser Thr Ser Thr Val Gly Tyr Pro Ala Lys Tyr Asp Ser Thr Ile Ala
                165                 170                 175

Val Ala Asn Val Asn Ser Ser Asn Val Arg Asn Ser Ser Ser Ala
            180                 185                 190

Gly Pro Glu Leu Asp Val Ser Ala Pro Gly Thr Ser Ile Leu Ser Thr
        195                 200                 205
```

```
Val Pro Ser Arg Gly Tyr Thr Ser Tyr Thr Gly Thr Ser Met Ala Ser
    210                 215                 220

Pro His Val Ala Gly Ala Ala Ala Leu Ile Leu Ser Lys Asn Pro Asn
225                 230                 235                 240

Leu Ser Asn Ser Gln Val Arg Gln Arg Leu Glu Asn Thr Ala Thr Pro
                245                 250                 255

Leu Gly Asn Ser Phe Tyr Tyr Gly Lys Gly Leu Ile Asn Val Gln Ala
                260                 265                 270

Ala Ser Asn
        275

<210> SEQ ID NO 32
<211> LENGTH: 276
<212> TYPE: PRT
<213> ORGANISM: Bacillus lehensis
<220> FEATURE:
<221> NAME/KEY: misc_feature
<222> LOCATION: (1)..(276)
<223> OTHER INFORMATION: B_lehensis_AFP23380

<400> SEQUENCE: 32

Met Ala Gln Thr Val Pro Tyr Gly Ile Pro Gln Ile Lys Ala Pro Ala
1               5                   10                  15

Val His Ala Gln Gly Tyr Lys Gly Ala Asn Val Lys Val Ala Val Leu
                20                  25                  30

Asp Thr Gly Ile His Ala Ala His Pro Asp Leu Asn Val Ala Gly Gly
                35                  40                  45

Ala Ser Phe Val Pro Ser Glu Pro Asn Ala Thr Gln Asp Phe Gln Ser
    50                  55                  60

His Gly Thr His Val Ala Gly Thr Ile Ala Ala Leu Asp Asn Thr Ile
65                  70                  75                  80

Gly Val Leu Gly Val Ala Pro Ser Ala Ser Leu Tyr Ala Val Lys Val
                85                  90                  95

Leu Asp Arg Tyr Gly Asp Gly Gln Tyr Ser Trp Ile Ile Ser Gly Ile
                100                 105                 110

Glu Trp Ala Val Ala Asn Asn Met Asp Val Ile Asn Met Ser Leu Gly
                115                 120                 125

Gly Pro Asn Gly Ser Thr Ala Leu Lys Asn Ala Val Asp Thr Ala Asn
    130                 135                 140

Asn Arg Gly Val Val Val Ala Ala Ala Gly Asn Ser Gly Ser Thr
145                 150                 155                 160

Gly Ser Thr Ser Thr Val Gly Tyr Pro Ala Lys Tyr Asp Ser Thr Ile
                165                 170                 175

Ala Val Ala Asn Val Asn Ser Asn Asn Val Arg Asn Ser Ser Ser Ser
                180                 185                 190

Ala Gly Pro Glu Leu Asp Val Ser Ala Pro Gly Thr Ser Ile Leu Ser
            195                 200                 205

Thr Val Pro Ser Ser Gly Tyr Thr Ser Tyr Thr Gly Thr Ser Met Ala
    210                 215                 220

Ser Pro His Val Ala Gly Ala Ala Ala Leu Ile Leu Ser Lys Tyr Pro
225                 230                 235                 240

Asn Leu Ser Thr Ser Gln Val Arg Gln Arg Leu Glu Asn Thr Ala Thr
                245                 250                 255

Pro Leu Gly Asn Ser Phe Tyr Tyr Gly Lys Gly Leu Ile Asn Val Gln
                260                 265                 270

Ala Ala Ser Asn
```

<210> SEQ ID NO 33
<211> LENGTH: 275
<212> TYPE: PRT
<213> ORGANISM: Bacillus stratosphericus
<220> FEATURE:
<221> NAME/KEY: misc_feature
<222> LOCATION: (1)..(275)
<223> OTHER INFORMATION: B_stratosphericus_WP_007497196

<400> SEQUENCE: 33

```
Ala Gln Thr Val Pro Tyr Gly Ile Pro Gln Ile Lys Ala Pro Ala Val
1               5                   10                  15

His Ala Gln Gly Tyr Lys Gly Ala Asn Val Lys Val Ala Val Leu Asp
            20                  25                  30

Thr Gly Ile His Ala Ala His Pro Asp Leu Asn Val Ala Gly Gly Ala
        35                  40                  45

Ser Phe Val Pro Ser Glu Pro Asn Ala Thr Gln Asp Phe Gln Ser His
    50                  55                  60

Gly Thr His Val Ala Gly Thr Ile Ala Ala Leu Asp Asn Thr Ile Gly
65              70                  75                  80

Val Leu Gly Val Ala Pro Ser Ala Ser Leu Tyr Ala Val Lys Val Leu
                85                  90                  95

Asp Arg Asn Gly Asp Gly Gln Tyr Ser Trp Ile Ile Ser Gly Ile Glu
            100                 105                 110

Trp Ala Val Ala Asn Asn Met Asp Val Ile Asn Met Ser Leu Gly Gly
        115                 120                 125

Pro Ser Gly Ser Thr Ala Leu Lys Asn Ala Val Asp Thr Ala Asn Asn
    130                 135                 140

Arg Gly Val Val Val Ala Ala Gly Asn Ser Gly Ser Thr Gly
145                 150                 155                 160

Ser Thr Ser Thr Val Gly Tyr Pro Ala Lys Tyr Asp Ser Thr Ile Ala
                165                 170                 175

Val Ala Asn Val Asn Ser Asn Asn Val Arg Asn Ser Ser Ser Ser Ala
            180                 185                 190

Gly Pro Glu Leu Asp Val Ser Ala Pro Gly Thr Ser Ile Leu Ser Thr
        195                 200                 205

Val Pro Ser Ser Gly Tyr Thr Ser Tyr Thr Gly Thr Ser Met Ala Ser
    210                 215                 220

Pro His Val Ala Gly Ala Ala Ala Leu Ile Leu Ser Lys Tyr Pro Asn
225                 230                 235                 240

Leu Ser Thr Ser Gln Val Arg Gln Arg Leu Glu Asn Thr Ala Thr Pro
                245                 250                 255

Leu Gly Asn Ser Phe Tyr Tyr Gly Lys Gly Leu Ile Asn Val Gln Ala
            260                 265                 270

Ala Ser Asn
        275
```

<210> SEQ ID NO 34
<211> LENGTH: 275
<212> TYPE: PRT
<213> ORGANISM: Bacillus pumilus
<220> FEATURE:
<221> NAME/KEY: misc_feature
<222> LOCATION: (1)..(275)
<223> OTHER INFORMATION: B_pumilus_ADK11996

<400> SEQUENCE: 34

Ala Gln Thr Val Pro Tyr Gly Ile Pro Gln Ile Lys Ala Pro Ala Val
1               5                   10                  15

His Ala Gln Gly Tyr Lys Gly Ala Asn Val Lys Val Ala Val Leu Asp
                20                  25                  30

Thr Gly Ile His Ala Ala His Pro Asp Leu Asn Val Ala Gly Gly Ala
            35                  40                  45

Ser Phe Val Pro Ser Glu Pro Asn Ala Thr Gln Asp Phe Gln Ser His
    50                  55                  60

Gly Thr His Val Ala Gly Thr Ile Ala Ala Leu Asp Asn Thr Ile Gly
65                  70                  75                  80

Val Leu Gly Val Ala Pro Ser Ala Ser Leu Tyr Ala Val Lys Val Leu
                85                  90                  95

Asp Arg Asn Gly Asp Gly Gln Tyr Ser Trp Ile Ile Ser Gly Ile Glu
                100                 105                 110

Trp Ala Val Ala Asn Asn Met Asp Val Ile Asn Met Ser Leu Gly Gly
                115                 120                 125

Ala Ser Gly Ser Thr Ala Leu Lys Asn Ala Val Asp Thr Ala Asn Asn
            130                 135                 140

Arg Gly Val Val Val Ala Ala Ala Gly Asn Ser Gly Ser Ser Ser Gly
145                 150                 155                 160

Ser Arg Ser Thr Val Gly Tyr Pro Ala Lys Tyr Glu Ser Thr Ile Ala
                165                 170                 175

Val Ala Asn Val Asn Ser Asn Asn Val Arg Asn Ser Ser Ser Ser Ala
                180                 185                 190

Gly Pro Glu Leu Asp Val Ser Ala Pro Gly Thr Ser Ile Leu Ser Thr
            195                 200                 205

Val Pro Ser Ser Gly Tyr Thr Ser Tyr Thr Gly Thr Ser Met Ala Ser
            210                 215                 220

Pro His Val Ala Gly Ala Ala Ala Leu Ile Leu Ser Lys Asn Pro Asn
225                 230                 235                 240

Leu Thr Asn Ser Gln Val Arg Gln Arg Leu Glu Asn Thr Ala Thr Pro
                245                 250                 255

Leu Gly Asp Ser Phe Tyr Tyr Gly Lys Gly Leu Ile Asn Val Gln Ala
                260                 265                 270

Ala Ser Asn
        275

<210> SEQ ID NO 35
<211> LENGTH: 275
<212> TYPE: PRT
<213> ORGANISM: Bacillus sp.
<220> FEATURE:
<221> NAME/KEY: misc_feature
<222> LOCATION: (1)..(275)
<223> OTHER INFORMATION: Bac_sp_HYC10_WP008359041

<400> SEQUENCE: 35

Ala Gln Thr Val Pro Tyr Gly Ile Pro Gln Ile Lys Ala Pro Ala Val
1               5                   10                  15

His Ala Gln Gly Tyr Lys Gly Ala Asn Val Lys Val Ala Val Leu Asp
                20                  25                  30

Thr Gly Ile His Ala Ala His Pro Asp Leu Asn Val Ala Gly Gly Ala
            35                  40                  45

Ser Phe Val Pro Ser Glu Pro Asn Ala Thr Gln Asp Phe Gln Ser His
    50                  55                  60

-continued

```
Gly Thr His Val Ala Gly Thr Ile Ala Ala Leu Asp Asn Thr Ile Gly
 65                  70                  75                  80

Val Leu Gly Val Ala Pro Ser Ala Ser Leu Tyr Ala Val Lys Val Leu
                 85                  90                  95

Asp Arg Asn Gly Asp Gly Gln Tyr Ser Trp Ile Ile Ser Gly Ile Glu
            100                 105                 110

Trp Ala Val Ala Asn Asn Met Asp Val Ile Asn Met Ser Leu Gly Gly
        115                 120                 125

Pro Ser Gly Ser Thr Ala Leu Lys Asn Ala Val Asp Thr Ala Asn Asn
    130                 135                 140

Arg Gly Val Val Val Ala Ala Gly Asn Ser Gly Ser Ser Gly
145                 150                 155                 160

Ser Thr Ser Thr Val Gly Tyr Pro Ala Lys Tyr Asp Ser Thr Ile Ala
                165                 170                 175

Val Ala Asn Val Asn Ser Asn Val Arg Asn Ser Ser Ser Ser Ala
            180                 185                 190

Gly Pro Glu Leu Asp Val Ser Ala Pro Gly Thr Ser Ile Leu Ser Thr
        195                 200                 205

Val Pro Ser Ser Gly Tyr Ala Ser Tyr Thr Gly Thr Ser Met Ala Ser
    210                 215                 220

Pro His Val Ala Gly Ala Ala Leu Ile Leu Ser Lys His Pro Asn
225                 230                 235                 240

Leu Thr Asn Thr Gln Val Arg Gln Arg Leu Glu Asn Thr Ala Thr Pro
                245                 250                 255

Leu Gly Ser Ser Phe Tyr Tyr Gly Lys Gly Leu Ile Asn Val Gln Ala
            260                 265                 270

Ala Ala Asn
        275

<210> SEQ ID NO 36
<211> LENGTH: 275
<212> TYPE: PRT
<213> ORGANISM: Bacillus atrophaeus
<220> FEATURE:
<221> NAME/KEY: misc_feature
<222> LOCATION: (1)..(275)
<223> OTHER INFORMATION: B_atrophaeus_YP003972439

<400> SEQUENCE: 36

Ala Gln Ser Val Pro Tyr Gly Ile Ser Gln Ile Lys Ala Pro Ala Val
 1               5                  10                  15

His Ser Gln Gly Tyr Thr Gly Ser Asn Val Lys Val Ala Val Ile Asp
                20                  25                  30

Ser Gly Ile Asp Ser Ser His Pro Asp Leu Lys Val Ser Gly Gly Ala
            35                  40                  45

Ser Phe Val Pro Ser Glu Pro Asn Pro Phe Gln Asp Gly Asn Ser His
        50                  55                  60

Gly Thr His Val Ala Gly Thr Val Ala Ala Leu Asn Asn Ser Val Gly
 65                  70                  75                  80

Val Leu Gly Val Ala Pro Ser Ala Ser Leu Tyr Ala Val Lys Val Leu
                 85                  90                  95

Ser Ser Ser Gly Ser Gly Asp Tyr Ser Trp Ile Ile Asn Gly Ile Glu
            100                 105                 110

Trp Ala Ile Ser Asn Asn Met Asp Val Ile Asn Met Ser Leu Gly Gly
        115                 120                 125

Pro Gln Gly Ser Thr Ala Leu Lys Ala Val Val Asp Lys Ala Val Ser
```

```
                130             135             140
Gln Gly Ile Val Val Ala Ala Gly Asn Ser Gly Ser Ser Gly
145                 150                 155                 160

Ser Thr Ser Thr Val Gly Tyr Pro Ala Lys Tyr Pro Ser Val Ile Ala
                165                 170                 175

Val Gly Ala Val Asp Ser Asn Asn Gln Arg Ala Ser Phe Ser Ser Ala
                180                 185                 190

Gly Ser Glu Leu Asp Val Met Ala Pro Gly Val Ser Ile Gln Ser Thr
                195                 200                 205

Leu Pro Gly Ser Ser Tyr Gly Ser Tyr Asn Gly Thr Ser Met Ala Ser
                210                 215                 220

Pro His Val Ala Gly Ala Ala Ala Leu Val Leu Ser Lys His Pro Asn
225                 230                 235                 240

Trp Thr Asn Ser Gln Val Arg Asn Ser Leu Glu Ser Thr Ala Thr Asn
                245                 250                 255

Leu Gly Asn Ser Phe Tyr Tyr Gly Lys Gly Leu Ile Asn Val Gln Ala
                260                 265                 270

Ala Ala Gln
        275

<210> SEQ ID NO 37
<211> LENGTH: 275
<212> TYPE: PRT
<213> ORGANISM: Bacillus amyloliquefaciens
<220> FEATURE:
<221> NAME/KEY: misc_feature
<222> LOCATION: (1)..(275)
<223> OTHER INFORMATION: B_amyloliquefaciens_CAA24990

<400> SEQUENCE: 37

Ala Gln Ser Val Pro Tyr Gly Val Ser Gln Ile Lys Ala Pro Ala Leu
1               5                   10                  15

His Ser Gln Gly Tyr Thr Gly Ser Asn Val Lys Val Ala Val Ile Asp
                20                  25                  30

Ser Gly Ile Asp Ser Ser His Pro Asp Leu Lys Val Ala Gly Gly Ala
                35                  40                  45

Ser Met Val Pro Ser Glu Thr Asn Pro Phe Gln Asp Asn Asn Ser His
50                  55                  60

Gly Thr His Val Ala Gly Thr Val Ala Ala Leu Asn Asn Ser Ile Gly
65                  70                  75                  80

Val Leu Gly Val Ala Pro Ser Ala Ser Leu Tyr Ala Val Lys Val Leu
                85                  90                  95

Gly Ala Asp Gly Ser Gly Gln Tyr Ser Trp Ile Ile Asn Gly Ile Glu
                100                 105                 110

Trp Ala Ile Ala Asn Asn Met Asp Val Ile Asn Met Ser Leu Gly Gly
                115                 120                 125

Pro Ser Gly Ser Ala Ala Leu Lys Ala Ala Val Asp Lys Ala Val Ala
                130                 135                 140

Ser Gly Val Val Val Ala Ala Gly Asn Glu Gly Thr Ser Gly
145                 150                 155                 160

Ser Ser Ser Thr Val Gly Tyr Pro Gly Lys Tyr Pro Ser Val Ile Ala
                165                 170                 175

Val Gly Ala Val Asp Ser Ser Asn Gln Arg Ala Ser Phe Ser Ser Val
                180                 185                 190

Gly Pro Glu Leu Asp Val Met Ala Pro Gly Val Ser Ile Gln Ser Thr
                195                 200                 205
```

```
Leu Pro Gly Asn Lys Tyr Gly Ala Tyr Asn Gly Thr Ser Met Ala Ser
        210                 215                 220

Pro His Val Ala Gly Ala Ala Leu Ile Leu Ser Lys His Pro Asn
225                 230                 235                 240

Trp Thr Asn Thr Gln Val Arg Ser Ser Leu Glu Asn Thr Thr Thr Lys
                245                 250                 255

Leu Gly Asp Ser Phe Tyr Tyr Gly Lys Gly Leu Ile Asn Val Gln Ala
            260                 265                 270

Ala Ala Gln
        275

<210> SEQ ID NO 38
<211> LENGTH: 275
<212> TYPE: PRT
<213> ORGANISM: Bacillus methylotrophicus
<220> FEATURE:
<221> NAME/KEY: misc_feature
<222> LOCATION: (1)..(275)
<223> OTHER INFORMATION: B_methylotrophicus_AGC81872

<400> SEQUENCE: 38

Ala Gln Ser Val Pro Tyr Gly Val Ser Gln Ile Lys Ala Pro Ala Leu
1               5                   10                  15

His Ser Gln Gly Phe Thr Gly Ser Asn Val Lys Val Ala Val Ile Asp
            20                  25                  30

Ser Gly Ile Asp Ser Ser His Pro Asp Leu Lys Val Ala Gly Gly Ala
        35                  40                  45

Ser Met Val Pro Ser Glu Thr Asn Pro Phe Gln Asp Arg Asn Ser His
50                  55                  60

Gly Thr His Val Ala Gly Thr Val Ala Ala Leu Asn Asn Ser Val Gly
65                  70                  75                  80

Val Leu Gly Val Ala Pro Ser Ala Ser Leu Tyr Ala Val Lys Val Leu
                85                  90                  95

Gly Ala Asp Gly Ser Gly Gln Tyr Ser Trp Ile Ile Asn Gly Ile Glu
            100                 105                 110

Trp Ala Ile Ala Asn Asn Met Asp Val Ile Asn Met Ser Leu Gly Gly
        115                 120                 125

Pro Ser Gly Ser Ala Ala Leu Lys Ala Ala Val Asp Lys Ala Val Ala
130                 135                 140

Ser Gly Val Val Val Ala Ala Ala Gly Asn Glu Gly Thr Ser Gly Ser
145                 150                 155                 160

Gly Ser Ser Thr Val Gly Tyr Pro Gly Lys Tyr Pro Ser Val Ile Ala
                165                 170                 175

Val Gly Ala Val Asn Ser Ser Asn Gln Arg Ala Ser Phe Ser Ser Val
            180                 185                 190

Gly Ser Glu Leu Asp Val Met Ala Pro Gly Val Ser Ile Gln Ser Thr
        195                 200                 205

Leu Pro Gly Asn Lys Tyr Gly Ala Tyr Asn Gly Thr Ser Met Ala Ser
210                 215                 220

Pro His Val Ala Gly Ala Ala Leu Ile Leu Ser Lys His Pro Asn
225                 230                 235                 240

Trp Thr Asn Thr Gln Val Arg Ser Ser Leu Glu Asn Thr Thr Thr Lys
                245                 250                 255

Leu Gly Asp Ala Phe Tyr Tyr Gly Lys Gly Leu Ile Asn Val Gln Ala
            260                 265                 270
```

Ala Ala Gln
    275

<210> SEQ ID NO 39
<211> LENGTH: 275
<212> TYPE: PRT
<213> ORGANISM: Geobacillus stearothermophilus
<220> FEATURE:
<221> NAME/KEY: misc_feature
<222> LOCATION: (1)..(275)
<223> OTHER INFORMATION: G_stearothermophilus_ABY25856

<400> SEQUENCE: 39

Ala Gln Ser Val Pro Tyr Gly Val Ser Gln Ile Lys Ala Pro Ala Leu
1               5                   10                  15

His Ser Gln Gly Phe Thr Gly Ser Asn Val Lys Val Ala Val Ile Asp
            20                  25                  30

Ser Gly Ile Asp Ser Ser His Pro Asp Leu Lys Val Ala Gly Gly Ala
        35                  40                  45

Ser Met Val Pro Ser Glu Thr Asn Pro Phe Gln Asp Asn Asn Ser His
    50                  55                  60

Gly Thr His Val Ala Gly Thr Val Ala Ala Leu Asn Asn Ser Val Gly
65                  70                  75                  80

Val Leu Gly Val Ala Pro Ser Ala Ser Leu Tyr Ala Val Lys Val Leu
                85                  90                  95

Gly Ala Asp Gly Ser Gly Gln Tyr Ser Trp Ile Ile Asn Gly Ile Glu
            100                 105                 110

Trp Ala Ile Ala Tyr Asn Met Asp Val Ile Asn Met Ser Leu Gly Gly
        115                 120                 125

Pro Ser Gly Ser Ala Ala Leu Lys Ala Ala Val Asp Lys Ala Val Ala
    130                 135                 140

Ser Gly Ile Val Val Ala Ala Ala Gly Asn Glu Gly Thr Ser Gly Ser
145                 150                 155                 160

Ser Ser Ser Thr Val Gly Tyr Pro Gly Lys Tyr Pro Ser Val Ile Ala
                165                 170                 175

Val Gly Ala Val Asn Ser Ser Asn Gln Arg Ala Ser Phe Ser Ser Val
            180                 185                 190

Gly Ser Glu Leu Asp Val Met Ala Pro Gly Val Ser Ile Gln Ser Thr
        195                 200                 205

Leu Pro Gly Asn Lys Tyr Gly Ala Tyr Asn Gly Thr Ser Met Ala Ser
    210                 215                 220

Pro His Val Ala Gly Ala Ala Ala Leu Ile Leu Ser Lys His Pro Asn
225                 230                 235                 240

Trp Thr Asn Thr Gln Val Arg Ser Ser Leu Glu Asn Thr Thr Thr Lys
                245                 250                 255

Leu Gly Asp Ala Phe Tyr Tyr Gly Lys Gly Leu Ile Asn Val Gln Ala
            260                 265                 270

Ala Ala Gln
    275

<210> SEQ ID NO 40
<211> LENGTH: 275
<212> TYPE: PRT
<213> ORGANISM: Bacillus vallismortis
<220> FEATURE:
<221> NAME/KEY: misc_feature
<222> LOCATION: (1)..(275)
<223> OTHER INFORMATION: B_vallismortis_WP010329279

<400> SEQUENCE: 40

```
Ala Gln Ser Val Pro Tyr Gly Ile Ser Gln Ile Lys Ala Pro Ala Leu
1               5                   10                  15

His Ser Gln Gly Tyr Thr Gly Ser Asn Val Lys Val Ala Val Ile Asp
            20                  25                  30

Ser Gly Ile Asp Ser Ser His Pro Asp Leu Asn Val Arg Gly Gly Ala
        35                  40                  45

Ser Phe Val Pro Ser Glu Thr Asn Pro Tyr Gln Asp Gly Ser Ser His
    50                  55                  60

Gly Thr His Val Ala Gly Thr Val Ala Ala Leu Asn Asn Ser Ile Gly
65                  70                  75                  80

Val Leu Gly Val Ala Pro Asn Ala Ser Leu Tyr Ala Val Lys Val Leu
                85                  90                  95

Asp Ser Thr Gly Asn Gly Gln Tyr Ser Trp Ile Ile Asn Gly Ile Glu
            100                 105                 110

Trp Ala Ile Ser Asn Lys Met Asp Val Ile Asn Met Ser Leu Gly Gly
        115                 120                 125

Pro Ser Gly Ser Thr Ala Leu Lys Ser Val Val Asp Arg Ala Val Ala
    130                 135                 140

Ser Gly Ile Val Val Ala Ala Ala Gly Asn Glu Gly Thr Ser Gly
145                 150                 155                 160

Ser Ser Ser Thr Ile Gly Tyr Pro Ala Lys Tyr Pro Ser Thr Ile Ala
            165                 170                 175

Val Gly Ala Val Asn Ser Ser Asn Gln Arg Gly Ser Phe Ser Ser Val
        180                 185                 190

Gly Pro Glu Leu Asp Val Met Ala Pro Gly Val Ser Ile Gln Ser Thr
    195                 200                 205

Leu Pro Gly Gly Thr Tyr Gly Ser Tyr Asn Gly Thr Ser Met Ala Thr
210                 215                 220

Pro His Val Ala Gly Ala Ala Ala Leu Ile Leu Ser Lys His Pro Thr
225                 230                 235                 240

Trp Thr Asn Thr Gln Val Arg Asn Arg Leu Glu Ser Thr Thr Thr Tyr
            245                 250                 255

Leu Gly Ser Ser Phe Tyr Tyr Gly Lys Gly Leu Ile Asn Val Gln Ala
        260                 265                 270

Ala Ala Gln
        275
```

<210> SEQ ID NO 41
<211> LENGTH: 275
<212> TYPE: PRT
<213> ORGANISM: Bacillus subtilis
<220> FEATURE:
<221> NAME/KEY: misc_feature
<222> LOCATION: (1)..(275)
<223> OTHER INFORMATION: B_subtilis_ACJ07037

<400> SEQUENCE: 41

```
Ala Gln Ser Val Pro Tyr Gly Ile Ser Gln Ile Lys Ala Pro Ala Leu
1               5                   10                  15

His Ser Gln Gly Tyr Thr Gly Ser Asn Val Lys Val Ala Val Ile Asp
            20                  25                  30

Ser Gly Ile Asp Ser Ser His Pro Asp Leu Asn Val Lys Gly Gly Ala
        35                  40                  45

Ser Phe Val Pro Ser Glu Thr Asn Pro Tyr Gln Asp Gly Ser Ser His
    50                  55                  60
```

Gly Thr His Val Ala Gly Thr Ile Ala Ala Leu Asn Asn Thr Ile Gly
 65                  70                  75                  80

Val Leu Gly Val Ala Pro Asn Ala Ser Leu Tyr Ala Val Lys Val Leu
                 85                  90                  95

Asp Ser Thr Gly Ser Gly Gln Tyr Ser Trp Ile Ile Asn Gly Ile Glu
            100                 105                 110

Trp Ala Ile Ser Asn Asn Met Asp Val Ile Asn Met Ser Leu Gly Gly
        115                 120                 125

Pro Ser Gly Ser Thr Ala Leu Lys Thr Val Val Asp Lys Ala Val Ser
130                 135                 140

Ser Gly Ile Val Ala Ala Ala Gly Asn Glu Gly Ser Ser Gly
145                 150                 155                 160

Ser Thr Ser Thr Val Gly Tyr Pro Ala Lys Tyr Pro Ser Thr Ile Ala
                165                 170                 175

Val Gly Ala Val Asn Ser Ser Asn Gln Arg Ala Ser Phe Ser Ser Ala
            180                 185                 190

Gly Ser Glu Leu Asp Val Met Ala Pro Gly Val Ser Ile Gln Ser Thr
        195                 200                 205

Leu Pro Gly Gly Thr Tyr Gly Ala Tyr Asn Gly Thr Ser Met Ala Thr
210                 215                 220

Pro His Val Ala Gly Ala Ala Ala Leu Ile Leu Ser Lys His Pro Thr
225                 230                 235                 240

Trp Thr Asn Ala Gln Val Arg Asp Arg Leu Glu Ser Thr Ala Thr Tyr
                245                 250                 255

Leu Gly Ser Ser Phe Tyr Tyr Gly Lys Gly Leu Ile Asn Val Gln Ala
            260                 265                 270

Ala Ala Gln
        275

<210> SEQ ID NO 42
<211> LENGTH: 275
<212> TYPE: PRT
<213> ORGANISM: Bacillus subtilis
<220> FEATURE:
<221> NAME/KEY: misc_feature
<222> LOCATION: (1)..(275)
<223> OTHER INFORMATION: B_subtilis_str168_CAA74536

<400> SEQUENCE: 42

Ala Gln Ser Val Pro Tyr Gly Ile Ser Gln Ile Lys Ala Pro Ala Leu
1               5                   10                  15

His Ser Gln Gly Tyr Thr Gly Ser Asn Val Lys Val Ala Val Ile Asp
            20                  25                  30

Ser Gly Ile Asp Ser Ser His Pro Asp Leu Asn Val Arg Gly Gly Ala
        35                  40                  45

Ser Phe Val Pro Ser Glu Thr Asn Pro Tyr Gln Asp Gly Ser Ser His
    50                  55                  60

Gly Thr His Val Ala Gly Thr Ile Ala Ala Leu Asn Asn Ser Ile Gly
 65                  70                  75                  80

Val Leu Gly Val Ser Pro Ser Ala Ser Leu Tyr Ala Val Lys Val Leu
                 85                  90                  95

Asp Ser Thr Gly Ser Gly Gln Tyr Ser Trp Ile Ile Asn Gly Ile Glu
            100                 105                 110

Trp Ala Ile Ser Asn Asn Met Asp Val Ile Asn Met Ser Leu Gly Gly
        115                 120                 125

```
Pro Thr Gly Ser Thr Ala Leu Lys Thr Val Val Asp Lys Ala Val Ser
130                 135                 140

Ser Gly Ile Val Val Ala Ala Ala Gly Asn Glu Gly Ser Ser Gly
145                 150                 155                 160

Ser Thr Ser Thr Val Gly Tyr Pro Ala Lys Tyr Pro Ser Thr Ile Ala
                165                 170                 175

Val Gly Ala Val Asn Ser Ser Asn Gln Arg Ala Ser Phe Ser Ser Ala
                180                 185                 190

Gly Ser Glu Leu Asp Val Met Ala Pro Gly Val Ser Ile Gln Ser Thr
            195                 200                 205

Leu Pro Gly Gly Thr Tyr Gly Ala Tyr Asn Gly Thr Ser Met Ala Thr
210                 215                 220

Pro His Val Ala Gly Ala Ala Ala Leu Ile Leu Ser Lys His Pro Thr
225                 230                 235                 240

Trp Thr Asn Ala Gln Val Arg Asp Arg Leu Glu Ser Thr Ala Thr Tyr
                245                 250                 255

Leu Gly Asn Ser Phe Tyr Tyr Gly Lys Gly Leu Ile Asn Val Gln Ala
            260                 265                 270

Ala Ala Gln
        275

<210> SEQ ID NO 43
<211> LENGTH: 275
<212> TYPE: PRT
<213> ORGANISM: Bacillus mojavensis
<220> FEATURE:
<221> NAME/KEY: misc_feature
<222> LOCATION: (1)..(275)
<223> OTHER INFORMATION: B_mojavensis_WP010333625

<400> SEQUENCE: 43

Ala Gln Ser Val Pro Tyr Gly Ile Ser Gln Ile Lys Ala Pro Ala Leu
1               5                   10                  15

His Ser Gln Gly Tyr Thr Gly Ser Asn Val Lys Val Ala Val Ile Asp
            20                  25                  30

Ser Gly Ile Asp Ser Ser His Pro Asp Leu Asn Val Arg Gly Gly Ala
        35                  40                  45

Ser Phe Val Pro Ser Glu Thr Asn Pro Tyr Gln Asp Gly Ser Ser His
50                  55                  60

Gly Thr His Val Ala Gly Thr Val Ala Ala Leu Asn Asn Thr Ile Gly
65                  70                  75                  80

Val Leu Gly Val Ala Pro Ser Ala Ser Leu Tyr Ala Val Lys Val Leu
                85                  90                  95

Asp Ser Thr Gly Ser Gly Gln Tyr Ser Trp Ile Ile Asn Gly Ile Glu
            100                 105                 110

Trp Ala Ile Ser Asn Asn Met Asp Val Ile Asn Met Ser Leu Gly Gly
        115                 120                 125

Pro Thr Gly Ser Thr Ala Leu Lys Thr Val Val Asp Lys Ala Val Ala
130                 135                 140

Ser Gly Ile Val Val Ala Ala Ala Gly Asn Glu Gly Ser Ser Gly
145                 150                 155                 160

Ser Thr Ser Thr Val Gly Tyr Pro Ala Lys Tyr Pro Ser Thr Ile Ala
                165                 170                 175

Val Gly Ala Val Asn Ser Ser Asn Gln Arg Ala Ser Phe Ser Ser Ala
                180                 185                 190

Gly Ser Glu Leu Asp Val Met Ala Pro Gly Val Ser Ile Gln Ser Thr
```

```
                195                 200                 205
Leu Pro Gly Gly Thr Tyr Gly Ala Tyr Asn Gly Thr Ser Met Ala Thr
    210                 215                 220

Pro His Val Ala Gly Ala Ala Leu Ile Leu Ser Lys His Pro Thr
225                 230                 235                 240

Trp Thr Asn Ala Gln Val Arg Asp Arg Leu Glu Ser Thr Ala Thr Tyr
                245                 250                 255

Leu Gly Ser Ser Phe Tyr Tyr Gly Lys Gly Leu Ile Asn Val Gln Ala
                260                 265                 270

Ala Ala Gln
        275

<210> SEQ ID NO 44
<211> LENGTH: 275
<212> TYPE: PRT
<213> ORGANISM: Bacillus subtilis
<220> FEATURE:
<221> NAME/KEY: misc_feature
<222> LOCATION: (1)..(275)
<223> OTHER INFORMATION: B_subtilis_BAN09118

<400> SEQUENCE: 44

Ala Gln Ser Val Pro Tyr Gly Ile Ser Gln Ile Lys Ala Pro Ala Leu
1               5                   10                  15

His Ser Gln Gly Tyr Thr Gly Ser Asn Val Lys Val Ala Val Ile Asp
                20                  25                  30

Ser Gly Ile Asp Ser Ser His Pro Asp Leu Asn Val Arg Gly Gly Ala
            35                  40                  45

Ser Phe Val Pro Ser Glu Thr Asn Pro Tyr Gln Asp Gly Ser Ser His
    50                  55                  60

Gly Thr His Val Ala Gly Thr Val Ala Ala Leu Asn Asn Thr Ile Gly
65                  70                  75                  80

Val Leu Gly Val Ala Pro Ser Ala Ser Leu Tyr Ala Val Lys Val Leu
                85                  90                  95

Asp Ser Thr Gly Ser Gly Gln Tyr Ser Trp Ile Ile Asn Gly Ile Glu
            100                 105                 110

Trp Ala Ile Ser Asn Asn Met Asp Val Ile Asn Met Ser Leu Gly Gly
        115                 120                 125

Pro Thr Gly Ser Thr Ala Leu Lys Thr Val Val Asp Lys Ala Val Ala
    130                 135                 140

Ser Gly Ile Val Val Ala Ala Ala Gly Asn Glu Gly Ser Ser Gly
145                 150                 155                 160

Ser Thr Ser Thr Val Gly Tyr Pro Ala Lys Tyr Pro Ser Thr Ile Ala
                165                 170                 175

Val Gly Ala Val Asn Ser Ser Asn Gln Arg Ala Ser Phe Ser Ser Ala
            180                 185                 190

Gly Ser Glu Leu Asp Val Met Ala Pro Gly Val Ser Ile Gln Ser Thr
        195                 200                 205

Leu Pro Gly Gly Thr Tyr Gly Ser Tyr Asn Gly Thr Ser Met Ala Thr
    210                 215                 220

Pro His Val Ala Gly Ala Ala Leu Ile Leu Ser Lys His Pro Thr
225                 230                 235                 240

Trp Ser Asn Ala Gln Val Arg Asp Arg Leu Glu Ser Thr Ala Thr Asn
                245                 250                 255

Leu Gly Ser Ser Phe Tyr Tyr Gly Lys Gly Leu Ile Asn Val Gln Ala
                260                 265                 270
```

```
Ala Ala Gln
        275

<210> SEQ ID NO 45
<211> LENGTH: 3
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<223> OTHER INFORMATION: Amino acid motif Tyr56-Asn57-Thr58 (amino
      acid positions correspond to numbering in amino acid sequence
      AprL protease shown in SEQ ID NO: 2). This motif starts at
      position 56 and ends at position 58

<400> SEQUENCE: 45

Tyr Asn Thr
1

<210> SEQ ID NO 46
<211> LENGTH: 3
<212> TYPE: PRT
<213> ORGANISM: Artificial Sequence
<220> FEATURE:
<223> OTHER INFORMATION: Synthetic peptide

<400> SEQUENCE: 46

Tyr Asn Thr
1

<210> SEQ ID NO 47
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (3)..(3)
<223> OTHER INFORMATION: Xaa is Ala or Ser
<220> FEATURE:
<221> NAME/KEY: misc_feature
<222> LOCATION: (6)..(6)
<223> OTHER INFORMATION: Xaa, if present, is any amino acid
<220> FEATURE:
<221> NAME/KEY: misc_feature
<222> LOCATION: (7)..(7)
<223> OTHER INFORMATION: Xaa is Ala or Ser

<400> SEQUENCE: 47

Phe Val Xaa Gly Glu Xaa Xaa Tyr Asn Thr
1               5                   10

<210> SEQ ID NO 48
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<223> OTHER INFORMATION: F50V51X152G53E54X355Y56 N57T58 (SEQ ID NO:48)
      motif, wherein X1 is an A or S and X3 is an A or S; and further
      wherein the amino acid positions are numbered by correspondence
      with the amino acid sequence of the AprL protease set forth in SEQ
      ID NO:2
<220> FEATURE:
<221> NAME/KEY: misc_feature
<222> LOCATION: (3)..(3)
<223> OTHER INFORMATION: Xaa is Ala or Ser
```

```
<220> FEATURE:
<221> NAME/KEY: misc_feature
<222> LOCATION: (6)..(6)
<223> OTHER INFORMATION: Xaa is Ala or Ser

<400> SEQUENCE: 48

Phe Val Xaa Gly Glu Xaa Tyr Asn Thr
1               5

<210> SEQ ID NO 49
<211> LENGTH: 4
<212> TYPE: PRT
<213> ORGANISM: Artificial Sequence
<220> FEATURE:
<223> OTHER INFORMATION: Synthetic peptide

<400> SEQUENCE: 49

Leu Ser Ala Ser
1

<210> SEQ ID NO 50
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<223> OTHER INFORMATION: Leu240-Ser241-Ala242-Ser243 motif (amino acid
      positions correspond to numbering in amino acid sequence AprL
      protease shown in SEQ ID NO: 2)

<400> SEQUENCE: 50

Leu Ser Ala Ser
1

<210> SEQ ID NO 51
<211> LENGTH: 11
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(4)
<223> OTHER INFORMATION: Xaa is any amino acid
<220> FEATURE:
<221> NAME/KEY: misc_feature
<222> LOCATION: (10)..(10)
<223> OTHER INFORMATION: Xaa is Val or Ile

<400> SEQUENCE: 51

Lys Xaa Xaa Xaa Leu Ser Ala Ser Gln Xaa Arg
1               5                   10

<210> SEQ ID NO 52
<211> LENGTH: 11
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<223> OTHER INFORMATION: K236XXXLSASQX5R246 (SEQ ID NO:52) motif,
      wherein X is any amino acid and X5 is an I or V; and further
      wherein the amino acid positions are numbered by correspondence
      with the amino acid sequence of the AprL protease set forth in SEQ
      ID NO:2.
<220> FEATURE:
<221> NAME/KEY: misc_feature
<222> LOCATION: (2)..(4)
```

```
<223> OTHER INFORMATION: Xaa is any amino acid
<220> FEATURE:
<221> NAME/KEY: misc_feature
<222> LOCATION: (10)..(10)
<223> OTHER INFORMATION: Xaa is Val or Ile

<400> SEQUENCE: 52

Lys Xaa Xaa Xaa Leu Ser Ala Ser Gln Xaa Arg
1               5                   10

<210> SEQ ID NO 53
<211> LENGTH: 254
<212> TYPE: PRT
<213> ORGANISM: Artificial Sequence
<220> FEATURE:
<223> OTHER INFORMATION: Synthetic consensus sequence

<400> SEQUENCE: 53

Ala Gln Thr Val Pro Tyr Gly Ile Ile Lys Ala Pro Val His Ala Gln
1               5                   10                  15

Gly Tyr Thr Gly Ser Asn Val Lys Val Ala Val Leu Asp Thr Gly Ile
            20                  25                  30

Ala Ser His Pro Asp Leu Asn Val Gly Gly Ala Ser Phe Val Pro Ser
        35                  40                  45

Glu Pro Gln Asp Gly Asn Gly His Gly Thr His Val Ala Gly Thr Val
    50                  55                  60

Ala Ala Leu Asn Asn Thr Ile Gly Val Leu Gly Val Ala Pro Ser Ala
65                  70                  75                  80

Ser Leu Tyr Ala Val Lys Val Leu Ala Ser Gly Ser Gly Ser Tyr Ser
                85                  90                  95

Ile Ile Gln Gly Ile Glu Trp Ala Ile Asn Asn Met Asp Val Ile Asn
            100                 105                 110

Met Ser Leu Gly Gly Pro Ser Gly Ser Thr Ala Leu Lys Gln Ala Val
        115                 120                 125

Asp Ala Ala Ser Gly Val Val Val Ala Ala Ala Gly Asn Ser Gly
    130                 135                 140

Ser Ser Gly Thr Thr Val Gly Tyr Pro Ala Lys Tyr Ser Val Ile Ala
145                 150                 155                 160

Val Gly Ala Val Asp Ser Asn Asn Asn Arg Ala Ser Phe Ser Ser Gly
                165                 170                 175

Ser Glu Leu Asp Val Met Ala Pro Gly Val Ser Ile Gln Ser Thr Leu
            180                 185                 190

Pro Gly Asn Tyr Ala Ser Tyr Asn Gly Thr Ser Met Ala Ser Pro His
        195                 200                 205

Val Ala Gly Ala Ala Ala Leu Ile Leu Ser Lys His Pro Ser Trp Ser
    210                 215                 220

Asn Ser Gln Val Arg Asn Arg Leu Asn Thr Ala Thr Leu Gly Ser Phe
225                 230                 235                 240

Tyr Tyr Gly Lys Gly Leu Ile Asn Val Glu Ala Ala Ala Gln
                245                 250

<210> SEQ ID NO 54
<211> LENGTH: 274
<212> TYPE: PRT
<213> ORGANISM: Artificial Sequence
<220> FEATURE:
<223> OTHER INFORMATION: Synthetic consensus sequence

<400> SEQUENCE: 54
```

-continued

```
Ala Gln Thr Val Pro Tyr Gly Ile Pro Leu Ile Lys Ala Asp Lys Val
1               5                   10                  15

Gln Ala Gln Gly Phe Lys Gly Ala Asn Val Lys Val Ala Val Leu Asp
            20                  25                  30

Thr Gly Ile Gln Ala Ser His Pro Asp Leu Asn Val Val Gly Gly Ala
        35                  40                  45

Ser Phe Val Ala Gly Glu Ala Tyr Asn Thr Asp Gly Asn Gly His Gly
    50                  55                  60

Thr His Val Ala Gly Thr Val Ala Ala Leu Asp Asn Thr Thr Gly Val
65                  70                  75                  80

Leu Gly Val Ala Pro Asn Val Ser Leu Tyr Ala Val Lys Val Leu Asn
                85                  90                  95

Ser Ser Gly Ser Gly Ser Tyr Ser Gly Ile Val Ser Gly Ile Glu Trp
            100                 105                 110

Ala Thr Thr Asn Gly Met Asp Val Ile Asn Met Ser Leu Gly Gly Pro
        115                 120                 125

Ser Gly Ser Thr Ala Met Lys Gln Ala Val Asp Asn Ala Tyr Ala Arg
    130                 135                 140

Gly Val Val Val Ala Ala Ala Gly Asn Ser Gly Ser Ser Gly Asn
145                 150                 155                 160

Thr Asn Thr Ile Gly Tyr Pro Ala Lys Tyr Asp Ser Val Ile Ala Val
                165                 170                 175

Gly Ala Val Asp Ser Asn Ser Asn Arg Ala Ser Phe Ser Ser Val Gly
            180                 185                 190

Ala Glu Leu Glu Val Met Ala Pro Gly Ala Gly Val Tyr Ser Thr Tyr
        195                 200                 205

Pro Thr Asn Thr Tyr Ala Thr Leu Asn Gly Thr Ser Met Ala Ser Pro
    210                 215                 220

His Val Ala Gly Ala Ala Ala Leu Ile Leu Ser Lys His Pro Asn Leu
225                 230                 235                 240

Ser Ala Ser Gln Val Arg Asn Arg Leu Ser Ser Thr Ala Thr Tyr Leu
                245                 250                 255

Gly Ser Ser Phe Tyr Tyr Gly Lys Gly Leu Ile Asn Val Glu Ala Ala
            260                 265                 270

Ala Gln
```

```
<210> SEQ ID NO 55
<211> LENGTH: 4
<212> TYPE: PRT
<213> ORGANISM: artificial sequence
<220> FEATURE:
<223> OTHER INFORMATION: motif
<220> FEATURE:
<221> NAME/KEY: MISC_FEATURE
<222> LOCATION: (3)..(3)
<223> OTHER INFORMATION: Xaa is Ala or Gly

<400> SEQUENCE: 55

Leu Ser Xaa Ser
1
```

```
<210> SEQ ID NO 56
<211> LENGTH: 4
<212> TYPE: PRT
<213> ORGANISM: artificial sequence
<220> FEATURE:
<223> OTHER INFORMATION: motif
<220> FEATURE:
<221> NAME/KEY: MISC_FEATURE
```

<223> OTHER INFORMATION: L240S241G242S243 (SEQ ID NO:56) motif, wherein
      the amino acid positions are numbered by correspondence with the
      amino acid sequence of AprL protease set forth in SEQ ID NO:2.

<400> SEQUENCE: 56

Leu Ser Gly Ser
1

<210> SEQ ID NO 57
<211> LENGTH: 11
<212> TYPE: PRT
<213> ORGANISM: artificial sequence
<220> FEATURE:
<223> OTHER INFORMATION: motif
<220> FEATURE:
<221> NAME/KEY: MISC_FEATURE
<222> LOCATION: (2)..(4)
<223> OTHER INFORMATION: Xaa is any amino acid
<220> FEATURE:
<221> NAME/KEY: MISC_FEATURE
<222> LOCATION: (7)..(7)
<223> OTHER INFORMATION: Xaa is Ala or Gly
<220> FEATURE:
<221> NAME/KEY: MISC_FEATURE
<222> LOCATION: (10)..(10)
<223> OTHER INFORMATION: Xaa is Ile or Val

<400> SEQUENCE: 57

Lys Xaa Xaa Xaa Leu Ser Xaa Ser Gln Xaa Arg
1               5                   10

<210> SEQ ID NO 58
<211> LENGTH: 4
<212> TYPE: PRT
<213> ORGANISM: artificial sequence
<220> FEATURE:
<223> OTHER INFORMATION: motif

<400> SEQUENCE: 58

Leu Ser Gly Ser
1

<210> SEQ ID NO 59
<211> LENGTH: 11
<212> TYPE: PRT
<213> ORGANISM: artificial sequence
<220> FEATURE:
<223> OTHER INFORMATION: motif
<220> FEATURE:
<221> NAME/KEY: MISC_FEATURE
<222> LOCATION: (2)..(4)
<223> OTHER INFORMATION: Xaa is any amino acid
<220> FEATURE:
<221> NAME/KEY: MISC_FEATURE
<222> LOCATION: (10)..(10)
<223> OTHER INFORMATION: Xaa is Ile or Val

<400> SEQUENCE: 59

Lys Xaa Xaa Xaa Leu Ser Gly Ser Gln Xaa Arg
1               5                   10

<210> SEQ ID NO 60
<211> LENGTH: 11
<212> TYPE: PRT
<213> ORGANISM: artificial sequence
<220> FEATURE:
<223> OTHER INFORMATION: motif
<220> FEATURE:
<221> NAME/KEY: MISC_FEATURE
<223> OTHER INFORMATION: K236XXXLSGSQX5R246 (SEQ ID NO:60) motif,
      wherein X is any amino acid and X5 is an I or V; and further

```
         wherein the amino acid positions are numbered by correspondence
         with the amino acid sequence of the AprL protease set forth in SEQ
         ID NO:2.
<220> FEATURE:
<221> NAME/KEY: MISC_FEATURE
<222> LOCATION: (2)..(4)
<223> OTHER INFORMATION: Xaa is any amino acid
<220> FEATURE:
<221> NAME/KEY: MISC_FEATURE
<222> LOCATION: (10)..(10)
<223> OTHER INFORMATION: Xaa is Ile or Val

<400> SEQUENCE: 60

Lys Xaa Xaa Xaa Leu Ser Gly Ser Gln Xaa Arg
1               5                   10
```

We claim:

1. A variant subtilisin enzyme or an active fragment thereof comprising one or more amino acid modification to a parent AprL-clade subtilisin enzyme, wherein the modification is T078I;
   wherein the amino acid positions of the subtilisin variant are numbered by correspondence with the amino acid sequence of *Bacillus* sp. AprL subtilisin set forth in SEQ ID NO:2, and wherein the variant has at least 95% sequence identity to the amino acid sequence of SEQ ID NO: 2.

2. The variant of claim 1, comprising one or more amino acid modification selected from:
   A001C, A048R, A052F, G099S, G099T, G101A, G127F, G127I, G127M, G127Q, G127T, G127V, I121M, L010M, L095A, L095F, L095Q, L095S, L125I, L125V, M123C, M123I, N025F, N025S, N116C, N140R, N184C, P238C, P238D, P238I, P238M, P238N, Q136A, S098F, S098H, S102D, S158Q, S241R, T077C, T077F, T215C, V026I, V026Q, V045R, and V149C;
   A024E, A128D, G053C, G101N, G165E, G203C, L125S, N061E, N116C, S098D, S102E, S104D, S129E, S155D, S158E, and V026T.

3. The variant of claim 1, comprising one or more amino acid modification selected from: A029T, A048K, A048R, A052F, A052R, A068G, A113C, D119H, E111Q, G099A, G099S, G127A, G127T, G165A, K012G, K012H, K027C, K027E, K027M, L095F, L125I, L125V, L240Q, N025F, N025G, N025L, N043R, N116R, N140R, N160C, N184C, N239K, P238C, P238I, P238M, Q136F, Q136H, Q136K, Q136R, Q136W, S098F, S098H, S104A, S158Q, S241R, V045R, and Y103M.

4. The variant of claim 1, comprising one or more amino acid modification selected from: A001C, A001D, A024E, A024G, A048C, A048D, A048K, A048N, A052F, A052M, A052V, A052Y, A055C, A072G, A091G, A113C, A128P, A128Q, A133G, A133S, A133T, A143E, A143F, A143H, A143N, A143S, A143W, A193D, A202C, A202D, A202E, A202Q, A227S, D119F, D119S, D119Y, G053C, G053E, G053N, G053Q, G060L, G060Y, G099A, G099T, G101A, G117D, G117V, G127A, G127S, G127T, G130D, G130H, G203A, G203C, G203E, G203M, H237I, I035A, I035C, I035M, I035T, I121M, K012N, K015M, K027C, K027L, K027M, K027R, K264A, K264S, L010M, L095F, L125V, L234Q, L240N, L249I, M123C, M123I, M123L, N025F, N025G, N025L, N025S, N057C, N061A, N076G, N096D, N096G, N116A, N116C, N116L, N116Y, N140A, N160C, N182C, N182D, N184C, N211S, N247F, N247H, N247I, N247L, N247Q, N247S, N247V, N247W, N247Y, P009E, P009T, P238A, P238C, P238D, P238F, P238I, P238R, Q017H, Q136A, Q136C, Q136F, Q136H, Q136K, Q136L, R144F, R144L, R248K, S086R, S088N, S088Y, S097G, S097H, S097Y, S098H, S098L, S100L, S102D, S102E, S102G, S102K, S129E, S129H, S155A, S155D, S155E, S155H, S157D, S158I, S158Q, S181A, S181Q, S183G, S241R, S241T, S243I, S243N, S243T, S243V, S243Y, S251E, S258C, S258D, S258P, T058C, T058D, T058F, T058I, T077C, T077F, T077L, T077M, T078Q, T132A, T132Q, T132V, T132Y, T161Q, T210I, T215C, V026Q, V026R, V026T, V028A, V028C, V045I, V071A, V071L, V120A, V120C, V120I, V146A, V146H, V146K, V147L, V149C, Y056H, and Y255C.

5. The variant of claim 1, wherein said parent subtilisin enzyme comprises an amino acid sequence of SEQ ID NO:2, 9, 12, 13, 14, 15, or 16.

6. The variant of claim 1, wherein said parent subtilisin enzyme and/or said variant comprises:
   (i) the YNT (SEQ ID NO:46) motif between Asp32 and His63;
   (ii) the Y56N57T58 (SEQ ID NO:45) motif;
   (iii) an F50V51X$_1$52G53E54X$_3$55Y56N57T58 (SEQ ID NO:48) motif, wherein X$_1$ is an A or S and X$_3$ is an A or S;
   (iv) an LSX$_4$S (SEQ ID NO:55) motif between Lys236 and Arg246, wherein X$_4$ is A or G;
   (v) the L240S241A242S243 (SEQ ID NO:50) motif;
   (vi) the L240S241G242S243(SEQ ID NO:56) motif;
   (vii) a KXXXLSX$_4$SQX$_5$R (SEQ ID NO:57) motif, wherein X is any amino acid, X$_4$ is A or G, and X$_5$ is an I or V;
   (viii) a K236XXXLSASQX$_5$R246 (SEQ ID NO: 52) motif, wherein X is any amino acid and X$_5$ is an I or V;
   (ix) K236XXXLSGSQX$_5$R246 (SEQ ID NO:60) motif, wherein X is any amino acid and X$_5$ is an I or V; or
   (x) a motif 1 selected from (i), (ii), and (iii) in combination with a motif 2 selected from (iv), (v), (vi), (vii), (viii), and (ix).

7. The variant of claim 1, wherein said parent subtilisin enzyme and/or said variant comprises a loop region between residues 52-60.

8. The variant of claim 1, wherein said parent subtilisin enzyme and/or said variant comprises an Arg248 residue.

9. The variant of claim 1, wherein said parent subtilisin enzyme and/or said variant comprises (i) the amino acid sequence of SEQ ID NO: 45, 46, 47, or 48; and (ii) the amino acid sequence of SEQ ID NO: 49, 50, 51, 52, 55, 56, 57, 58, 59, or 60.

10. A composition comprising at least one variant of claim 1.

11. The composition of claim 10, wherein said composition is a cleaning composition or a detergent composition.

12. The composition of claim 11, wherein said detergent composition is selected from the group consisting of a laundry detergent, a fabric softening detergent, a dishwashing detergent, and a hard-surface cleaning detergent.

13. The composition of claim 10, wherein said composition further comprises a surfactant; at least one stabilizer; at least one bleaching agent; at least one adjunct ingredient; one or more additional enzymes or enzyme derivatives selected from the group consisting of acyl transferases, alpha-amylases, beta-amylases, alpha-galactosidases, arabinosidases, aryl esterases, beta-galactosidases, carrageenases, catalases, cellobiohydrolases, cellulases, chondroitinases, cutinases, endo-beta-1, 4-glucanases, endo-beta-mannanases, esterases, exo-mannanases, galactanases, glucoamylases, hemicellulases, hyaluronidases, keratinases, laccases, lactases, ligninases, lipases, lipoxygenases, mannanases, oxidases, pectate lyases, pectin acetyl esterases, pectinases, pentosanases, peroxidases, phenoloxidases, phosphatases, phospholipases, phytases, polygalacturonases, proteases, pullulanases, reductases, rhamnogalacturonases, beta-glucanases, tannases, transglutaminases, xylan acetyl-esterases, xylanases, xyloglucanases, and xylosidases, additional metallopotease enzymes and combinations thereof.

14. The composition of claim 10, wherein said cleaning composition contains phosphate.

15. The composition of claim 10, wherein said cleaning composition contains borate.

16. The composition of claim 10, wherein said composition is a granular, powder, solid, bar, liquid, tablet, gel, unit dose or paste composition.

* * * * *